US008933096B2

(12) United States Patent
Lavoie et al.

(10) Patent No.: US 8,933,096 B2
(45) Date of Patent: Jan. 13, 2015

(54) ANTIMICROBIAL AGENTS

(75) Inventors: Edmond J. Lavoie, Princeton Jct, NJ (US); Ajit Parhi, Highland Park, NJ (US); Daniel S. Pilch, Highland Park, NJ (US)

(73) Assignees: Rugers, The State University of New Jersey, New Brunswick, NJ (US); University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 13/702,936

(22) PCT Filed: Jun. 9, 2011

(86) PCT No.: PCT/US2011/039839
§ 371 (c)(1),
(2), (4) Date: Dec. 7, 2012

(87) PCT Pub. No.: WO2011/156626
PCT Pub. Date: Dec. 15, 2011

(65) Prior Publication Data
US 2013/0116278 A1    May 9, 2013

Related U.S. Application Data

(60) Provisional application No. 61/353,107, filed on Jun. 9, 2010, provisional application No. 61/355,408, filed on Jun. 16, 2010, provisional application No. 61/372,755, filed on Aug. 11, 2010, provisional application No. 61/372,770, filed on Aug. 11, 2010.

(51) Int. Cl.
| C07D 217/22 | (2006.01) |
| A61K 31/47 | (2006.01) |
| C07D 217/14 | (2006.01) |
| C07D 405/10 | (2006.01) |

(52) U.S. Cl.
CPC ............ C07D 405/10 (2013.01); C07D 217/14 (2013.01); C07D 217/22 (2013.01)
USPC ........... 514/307; 514/309; 514/310; 546/141; 546/143; 546/144

(58) Field of Classification Search
None
See application file for complete search history.

(56) References Cited

U.S. PATENT DOCUMENTS

| 4,309,539 | A | 1/1982 | Boller et al. |
| 4,782,058 | A | 11/1988 | Griffith |
| 5,177,067 | A | 1/1993 | Guerry et al. |
| 5,177,075 | A | 1/1993 | Suto et al. |
| 2002/0035090 | A1 | 3/2002 | Zeldis et al. |
| 2002/0077333 | A1 | 6/2002 | Dey et al. |
| 2006/0183943 | A1 | 8/2006 | Hu |
| 2008/0027028 | A1 | 1/2008 | Chichak |
| 2008/0300239 | A1 | 12/2008 | Adams et al. |
| 2009/0076074 | A1 | 3/2009 | Jung et al. |
| 2009/0312319 | A1 | 12/2009 | Ren et al. |
| 2010/0120810 | A1 | 5/2010 | Leblond et al. |
| 2012/0022061 | A1 | 1/2012 | LaVoie |
| 2012/0059026 | A1 | 3/2012 | LaVoie |
| 2013/0109713 | A1 | 5/2013 | LaVoie |

FOREIGN PATENT DOCUMENTS

| DE | 4327748 A1 | 2/1995 |
| EP | 0719764 A1 | 7/1996 |
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 2004/000814 A1 | 12/2003 |
| WO | WO 2004/005472 A2 | 1/2004 |
| WO | WO 2004/041210 A2 | 5/2004 |
| WO | WO 2004/087145 A2 | 10/2004 |
| WO | WO 2005/075428 A1 | 8/2005 |
| WO | WO 2006/067048 A1 | 6/2006 |
| WO | WO 2006/105289 A1 | 10/2006 |
| WO | WO 2008/016596 A2 | 2/2008 |
| WO | WO 2010/127307 A1 | 11/2010 |

OTHER PUBLICATIONS

Wu et al., Toxicology, 236, pp. 1-6, 2007.*
Roesch et al, Journal of Organic Chemistry (2001), 66(24), pp. 8042-8051.*
Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", Bull. Chem. Soc. Japan, 57 (8), 2188-2192 (1984).
Augstein et al., "Synthesis of 11-Hydroxy-2,3,9,10-tetramethoxy-5,6,13,13a-tetrahydro-8H-dibenzo[a,g]quinolizine. A Contribution to the Structure of Stepharotine", Stepharotine, vol. 34, No. 5, 1349-1352 (1969).
Bedi et al., "Synthesis and biological activity of novel antibacterial quinazolines", Bioorganic & Medicinal Chemistry Letters, vol. 14 (20), 5211-5213 (2004).

(Continued)

Primary Examiner — Zinna Northington Davis
(74) Attorney, Agent, or Firm — Viksnins Harris & Padys PLLP

(57) ABSTRACT

The invention provides a compound of formula (I): or a salt or prodrug thereof, wherein $R^1$, $R^4$-$R^8$, $R^{10}$, $R^{2'}$-$R^{6'}$, W, and A have any of the values described in the specification, as well as compositions comprising a compound of formula (I). The compounds are useful as antibacterial agents.

(I)

27 Claims, No Drawings

(56) References Cited

OTHER PUBLICATIONS

Beilstein, Database Beilstein Institute for Organic Chemistry, XP002591901, Database Accession No. 3834367 (BRN) abstract (1918).
Beilstein, Database Beilstein Institute for Organic Chemistry, XP002591900, Database Accession No. 3837583(BNR) abstract (1930).
Beuria, T.K. et al., "Sanguinarine Blocks Cytokinesis in Bacteria by Inhibiting FtsZ Assembly and Bundling", *Biochemistry*, 44, 16584-16593 (2005).
Bild et al., "Discovery of Inhibitors of MCF-7 Tumor Cell Adhesion to Endothelial Cells and Investigation on their Mode of Action", *Archiv Der Pharmazie*, vol. 337 (12), 687-694 (2004).
Chen et al., "Synthesis and Antibacterial Evaluation of Certain Quinolone Derivatives", *J. Med. Chem.*, 44, 2374-2377 (2001).
Cole et al., "Potential Tumor-Selective Nitroimidazolylmethyluracil Prodrug Derivatives: Inhibitors of the Angiogenic Enzyme Thymidine Phosphorylase", J. Med. Chem., 46, 207-209 (2003).
Database Registry [Online], Chemical Abstracts Service, XP002570845, Database accession No. 1043562-34-0/RN, abstract (2008).
Denes et al., "The chemistry of sanguinarine", XP002570844, Chemical Abstracts Service, Database accession No. 1960:91836, abstract, *Magyar Kemiai Folyoirat*, 64, 125-130 (1958).
Dyke et al., "The Chemistry of Cryptopine—I The Epicryptopines", *Tetrahedr0n*, vol. 24, No. 3, 1455-1465 (1968).
Dyke et al., "The Chemistry of Cryptopine—II Pseudocryptopine Chloride", *Tetrahedron*, vol. 25, 5375-5381 (1969).
Dykhuizen, "Santa Rosalia revisited: Why are there so many species of bacteria?", *Antonie van Leeuwenhock*, 73, 25-33 (1998).
Foroumadi et al., "Synthesis and in vitro antibacterial N-[5-(5-nitro-2-thienyl)-1,3,4-thiadiazole-2-yl] piperazinyl pquinolones", *European Journal of Medicinal Chemistry*, 38, 851-854 (2003).
Gopinath et al., "Dehydrogenation cyclization of 2-aryl-1-tetralone oxime acetates", XP002570843, Chemical Abstracts Service, Database accession No. 1960:23123, abstract, *Current Science*, 28, 241-242 (1959).
Huecas et al., "Protein Structure and Folding: The Interactions of Cell Division Protein FtsZ with Guanine Nucleotides", *J. Biol. Chem.*,282, 37515-37528 (2007).
Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", *Chem. Pharm. Bull.*, 32(8), 2984-2994 (1984).
Ito et al., "A medium-term rat liver bioassay for rapid in vivo detection of carcinogenic potential of chemicals", *Cancer Sci*, vol. 94 (1), 3-8 (2003).
Jackson et al., "Non-Steroidal Aromatase Inhibitors Based on a Biphenyl Scaffold: Synthesis, in vitro SAR, and Molecular Modelling", *Chem. Med. Chem.*, vol. 3, (4), 603-618 (2008).
Kaul et al., "A Bactericidal Guanidinomethyl Biaryl That Alters the Dynamics of Bacterial FtsZ Polymerization", *Journal of Medicinal Chemistry*, 55(22), 10160-10176 (2012).
Leroux et al., "N-(4-Biphenylmethyl)imidazoles as Potential Therapeutics for the Treatment of Prostate Cancer: Metabolic Robustness Due to Fluorine Substituion?", *Helvetica Chimica Acta, Verlag Helvetica*, vol. 86, 2671-2686 (2003).
Okudaira et al., "A Study of the Intestinal Absorption of an Ester-Type Prodrug, ME3229, in Rats: Active Efflux Transport as a Cause of Poor Bioavailability of the Active Drug", *Journal of Pharmacology and Experimental Therapeutics*, vol. 294 (2), 580-587 (2000).
Patent Cooperation Treaty, International Searching Authority, Search Report and Written Opinion for PCT/2011/039839, 13 pages, dated Oct. 17, 2011.
Sanders et al., "Selective Cytotoxicity of Topoisomerase-Directed Protoberberines against Glioblastoma Cells", *Biochemical Pharmacology*, vol. 56, 1157-1166 (1998).
Sethi, "Enzyme Inhibition VIII: Mode of Inhibition of Reverse Transcriptase Activity by Analogues, Isomers, and Related Alkaloids of Coralyne", *Journal of Pharmaceutical Sciences*, vol. 74 (8), 889-891 (1985).
Wachall et al., "Imidazole Substitued Biphenyls: A new Class o Highly Potent and in Vivo Active Inhibitors of P450 17 as Potential Therapeutics for Treatment of Prostate Cancer", *Bioorganic & Medicinal Chemistry*, vol. 7 (9), 1913-1924 (1999).
Yaeko et al., "Studies on the constituents of *Bocconia cordata*. IV. Transformation of sanguinarine into bocconine", XP002570841, Chemical Abstracts Service, Database accession No. 1992:129332, abstract, *Journal of Heterocyclic Chemistry*, 28(8), 1841-1843 (1991).
Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", *Chem. Pharm. Bull.*, 31(5), 1601-1611 (1983).

* cited by examiner

ANTIMICROBIAL AGENTS

PRIORITY OF INVENTION

This application is a 371 PCT/US11/39839 filed Jun. 9, 2001, which claims priority to United States Provisional Application No. 61/353,107, filed 9 Jun. 2010; 61/355,408, filed 16 Jun. 2010; 61/372,770, filed 11 Aug. 2010; and 61/372,755, filed 11 Aug. 2010.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need to expand currently available antimicrobials. In this connection, there is a pressing need for new antibiotics that exhibit novel mechanisms of action or that are able to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

SUMMARY OF THE INVENTION

In one embodiment the invention provides compounds that display antimicrobial activity. Accordingly, the invention provides a compound of formula I:

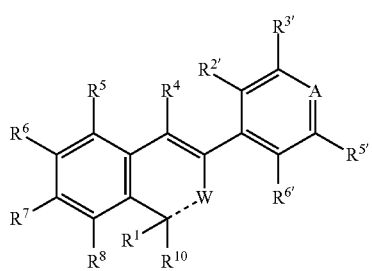

wherein $R^1$, $R^4$-$R^8$, $R^{10}$, $R^{2'}$-$R^{6'}$, W, and A have the values defined in a), b), and c) below:

a) when the dashed line - - - is a single bond, $R^{10}$ is present, then W is $NR^9$ or $(NR^9R^a)^+X^-$ and $R^9$ and $R^{6'}$ taken together are —$(CR^{13}{}_2)_2$— or —$CR^{14}$=$CR^{14}$—; or
when the dashed line - - - is a single bond, $R^{10}$ is present, then W is $NR^b$ or $(NR^cR^d)^+X^-$;

when the dashed line - - - is a double bond, and $R^{10}$ is absent, then W is $(NR^9)^+X^-$ and $R^9$ and $R^{6'}$ taken together are —$(CR^{13}{}_2)_2$— or —$CR^{14}$=$CR^{14}$—; or
when the dashed line - - - is a double bond, and $R^{19}$ is absent, then W is N or $(NR^a)^+X^-$; or
when the dashed line - - - is a single bond, $R^1$ is $R^{20}$, and $R^{11}$, then W is $NR^9$ or $(NR^9R^a)^+X^-$ and $R^9$ and $R^{6'}$ taken together are —$(CR^{13}{}_2)_2$—; or
when the dashed line - - - is a single bond, $R^1$ is $R^{20}$, and $R^{10}$ is $R^{11}$, then W is $NR^b$ or $(NR^cR^d)^+X^-$;
when the dashed line - - - is a single bond, $R^1$ is $R^{21}$, and $R^{10}$ is $R^{11}$, then W is $NR^9$ or $(NR^9R^a)^+X^-$ and $R^9$ and $R^{6'}$ taken together are —$(CR^{13}{}_2)_2$— or —$CR^{14}$=$CR^{14}$—; or
when the dashed line - - - is a single bond, $R^1$ is $R^{21}$, and $R^{10}$ is $R^{11}$, then W is $NR^b$ or $(NR^cR^d)^+X^-$;
$X^-$ is a counterion;
A is N or $CR^{4'}$;
$R^1$ is H, $(C_1$-$C_6)$alkyl, $(C_1$-$C_6)$alkoxy, $(C_1$-$C_6)$alkylthio, aryloxy or arylthio; and $R^{10}$ is H or $(C_1$-$C_6)$alkyl, wherein any $(C_1$-$C_6)$alkyl, $(C_1$-$C_6)$alkoxy, and $(C_1$-$C_6)$alkylthio of $R^1$ and $R^{10}$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^eR^f$, and wherein any aryloxy, or arylthio of $R^1$ and $R^{10}$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^eR^f$; or $R^1$ and $R^{10}$ together with the carbon to which they are attached form a carbonyl group;

at least one of $R^4$, $R^5$, $R^{2'}$, and $R^{3'}$ is aryl substituted with one or more $R^{cc}$ and optionally substituted with one or more groups independently selected from $(C_1$-$C_6)$alkyl, halo, hydroxy, cyano, nitro, $(C_1$-$C_6)$alkoxy, $(C_3$-$C_6)$cycloalkyl, carboxy, aryloxy, nitro, sulfo, —$S(O)_2NR^gR^h$, —$N(R^j)$ $S(O)_2R^k$, and —$NR^gR^h$; or at least one of $R^4$, $R^5$, $R^{2'}$, and $R^{3'}$ is aryl substituted with one or more $(C_1$-$C_6)$alkoxy and optionally substituted with one or more $R^{ee}$; or at least one of $R^4$, $R^5$, $R^{2'}$, and $R^{3'}$ is heteroaryl substituted with one or more $R^{dd}$ and optionally substituted with one or more groups independently selected from $(C_1$-$C_6)$alkyl, halo, hydroxy, cyano, nitro, $(C_1$-$C_6)$alkoxy, $(C_3$-$C_6)$cycloalkyl, carboxy, aryloxy, nitro, sulfo, —$S(O)_2NR^gR^h$, —$N(R^j)S(O)_2R^k$, and —$NR^gR^h$; or at least one of $R^4$, $R^5$, $R^{2'}$, and $R^{3'}$ is aryl($C_1$-$C_6$)alkoxy; and the remainder of $R^4$, $R^5$, $R^{2'}$, and $R^{3'}$ are each independently selected from hydrogen, halo, hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, aryl($C_1$-$C_6)$alkyl, aryl($C_1$-$C_6)$alkoxy, heteroaryl($C_1$-$C_6)$alkoxy, aryl, heteroaryl, heteroaryl($C_1$-$C_6)$alkyl, aryl($C_1$-$C_6)$alkanoyl, and heteroaryl($C_1$-$C_6)$alkanoyl; wherein each $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, and $(C_1$-$C_6)$alkanoyl of $R^4$, $R^5$, $R^{2'}$, and $R^{3'}$ is optionally substituted with one or more groups independently selected from halo, hydroxy, cyano, nitro, $(C_1$-$C_6)$alkoxy, $(C_3$-$C_6)$cycloalkyl, oxo, carboxy, aryloxy, sulfo, —$S(O)_2NR^gR^h$, —$N(R^j)S(O)_2R^k$, and —$NR^gR^h$; and wherein each aryl, and heteroaryl of $R^4$, $R^5$, $R^{2'}$, and $R^{3'}$ is optionally substituted with one or more groups independently selected from $(C_1$-$C_6)$alkyl, halo, hydroxy, cyano, nitro, $(C_1$-$C_6)$ alkoxy, $(C_3$-$C_6)$cycloalkyl, carboxy, aryloxy, nitro, sulfo, $R^{aa}$, —$S(O)_2NR^gR^h$, —$N(R^j)S(O)_2R^k$, and —$NR^gR^h$;

any adjacent $R^6$, $R^7$, $R^8$, $R^{4'}$, and $R^{5'}$ taken together can optionally be methylenedioxy and each remaining $R^6$, $R^7$, $R^8$, $R^{4'}$, and $R^{5'}$ is independently selected from H, $R^{bb}$, and B—$R^x$;

each B is independently selected from —O—, —S—, and —N($R^y$)—;

$R^{6'}$ is H, alkyl, halo, —NR$^e$R$^f$, NO$_2$, aryl, heteroaryl, aryl($C_1$-$C_6$)alkyl, heteroaryl($C_1$-$C_6$)alkyl, aryl($C_1$-$C_6$)alkanoyl or heteroaryl($C_1$-$C_6$)alkanoyl wherein alkyl, aryl, heteroaryl, aryl($C_1$-$C_6$)alkyl, heteroaryl($C_1$-$C_6$)alkyl, aryl($C_1$-$C_6$)alkanoyl or heteroaryl($C_1$-$C_6$)alkanoyl are optionally substituted with one or more groups selected from halo, cyano, ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

each $R^{13}$ is independently H, ($C_1$-$C_6$)alkyl, ($C_1$-$C_6$)alkoxy, ($C_1$-$C_6$)alkylthio, aryloxy or arylthio wherein any ($C_1$-$C_6$)alkyl, ($C_1$-$C_6$)alkoxy, and ($C_1$-$C_6$)alkylthio of $R^{13}$ is optionally substituted with one or more groups selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$, and wherein any aryloxy, or arylthio of $R^{13}$ is optionally substituted with one or more groups selected from halo, cyano, ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

each $R^{14}$ is independently H, ($C_1$-$C_6$)alkyl, ($C_1$-$C_6$)alkoxy, ($C_1$-$C_6$)alkylthio, aryloxy or arylthio wherein any ($C_1$-$C_6$)alkyl, ($C_1$-$C_6$)alkoxy, and ($C_1$-$C_6$)alkylthio of $R^{14}$ is optionally substituted with one or more groups selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$, and wherein any aryloxy, or arylthio of $R^{14}$ is optionally substituted with one or more groups selected from halo, cyano, ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^{20}$ is —NR$^{gg}$R$^{gh}$ and $R^{11}$ is H or ($C_1$-$C_6$)alkyl, wherein any ($C_1$-$C_6$)alkyl, of $R^{11}$ is optionally substituted with one or more groups selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^{21}$ is —NR$^{he}$—C(=NR$^{hb}$)—NR$^{hc}$R$^{hd}$, —C(=NR$^{hb}$)—NR$^{hc}$R$^{hd}$, —NR$^{ke}$—C(=NR$^{kb}$)R$^{ke}$, or —NR$^{ke}$—C(=O)—NR$^{kc}$R$^{kd}$, and $R^{11}$ is H or ($C_1$-$C_6$)alkyl, wherein any ($C_1$-$C_6$)alkyl, of $R^{11}$ is optionally substituted with one or more groups selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^a$ is ($C_1$-$C_6$)alkyl wherein ($C_1$-$C_6$)alkyl is optionally substituted with one or more groups independently selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^b$ is H or ($C_1$-$C_6$)alkyl wherein ($C_1$-$C_6$)alkyl is optionally substituted with one or more groups independently selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^c$ and $R^d$ are each independently selected from ($C_1$-$C_6$)alkyl wherein ($C_1$-$C_6$)alkyl is optionally substituted with one or more groups independently selected from halo, cyano, oxo (=O), ($C_1$-$C_6$)alkyl, ($C_3$-$C_6$)cycloalkyl, carboxy, NO$_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^e$R$^f$;

$R^e$ and $R^f$ are each independently H, ($C_1$-$C_6$)alkyl, aryl, heteroaryl, aryl($C_1$-$C_6$) alkyl or heteroaryl($C_1$-$C_6$) alkyl; or $R^e$ and $R^f$ together with the nitrogen to which they are attached form a morpholino, piperazino, pyrrolidino or piperidino;

each $R^g$ and $R^h$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^g$ and $R^h$ together with the nitrogen to which they are attached form a aziridino, azetidino, morpholino, piperazino, pyrrolidino or piperidino;

each $R^j$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^k$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^u$ and $R^v$ is independently selected from H and ($C_1$-$C_6$)alkyl;

each $R^x$ is independently selected from ($C_1$-$C_6$)alkyl, ($C_1$-$C_6$)alkanoyl, and —C(=O)NR$^u$R$^v$;

each $R^y$ is independently selected from H and ($C_1$-$C_6$) alkyl;

each $R^{aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, ($C_3$-$C_6$) cycloalkyl, carboxy, aryloxy, nitro, sulfo, —S(O)$_2$NR$^g$R$^h$, —N(R$^j$)S(O)$_2$R$^k$, and —NR$^g$R$^h$; and
and each $R^{bb}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, ($C_3$-$C_6$) cycloalkyl, carboxy, aryloxy, nitro, sulfo, —S(O)$_2$NR$^g$R$^h$, —N(R$^j$)S(O)$_2$R$^k$, and —NR$^g$R$^h$;

each $R^{cc}$ is independently selected from a) aryl that is substituted with one or more groups independently selected from ($C_1$-$C_6$)alkyl, halo, hydroxy, cyano, nitro, ($C_1$-$C_6$) alkoxy, ($C_3$-$C_6$)cycloalkyl, carboxy, aryloxy, nitro, sulfo, —S(O)$_2$NR$^g$R$^h$, —N(R$^j$)S(O)$_2$R$^k$, and —NR$^g$R$^h$; b) heteroaryl that is optionally substituted with one or more groups independently selected from ($C_1$-$C_6$)alkyl, halo, hydroxy, cyano, nitro, ($C_1$-$C_6$)alkoxy, ($C_3$-$C_6$)cycloalkyl, carboxy, aryloxy, nitro, sulfo, —S(O)$_2$NR$^g$R$^h$, —N(R$^j$)S(O)$_2$R$^k$, and —NR$^g$R$^h$; or c) aryl($C_1$-$C_6$)alkyl, aryl($C_1$-$C_6$)alkoxy; and each $R^{dd}$ is independently aryl or heteroaryl, which aryl or heteroaryl is optionally substituted with one or more groups independently selected from ($C_1$-$C_6$)alkyl, halo, hydroxy, cyano, nitro, ($C_1$-$C_6$)alkoxy, ($C_3$-$C_6$)cycloalkyl, carboxy, aryloxy, nitro, sulfo, —S(O)$_2$NR$^g$R$^h$, —N(R$^j$)S(O)$_2$R$^k$, and —NR$^g$R$^h$;

each $R^{ee}$ is independently aryl that is optionally substituted with one or more groups independently selected from ($C_1$-$C_6$)alkyl, halo, hydroxy, cyano, nitro, ($C_1$-$C_6$)alkoxy, ($C_3$-$C_6$) cycloalkyl, carboxy, nitro, sulfo, —S(O)$_2$NR$^g$R$^h$, —N(R$^j$)S(O)$_2$R$^k$, and —NR$^g$R$^h$;

each $R^{gg}$ and $R^{gh}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-

$C_6$) alkyl; or $R^g$ and $R^h$ together with the nitrogen to which they are attached form a aziridino, azetidino, morpholino, piperazino, pyrrolidino or piperidino;

each $R^{hb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{hc}$ and $R^{hd}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{hc}$ and $R^{hd}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{hc}$ and $R^{hd}$ is optionally substituted with one or more groups independently selected from hydroxy, carboxy, and $NR^{hm}R^{hn}$;

each $R^{he}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{hm}$ and $R^{hn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{hm}$ and $R^{hn}$ together with the nitrogen to which they are attached form a aziridino, azetidino, morpholino, piperazino, pyrrolidino or piperidino;

each $R^{kb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{kc}$ and $R^{kd}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{kc}$ and $R^{kd}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{kc}$ and $R^{kd}$ is optionally substituted with one or more groups independently selected from hydroxy, carboxy, and $NR^{km}R^{kn}$;

each $R^{ke}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^{km}$ and $R^{kn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{km}$ and $R^{kn}$ together with the nitrogen to which they are attached form a aziridino, azetidino, morpholino, piperazino, pyrrolidino or piperidino; or b) the bond represented by - - - is present, $R^{10}$ is absent, and W is $(NR^{30})^+D^-$ except as defined below when $R^{30}$ and $R^{3a}$ taken together with the atoms to which they are attached form a 5- or 6-membered heterocyclic ring or a 5- or 6-membered heteroaromatic ring;

$R^1$ is $-NR^{3a}R^{3b}$, $-C(=NR^{3cb})-NR^{3cc}R^{3cd}$, aryloxy, cyano, or $(C_1-C_6)$alkyl that is substituted with one or more $-NR3^{ce}-C(=NR^{3cb})R^{3ce}$, $-C(=NR^{3cb})-NR^{3cc}R^{3cd}$, $-NR^{3ce}-C(=NR^{3cb})-NR^{3cc}R^{3cd}$, and $-NR^{3ce}-C(=O)-NR^{3cc}R^{3cd}$;

at least one of $R^4$, $R^5$, $R^{2'}$, $R^{3'}$, and $R^{6'}$ is selected from hydroxy, carboxy, cyano, $CF_3SO_3-$, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; and the remainder of $R^4$, $R^5$, $R^{2'}$, $R^{3'}$, and $R^{6'}$ are independently selected from hydrogen, halo, hydroxy, carboxy, cyano, $CF_3SO_3-$, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, cycloalkyl, and $(C_1-C_6)$alkanoyl of $R^4$, $R^5$, $R^{2'}$, $R^{3'}$, and $R^{6'}$ is optionally substituted with one or more groups independently selected from halo, hydroxy, cyano, nitro, $(C_1-C_6)$alkoxy, cycloalkyl, oxo, carboxy, aryloxy, sulfo, $-S(O)_2NR^{3g}R^{3h}$, $-N(R^j)S(O)_2R^{3k}$, and $-NR^{3g}R^{3h}$; and wherein each aryl, and heteroaryl of $R^4$, $R^5$, $R^{2'}$, $R^{3'}$, and $R^{6'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{3aa}$, $-S(O)_2NR^{3g}R^{3h}$, $-N(R^{3j})S(O)_2R^{3k}$, and $-NR^{3g}R^{3h}$;

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, $R^{3bb}$, and $Z-R^{3x}$;

each Z is independently selected from $-O-$, $-S-$, and $-N(R^{3y})-$;

$R^{30}$ is absent and is absent; or $R^{30}$ is H or $(C_1-C_6)$alkyl and $D^-$ is counterion;

or $R^{30}$ and $R^{3a}$ taken together with the atoms to which they are attached form a 5- or 6-membered heterocyclic ring or a 5- or 6-membered heteroaromatic ring, wherein a) when the bond represented by - - - is present in the 5- or 6-membered heterocyclic ring or the 5- or 6-membered heteroaromatic ring, then W is $(NR^{30})^+D^-$ and $D^-$ is a counterion, b) when the bond represented by - - - is absent in the 5- or 6-membered heterocyclic ring or the 5- or 6-membered heteroaromatic ring, then W is $(NR^{30}R^{31})^+D^-R^{31}$ is $(C_1-C_6)$alkyl and $D^-$ is a counterion, or c) when the bond represented by - - - is absent in the 5- or 6-membered heterocyclic ring or the 5- or 6-membered heteroaromatic ring, then W is $(NR^{30})$;

A is N or $C-R^{4'}$;

$R^{3a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^a$ is optionally substituted with one or more groups selected from halo, hydroxy, cyano, nitro, $(C_1-C_6)$alkoxy, cycloalkyl, oxo, carboxy, $-NR^{3da}R^{3db}$, and aryloxy, and wherein each aryl and heteroaryl of $R^{3a}$ is optionally substituted with one or more groups selected from $(C_1-C_6)$alkyl, halo, hydroxy, cyano, nitro, $(C_1-C_6)$alkoxy, cycloalkyl, carboxy, and aryloxy; and $R^{3b}$ is hydrogen, $(C_1-C_6)$alkyl, aryl, aryl$(C_1-C_6)$alkyl, heteroaryl, heteroaryl$(C_1-C_6)$alkyl, $-C(=NR^{3cb})-NR^{3cc}R^{3cd}$, $-C(=NR^{3cb})-R^{3ea}$, $-C(=O)-R^{3m}$, $-C(=O)-OR^{3n}$, $-C(=O)-SR^{3p}$, $-C(=O)-NR^{3q}R^{3r}$, $-C(=S)-R^{3m}$, $-C(=S)-OR^{3n}$, $-C(=S)-SR^{3p}$, or $-C(=S)-NR^{3q}R^{3r}$; wherein each $(C_1-C_6)$alkyl of $R^{3b}$ is optionally substituted with one or more groups independently selected from halo, hydroxy, cyano, nitro, $(C_1-C_6)$alkoxy, cycloalkyl, oxo, carboxy, $-NR^{3da}R^{3db}$, and aryloxy; and wherein each aryl, and heteroaryl of $R^b$ is optionally substituted with one or more groups independently selected from $(C_1-C_6)$alkyl, halo, hydroxy, cyano, nitro, $(C_1-C_6)$alkoxy, cycloalkyl, carboxy, and aryloxy; or $R^{3a}$ and $R^{3b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{3c}$ is hydrogen, $(C_1-C_6)$alkyl, aryl, or heteroaryl;

$R^{3d}$ is hydrogen, $(C_1-C_6)$alkyl, $(C_1-C_6)$alkoxy, $(C_1-C_6)$alkylthio, $(C_1-C_6)$alkanoyl, or $-NR^{3e}R^{3f}$;

$R^{3e}$ and $R^{3f}$ are each independently selected from H, $(C_1-C_6)$alkyl, cycloalkyl, cycloalkyl$(C_1-C_6)$alkyl, aryl, heteroaryl, aryl($C_1$-$C_6$) alkyl and heteroaryl($C_1$-$C_6$)alkyl; or $R^{3e}$ and $R^{3f}$ together with the nitrogen to which they are attached form a aziridino, azetidino, morpholino, piperazino, pyrrolidino or piperidino;

each $R^{3g}$ and $R^{3h}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$) alkyl; or $R^{3g}$ and $R^{3h}$ together with the nitrogen to which they are attached form a aziridino, azetidino, morpholino, piperazino, pyrrolidino or piperidino;

each $R^{3j}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl;

each $R^{3k}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl;

each $R^{3m}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl;

each $R^{3n}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl, wherein each aryl, and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$;

each $R^{3p}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl, wherein each aryl, and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$;

each $R^{3q}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl; and each $R^{3r}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$)alkyl; or $R^{3q}$ and $R^{3r}$ together with the nitrogen to which they are attached form a aziridino, azetidino, morpholino, piperazino, pyrrolidino or piperidino;

each $R^{3u}$ and $R^{3v}$ is independently selected from H and ($C_1$-$C_6$)alkyl;

each $R^{3x}$ is independently selected from ($C_1$-$C_6$)alkyl, ($C_1$-$C_6$)alkanoyl, and —C(=O)NR$^{3u}$R$^{3v}$;

each $R^{3y}$ is independently selected from H and ($C_1$-$C_6$) alkyl;

each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$; and each $R^{3bb}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$;

each $R^{3cb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{3cc}$ and $R^{3cd}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{3cc}$ and $R^{3cd}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{3cc}$ and $R^{3cd}$ is optionally substituted with one or more groups independently selected from hydroxy, carboxy, and NR$^{3cm}$R$^{3cn}$;

each $R^{3ce}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{3cg}$ and $R^{3ch}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{3cg}$ and $R^{3ch}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{3cg}$ and $R^{3ch}$ is optionally substituted with one or more groups independently selected from hydroxy, carboxy, and NR$^{3cm}$R$^{3cn}$;

each $R^{3cm}$ and $R^{3cn}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{cm}$ and $R^{cn}$ together with the nitrogen to which they are attached form a aziridino, azetidino, morpholino, piperazino, pyrrolidino or piperidino;

each $R^{3da}$ and $R^{3db}$ is independently selected from H, ($C_1$-$C_6$)alkyl, cycloalkyl, cycloalkyl($C_1$-$C_6$)alkyl, aryl, heteroaryl, aryl($C_1$-$C_6$) alkyl and heteroaryl($C_1$-$C_6$) alkyl; or $R^{3da}$ and $R^{3db}$ together with the nitrogen to which they are attached form a aziridino, azetidino, morpholino, piperazino, pyrrolidino or piperidino;

$R^{ea}$ is H, ($C_1$-$C_6$)alkyl, ($C_1$-$C_6$)alkoxy, ($C_1$-$C_6$)alkylthio, or ($C_1$-$C_6$)alkanoyl;

or c) when the dashed line - - - is a double bond, and $R^{10}$ is absent, then W is (NR$^{41}$)$^+$W$^-$ and $R^{41}$ and $R^{6\prime}$ taken together are —CHR$^{43}$—CHR$^{42}$—, or —CR$^{43}$=CR$^{42}$—;

$R^1$ is —NR$^{4a}$R$^{4b}$, —C(=NR$^{4cb}$)—NR$^{4cc}$R$^{4cd}$, cyano, or ($C_1$-$C_6$)alkyl that is substituted with one or more —NR$^{4ce}$—C(=NR$^{4cb}$)R$^{4ce}$; —C(=NR$^{4cb}$)—NR$^{4cc}$R$^{4cd}$; and —NR$^{4ce}$—C(=NR$^{4cb}$)—NR$^{4cc}$R$^{4cd}$;

$R^{4\prime}$, $R^{5\prime}$, $R^6$, $R^7$ and $R^8$ are each indepentyl selected from H and Z—R$^x$; or $R^{4\prime}$ and $R^{5\prime}$ taken together are methylenedioxy and $R^6$, $R^7$, and $R^8$ are each indepentyl selected from H and Z—R$^x$; or $R^8$ and 7 taken together are methylenedioxy and $R^{4\prime}$, $R^{5\prime}$, and $R^6$ are each indepentyl selected from H and Z—R$^x$; or $R^7$ and $R^6$ taken together are methylenedioxy and $R^{4\prime}$, $R^{5\prime}$, and $R^8$ are each indepentyl selected from H and —Z—R$^{4x}$;

each Z is independently selected from —O—, —S—, and —N(R$^{4y}$)—;

at least one of $R^{2\prime}$, $R^{3\prime}$, $R^4$, and $R^5$ is selected from hydroxy, carboxy, cyano, CF$_3$SO$_3$—, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$)alkyl, aryl, heteroaryl, heteroaryl($C_1$-$C_6$)alkyl, arylalkanoyl, and heteroarylalkanoyl; and the remainder of $R^{2\prime}$, $R^{3\prime}$, $R^4$, and $R^5$ are independently selected from H, hydroxy, carboxy, cyano, CF$_3$SO$_3$—, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$) alkyl, aryl, heteroaryl, heteroaryl($C_1$-$C_6$)alkyl, aryl($C_1$-$C_6$) alkanoyl, and heteroaryl($C_1$-$C_6$)alkanoyl; wherein each ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, and ($C_1$-$C_6$)alkanoyl of $R^{2\prime}$, $R^{3\prime}$, $R^4$, and $R^5$ is optionally substituted with one or more groups independently selected from halo, hydroxy, cyano, nitro, $(C_1-C_6)$ alkoxy, $(C_3-C_6)$cycloalkyl, oxo, carboxy, aryloxy, sulfo, $-S(O)_2NR^{4g}R^{4h}$, $-N(R^{4j})S(O)_2R^{4k}$, and $-NR^{4g}R^{4h}$; and wherein each aryl and heteroaryl of $R^{2t}$, $R^{3t}$, $R^4$, and $R^5$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $-S(O)_2NR^{4g}R^{4h}$, $-N(R^{4j})S(O)_2R^{4k}$, $R^{4s}$, and $-NR^{4g}R^{4h}$;

$R^{42}$ is H, $(C_1-C_6)$alkyl, aryl, heteroaryl, or aryl$(C_1-C_6)$alkyl;

$R^{43}$ is H, $(C_1-C_6)$alkyl, aryl, heteroaryl, or aryl$(C_1-C_6)$alkyl;

$R^{4a}$ is H, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^{4a}$ is optionally substituted with one or more groups selected from halo, hydroxy, cyano, nitro, $(C_1-C_6)$alkoxy, $(C_3-C_6)$cycloalkyl, oxo, carboxy, and aryloxy, and wherein each aryl and heteroaryl of $R^{4a}$ is optionally substituted with one or more groups selected from $(C_1-C_6)$alkyl, halo, hydroxy, cyano, nitro, $(C_1-C_6)$alkoxy, $(C_3-C_6)$cycloalkyl, carboxy, and aryloxy; and $R^{4b}$ is H, $(C_1-C_6)$alkyl, aryl, aryl$(C_1-C_6)$alkyl, heteroaryl, heteroaryl$(C_1-C_6)$alkyl, $-C(=O)-R^{4m}$, $-C(=O)-OR^{4n}$, $-C(=O)-SR^{4p}$, $-C(=O)-NR^{4q}R^{4r}$, $-C(=S)-R^{4m}$, $-C(=S)-OR^{4n}$, $-C(=S)-SR^{4p}$, $-C(=S)-NR^{4q}R^{4r}$, or $-C(=NR^{4c})-R^{4d}$; wherein each $(C_1-C_6)$alkyl of $R^{4b}$ is optionally substituted with one or more groups independently selected from halo, hydroxy, cyano, nitro, $(C_1-C_6)$alkoxy, $(C_3-C_6)$cycloalkyl, oxo, carboxy, and aryloxy; and wherein each aryl, and heteroaryl of $R^b$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, and aryloxy; or $R^{4a}$ and $R^{4b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one of more $(C_1-C_6)$alkyl;

$R^{4c}$ is H, $(C_1-C_6)$alkyl, aryl, or heteroaryl;

$R^{4d}$ is H, $(C_1-C_6)$alkyl, $(C_1-C_6)$alkoxy, $(C_1-C_6)$alkylthio, $(C_1-C_6)$alkanoyl, or $-NR^{4e}R^{4f}$;

$R^{4e}$ and $R^{4f}$ are each independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^{4e}$ and $R^{4f}$ together with the nitrogen to which they are attached form a aziridino, azetidino, morpholino, piperazino, pyrrolidino or piperidino;

each $R^{4g}$ and $R^{4h}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^g$ and $R^h$ together with the nitrogen to which they are attached form a aziridino, azetidino, morpholino, piperazino, pyrrolidino or piperidino;

each $R^{4j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4k}$ is independently selected from $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4m}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4n}$ is independently selected from $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4p}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4q}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^r$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^q$ and $R^r$ together with the nitrogen to which they are attached form a aziridino, azetidino, morpholino, piperazino, pyrrolidino or piperidino;

each $R^{4s}$ is independently trifluoromethyl, trifluoromethoxy, or aryl optionally substituted with one or more $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $-S(O)_2NR^{4g}R^{4h}$, $-N(R^{4j})S(O)_2R^{4k}$, trifluoromethyl, trifluoromethoxy, and $-NR^{4g}R^{4h}$;

each $R^{4u}$ and $R^{4v}$ is independently selected from H and $(C_1-C_6)$alkyl;

each $R^{4x}$ is independently selected from $(C_1-C_6)$alkyl, $(C_1-C_6)$alkanoyl, and $-C(=O)NR^{4u}R^{4v}$;

each $R^{4y}$ is independently selected from H and $(C_1-C_6)$alkyl;

each $R^{4cb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4cc}$ and $R^{cd}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{4cc}$ and $R^{4cd}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{4cc}$ and $R^{4cd}$ is optionally substituted with one or more groups independently selected from hydroxy, carboxy, and $NR^{4cm}R^{4n}$;

each $R^{4ce}$ is independently selected from H, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{4cg}$ and $R^{4ch}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{4cg}$ and $R^{4ch}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{4ch}$ and $R^{4ch}$ is optionally substituted with one or more groups independently selected from hydroxy, carboxy, and $NR^{4cm}R^{4cn}$;

each $R^{4cm}$ and $R^{4cn}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{4cm}$ and $R^{4cn}$ together with the nitrogen to which they are attached form a aziridino, azetidino, morpholino, piperazino, pyrrolidino or piperidino; and $W^-$ is a counter anion;

or a salt or prodrug thereof.

In one embodiment the invention provides a compound of formula (I) which is a compound of the following formula:

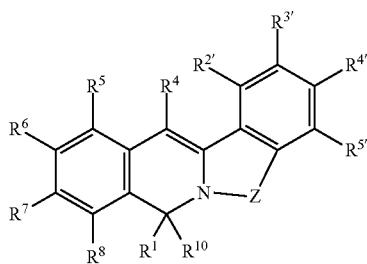

Ia wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of the following formula:

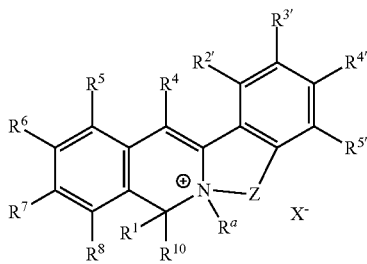

Ib wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of the following formula:

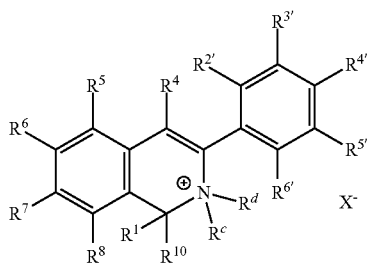

Ic or a pharmaceutically acceptable salt or prodrug thereof.

In one embodiment the invention provides a compound of formula (I) which is a compound of the following formula:

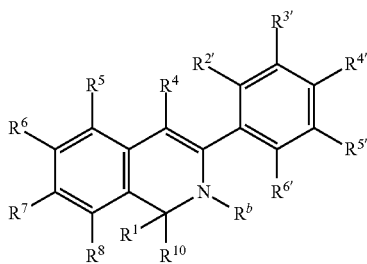

Id or a pharmaceutically acceptable salt or prodrug thereof.

In one embodiment the invention provides a compound of formula (I) which is a compound of the following formula:

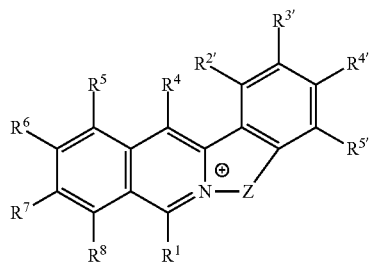

Ie wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of the following formula:

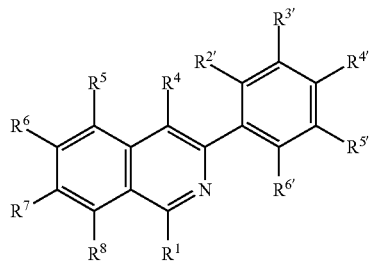

If or a pharmaceutically acceptable salt or prodrug thereof.

In one embodiment the invention provides a compound of formula (I) which is a compound of the following formula:

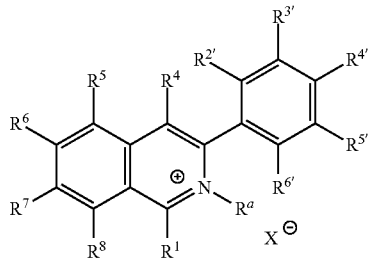

Ig or a pharmaceutically acceptable salt or prodrug thereof.

In one embodiment the invention provides a compound of formula (I) which is a compound of formula Ih:

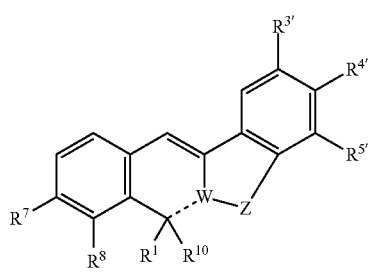

Ih wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of formula Ij:

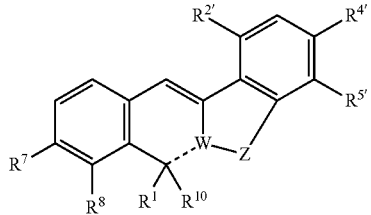

wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of formula Ik:

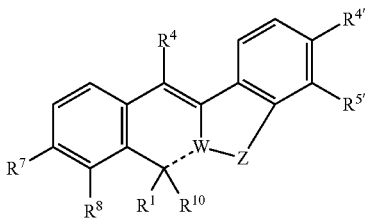

wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of formula Im:

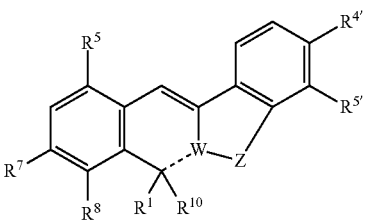

wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of formula Ip:

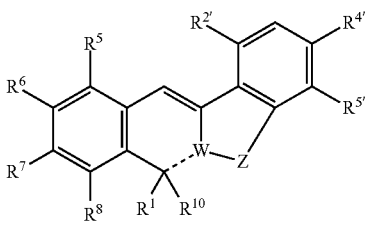

wherein Z is —(CR$^{13}_2$)$_2$— or —CR$^{14}$=CR$^{14}$—; or a pharmaceutically acceptable salt or prodrug thereof.

In one embodiment the invention provides a compound of formula (I) which is a compound of formula Ir:

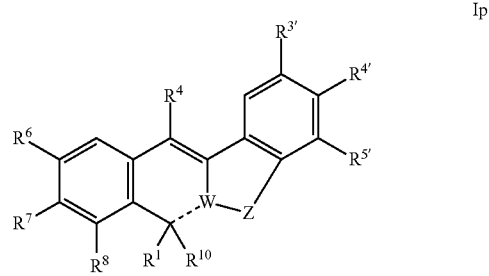

wherein Z is —(CR$^{13}_2$)$_2$— or —CR$^{14}$=CR$^{14}$—; or a pharmaceutically acceptable salt or prodrug thereof.

In one specific embodiment of the invention at least one B is —O—.

In one specific embodiment of the invention at least one B is —S—.

In one specific embodiment of the invention at least one B is —N(R$^y$)—.

In one specific embodiment of the invention R$^x$ is (C$_1$-C$_6$)alkyl.

In one specific embodiment of the invention R$^1$ is cyano.

In one specific embodiment of the invention R$^1$ is aryloxy.

In one specific embodiment of the invention R$^1$ is phenoxy.

In one specific embodiment of the invention R$^1$ is —NR$^{3a}$R$^{3b}$.

In one specific embodiment of the invention R$^1$ is —NR$^{3a}$R$^{3b}$; R$^{3a}$ is hydrogen or (C$_1$-C$_6$)alkyl; and R$^{3b}$ is (C$_1$-C$_6$)alkyl that is substituted with one or more —NR$^{3da}$R$^{3db}$.

In one specific embodiment of the invention R$^1$ is —NR$^{3a}$R$^{3b}$; R$^{3a}$ is hydrogen; and R$^{3b}$ is (C$_1$-C$_6$)alkyl that is substituted with —NH$_2$.

In one specific embodiment of the invention R$^1$ is —NR$^{3a}$R$^{3b}$; R$^{3a}$ is hydrogen; and R$^{3b}$ is 2-aminoethyl.

In one specific embodiment of the invention R$^1$ is —NR$^{3a}$—C(=NR$^{3cb}$)—NR$^{3cc}$R$^{3cd}$.

In one specific embodiment of the invention R$^1$ is —NH—C(=NH)—NH$_2$.

In one specific embodiment of the invention R$^8$ is (C$_1$-C$_3$)alkoxy.

In one specific embodiment of the invention R$^8$ is methoxy.

In one specific embodiment of the invention R$^7$ is (C$_1$-C$_3$)alkoxy.

In one specific embodiment of the invention R$^7$ is methoxy.

In one specific embodiment of the invention R$^6$ is (C$_1$-C$_3$)alkoxy.

In one specific embodiment of the invention R$^6$ is methoxy.

In one specific embodiment of the invention R$^{4\prime}$ is (C$_1$-C$_3$)alkoxy.

In one specific embodiment of the invention R$^{4\prime}$ is methoxy.

In one specific embodiment of the invention R$^{5\prime}$ is (C$_1$-C$_3$)alkoxy.

In one specific embodiment of the invention R$^{5\prime}$ is methoxy.

In one specific embodiment of the invention R$^6$, R$^7$, R$^8$, R$^{4\prime}$ and R$^{5\prime}$ are each independently (C$_1$-C$_3$)alkoxy.

In one specific embodiment of the invention R$^6$, R$^7$, R$^8$, R$^{4\prime}$ and R$^{5\prime}$ are each methoxy.

In one specific embodiment of the invention R$^7$, R$^8$, R$^{4\prime}$ and R$^{5\prime}$ are each methoxy.

In one specific embodiment of the invention R$^7$ and R$^8$ taken together are methylenedioxy.

In one specific embodiment of the invention R$^6$ and R$^7$ taken together are methylenedioxy.

In one specific embodiment of the invention $R^{4'}$ and $R^{5'}$ taken together are methylenedioxy.

In one specific embodiment of the invention $R^6$ and $R^7$ taken together are methylenedioxy and $R^{4'}$ and $R^{5'}$ taken together are methylenedioxy.

In one specific embodiment of the invention $R^1$ is methyl.

In one specific embodiment of the invention at least one of $R^4$, $R^5$, $R^{2'}$ and $R^{3'}$ is aryl substituted with one or more $R^{cc}$ and optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention at least one of $R^4$, $R^5$, $R^{2'}$ and $R^{3'}$ is phenyl substituted with one or more $R^{cc}$ and optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{cc}$ is aryl that is substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{cc}$ is heteroaryl that is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{cc}$ is phenyl that is substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{cc}$ is pyridyl or furyl that is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention at least one of $R^4$, $R^5$, $R^{2'}$ and $R^{3'}$ is heteroaryl substituted with one or more $R^{dd}$ and optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention at least one of $R^4$, $R^5$, $R^{2'}$ and $R^{3'}$ is pyridyl or furyl substituted with one or more $R^{dd}$ and optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention at least one of $R^4$, $R^5$, $R^{2'}$, and $R^{3'}$ is aryl$(C_1-C_6)$alkoxy.

In one specific embodiment of the invention at least one of $R^4$, $R^5$, $R^{2'}$, and $R^{3'}$ is benzyloxy.

In one specific embodiment of the invention each $R^{dd}$ is independently aryl, which is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{dd}$ is independently heteroaryl, which is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{dd}$ is independently phenyl, which is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$.

In one specific embodiment of the invention each $R^{dd}$ is independently pyridyl or furyl, which pyridyl or furyl is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $—S(O)_2NR^gR^h$, $—N(R^j)S(O)_2R^k$, and $—NR^gR^h$;

In one specific embodiment of the invention at least one of $R^4$, $R^5$, $R^{2'}$ and $R^{3'}$ is 4-(3-dimethylaminophenyl)phenyl, 2-phenyl-pyrid-5-yl, 2-(3-methoxyphenyl)pyrid-5-yl, 2-phenyl-furan-4-yl, 2-(pyrid-4-yl)pyrid-5-yl, 4-phenylpyrid-2-yl, 2,6-diphenylpyrid-4-yl, 3-phenylphenyl, or 3,5-diphenylphenyl.

In one embodiment the invention provides a compound of formula (I) which is:

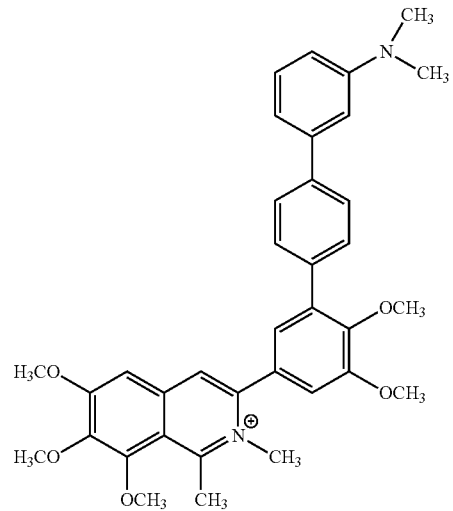

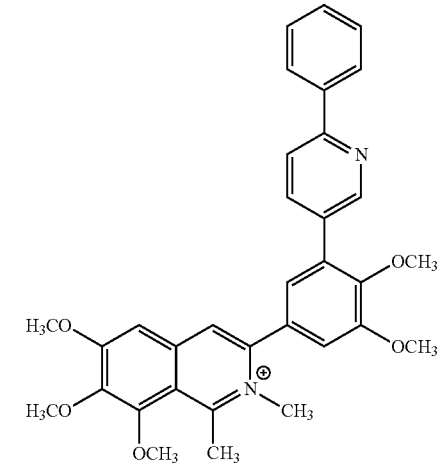

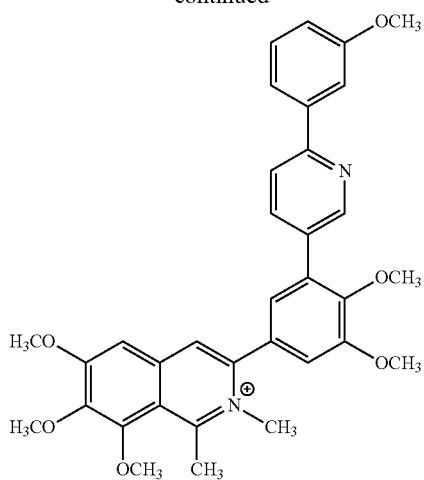
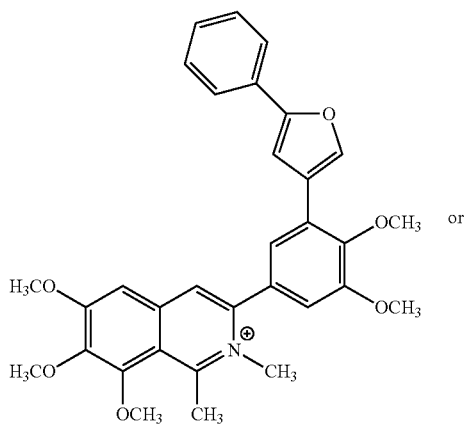
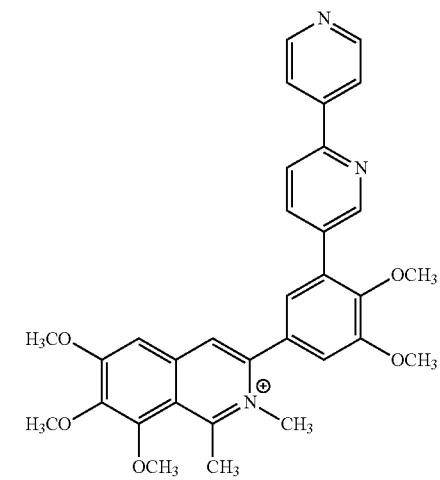
or a salt or prodrug thereof.
In one embodiment the invention provides a compound of formula (I) which is:
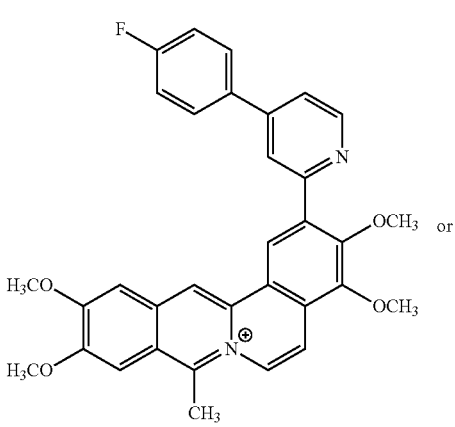
or a salt or prodrug thereof.
In one embodiment the invention provides a compound of formula (I) which is:

-continued

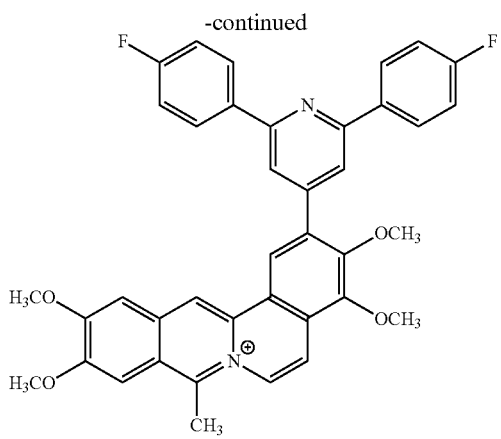

or a salt or prodrug thereof.

In one embodiment the invention provides a compound of formula (I) wherein:

the bond represented by - - - is present, $R^{10}$ is absent, and W is $(NR^{30})^+D^-$ except as defined below when $R^{30}$ and $R^{3a}$ taken together with the atoms to which they are attached form a 5- or 6-membered heterocyclic ring or a 5- or 6-membered heteroaromatic ring;

$R^1$ is —$NR^{3a}R^{3b}$ or cyano;

at least one of $R^4$, $R^5$, $R^{2'}$, $R^{3'}$, and $R^{6'}$ is selected from hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; and the remainder of $R^4$, $R^5$, $R^{2'}$, $R^{3'}$, and $R^{6'}$ are independently selected from hydrogen, halo, hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, cycloalkyl, and $(C_1-C_6)$alkanoyl of $R^4$, $R^5$, $R^{2'}$, $R^{3'}$, and $R^{6'}$ is optionally substituted with one or more groups independently selected from halo, hydroxy, cyano, nitro, $(C_1-C_6)$alkoxy, cycloalkyl, oxo, carboxy, aryloxy, sulfo, —$S(O)_2NR^{3g}R^{3h}$, —$N(R^j)S(O)_2R^{3k}$, and —$NR^{3g}R^{3h}$; and wherein each aryl, and heteroaryl of $R^4$, $R^5$, $R^{2'}$, $R^{3'}$, and $R^{6'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{3aa}$, —$S(O)_2NR^{3g}R^{3h}$, —$N(R^{3j})S(O)_2R^{3k}$, and —$NR^{3g}R^{3h}$;

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, $R^{3bb}$, and Z—$R^{3x}$;

each Z is independently selected from —O—, —S—, and —$N(R^{3y})$—;

$R^{30}$ is absent and if is absent; or $R^{30}$ is H or $(C_1-C_6)$alkyl and if is counterion;

or $R^{30}$ and $R^{3a}$ taken together with the atoms to which they are attached form a 5- or 6-membered heterocyclic ring or a 5- or 6-membered heteroaromatic ring, wherein a) when the bond represented by - - - is present in the 5- or 6-membered heterocyclic ring or the 5- or 6-membered heteroaromatic ring, then W is $(NR^{30})^+D^-$ and $D^-$ is a counterion, b) when the bond represented by - - - is absent in the 5- or 6-membered heterocyclic ring or the 5- or 6-membered heteroaromatic ring, then W is $(NR^{30}R^{31})^+D^-R^{31}$ is $(C_1-C_6)$alkyl and if is a counterion, or c) when the bond represented by - - - is absent in the 5- or 6-membered heterocyclic ring or the 5- or 6-membered heteroaromatic ring, then W is $(NR^{30})$;

A is N or C—$R^{4'}$;

$R^{3a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^a$ is optionally substituted with one or more groups selected from halo, hydroxy, cyano, nitro, $(C_1-C_6)$alkoxy, cycloalkyl, oxo, carboxy, and aryloxy, and wherein each aryl and heteroaryl of $R^{3a}$ is optionally substituted with one or more groups selected from $(C_1-C_6)$alkyl, halo, hydroxy, cyano, nitro, $(C_1-C_6)$alkoxy, cycloalkyl, carboxy, and aryloxy; and $R^{3b}$ is hydrogen, $(C_1-C_6)$alkyl, aryl, aryl$(C_1-C_6)$alkyl, heteroaryl, heteroaryl$(C_1-C_6)$alkyl, —$C(=O)$—$R^{3m}$, —$C(=O)$—$OR^{3n}$, —$C(=O)$—$SR^{3p}$, —$C(=O)$—$NR^{3q}R^{3r}$, —$C(=S)$—$R^{3m}$, —$C(=S)$—$OR^{3n}$, —$C(=S)$—$SR^{3p}$, —$C(=S)$—$NR^{3q}R^{3r}$, or —$C(=NR^{3c})$—$R^{3d}$; wherein each $(C_1-C_6)$alkyl of $R^{3b}$ is optionally substituted with one or more groups independently selected from halo, hydroxy, cyano, nitro, $(C_1-C_6)$alkoxy, cycloalkyl, oxo, carboxy, and aryloxy; and wherein each aryl, and heteroaryl of $R^b$ is optionally substituted with one or more groups independently selected from $(C_1-C_6)$alkyl, halo, hydroxy, cyano, nitro, $(C_1-C_6)$alkoxy, cycloalkyl, carboxy, and aryloxy; or $R^{3a}$ and $R^{3b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{3c}$ is hydrogen, $(C_1-C_6)$alkyl, aryl, or heteroaryl;

$R^{3d}$ is hydrogen, $(C_1-C_6)$alkyl, $(C_1-C_6)$alkoxy, $(C_1-C_6)$alkylthio, $(C_1-C_6)$alkanoyl, or —$NR^{3e}R^{3f}$;

$R^{3e}$ and $R^{3f}$ are each independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; or $R^{3e}$ and $R^{3f}$ together with the nitrogen to which they are attached form a aziridino, azetidino, morpholino, piperazino, pyrrolidino or piperidino;

each $R^{3g}$ and $R^{3h}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$ alkyl; or $R^{3g}$ and $R^{3h}$ together with the nitrogen to which they are attached form a aziridino, azetidino, morpholino, piperazino, pyrrolidino or piperidino;

each $R^{3j}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3k}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3m}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3n}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{3g}R^{3h}$, —$N(R^{3j})S(O)_2R^{3k}$, and —$NR^{3g}R^{3h}$;

each $R^{3p}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{3g}R^{3h}$, $-N(R^{3j})S(O)_2R^{3k}$, and $-NR^{3g}R^{3h}$;

each $R^{3q}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; and each $R^{3r}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; or $R^{3r}$ and $R^{3r}$ together with the nitrogen to which they are attached form a aziridino, azetidino, morpholino, piperazino, pyrrolidino or piperidino;

each $R^{3u}$ and $R^{3v}$ is independently selected from H and $(C_1-C_6)$alkyl;

each $R^{3x}$ is independently selected from $(C_1-C_6)$alkyl, $(C_1-C_6)$alkanoyl, and $-C(=O)NR^{3u}R^{3v}$;

each $R^{3y}$ is independently selected from H and $(C_1-C_6)$ alkyl;

each $R^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{3g}R^{3h}$, $-N(R^{3j})S(O)_2R^{3k}$, and $-NR^{3g}R^{3h}$; and each $R^{3bb}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{3g}R^{3h}$, $-N(R^{3j})S(O)_2R^{3k}$, and $-NR^{3g}R^{3h}$.

In one embodiment the invention provides a compound of formula (I) wherein:

the bond represented by - - - is present, $R^{10}$ is absent, and W is $(NR^{30})^+D^-$;

$R^6$ $R^7$, $R^8$, $R^{4'}$ and $R^{5'}$ are each indepentyl selected from H and $Z-R^x$; or $R^6$ and $R^7$ taken together are methylenedioxy and $R^8$, $R^{4'}$, and $R^{5'}$ are each indepentyl selected from H and $Z-R^x$; or $R^7$ and $R^8$ taken together are methylenedioxy and $R^6$, $R^{4'}$ and $R^{5'}$ are each indepentyl selected from H and $Z-R^x$; or $R^{4'}$ and $R^{5'}$ taken together are methylenedioxy and $R^6$, $R^7$, and $R^8$ are each indepentyl selected from H and $-Z-R^x$;

each Z is independently selected from $-O-$, $-S-$, and $-N(R^y)-$;

at least one of $R^4$, $R^5$, $R^{2'}$, $R^{3'}$, and $R^{6'}$ is selected from hydroxy, carboxy, cyano, $CF_3SO_3-$, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, arylalkanoyl, and heteroarylalkanoyl; and the remainder of $R^4$, $R^5$, $R^{2'}$, $R^{3'}$, and $R^{6'}$ are independently selected from hydrogen, hydroxy, carboxy, cyano, $CF_3SO_3-$, $(C_1-C_6)$ alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl of $R^4$, $R^5$, $R^{2'}$, $R^{3'}$, and $R^{6'}$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, $-S(O)_2NR^{3g}R^{3h}$, $-N(R^{3j})S(O)_2R^{3k}$, and $-NR^{3g}R^{3h}$; and wherein each aryl, and heteroaryl of $R^4$, $R^5$, $R^{2'}$, $R^{3'}$, and $R^{6'}$ is optionally substituted with one or more groups independently selected from $(C_1-C_6)$alkyl, halo, hydroxy, cyano, nitro, $(C_1-C_6)$alkoxy, $(C_3-C_6)$ cycloalkyl, carboxy, aryloxy, nitro, sulfo, $-S(O)_2NR^{3g}R^{3h}$, $-N(R^{3j})S(O)_2R^{3k}$, and $-NR^{3g}R^{3h}$;

$R^{30}$ is absent and r is absent; or $R^{30}$ is H or $(C_1-C_6)$alkyl and $X^-$ is counterion;

$R^{11}$ is $-NR^{3a}R^{3b}$ or cyano;

$R^{3a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$ alkyl of $R^{3a}$ is optionally substituted with one or more groups selected from halo, hydroxy, cyano, nitro, $(C_1-C_6)$alkoxy, $(C_3-C_6)$cycloalkyl, oxo, carboxy, and aryloxy, and wherein each aryl and heteroaryl of $R^{3a}$ is optionally substituted with one or more groups selected from $(C_1-C_6)$alkyl, halo, hydroxy, cyano, nitro, $(C_1-C_6)$alkoxy, $(C_3-C_6)$cycloalkyl, carboxy, and aryloxy; and $R^{3b}$ is hydrogen, $(C_1-C_6)$alkyl, aryl, aryl$(C_1-C_6)$alkyl, heteroaryl, heteroaryl$(C_1-C_6)$alkyl, $-C(=O)-R^{3m}$, $-C(=O)-OR^{3n}$, $-C(=O)-S3p^p$, $-C(=O)-NR^{3q}R^{3r}$, $-C(=S)-R^{3m}$, $-C(=S)-OR^{3n}$, $-C(=S)-SR^{3p}$, $-C(=S)-NR^{3q}R^{3r}$, or $-C(=NR^{3c})-R^{3d}$; wherein each $(C_1-C_6)$alkyl of $R^{3b}$ is optionally substituted with one or more groups independently selected from halo, hydroxy, cyano, nitro, $(C_1-C_6)$alkoxy, $(C_3-C_6)$cycloalkyl, oxo, carboxy, and aryloxy; and wherein each aryl, and heteroaryl of $R^{3b}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, and aryloxy; or $R^{3a}$ and $R^{3b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one of more $(C_1-C_6)$alkyl;

$R^{3c}$ is hydrogen, $(C_1-C_6)$alkyl, aryl, or heteroaryl;

$R^{3d}$ is hydrogen, $(C_1-C_6)$alkyl, $(C_1-C_6)$alkoxy, $(C_1-C_6)$ alkylthio, $(C_1-C_6)$alkanoyl, or $-NR^{3e}R^{3f}$;

$R^{3e}$ and $R^{3f}$ are each independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$alkyl; or $R^e$ and $R^f$ together with the nitrogen to which they are attached form a aziridino, azetidino, morpholino, piperazino, pyrrolidino or piperidino;

each $R^{3g}$ and $R^{3h}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{3g}$ and $R^{3h}$ together with the nitrogen to which they are attached form a aziridino, azetidino, morpholino, piperazino, pyrrolidino or piperidino;

each $R^{3j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3k}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3m}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3n}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3p}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3q}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^{3r}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^{3q}$ and $R^{3r}$ together with the nitrogen to which they are attached form a aziridino, azetidino, morpholino, piperazino, pyrrolidino or piperidino;

each $R^{3u}$ and $R^{3v}$ is independently selected from H and $(C_1\text{-}C_6)$alkyl;

each $R^{3x}$ is independently selected from $(C_1\text{-}C_6)$alkyl, $(C_1\text{-}C_6)$alkanoyl, and $-C(=O)NR^{3u}R^{3v}$; and each $R^{3y}$ is independently selected from H and $(C_1\text{-}C_6)$alkyl.

In one embodiment the invention provides a compound of formula (I) which is a compound of formula (IIIa):

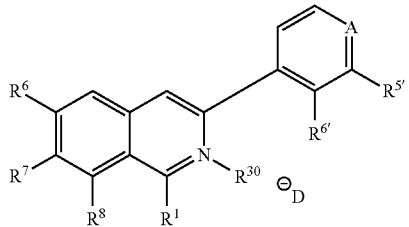

(IIIa)

wherein $R^{6\prime}$ is selected from hydroxy, carboxy, cyano, $CF_3SO_3-$, $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, aryl$(C_1\text{-}C_6)$alkyl, aryl, heteroaryl, heteroaryl$(C_1\text{-}C_6)$alkyl, arylalkanoyl, and heteroarylalkanoyl; wherein each $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, and $(C_1\text{-}C_6)$alkanoyl of $R^{6\prime}$ is optionally substituted with one or more groups independently selected from halo, hydroxy, cyano, nitro, $(C_1\text{-}C_6)$alkoxy, cycloalkyl, oxo, carboxy, aryloxy, sulfo, $-S(O)_2NR^{3g}R^{3h}$, $-N(R^{3j})S(O)_2R^{3k}$, and $-NR^{3g}R^{3h}$; and wherein each aryl, and heteroaryl of $R^{6\prime}$ is optionally substituted with one or more groups independently selected from $(C_1\text{-}C_6)$alkyl, halo, hydroxy, cyano, nitro, $(C_1\text{-}C_6)$alkoxy, cycloalkyl, carboxy, aryloxy, nitro, sulfo, $R^{3aa}$, $-S(O)_2NR^{3g}R^{3h}$, $-N(R^{3j})S(O)_2R^{3k}$, and $-NR^{3g}R^{3h}$; or a salt or prodrug thereof.

In one embodiment the invention provides a compound of formula (I) which is a compound of formula (IIIb):

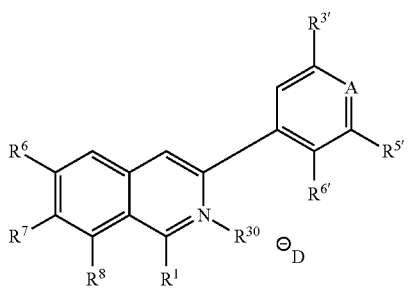

(IIIb)

wherein $R^{3\prime}$ is selected from hydroxy, carboxy, cyano, $CF_3SO_3-$, $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, aryl$(C_1\text{-}C_6)$alkyl, aryl, heteroaryl, heteroaryl$(C_1\text{-}C_6)$alkyl, arylalkanoyl, and heteroarylalkanoyl; wherein each $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, and $(C_1\text{-}C_6)$alkanoyl of $R^{3\prime}$ is optionally substituted with one or more groups independently selected from halo, hydroxy, cyano, nitro, $(C_1\text{-}C_6)$alkoxy, cycloalkyl, oxo, carboxy, aryloxy, sulfo, $-S(O)_2NR^{3g}R^{3h}$, $-N(R^{3j})S(O)_2R^{3k}$, and $-NR^{3g}R^{3h}$; and wherein each aryl, and heteroaryl of $R^{3\prime}$ is optionally substituted with one or more groups independently selected from $(C_1\text{-}C_6)$alkyl, halo, hydroxy, cyano, nitro, $(C_1\text{-}C_6)$alkoxy, cycloalkyl, carboxy, aryloxy, nitro, sulfo, $R^{3aa}$, $-S(O)_2NR^{3g}R^{3h}$, $-N(R^{3j})S(O)_2R^{3k}$, and $-NR^{3g}R^{3h}$; or a salt or prodrug thereof.

In one embodiment the invention provides a compound of formula (I) which is a compound of formula (IIIc):

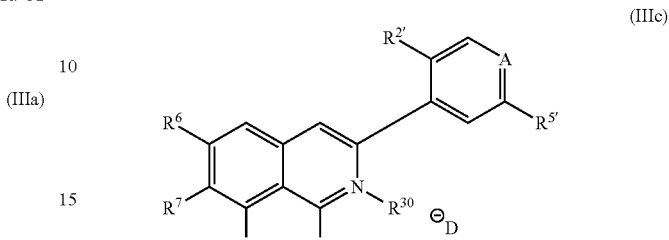

(IIIc)

wherein $R^{2\prime}$ is selected from hydroxy, carboxy, cyano, $CF_3SO_3-$, $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, aryl$(C_1\text{-}C_6)$alkyl, aryl, heteroaryl, heteroaryl$(C_1\text{-}C_6)$alkyl, arylalkanoyl, and heteroarylalkanoyl; wherein each $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, and $(C_1\text{-}C_6)$alkanoyl of $R^{2\prime}$ is optionally substituted with one or more groups independently selected from halo, hydroxy, cyano, nitro, $(C_1\text{-}C_6)$alkoxy, cycloalkyl, oxo, carboxy, aryloxy, sulfo, $-S(O)_2NR^{3g}R^{3h}$, $-N(R^{3j})S(O)_2Rv^k$, and $-NR^{3g}R^{3h}$; and wherein each aryl, and heteroaryl of $R^{2\prime}$ is optionally substituted with one or more groups independently selected from $(C_1\text{-}C_6)$alkyl, halo, hydroxy, cyano, nitro, $(C_1\text{-}C_6)$alkoxy, cycloalkyl, carboxy, aryloxy, nitro, sulfo, $R^{3aa}$, $-S(O)_2NR^{3g}R^{3h}$, $-N(R^{3j})S(O)_2R^{3k}$, and $-NR^{3g}R^{3h}$; or a salt or prodrug thereof.

In one embodiment the invention provides a compound of formula (I) which is a compound of formula (IIId):

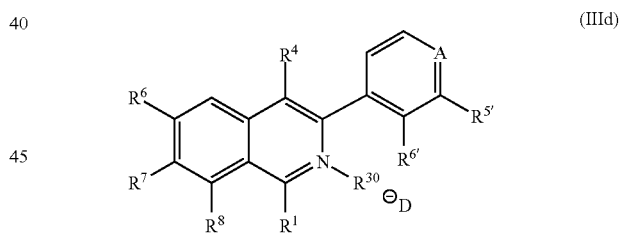

(IIId)

wherein $R^4$ is selected from hydroxy, carboxy, cyano, $CF_3SO_3-$, $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, aryl$(C_1\text{-}C_6)$alkyl, aryl, heteroaryl, heteroaryl$(C_1\text{-}C_6)$alkyl, arylalkanoyl, and heteroarylalkanoyl; wherein each $(C_1\text{-}C_6)$alkyl, $(C_2\text{-}C_6)$alkenyl, $(C_2\text{-}C_6)$alkynyl, $(C_1\text{-}C_6)$alkoxy, cycloalkyl, and $(C_1\text{-}C_6)$alkanoyl of $R^4$ is optionally substituted with one or more groups independently selected from halo, hydroxy, cyano, nitro, $(C_1\text{-}C_6)$alkoxy, cycloalkyl, oxo, carboxy, aryloxy, sulfo, $-S(O)_2NR^{3g}R^{3h}$, $-N(R^{3j})S(O)_2R^{3k}$, and $-NR^{3g}R^{3h}$; and wherein each aryl, and heteroaryl of $R^4$ is optionally substituted with one or more groups independently selected from $(C_1\text{-}C_6)$alkyl, halo, hydroxy, cyano, nitro, $(C_1\text{-}C_6)$alkoxy, cycloalkyl, carboxy, aryloxy, nitro, sulfo, $R^{3aa}$, $-S(O)_2NR^{3g}R^{3h}$, $-N(R^{3j})S(O)_2R^{3k}$, and $-NR^{3g}R^{3h}$; or a salt or prodrug thereof.

In one embodiment the invention provides a compound of formula (I) which is a compound of formula (IIIe):

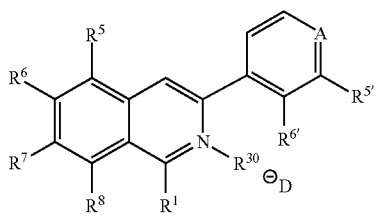

(IIIe)

wherein $R^5$ is selected from hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; wherein each $(C_1-C_6)$alkyl, $(C_2-C_6)$alkenyl, $(C_2-C_6)$alkynyl, $(C_1-C_6)$alkoxy, cycloalkyl, and $(C_1-C_6)$alkanoyl of $R^5$ is optionally substituted with one or more groups independently selected from halo, hydroxy, cyano, nitro, $(C_1-C_6)$alkoxy, cycloalkyl, oxo, carboxy, aryloxy, sulfo, —$S(O)_2$$NR^{3g}R^{3h}$, —$N(R^{3j})S(O)_2R^{3k}$, and —$NR^{3g}R^{3h}$; and wherein each aryl, and heteroaryl of $R^5$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{3aa}$, —$S(O)_2NR^{3g}R^{3h}$, —$N(R^{3j})S(O)_2R^{3k}$, and —$NR^{3g}R^{3h}$; or a salt or prodrug thereof.

In one specific embodiment of the invention $R^{30}$ is $(C_1-C_6)$alkyl and $D^-$ is counterion.

In one specific embodiment of the invention $R^{30}$ is absent and $D^-$ is absent.

In one specific embodiment of the invention at least one Z is —O—.

In one specific embodiment of the invention at least one Z is —S—.

In one specific embodiment of the invention at least one Z is —$N(R^{3y})$—.

In one specific embodiment of the invention each Z is —O—.

In one specific embodiment of the invention each Z is —S—.

In one specific embodiment of the invention each Z is —$N(R^{3y})$—.

In one specific embodiment of the invention $R^{3x}$ is $(C_1-C_6)$alkyl.

In one specific embodiment of the invention $R^{3a}$ is hydrogen or methyl.

In one specific embodiment of the invention $R^{3b}$ is hydrogen, $(C_1-C_6)$alkyl, aryl, aryl$(C_1-C_6)$alkyl, heteroaryl, or heteroaryl$(C_1-C_6)$alkyl.

In one specific embodiment of the invention $R^{3b}$ is hydrogen, methyl, phenyl, or benzyl.

In one specific embodiment of the invention $R^{3b}$ is —C(=$NR^{3c}$)—$R^{3d}$.

In one specific embodiment of the invention $R^{3a}$ and $R^{3b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one or more $(C_1-C_6)$alkyl.

In one specific embodiment of the invention $R^{3c}$ is hydrogen.

In one specific embodiment of the invention $R^{3d}$ is methyl or amino.

In one embodiment the invention provides a compound of formula (I) which is:

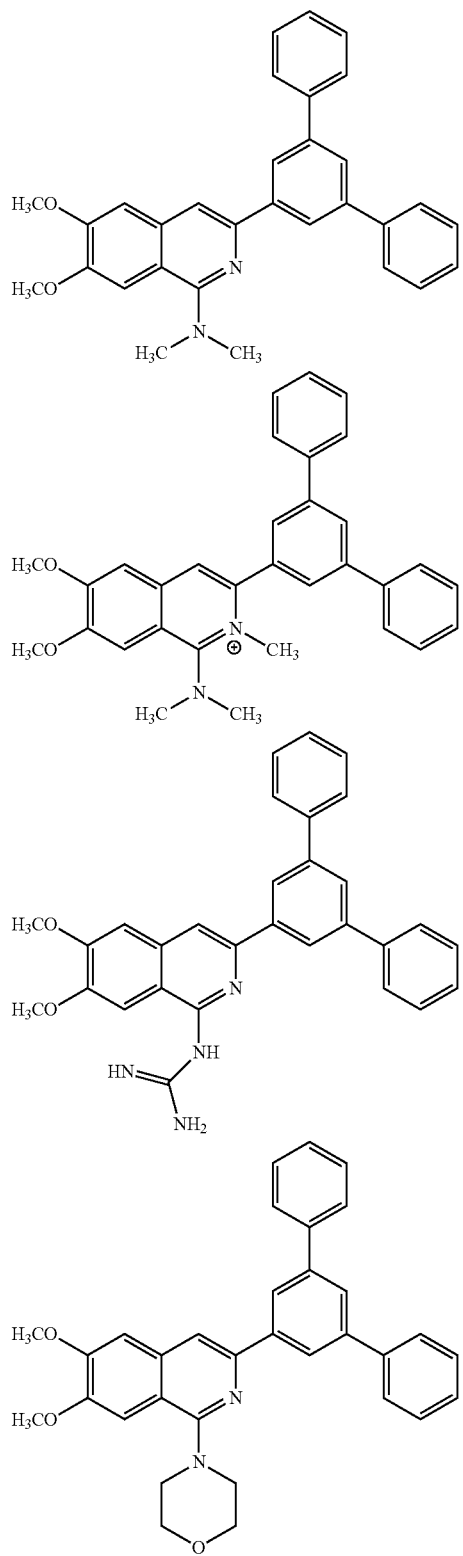 [SMILES: COc1cc2cc(-c3cc(-c4ccccc4)cc(-c4ccccc4)c3)nc(N(C)C)c2cc1OC ; COc1cc2cc(-c3cc(-c4ccccc4)cc(-c4ccccc4)c3)[n+](C)c(N(C)C)c2cc1OC ; COc1cc2cc(-c3cc(-c4ccccc4)cc(-c4ccccc4)c3)nc(NC(=N)N)c2cc1OC ; COc1cc2cc(-c3cc(-c4ccccc4)cc(-c4ccccc4)c3)nc(N3CCOCC3)c2cc1OC]

27
-continued
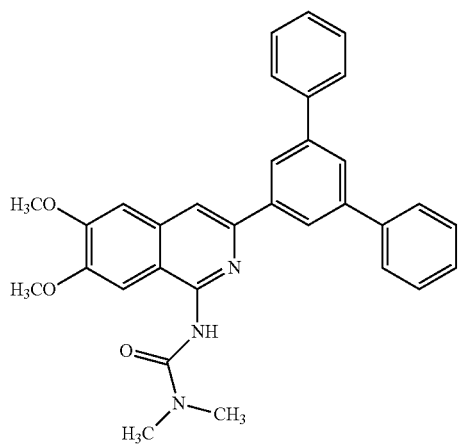
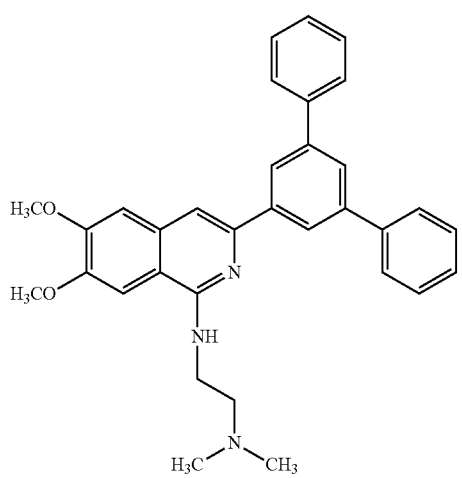
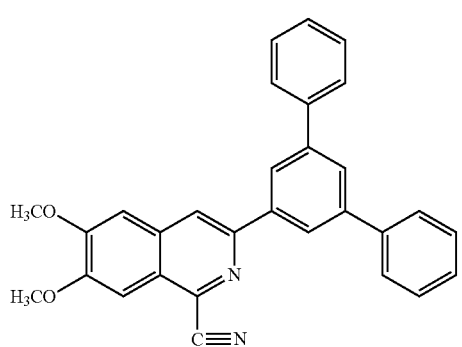
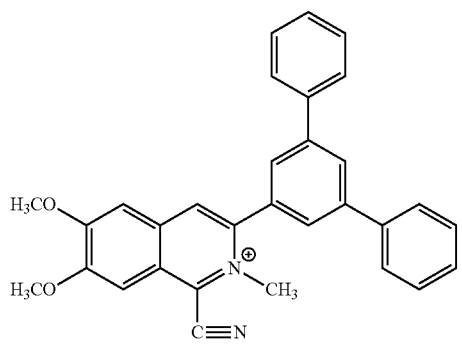
28
-continued
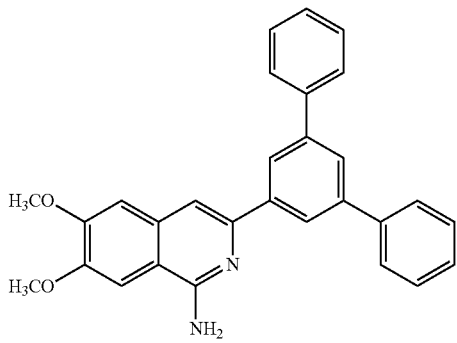
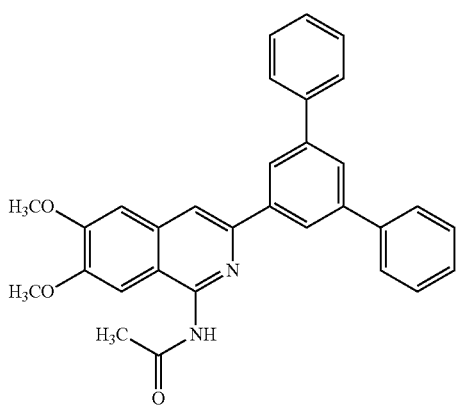
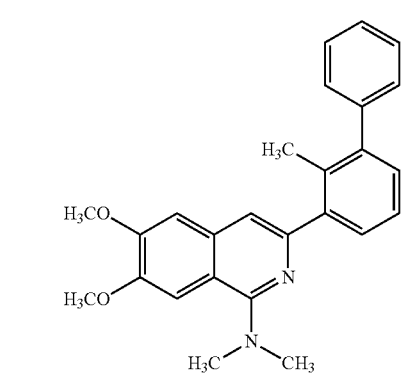
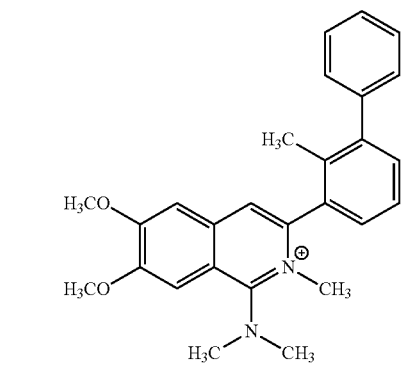

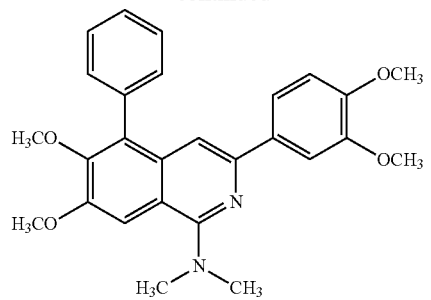
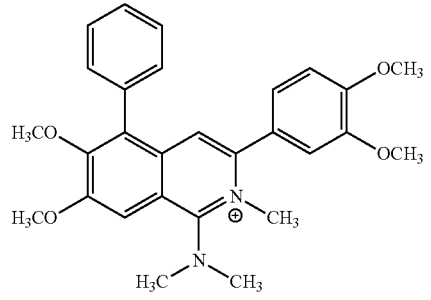
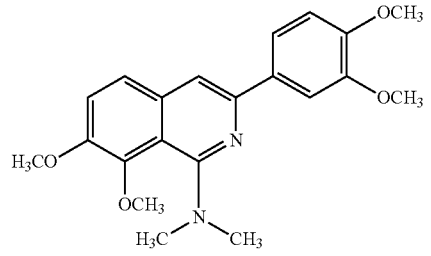
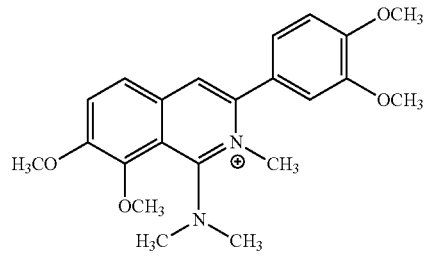
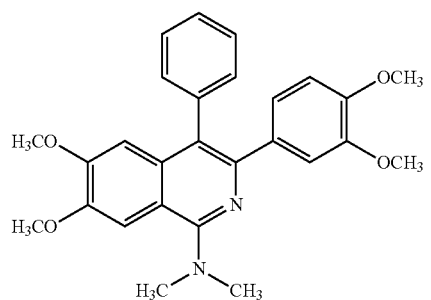
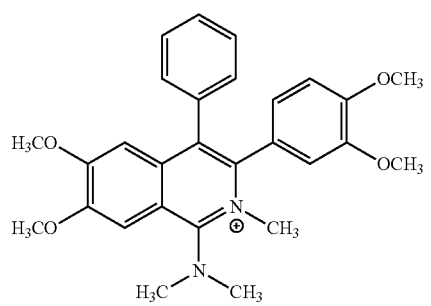
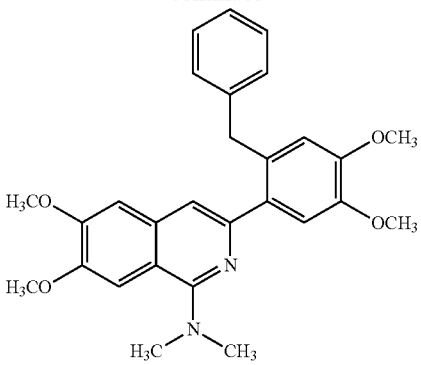
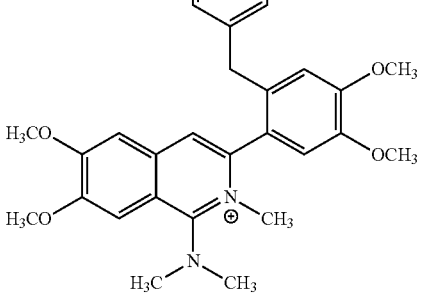
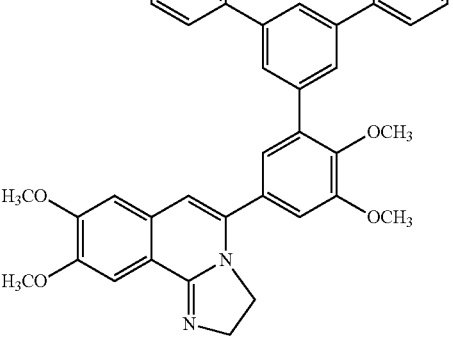
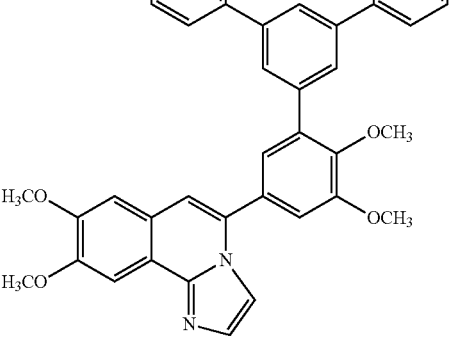

-continued

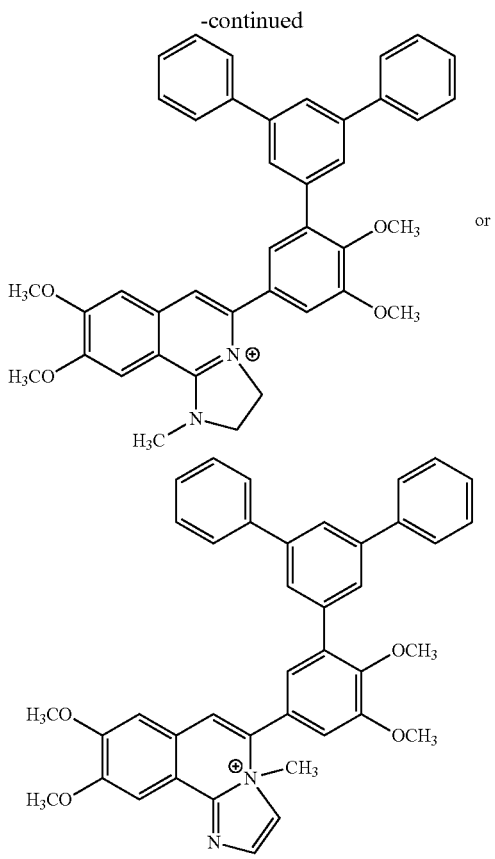

or a salt or prodrug thereof.

In one specific embodiment of the invention $R^{6'}$ is selected from aryl and heteroaryl, which aryl, and heteroaryl of $R^{6'}$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^{3'}$ is selected from aryl and heteroaryl, which aryl, and heteroaryl of $R^{3'}$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, R$^{aa}$, —S(O)$_2$NR$^g$R$^h$, —N(R$^j$)S(O)$_2$R$^k$, and —NR$^g$R$^h$; and each R$^{aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^g$R$^h$, —N(R$^j$)S(O)$_2$R$^k$, and —NR$^g$R$^h$.

In one specific embodiment of the invention $R^{2'}$ is selected from aryl and heteroaryl, which aryl, and heteroaryl of $R^{2'}$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$Rv$^k$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^j$)S(O)$_2$R$^{3k}$, and —NR$^{3g}$R$^{3h}$.

In one specific embodiment of the invention $R^4$ is selected from aryl and heteroaryl, which aryl, and heteroaryl of $R^4$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$; —N(R$^{3j}$)S(O)$_2$R$^{3k}$; and —NR$^{3g}$R$^{3h}$; each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^5$ is selected from aryl and heteroaryl, which aryl, and heteroaryl of $R^5$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —N$^3$R$^g$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^{6'}$ is selected from phenyl, pyridyl and furanyl and is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$Rv$^h$, —N(R$^{3j}$)S(O)$_2$R$^{3k}$, and —NR$^{3g}$Rv$^h$.

In one specific embodiment of the invention $R^{3'}$ is selected from phenyl, pyridyl and furanyl and is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and NR$^{3g}$R$^{3h}$.

In one specific embodiment of the invention $R^{2'}$ is selected from aryl and heteroaryl, which aryl, and heteroaryl of $R^{2'}$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^4$ is selected from phenyl, pyridyl and furanyl and is optionally substituted with one or more groups independently selected from ($C_1$-

$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —$^N$(R$^{3j}$)S(O)$_2$R$^{3k}$, and —NR$^{3g}$R$^{3h}$; And each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^5$ is selected from phenyl, pyridyl and furanyl and is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{3aa}$, —S(O)$_2$NR$^{3g}$R$^{3h}$, —N(R$^{3j}$)S(O)$_2$R$^{3k}$, and —NR$^{3g}$R$^{3h}$; and each $R^{3aa}$ is independently selected from aryl and heteroaryl, which aryl and heteroaryl is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

In one specific embodiment of the invention $R^{6'}$ is selected from phenyl, pyridyl and furanyl and is optionally substituted with one or more groups independently selected from phenyl, pyridyl, —NR$^{3g}$R$^{3h}$, ($C_1$-$C_6$)alkoxy, dimethylaminophenyl, and halo.

In one specific embodiment of the invention $R^{3'}$ is selected from phenyl, pyridyl and furanyl and is optionally substituted with one or more groups independently selected from phenyl, pyridyl, —NR$^{3g}$R$^{3h}$, ($C_1$-$C_6$)alkoxy, dimethylaminophenyl, and halo.

In one specific embodiment of the invention $R^{2'}$ is selected from phenyl, pyridyl and furanyl and is optionally substituted with one or more groups independently selected from phenyl, pyridyl, —NR$^{3g}$R$^{3h}$, ($C_1$-$C_6$)alkoxy, dimethylaminophenyl, and halo.

In one specific embodiment of the invention $R^4$ is selected from phenyl, pyridyl and furanyl and is optionally substituted with one or more groups independently selected from phenyl, pyridyl, —NR$^{3g}$R$^{3h}$, ($C_1$-$C_6$)alkoxy, dimethylaminophenyl, and halo.

In one specific embodiment of the invention $R^5$ is selected from phenyl, pyridyl and furanyl and is optionally substituted with one or more groups independently selected from phenyl, pyridyl, —NR$^{3g}$R$^{3h}$, ($C_1$-$C_6$)alkoxy, dimethylaminophenyl, and halo.

In one specific embodiment of the invention at least one of $R^4$, $R^5$, $R^{2'}$, $R^{3'}$, and $R^{6'}$ is selected from 3-biphenyl, 3-(4'-fluoro)biphenyl, 4-biphenyl, 4-(4'-fluoro)biphenyl, 3,5-bis (4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenypphenyl, 4-(3-furanyl)phenyl, 2-phenylpyrid-4-yl, 2-(3-methoxyphenyl)pyrid-3-yl, 2-phenylfur-4-yl, and 2-pyrid-4-yl)pyrid-5-yl.

In one specific embodiment of the invention A is N.

In one specific embodiment of the invention A is C—R$^{4'}$.

In one embodiment the invention provides a compound of formula (I) wherein:

the dashed line - - - is a double bond, $R^{10}$ is absent, W is (NR$^{41}$)$^+$W$^-$ and $R^{41}$ and $R^{6'}$ taken together are —CHR$^{43}$—CHR$^{42}$—, or —CR$^{43}$═CR$^{42}$—;

$R^{4'}$, $R^{5'}$, $R^6$, $R^7$ and $R^8$ are each indepentyl selected from H and Z—R$^{4x}$; or R$^{4'}$ and R$^{5'}$ taken together are methylenedioxy and R$^6$, R$^7$, and R$^8$ are each indepentyl selected from H and Z—R$^{4x}$; or R$^7$ and R$^8$ taken together are methylenedioxy and R$^{4'}$, R$^{5'}$, and R$^6$ are each indepentyl selected from H and Z—R$^{4x}$; or R$^6$ and R$^7$ taken together are methylenedioxy and R$^{4'}$, R$^{5'}$, and R$^8$ are each indepentyl selected from H and —Z—R$^{4x}$;

each Z is independently selected from —O—, —S—, and —N(R$^{4y}$)—;

at least one of R$^{2'}$, R$^{3'}$, R$^4$, and R$^5$ is selected from hydroxy, carboxy, cyano, CF$_3$SO$_3$—, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$)alkyl, aryl, heteroaryl, heteroaryl($C_1$-$C_6$)alkyl, arylalkanoyl, and heteroarylalkanoyl; and the remainder of R$^{2'}$, R$^{3'}$, R$^4$, and R$^5$ are independently selected from H, hydroxy, carboxy, cyano, CF$_3$SO$_3$—, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$) alkyl, aryl, heteroaryl, heteroaryl($C_1$-$C_6$)alkyl, aryl($C_1$-$C_6$) alkanoyl, and heteroaryl($C_1$-$C_6$)alkanoyl; wherein each ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, and ($C_1$-$C_6$)alkanoyl of R$^{2'}$, R$^{3'}$, R$^4$, and R$^5$ is optionally substituted with one or more groups independently selected from halo, hydroxy, cyano, nitro, ($C_1$-$C_6$) alkoxy, ($C_3$-$C_6$)cycloalkyl, oxo, carboxy, aryloxy, sulfo, —S(O)$_2$NR$^{4g}$R$^{4h}$, —N(R$^{4j}$)S(O)$_2$R$^{4k}$, and —NR$^{4g}$R$^{4h}$; and wherein each aryl and heteroaryl of R$^{2'}$, R$^{3'}$, R$^4$, and R$^5$ is optionally substituted with one or more groups independently selected from ($C_1$-$C_6$)alkyl, halo, hydroxy, cyano, nitro, ($C_1$-$C_6$)alkoxy, ($C_3$-$C_6$)cycloalkyl, carboxy, aryloxy, nitro, sulfo, —S(O)$_2$NR$^{4g}$R$^{4h}$, —N(R$^{4j}$)S(O)$_2$R$^{4k}$, R$^{4s}$, and —NR$^{4g}$R$^{4h}$;

$R^{42}$ is H, ($C_1$-$C_6$)alkyl, aryl, heteroaryl, or aryl($C_1$-$C_6$) alkyl;

$R^{43}$ is H, ($C_1$-$C_6$)alkyl, aryl, heteroaryl, or aryl($C_1$-$C_6$) alkyl;

$R^1$ is —NR$^a$R$^b$ or cyano;

$R^{4a}$ is H, ($C_1$-$C_6$)alkyl, aryl, aryl($C_1$-$C_6$)alkyl, heteroaryl, or heteroaryl($C_1$-$C_6$)alkyl; wherein each ($C_1$-$C_6$)alkyl of R$^a$ is optionally substituted with one or more groups selected from halo, hydroxy, cyano, nitro, ($C_1$-$C_6$)alkoxy, ($C_3$-$C_6$)cycloalkyl, oxo, carboxy, and aryloxy, and wherein each aryl and heteroaryl of R$^{4a}$ is optionally substituted with one or more groups selected from ($C_1$-$C_6$)alkyl, halo, hydroxy, cyano, nitro, ($C_1$-$C_6$)alkoxy, ($C_3$-$C_6$)cycloalkyl, carboxy, and aryloxy; and $R^{4b}$ is H, ($C_1$-$C_6$)alkyl, aryl, aryl($C_1$-$C_6$)alkyl, heteroaryl, heteroaryl($C_1$-$C_6$)alkyl, —C(═O)—R$^{4m}$, —C(═O)—OR$^{4n}$, —C(═O)—SR$^{4p}$, —C(═O)—NR$^{4q}$R$^{4r}$, —C(═S)—R$^{4m}$, —C(═S)—OR$^{4n}$, —C(═S)—SR$^{4p}$, —C(═S)—NR$^{4q}$R$^{4r}$, or —C(═NR$^{4c}$)—R$^{4d}$; wherein each ($C_1$-$C_6$)alkyl of R$^{4b}$ is optionally substituted with one or more groups independently selected from halo, hydroxy, cyano, nitro, ($C_1$-$C_6$)alkoxy, ($C_3$-$C_6$)cycloalkyl, oxo, carboxy, and aryloxy; and wherein each aryl, and heteroaryl of R$^{4b}$ is optionally substituted with one or more groups independently selected from ($C_1$-$C_6$)alkyl, halo, hydroxy, cyano, nitro, ($C_1$-$C_6$)alkoxy, ($C_3$-$C_6$)cycloalkyl, carboxy, and aryloxy; or R$^{4a}$ and R$^{4b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one or more ($C_1$-$C_6$)alkyl;

$R^{4c}$ is H, ($C_1$-$C_6$)alkyl, aryl, or heteroaryl;

$R^{4d}$ is H, ($C_1$-$C_6$)alkyl, ($C_1$-$C_6$)alkoxy, ($C_1$-$C_6$)alkylthio, ($C_1$-$C_6$)alkanoyl, or —NR$^e$R$^f$;

$R^{4e}$ and $R^{4f}$ are each independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$)alkyl; or $R^{4e}$ and $R^{4f}$ together with the nitrogen to which they are attached form a aziridino, azetidino, morpholino, piperazino, pyrrolidino or piperidino;

each $R^{4g}$ and $R^{4h}$ is independently selected from H, ($C_1$-$C_6$)alkyl, ($C_3$-$C_6$)cycloalkyl, ($C_3$-$C_6$)cycloalkyl($C_1$-$C_6$)

alkyl, aryl, heteroaryl, aryl(C₁-C₆) alkyl and heteroaryl(C₁-C₆) alkyl; or $R^{4g}$ and $R^{4h}$ together with the nitrogen to which they are attached form a aziridino, azetidino, morpholino, piperazino, pyrrolidino or piperidino;

each $R^{4j}$ is independently selected from H, (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl;

each $R^{4k}$ is independently selected from (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl;

each $R^{4m}$ is independently selected from H, (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl;

each $R^{4n}$ is independently selected from (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl;

each $R^{4p}$ is independently selected from H, (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl;

each $R^{4q}$ is independently selected from H, (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl; and each $R^r$ is independently selected from H, (C₁-C₆)alkyl, (C₃-C₆)cycloalkyl, (C₃-C₆)cycloalkyl(C₁-C₆)alkyl, aryl, heteroaryl, aryl(C₁-C₆) alkyl and heteroaryl(C₁-C₆)alkyl; or $R^{4q}$ and $R^{4r}$ together with the nitrogen to which they are attached form a aziridino, azetidino, morpholino, piperazino, pyrrolidino or piperidino;

each $R^{4s}$ is independently trifluoromethyl, trifluoromethoxy, or aryl optionally substituted with one or more (C₁-C₆)alkyl, halo, hydroxy, cyano, nitro, (C₁-C₆)alkoxy, (C₃-C₆)cycloalkyl, carboxy, aryloxy, nitro, sulfo, —S(O)₂$R^{4g}R^{4h}$, —N($R^{4j}$)S(O)₂$R^{4k}$, trifluoromethyl, trifluoromethoxy, and —N$R^{4g}R^{4h}$;

each $R^{4u}$ and $^4R^v$ is independently selected from H and (C₁-C₆)alkyl;

each $R^{4x}$ is independently selected from (C₁-C₆)alkyl, (C₁-C₆)alkanoyl, and —C(=O)N$R^uR^v$;

each $R^{4y}$ is independently selected from H and (C₁-C₆) alkyl; and

W⁻ is a counter anion;

or a salt or prodrug thereof.

In one embodiment the invention provides a compound of formula (I) which is a compound of formula (IVa):

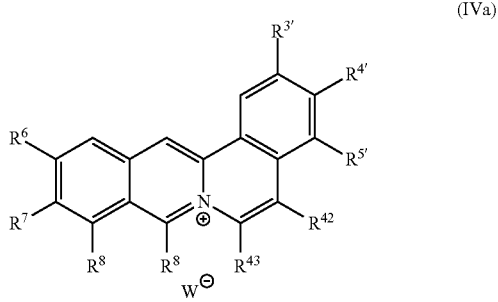

(IVa)

or a salt or prodrug thereof.

In one embodiment the invention provides a compound of formula (I) which is a compound of formula (IVb):

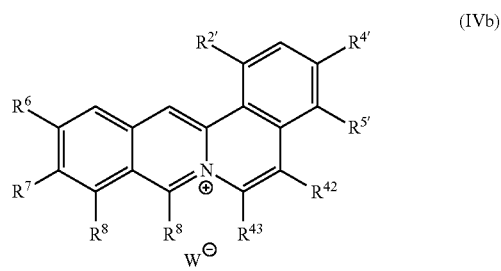

(IVb)

or a salt or prodrug thereof.

In one embodiment the invention provides a compound of formula (I) which is a compound of formula (IVc):

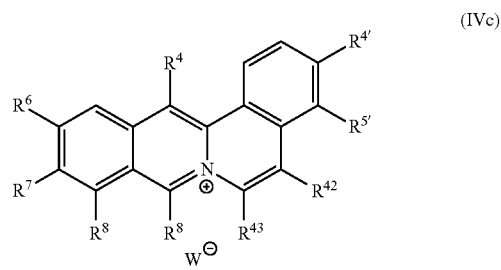

(IVc)

or a salt or prodrug thereof.

In one embodiment the invention provides a compound of formula (I) which is a compound of formula (IVd):

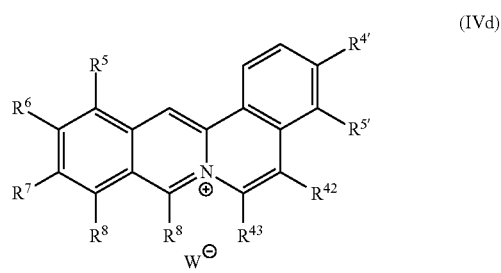

(IVd)

or a salt or prodrug thereof.

In one embodiment the invention provides a compound of formula (I) which is a compound of formula (IVe):

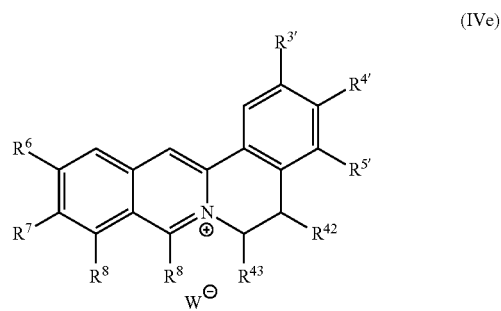

(IVe)

or a salt or prodrug thereof.

121. The compound of claim 1 which is a compound of formula (IVf):

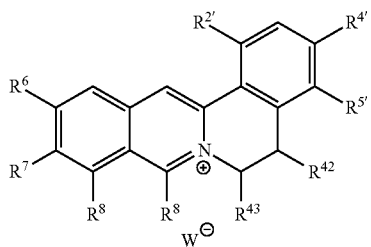

or a salt or prodrug thereof.

In one embodiment the invention provides a compound of formula (I) which is a compound of formula (IVg):

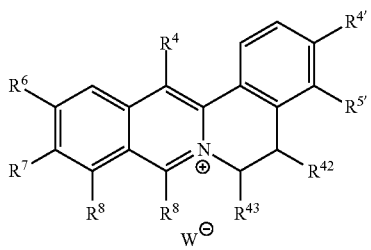

or a salt or prodrug thereof.

In one embodiment the invention provides a compound of formula (I) which is a compound of formula (Ih):

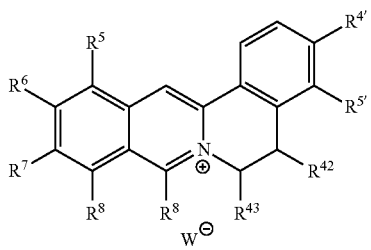

or a salt or prodrug thereof.

In one specific embodiment of the invention at least one Z is —N($R^{4y}$)—.

In one specific embodiment of the invention each Z is —N($R^{4y}$)—.

In one specific embodiment of the invention $R^{4x}$ is ($C_1$-$C_6$)alkyl.

In one specific embodiment of the invention $R^{4'}$, $R^{5'}$, $R^6$, and $R^7$ are each methoxy.

In one specific embodiment of the invention $R^1$ is —$NR^{4a}R^{4b}$.

In one specific embodiment of the invention $R^{4a}$ is hydrogen or methyl.

In one specific embodiment of the invention $R^{4b}$ is H, ($C_1$-$C_6$)alkyl, aryl, aryl($C_1$-$C_6$)alkyl, heteroaryl, or heteroaryl($C_1$-$C_6$)alkyl.

In one specific embodiment of the invention $R^{4b}$ is H, methyl, phenyl, or benzyl.

In one specific embodiment of the invention $R^{4b}$ is —C(=$NR^{4c}$)—$R^{4d}$.

In one specific embodiment of the invention $R^{4a}$ and $R^{4b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one or more ($C_1$-$C_6$)alkyl.

In one specific embodiment of the invention $R^{4c}$ is hydrogen.

In one specific embodiment of the invention $R^{4d}$ is methyl or amino.

In one specific embodiment of the invention $R^{42}$ and $R^{43}$ are each H.

In one embodiment the invention provides a compound of formula (I) which is:

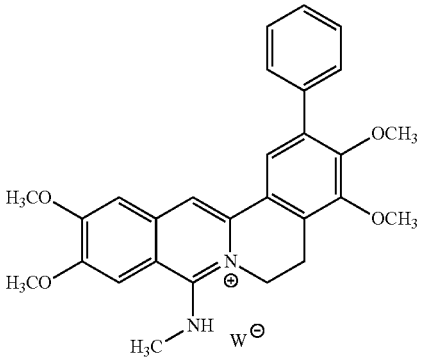

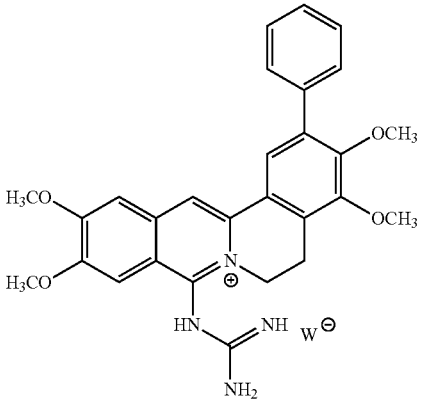

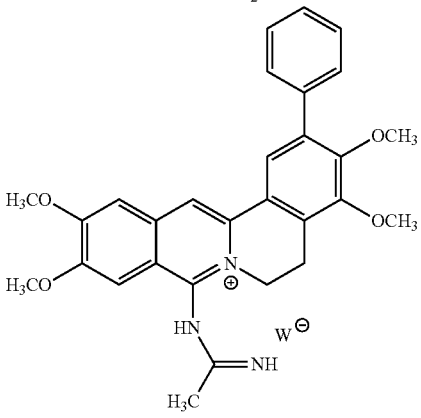

-continued
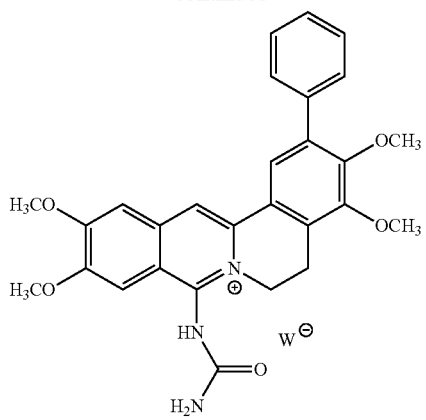
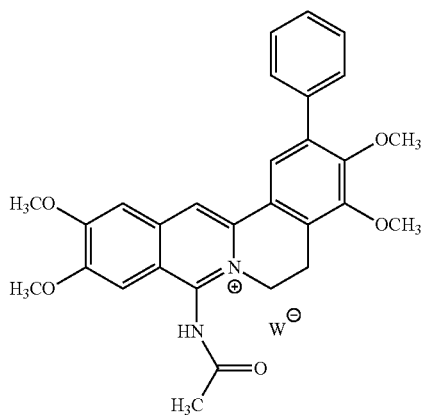
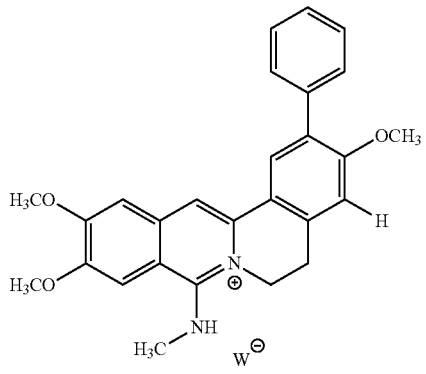
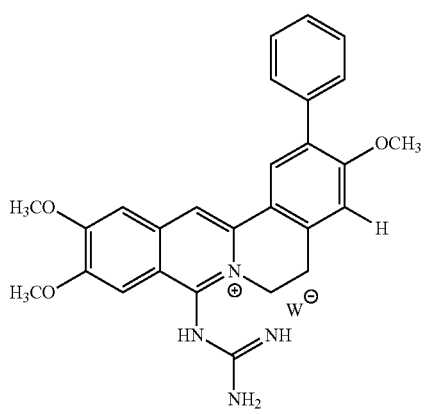
-continued
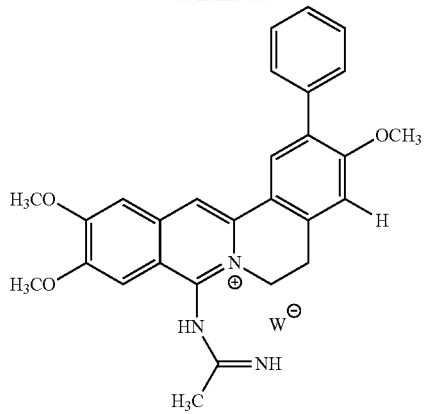
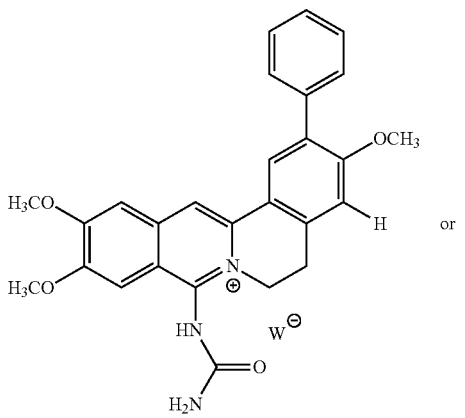
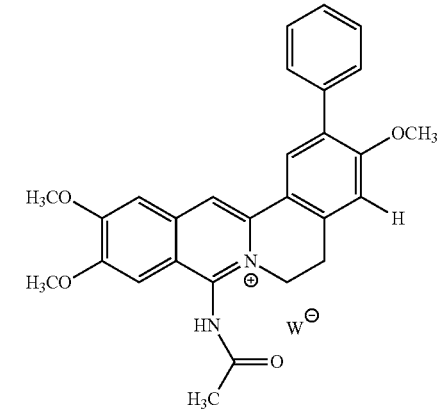
or a salt or prodrug thereof.
In one embodiment the invention provides a compound of formula (I) which is:
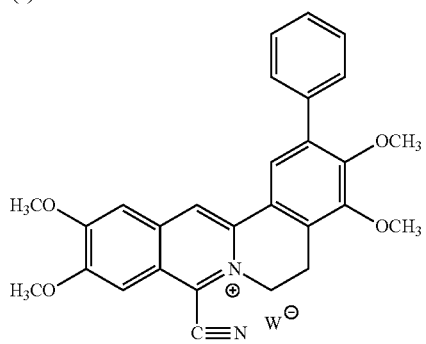

41
-continued
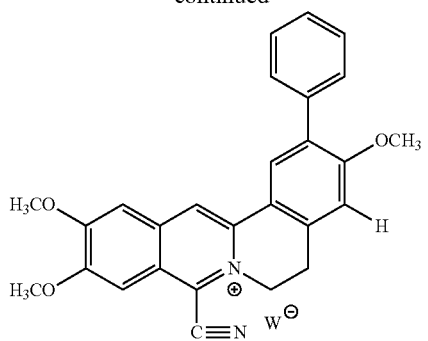
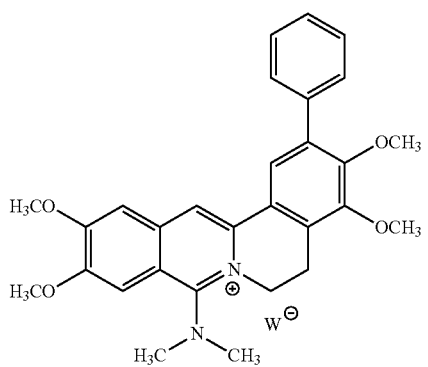
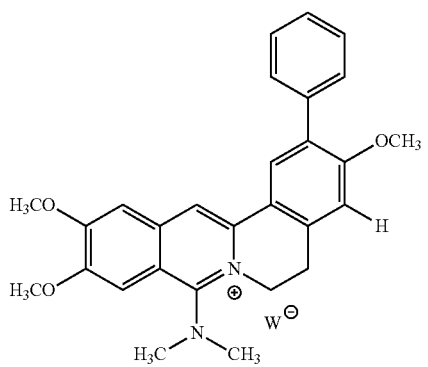
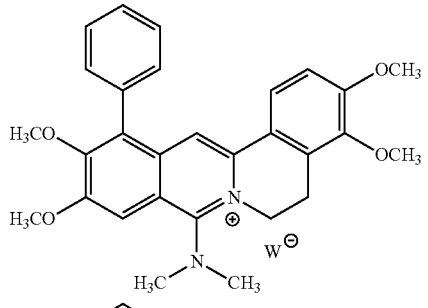
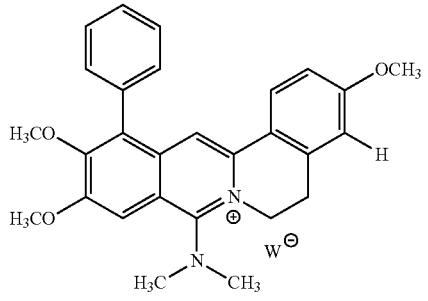
42
-continued
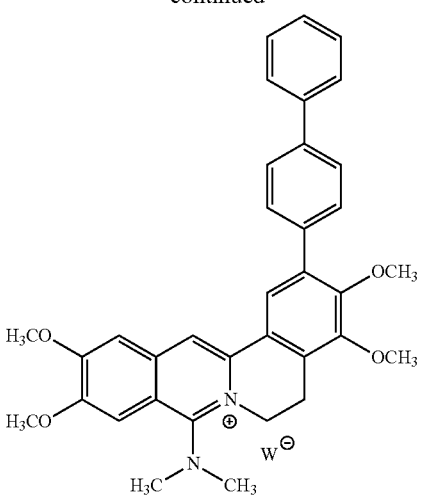
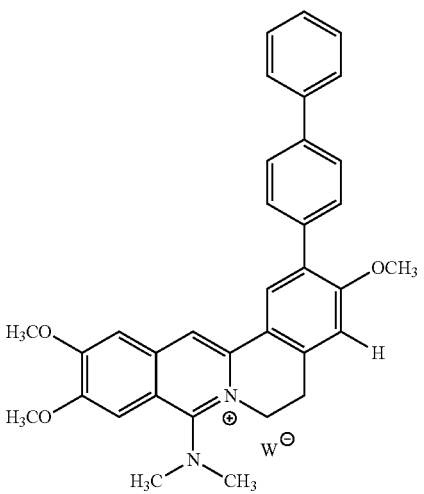
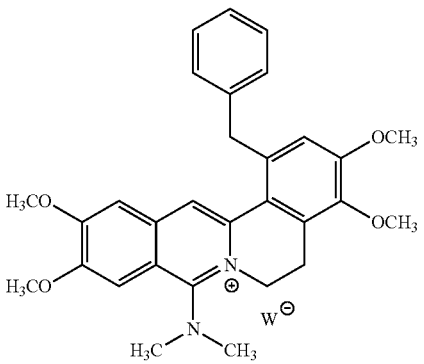
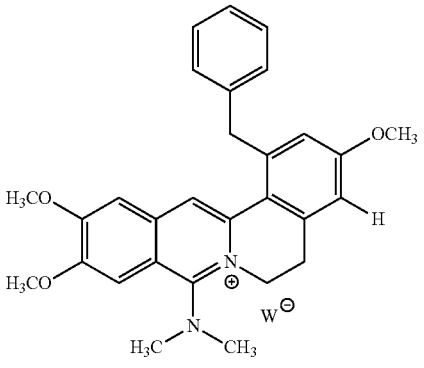

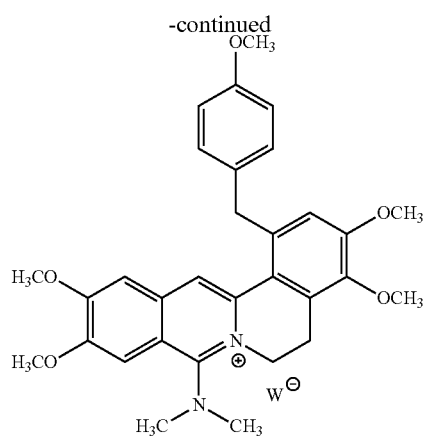
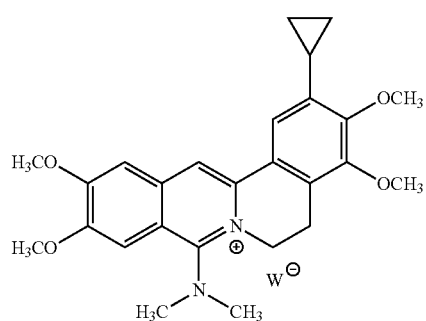
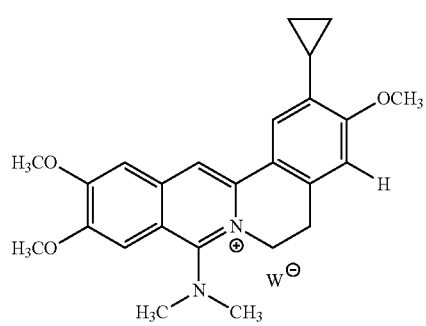
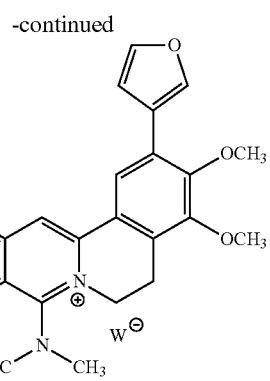
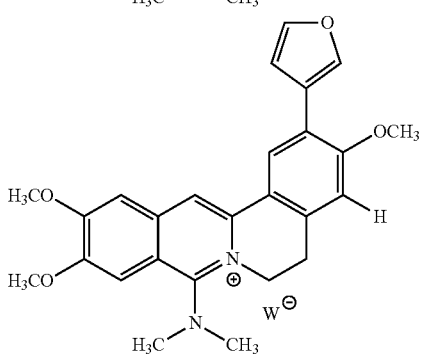
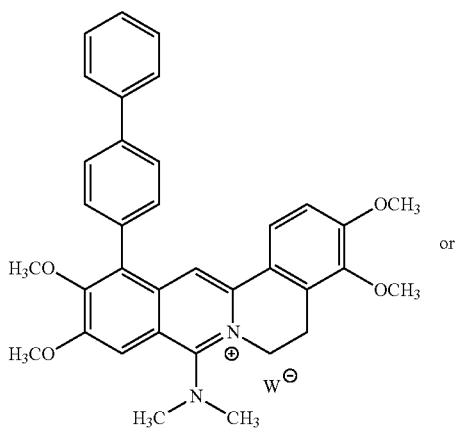
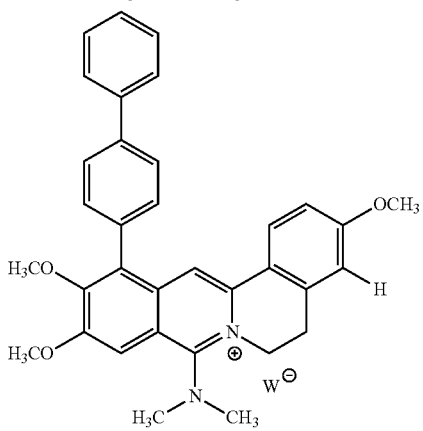
or a salt or prodrug thereof.
In one embodiment the invention provides a compound of formula (I) which is:

45
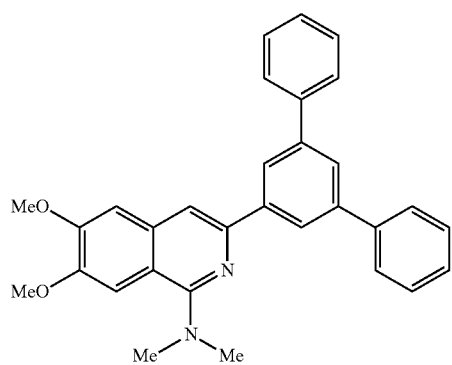
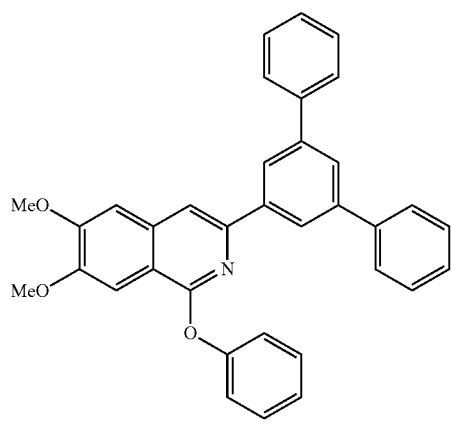
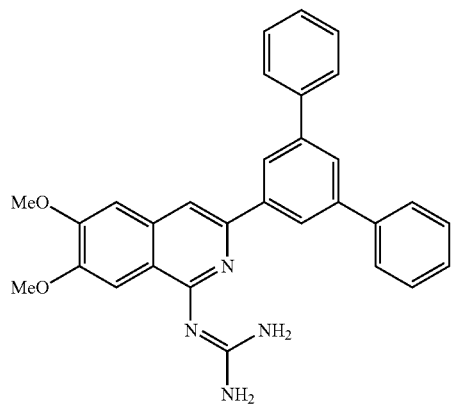
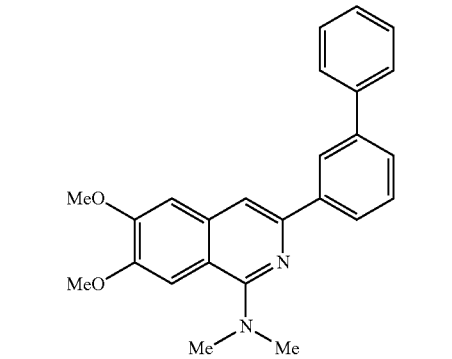
46
-continued
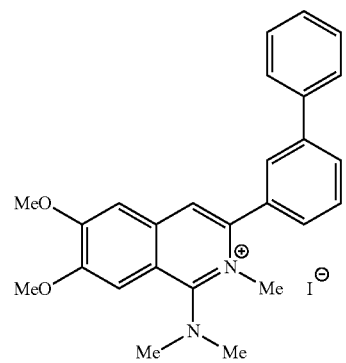
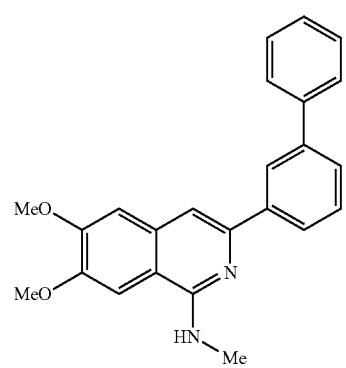
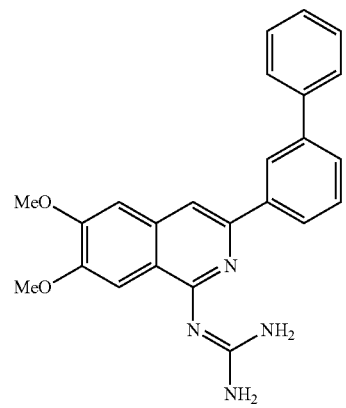
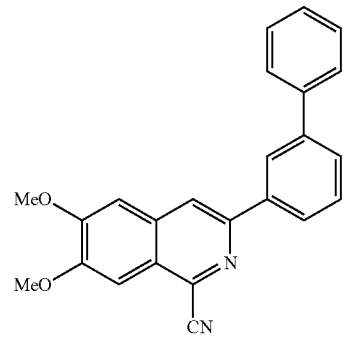

47
-continued
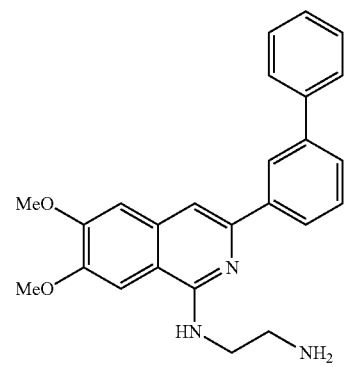
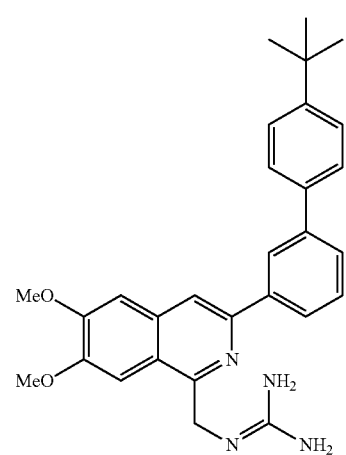
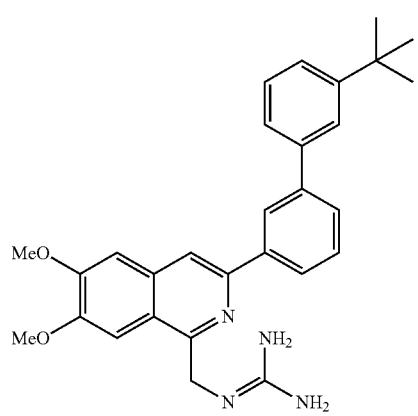
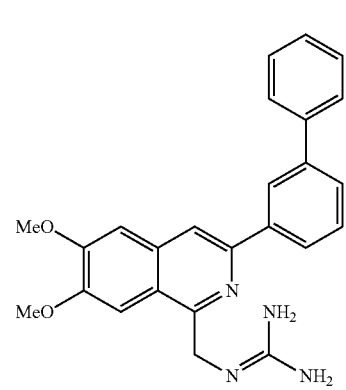
48
-continued
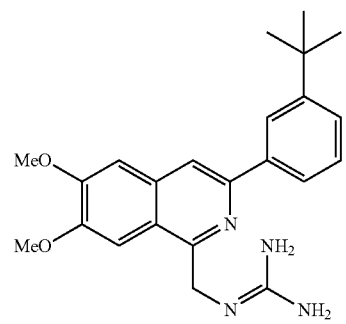
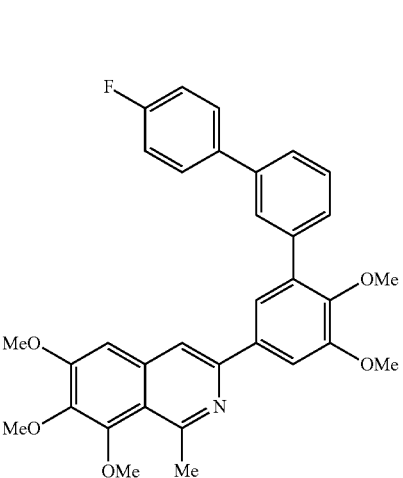
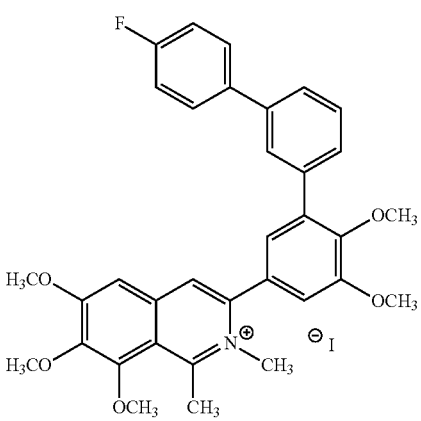
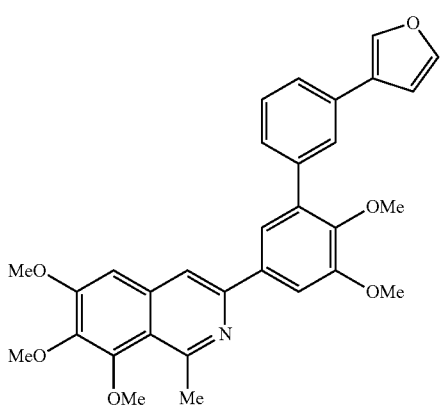

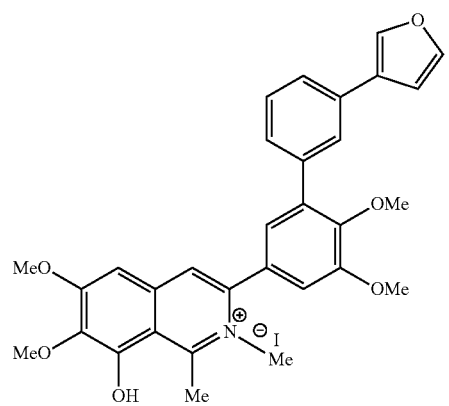

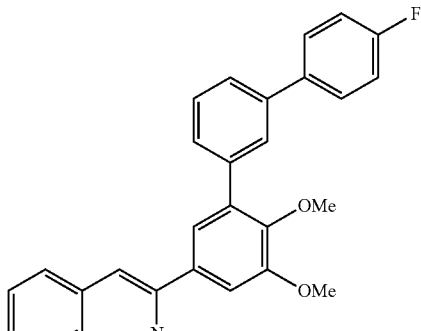

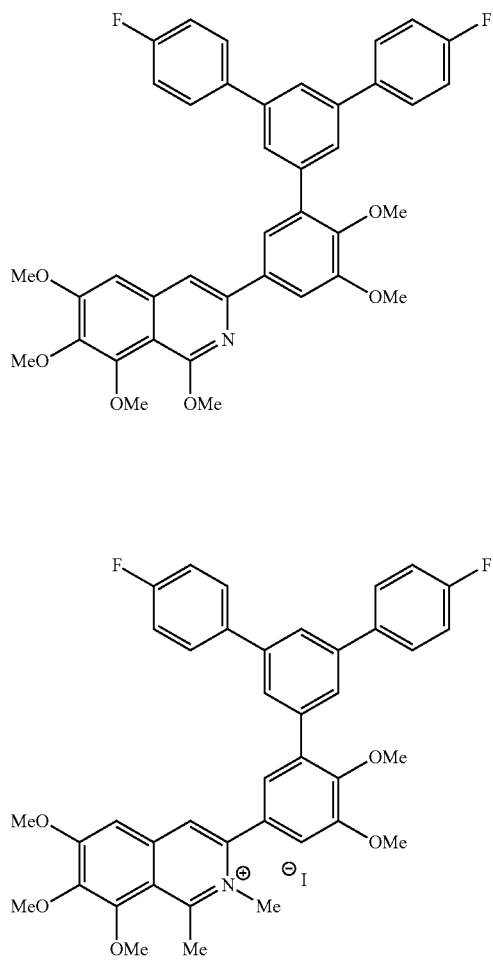

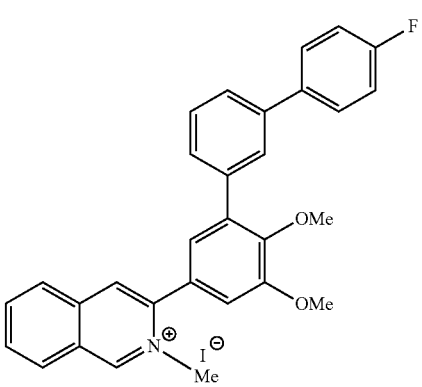

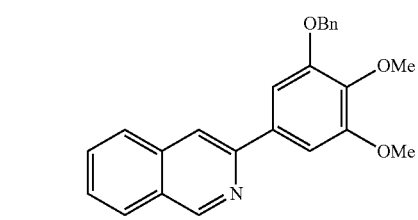

or a salt or prodrug thereof.

Generally, compounds of the invention including compounds of formula I set a), as well as synthetic intermediates that can be used for preparing compounds of formula I, can be prepared as illustrated in the following Schemes. It is understood that groups $R^1$-$R^{12}$, W, Y, and Z shown in the Schemes below can represent the final groups present in a corresponding compound of formula I or that these groups can represent groups that can be converted to the final groups present in a corresponding compound of formula I at a convenient point in a synthetic sequence. For example, in the Schemes below, the groups $R^1$-$R^{12}$, W, Y, and Z can comprise one or more protecting groups that can be removed at a convenient point in a synthetic sequence to provide the corresponding final groups in the compound of formula I.

Scheme 1

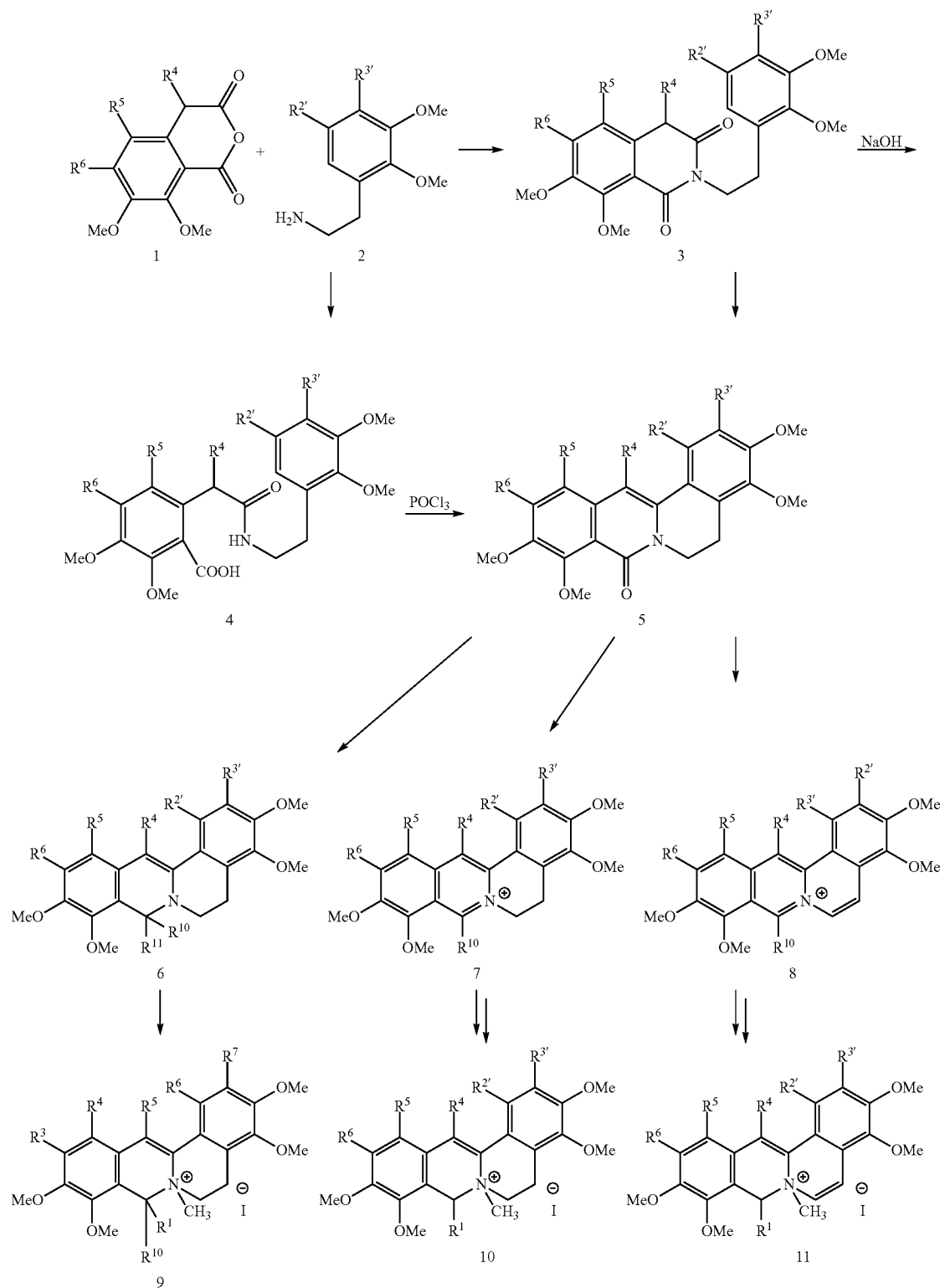

Condensation of readily available anhydride 1 and amine 2 can furnish imide 3. The resulting imide 3 can then be hydrolyzed to the corresponding acid amide 4. Acid catalyzed cyclization of 4 can then lead to oxypseudoberbernine 5. The key intermediate compound 5 can then be converted to compound 6, 7, and 8 using conventional chemistry. Each of these compounds can then be quaternized to afford the desired compounds 9, 10, and 11 respectively.

Scheme 2

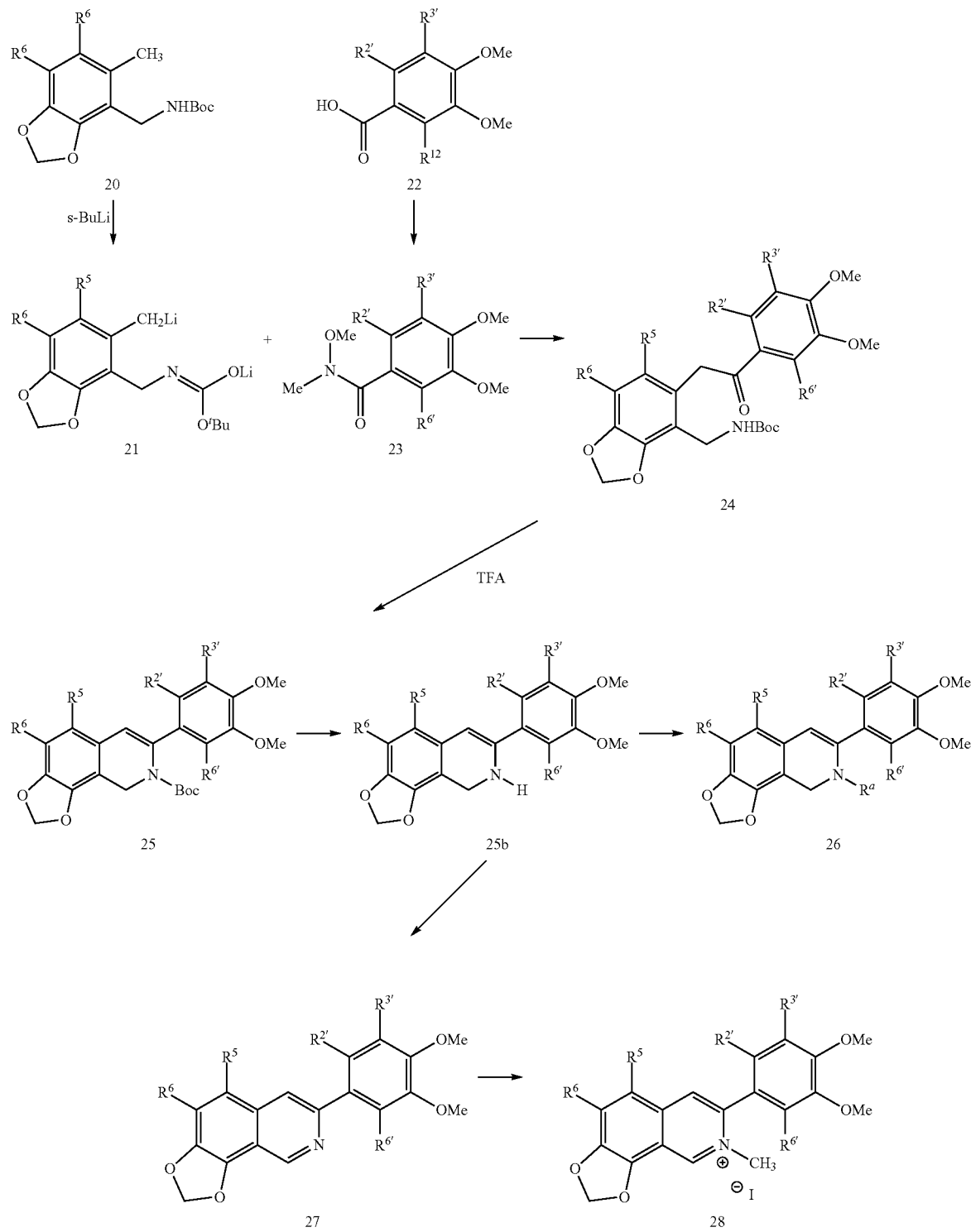

The substituted N-Boc protected benzylamine 20 can be converted to the dilithio 21 by treatment with two equivalents of sec-butyllithium. Acylation of dianion 21 can be accomplished by treatment with N-methoxy-N-methylamides derivative 23 (made from the corresponding acid 22) to afford the key intermediate compound 24. Exposure of ketone 24 to a catalytic amount of TFA can provide the Boc-1,2-dihydroisoquinoline 25. The Boc group in 25 can be removed to provide 25a and the resulting free amine can be functionalized to 26 by various electrophilic reagents. Alternatively 26 can be converted to compound 28.

Scheme 3

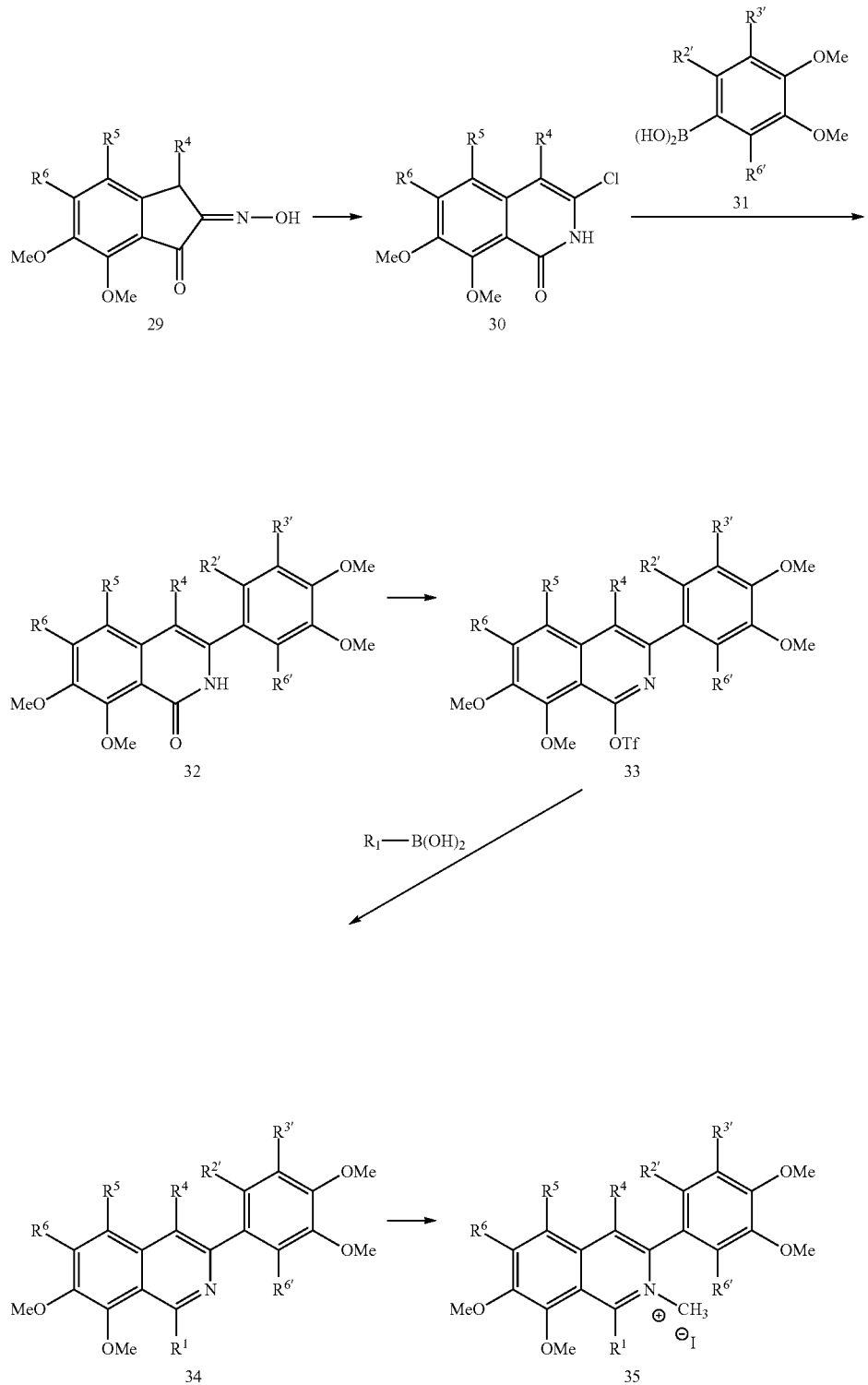

Beckmann rearrangement of α-ketooxime 29 with phosphorus pentachloride can produce 3-chloro-1(2H)isoquinolone 30 using literature methods. Suzuki coupling of 30 with boronic acid 31 can afford the key compound 32. Compound 32 can then be converted to triflate 33 which in turn can undergo a second Suzuki reaction with a boronic acid to afford compound 34. Quaternization of 34 can then lead to compound 35.

Scheme 4 illustrates methods and intermediates that are useful for preparing $R^{3'}$ substituted compounds of the invention.

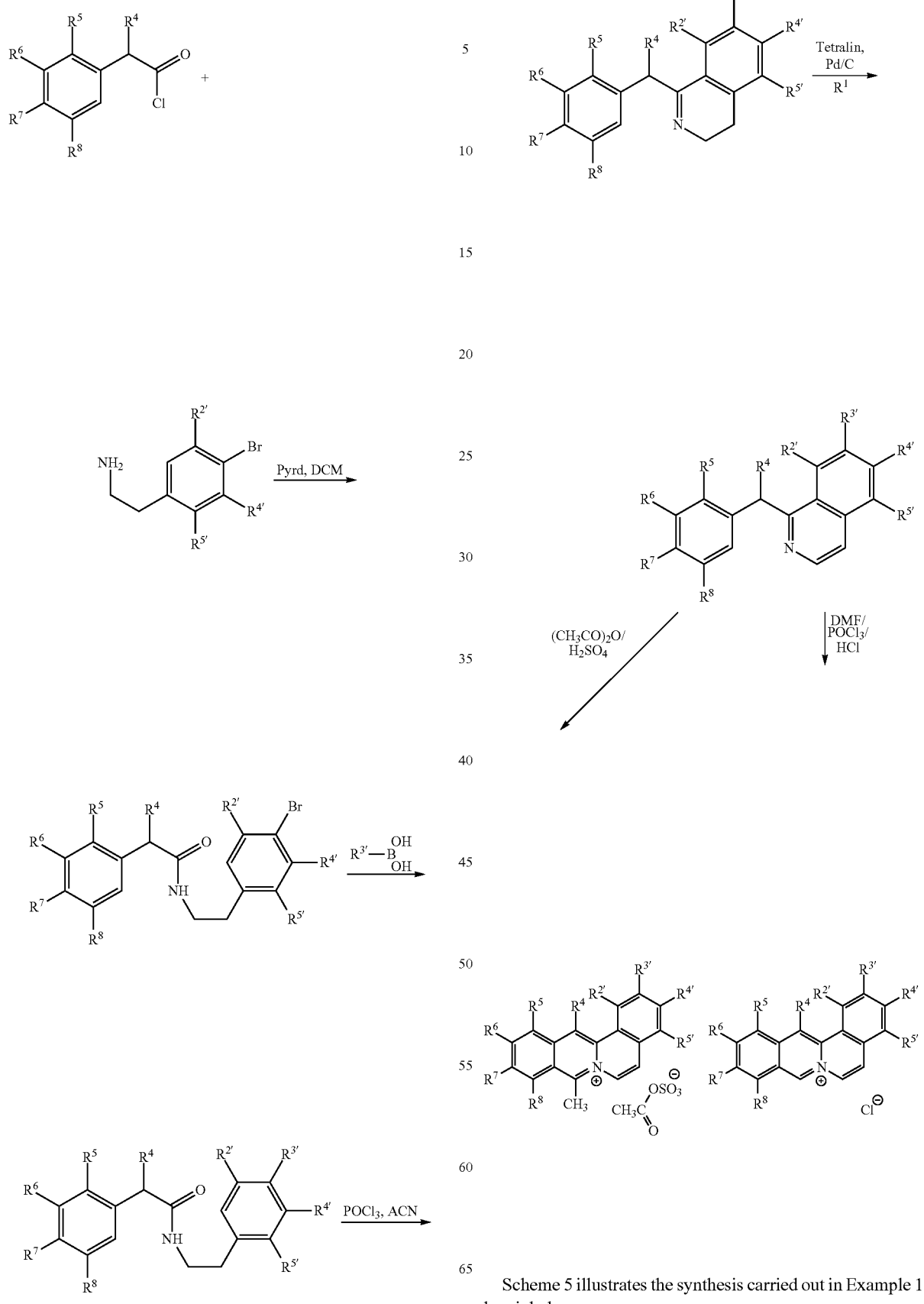
Scheme 5 illustrates the synthesis carried out in Example 1 hereinbelow.

Scheme 5
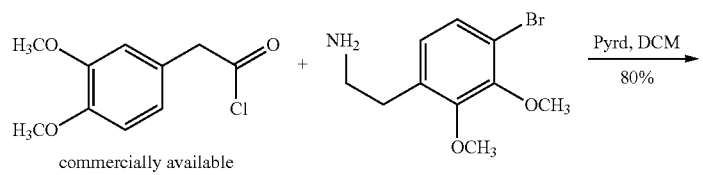
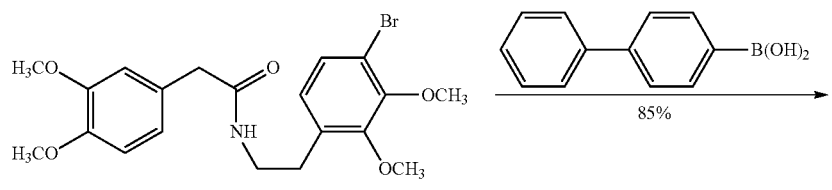
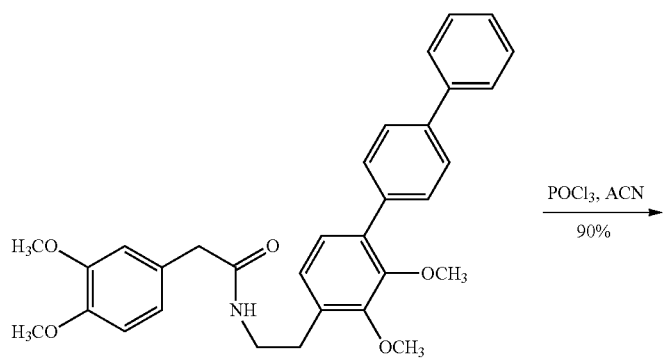
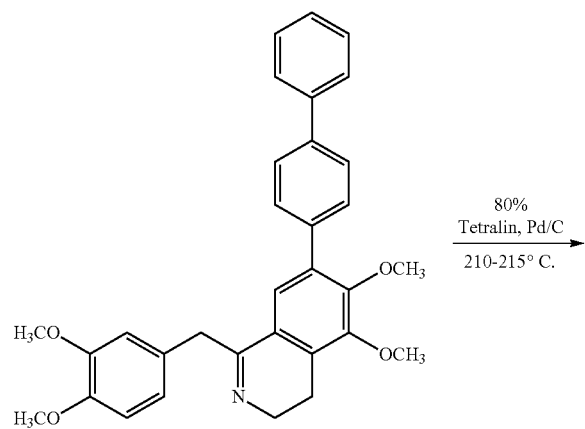

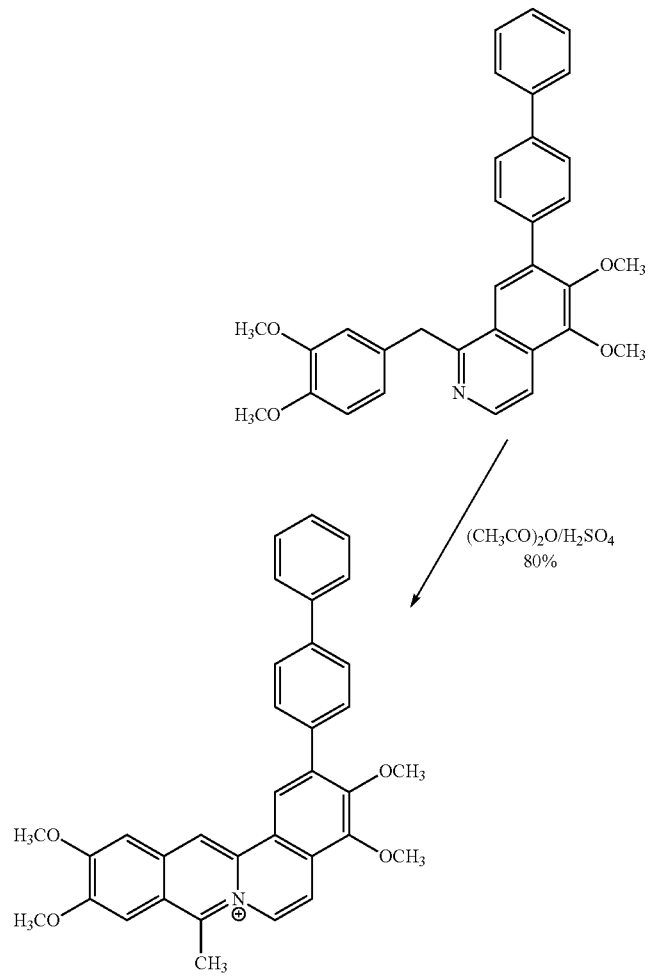 [SMILES: COc1ccc(Cc2nccc3c(OC)c(OC)c(-c4ccc(-c5ccccc5)cc4)cc23)cc1OC ; COc1cc2cc3c4cc(-c5ccc(-c6ccccc6)cc5)c(OC)c(OC)c4cc[n+]3c(C)c2cc1OC]
Scheme 6 illustrates methods and intermediates that are useful for preparing $R^4$ substituted compounds of the invention.
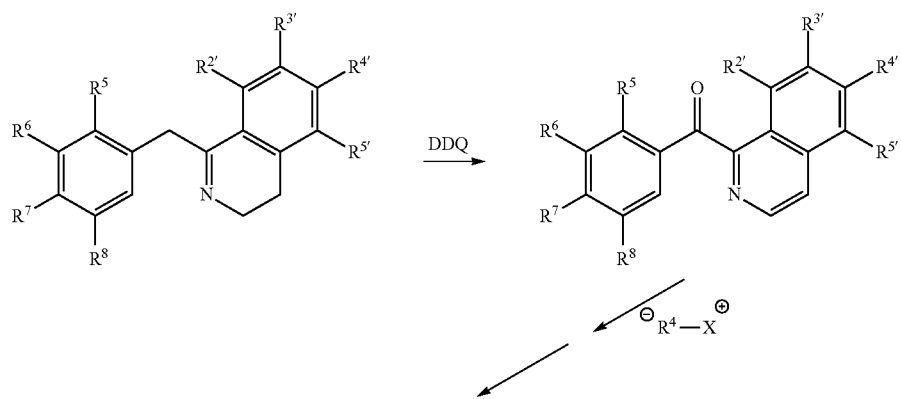

-continued
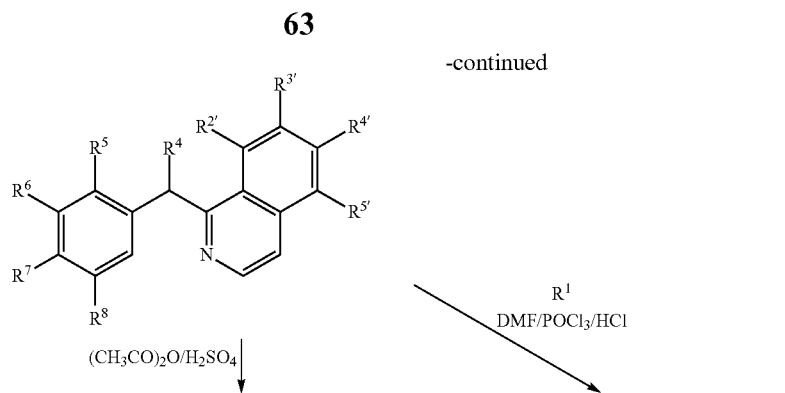
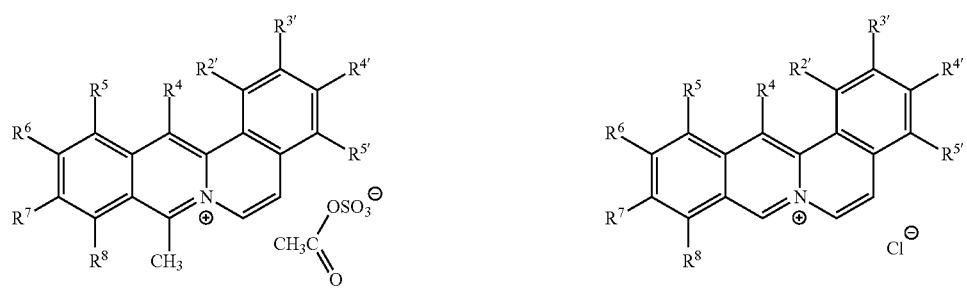
Scheme 7 illustrates methods and intermediates that are useful for preparing compounds that are substituted at $R^4$ and $R^{3'}$.
Scheme 7
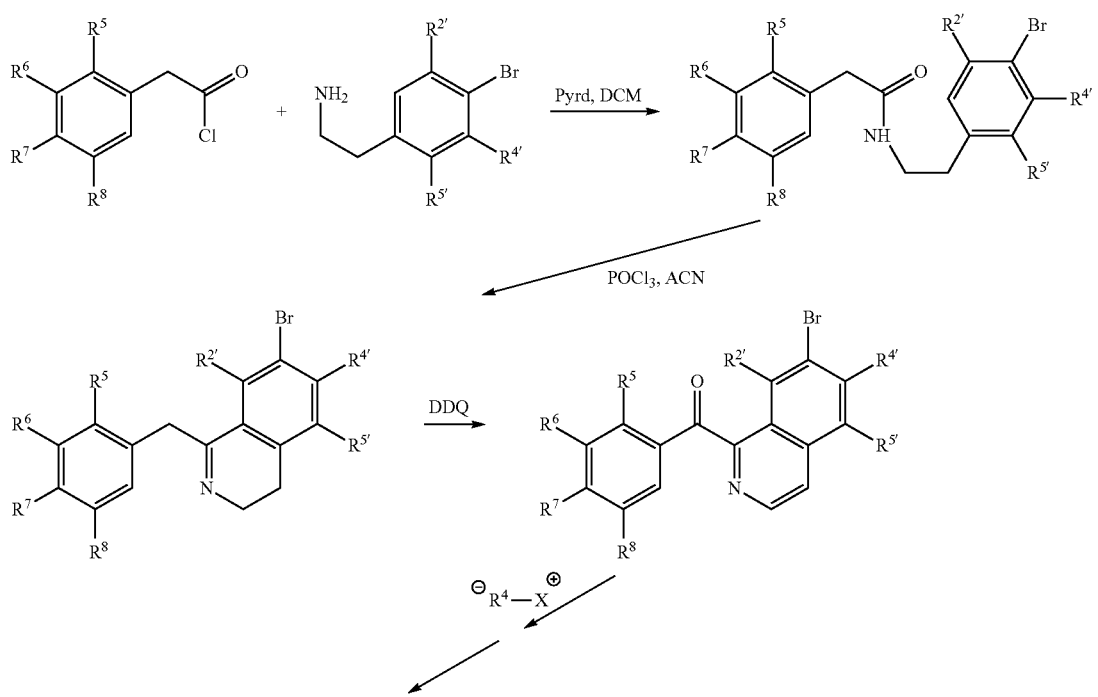

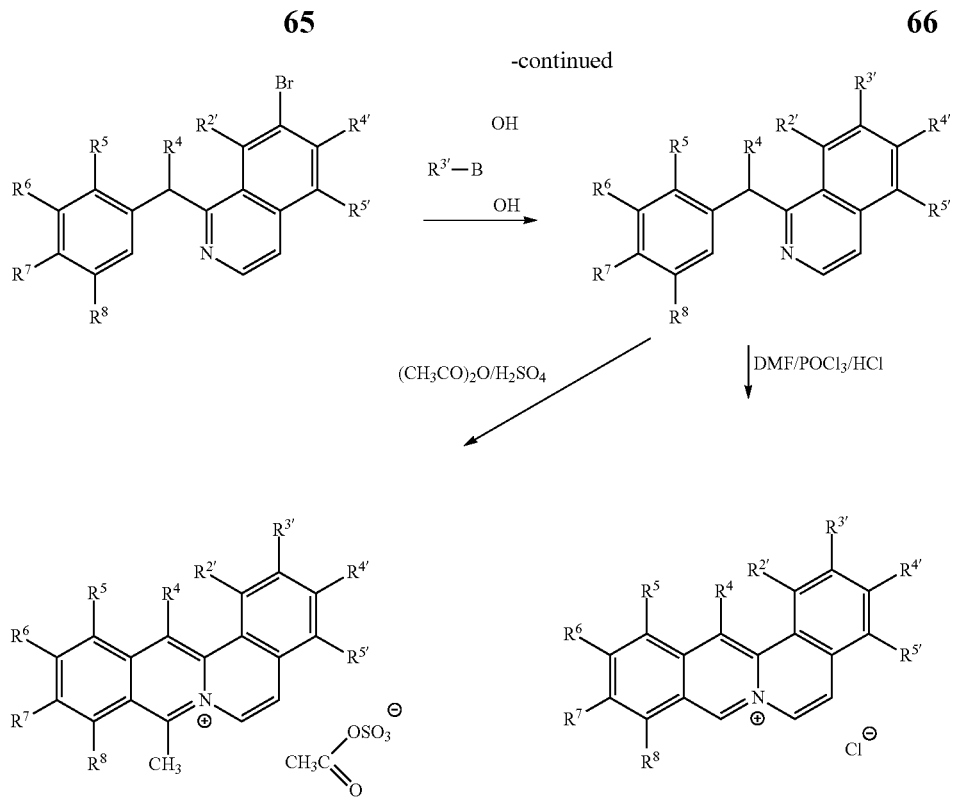

Scheme 8 illustrates the preparation of an intermediate phenethylamine that is useful for preparing compounds of the invention.

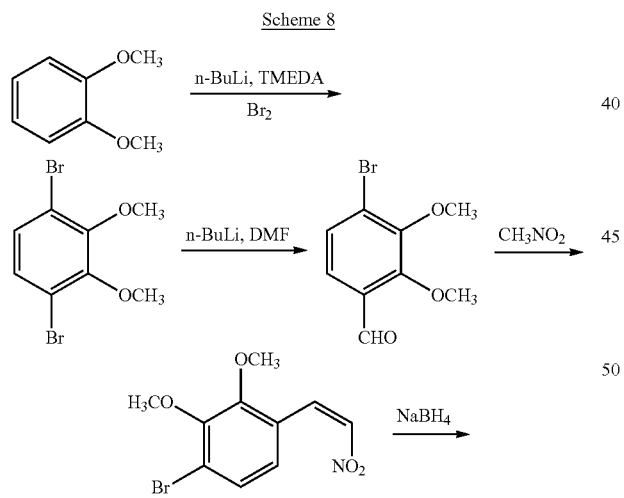

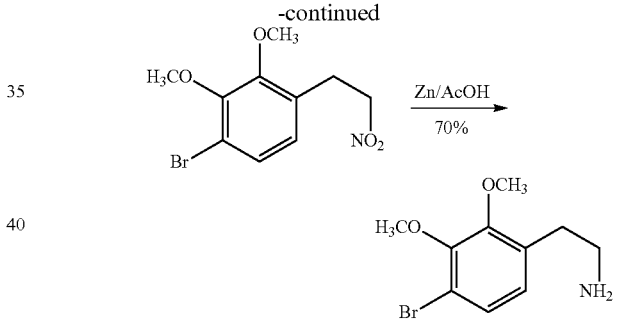

Scheme 8a illustrates methods for the preparation of phenethylamine intermediates that have $R^{14}$ substituents. The formation of β-substituted derivatives uses a nucleophile in a Michael addition reaction and the α-substituted derivatives is formed from a carbanion generated at the position adjacent to the nitro substituent, followed by reaction with an appropriate electrophile.

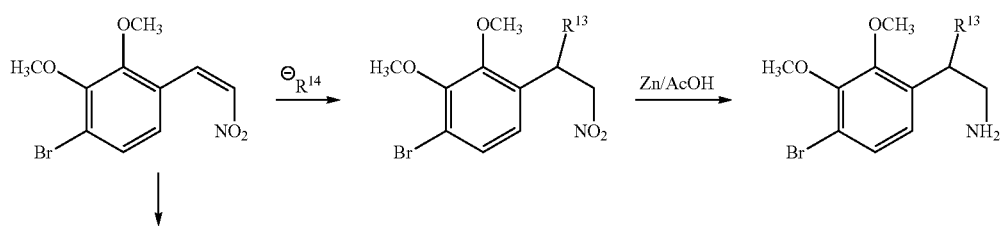

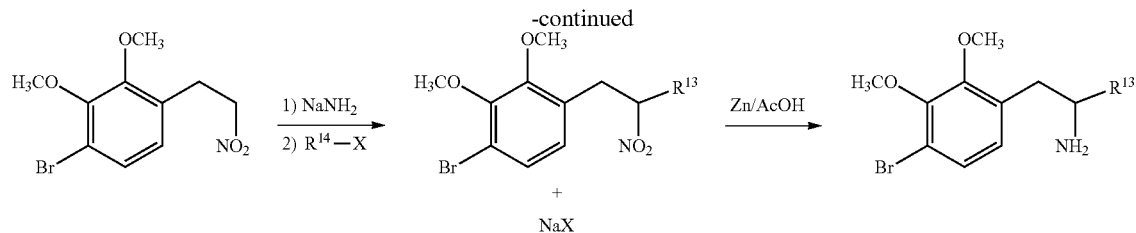
Scheme 9 illustrates methods and intermediates that are useful for preparing compounds of the invention.
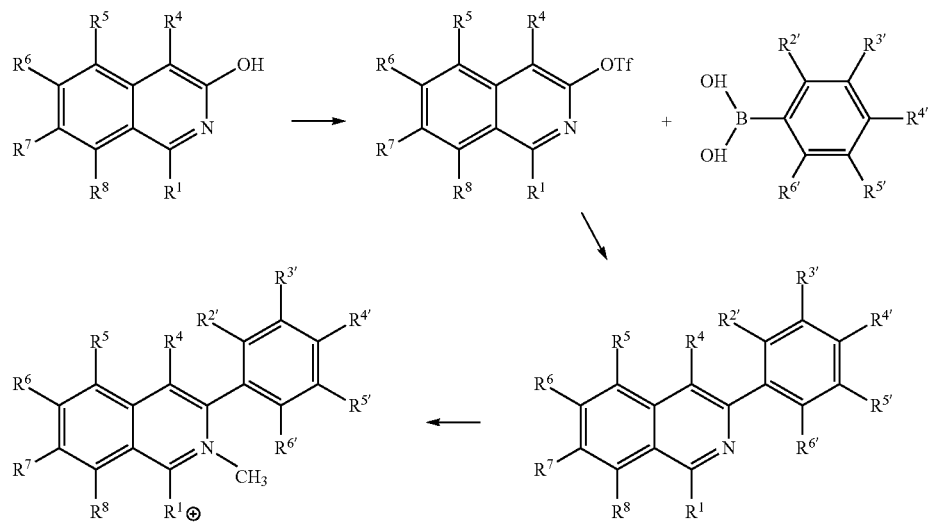
Scheme 10 illustrates methods and intermediates that are useful for preparing $R^7$ substituted compounds of the invention.
Scheme 11 illustrates the preparation of isoquinoline intermediates that are useful for preparing compounds of the invention.
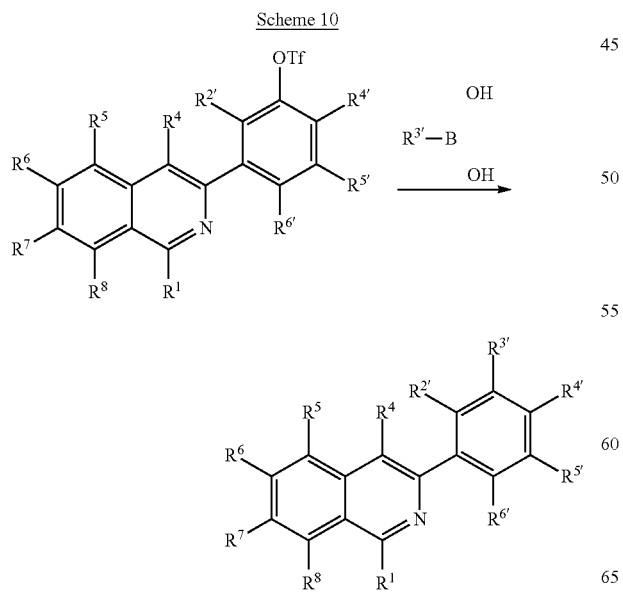
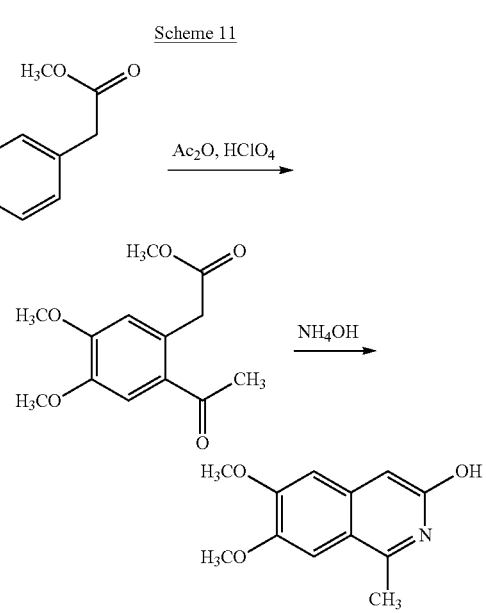

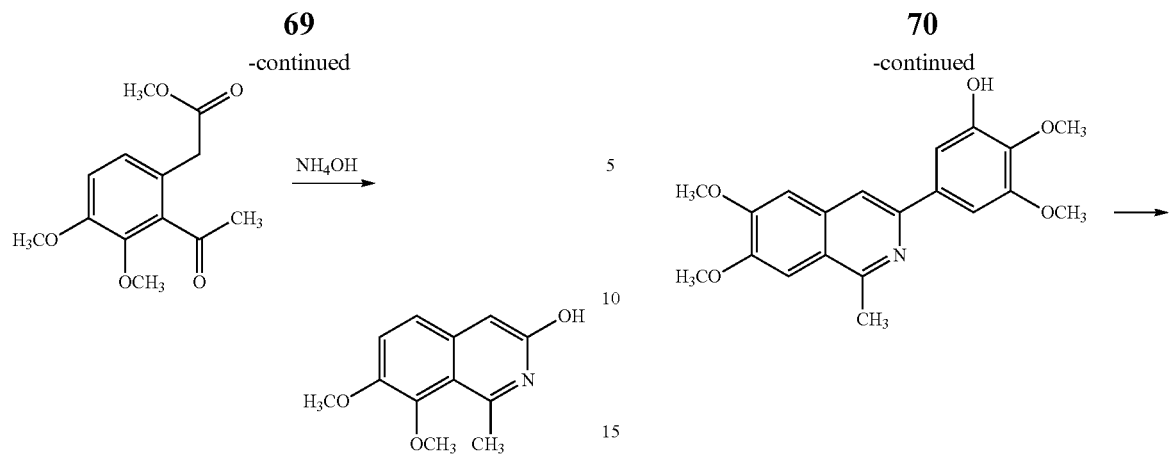
Scheme 12 illustrates the preparation of a triflate intermediate that is useful for preparing compounds of the invention.
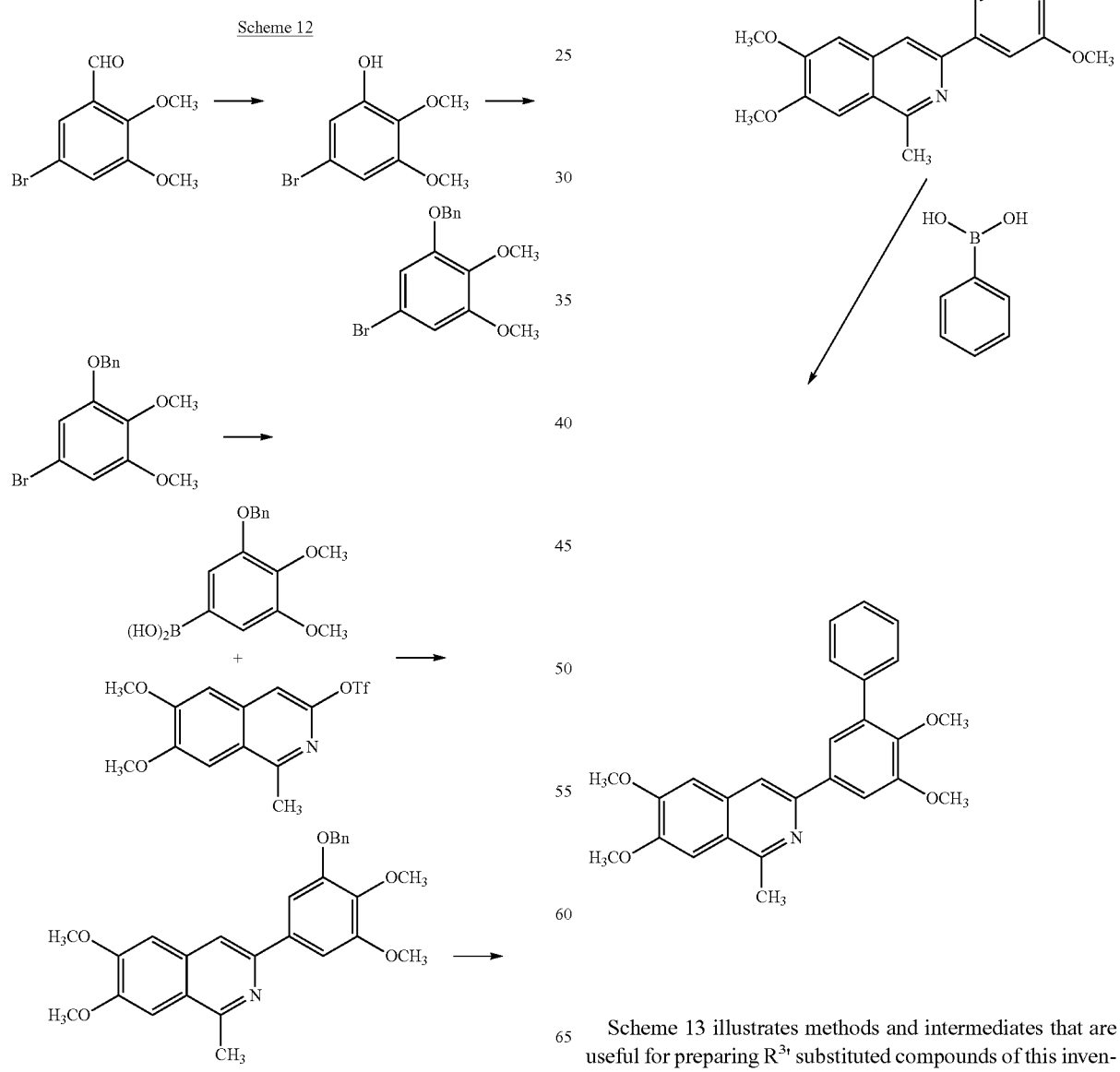
Scheme 13 illustrates methods and intermediates that are useful for preparing $R^{3'}$ substituted compounds of this invention.

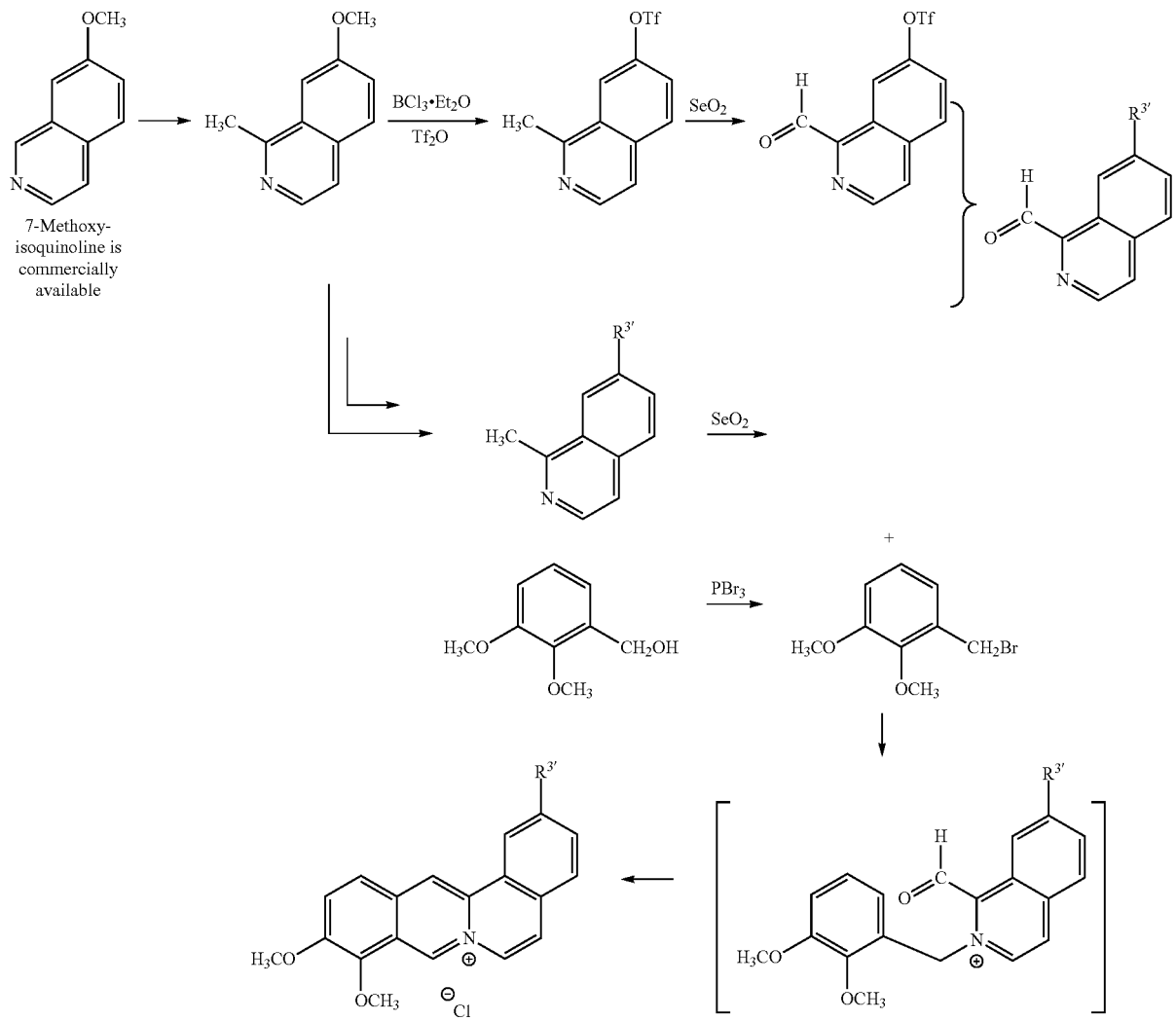
Scheme 14 illustrates methods and intermediates that are useful for preparing $R^{2'}$ substituted compounds of the invention.
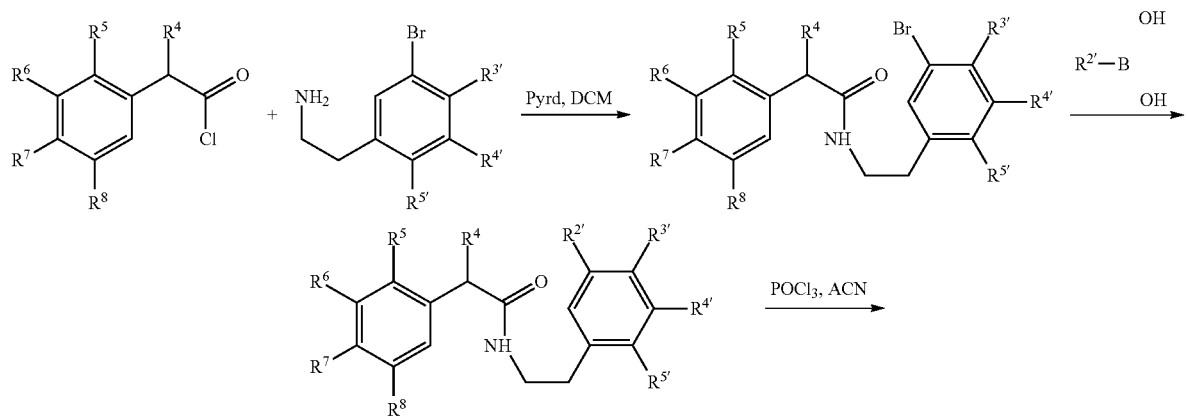

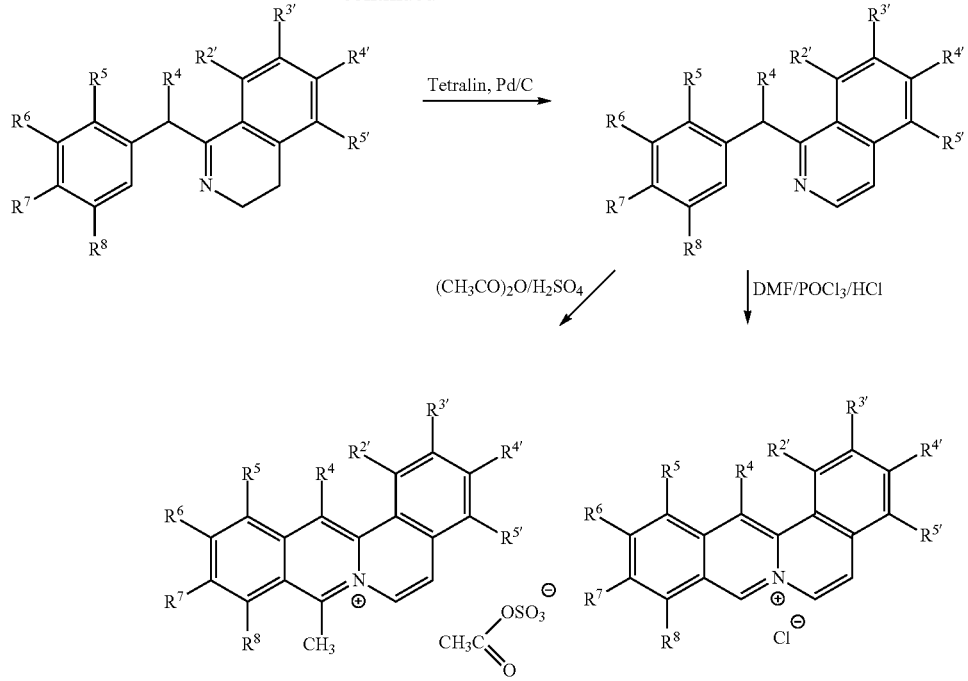
Scheme 15 illustrates methods and intermediates that are useful for preparing R[3'] substituted compounds of the invention.
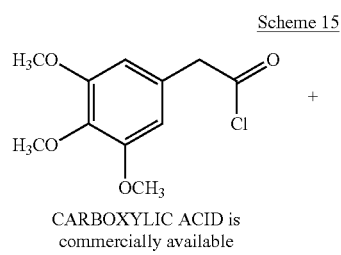
Scheme 15
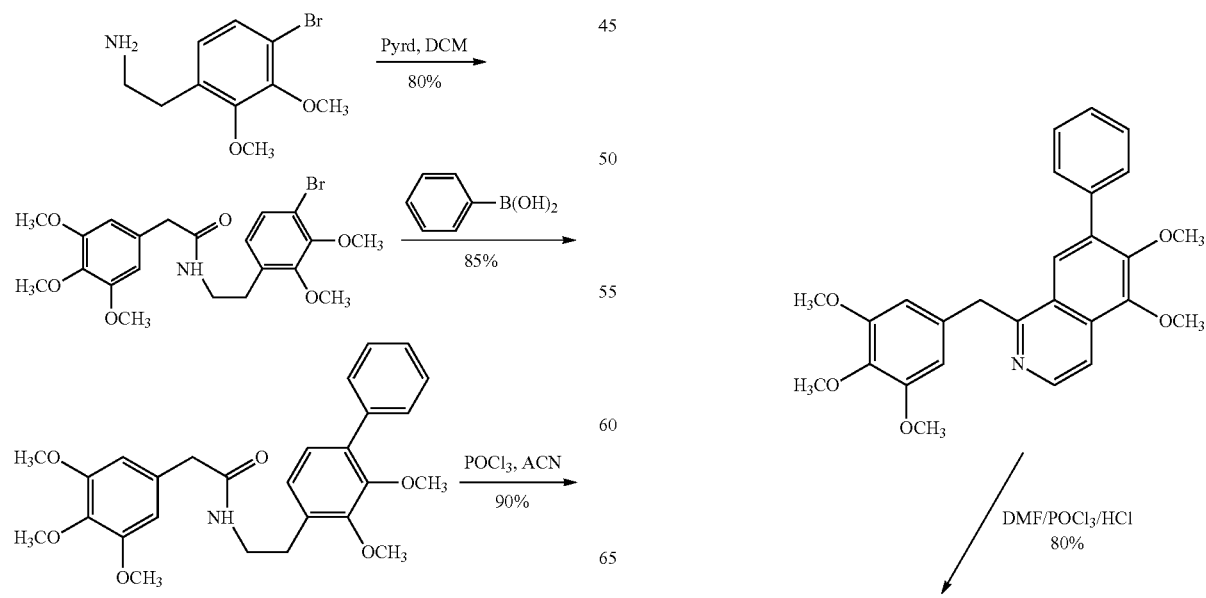

-continued
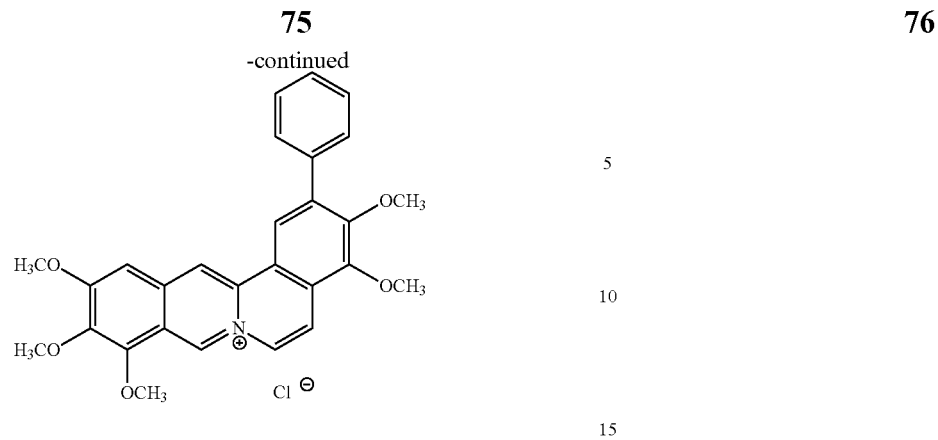
Scheme 16 illustrates methods and intermediates that are useful for preparing $R^{3'}$ substituted compounds of the invention.
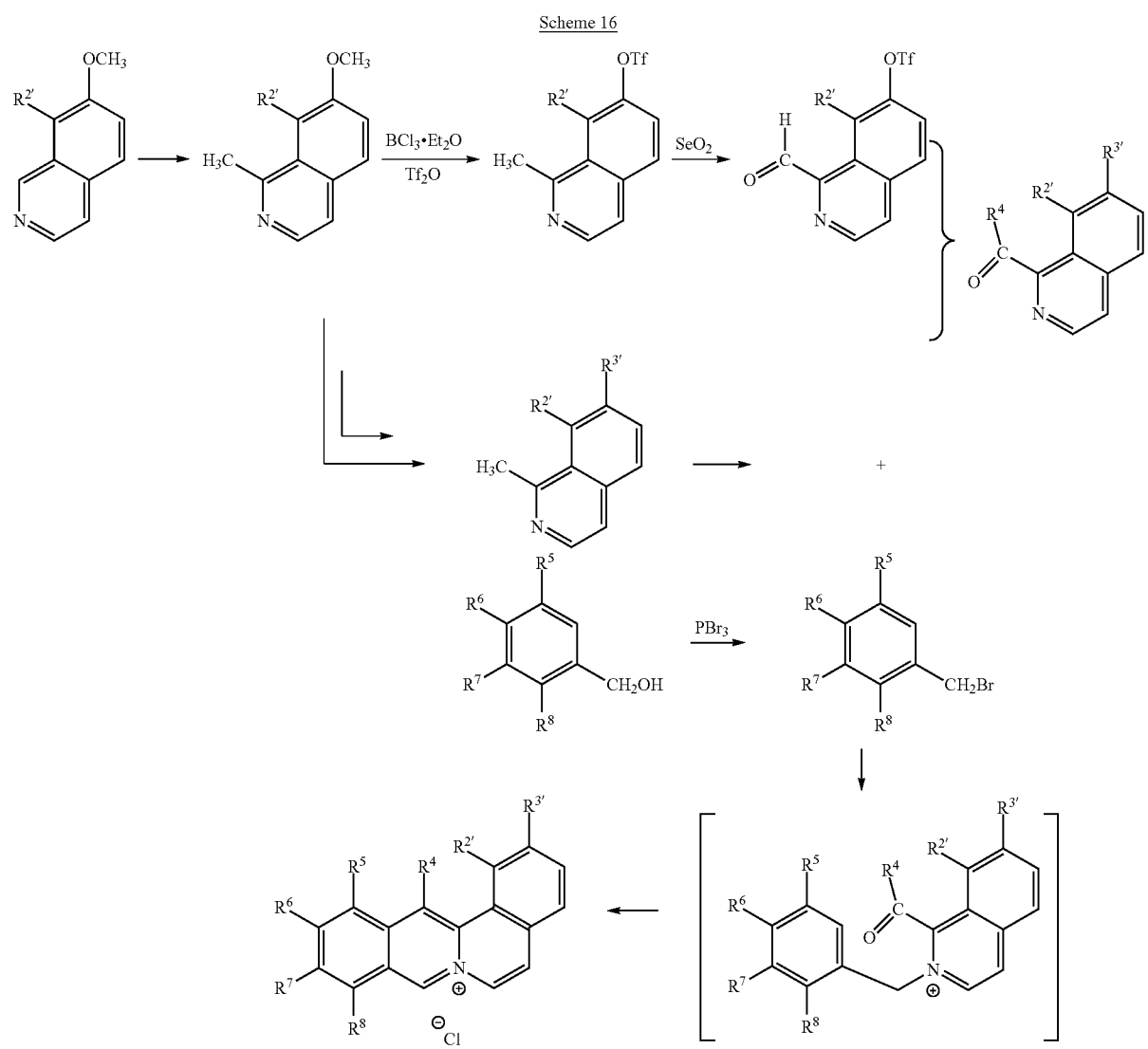
Scheme 17 illustrates methods and intermediates that are useful for preparing $R^{2'}$ substituted compounds of the invention.

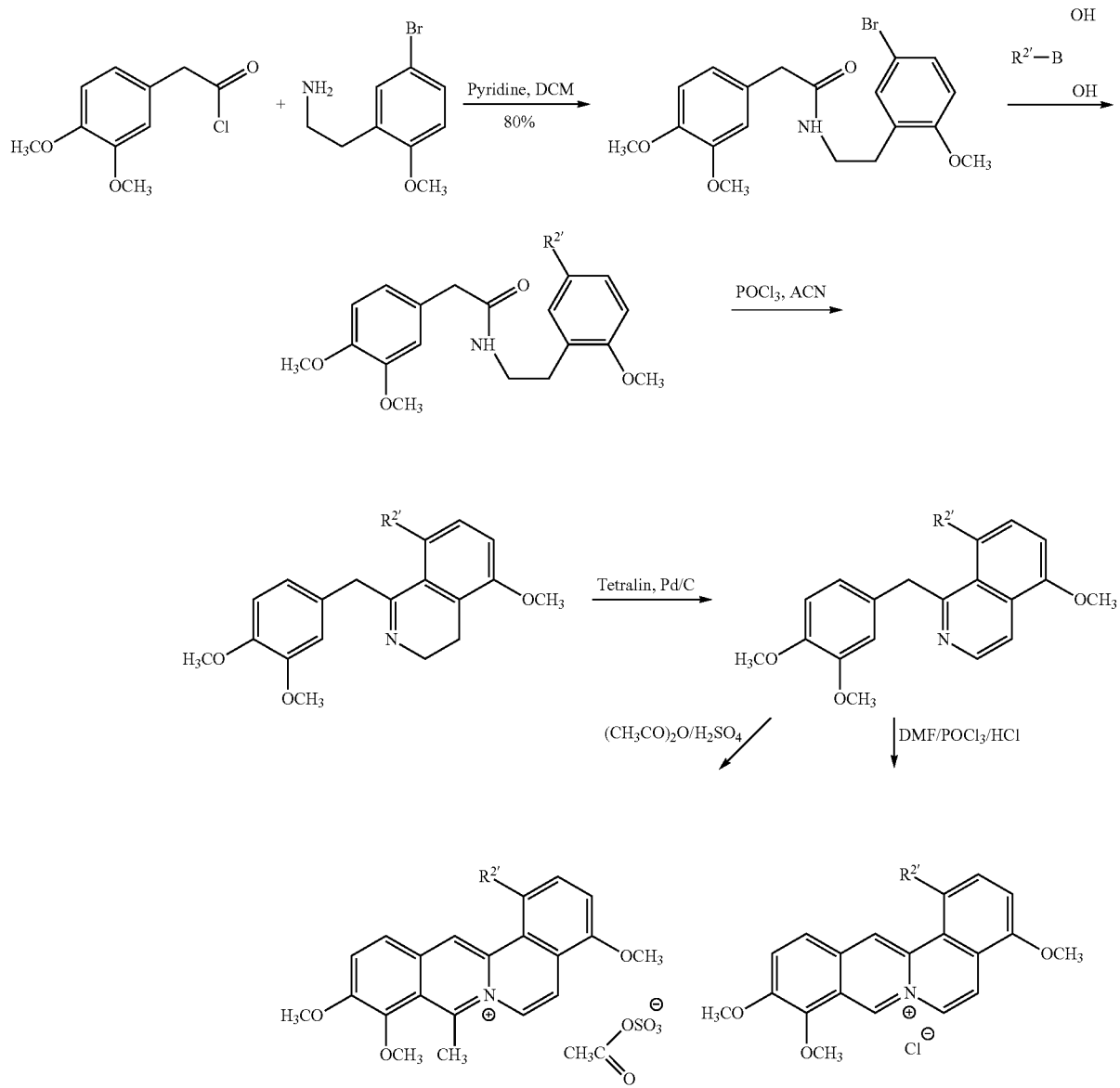
Scheme 18 illustrates methods and intermediates that are useful for preparing R[5] substituted compounds of the invention.
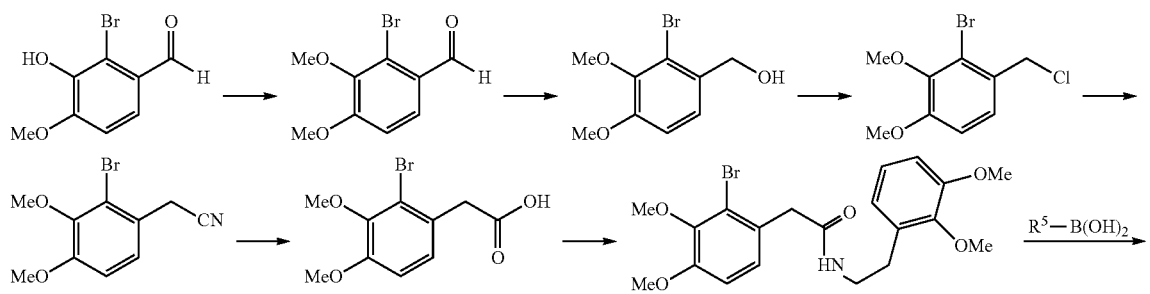

-continued
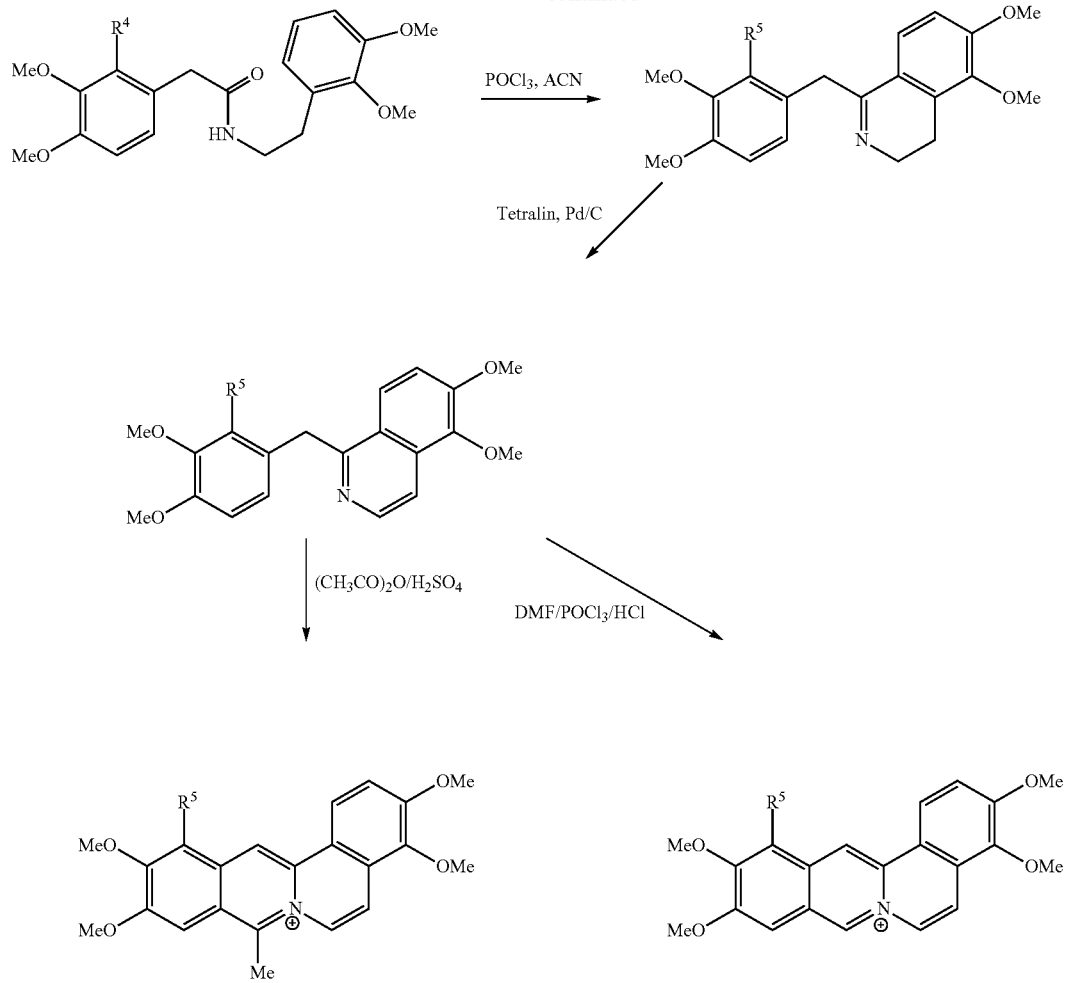
Compounds of formula I wherein $R^{2'}$ is other than hydrogen can be prepared as illustrated in Scheme 19.
Scheme 19
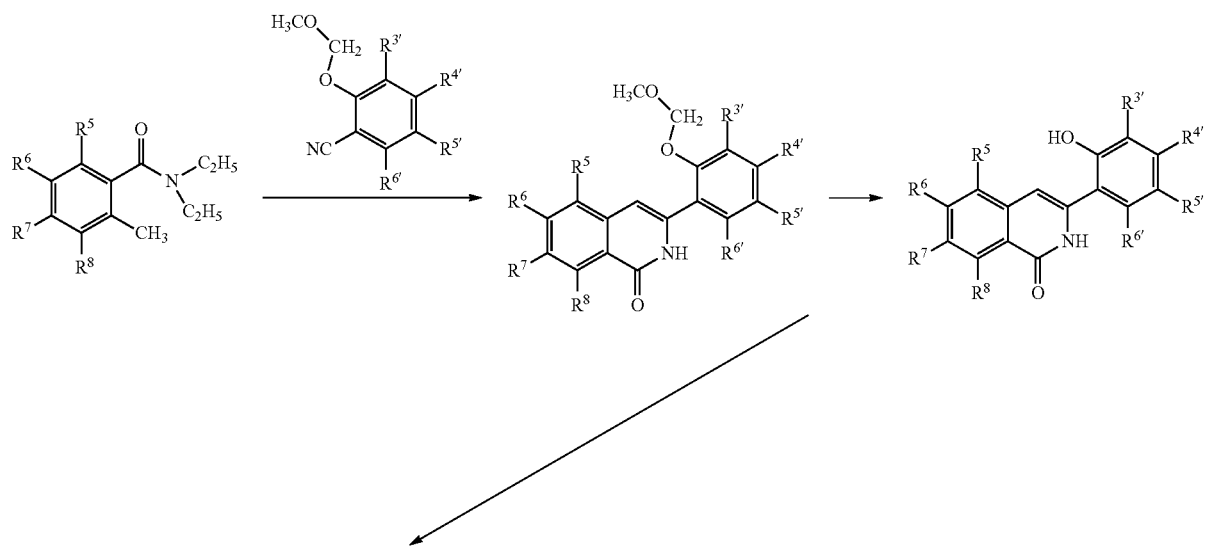

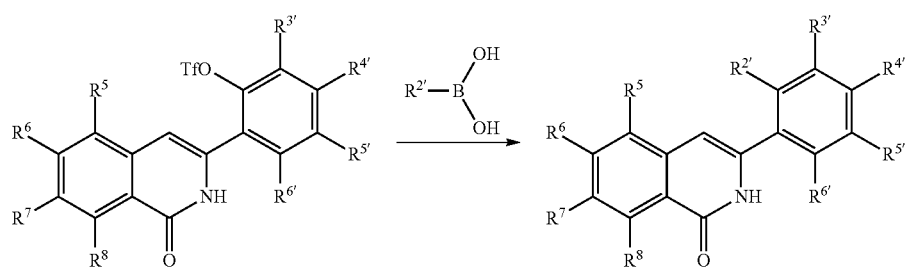
Scheme 20
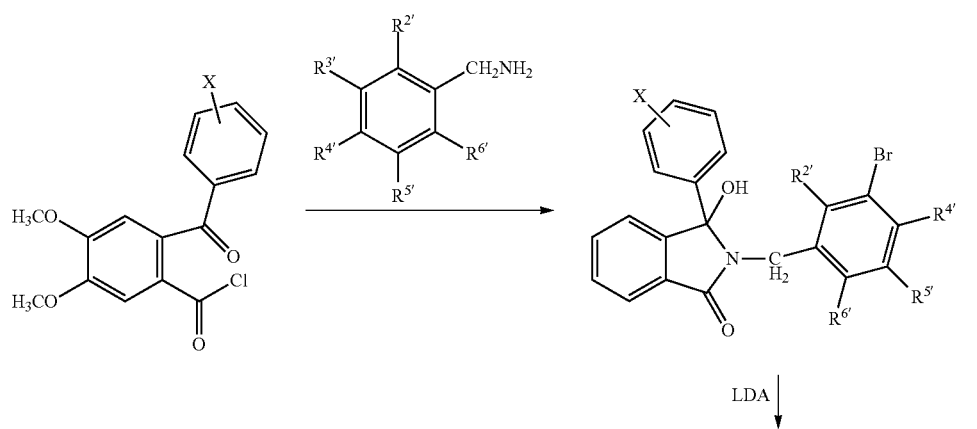
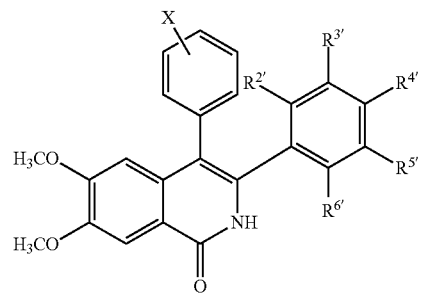

83 84
Scheme 21
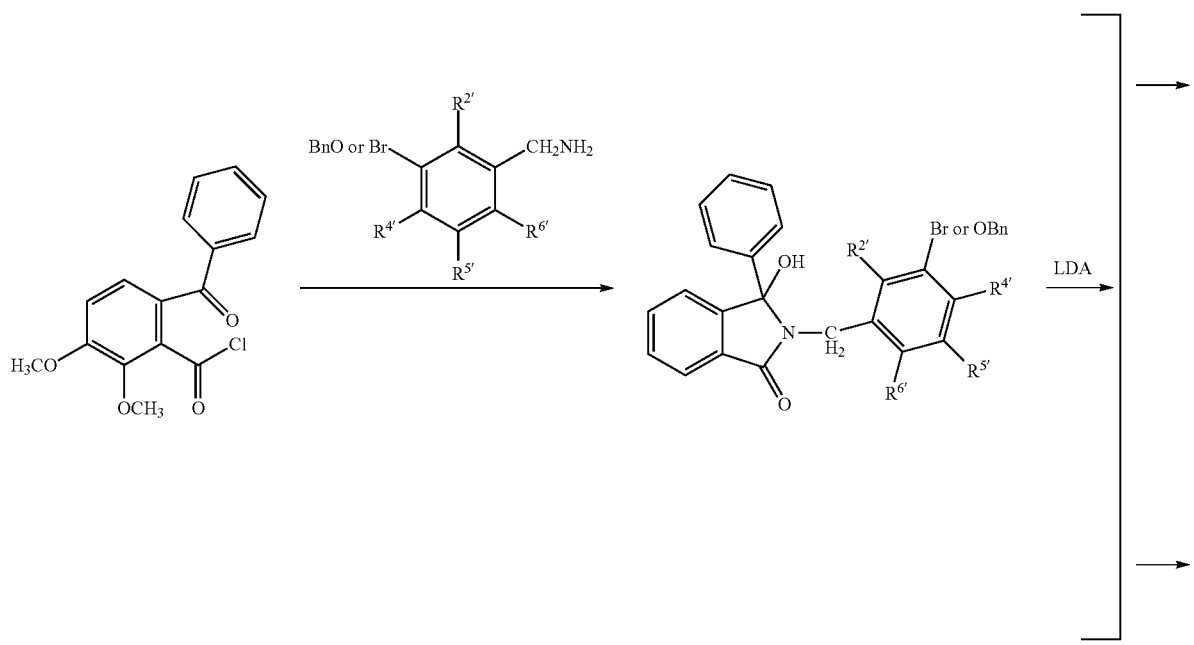
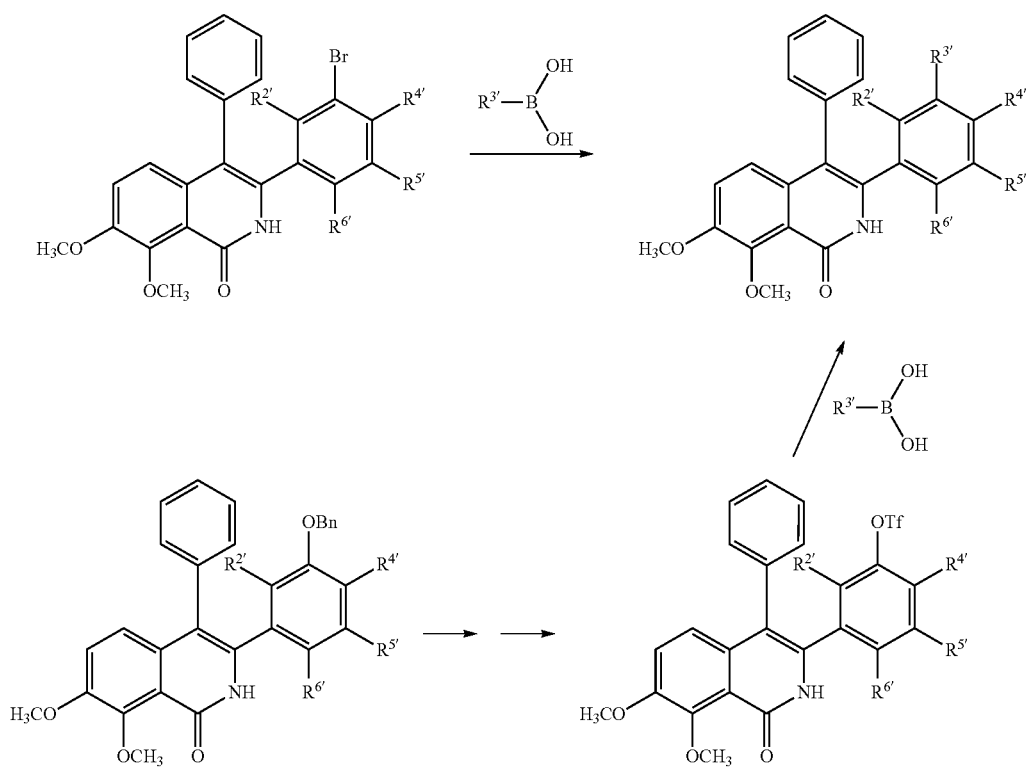

85 86
Scheme 22
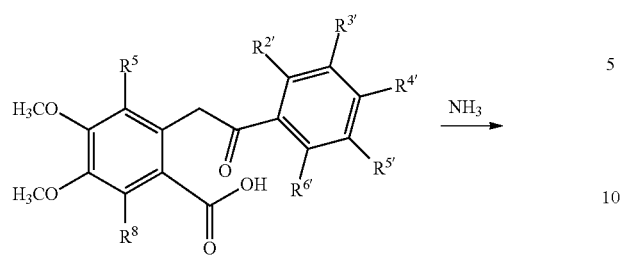
Scheme 23
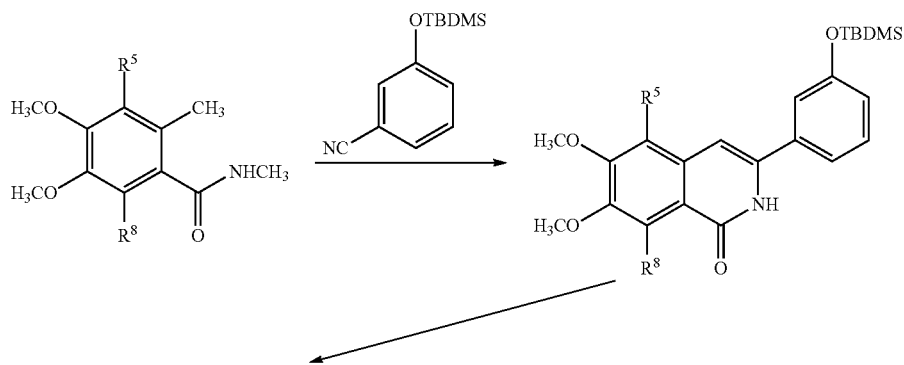
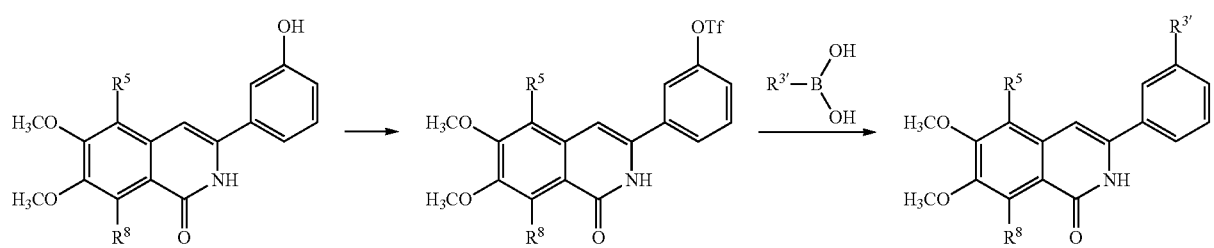

Scheme 24
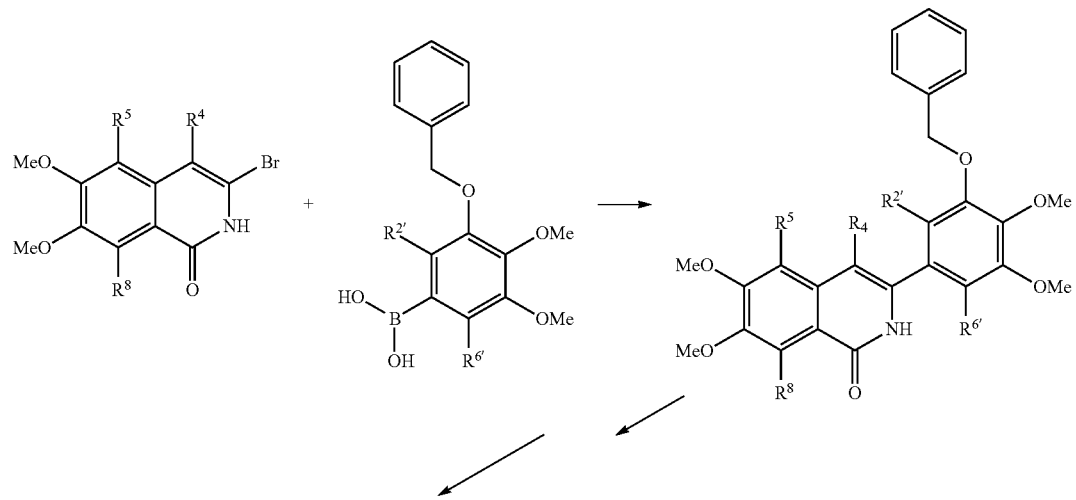
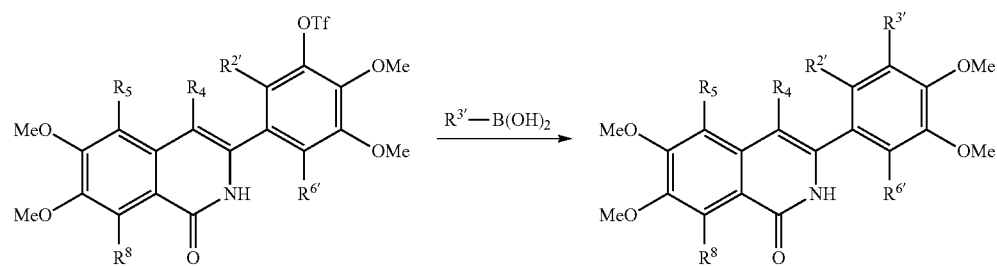
Scheme 25
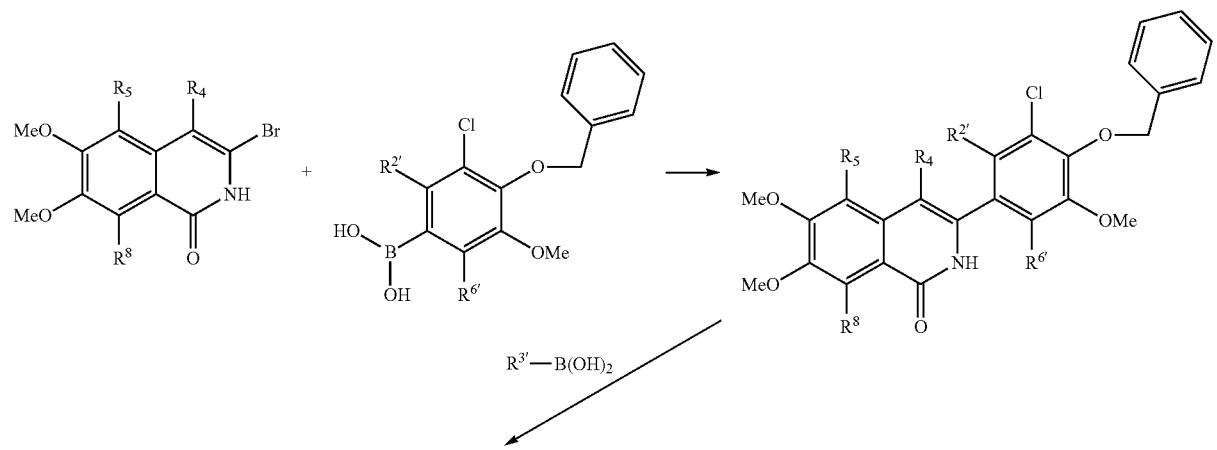

89 90
-continued
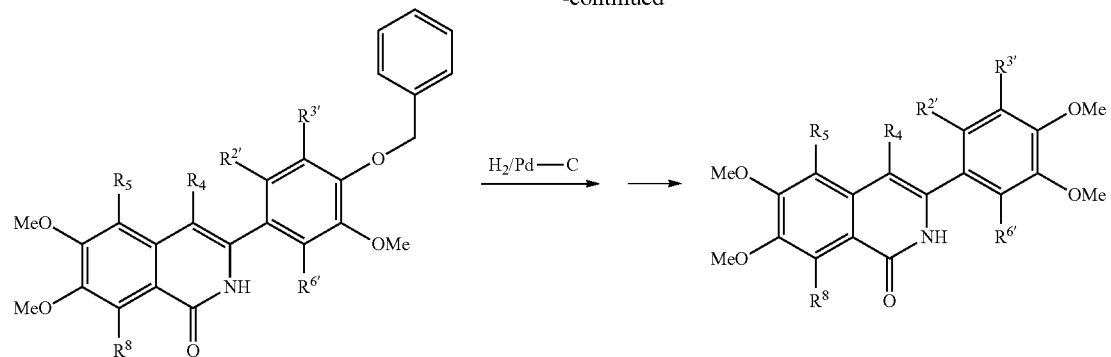
Scheme 26
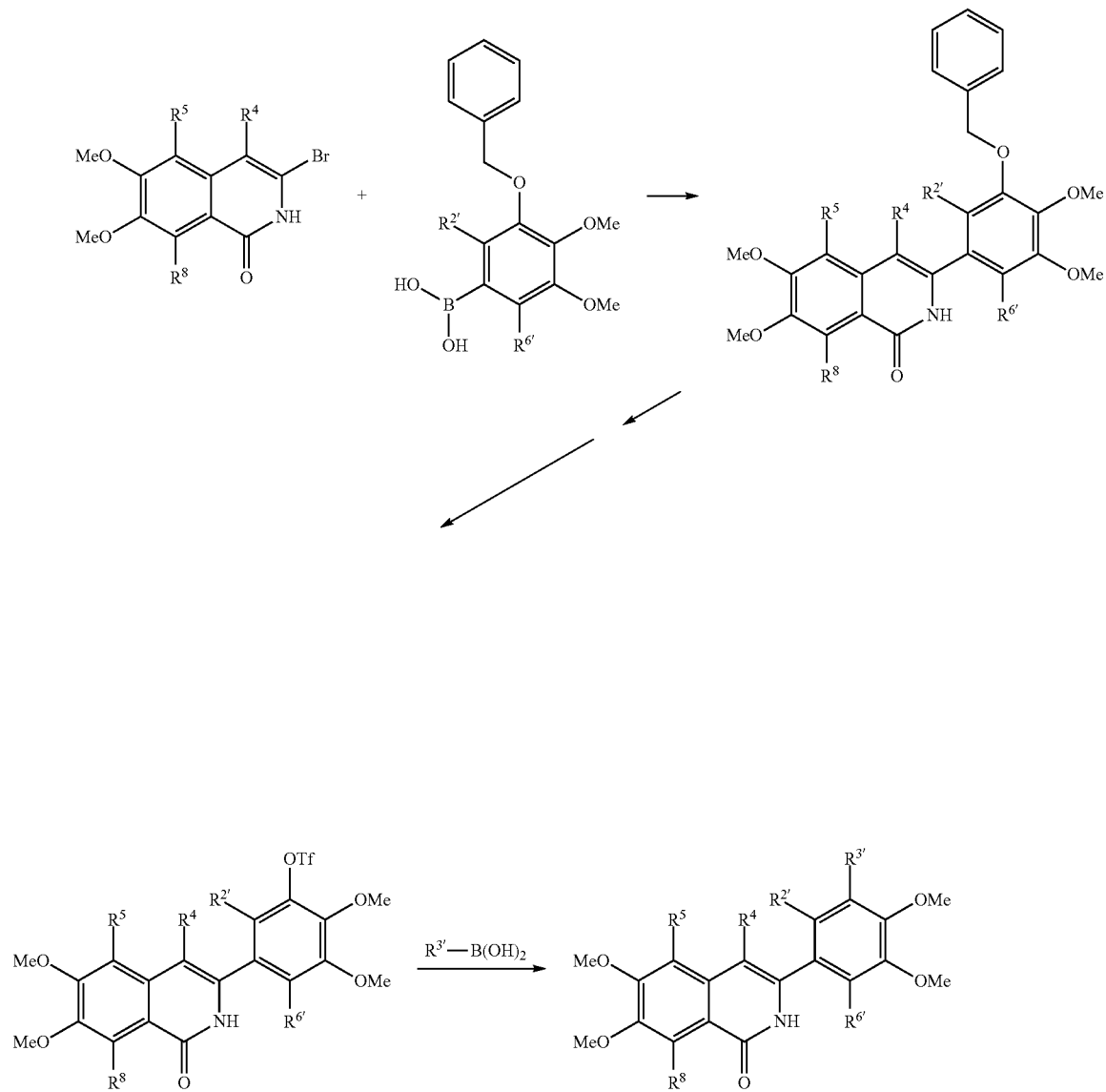

91 92
Scheme 27
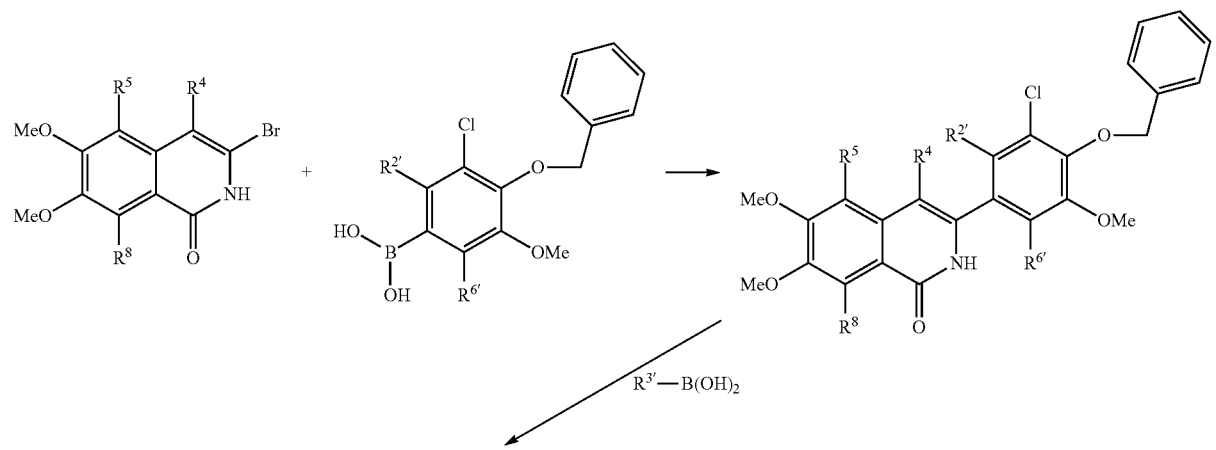
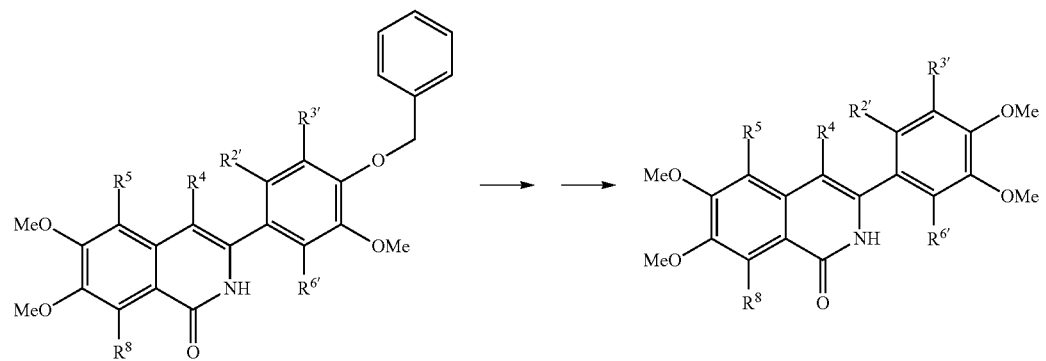
Scheme 28
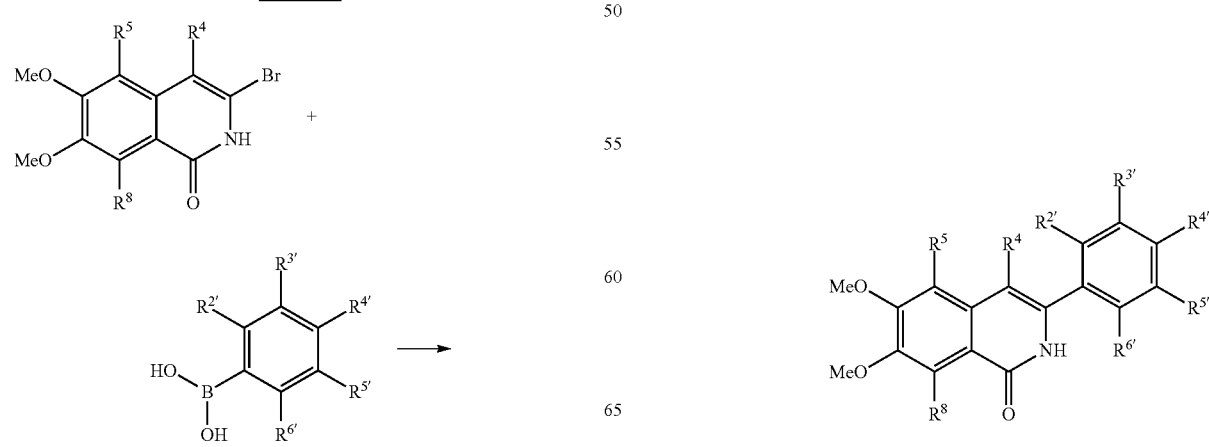

Scheme 29
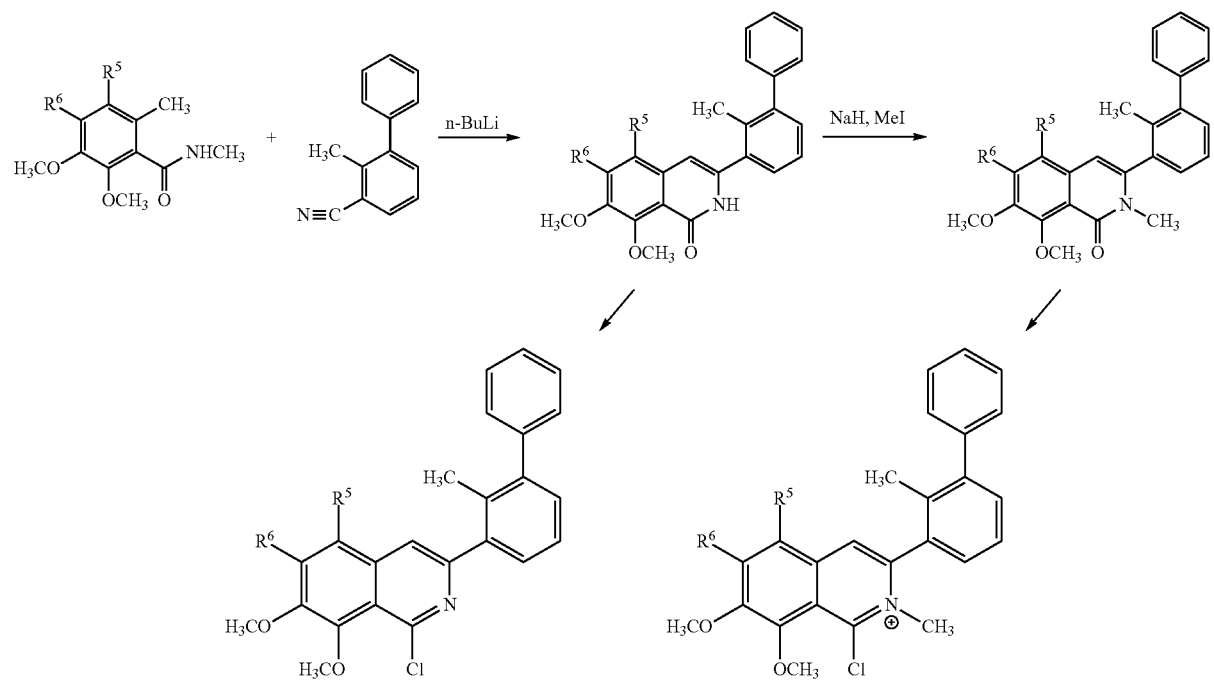
Scheme 30
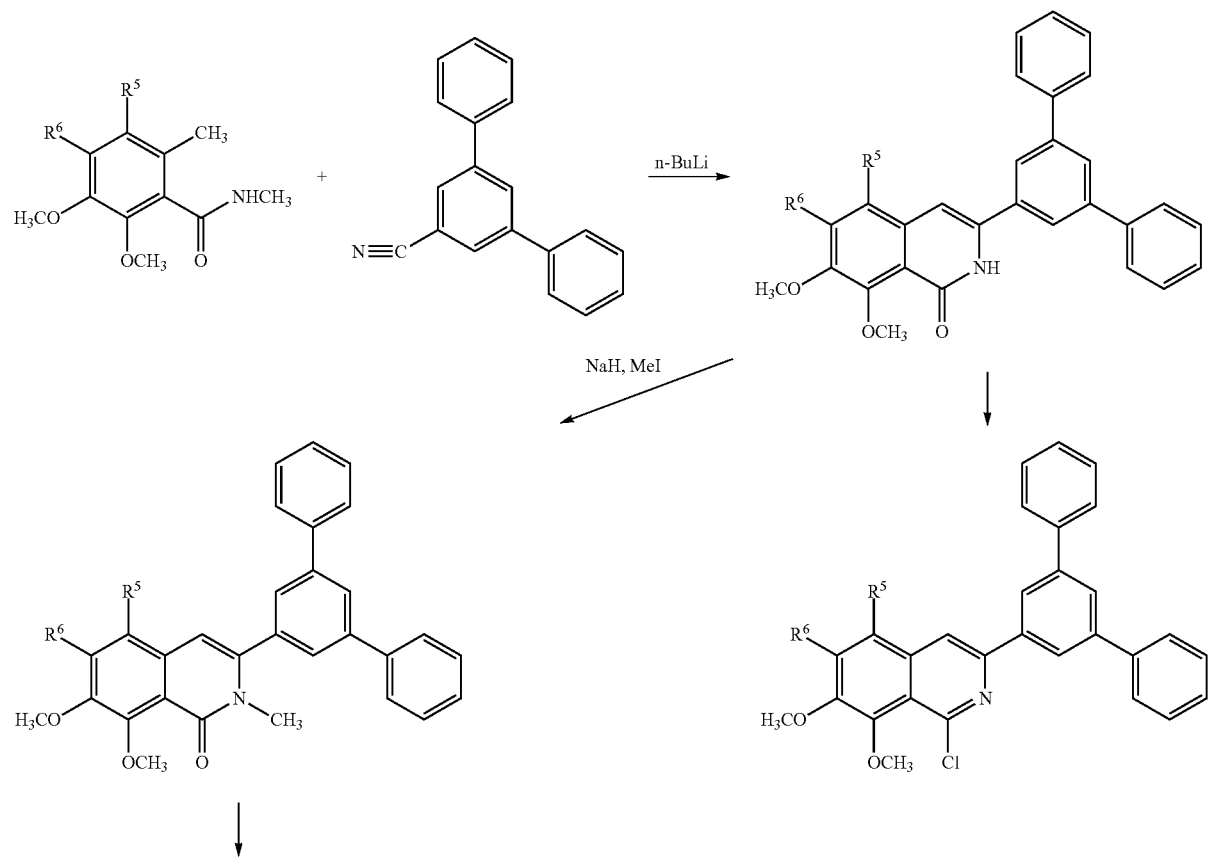

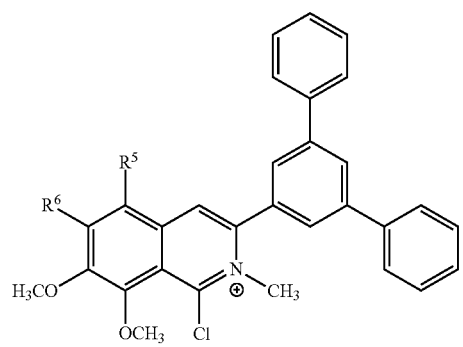
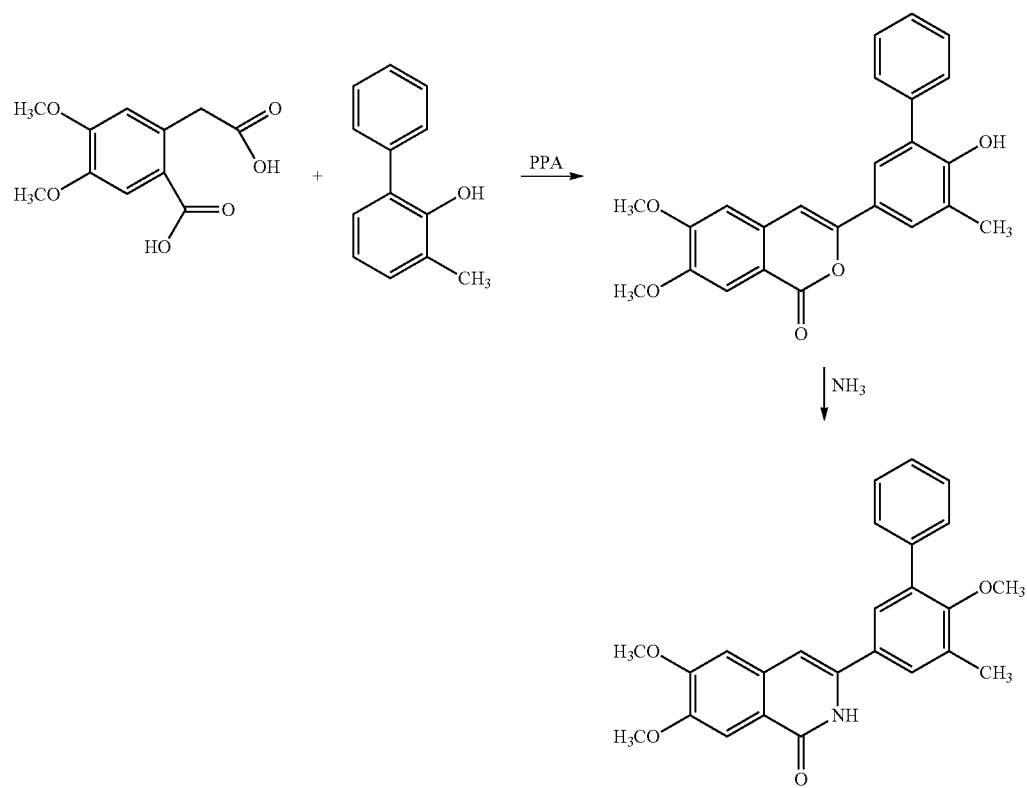
Scheme 31
Scheme 32
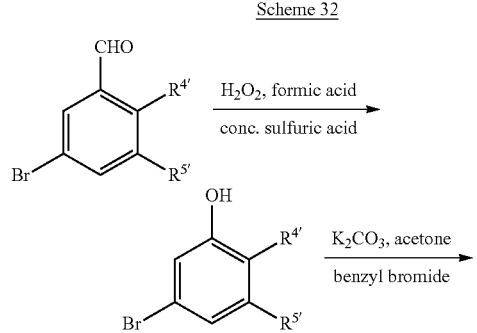
-continued
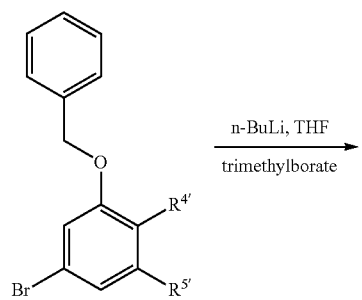

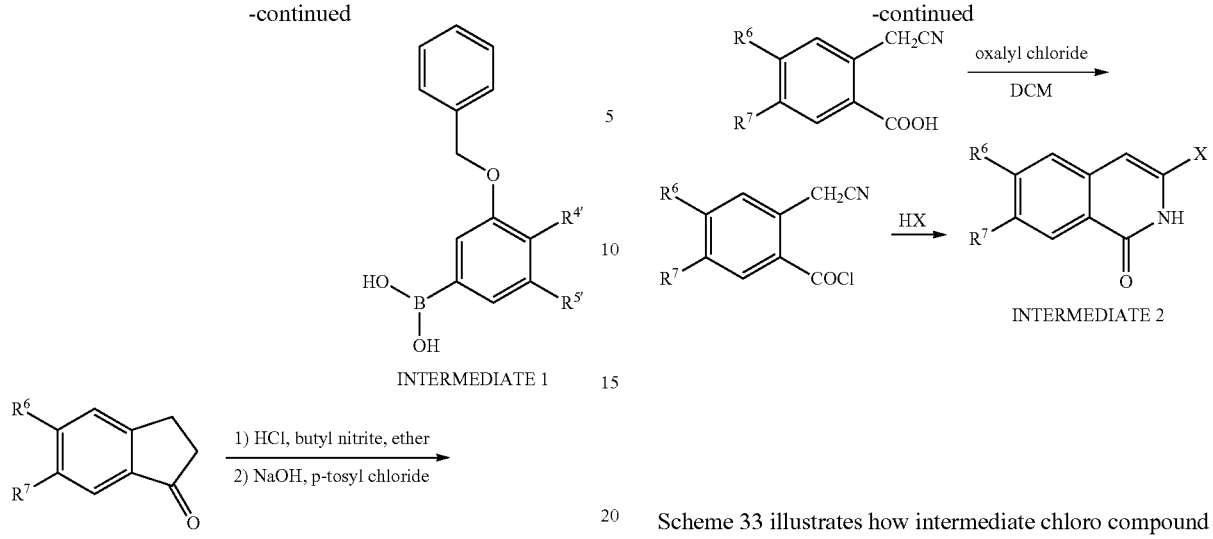
Scheme 33 illustrates how intermediate chloro compound 3 can be used for preparing compounds of formula I.
Scheme 33
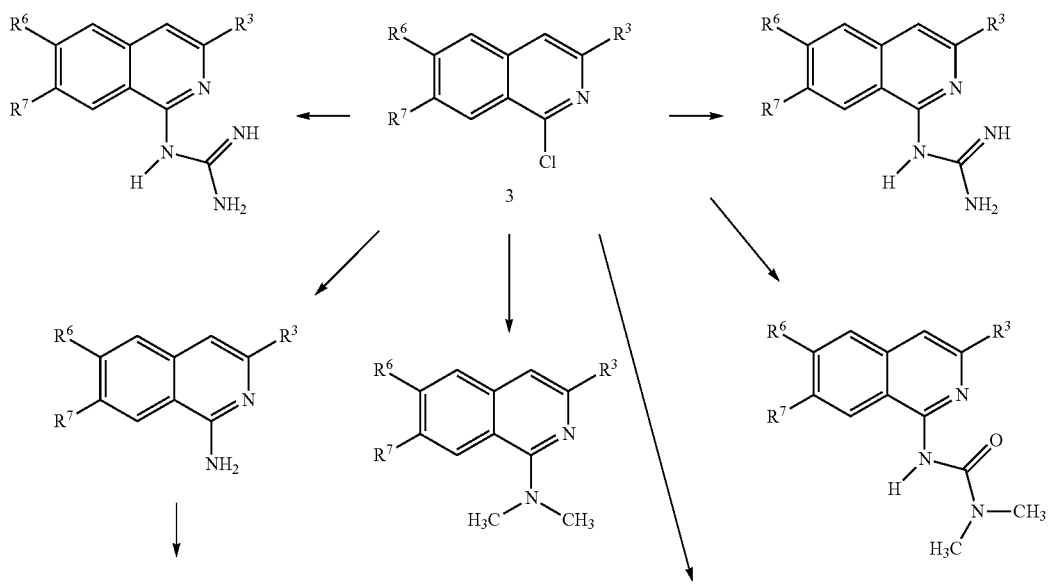
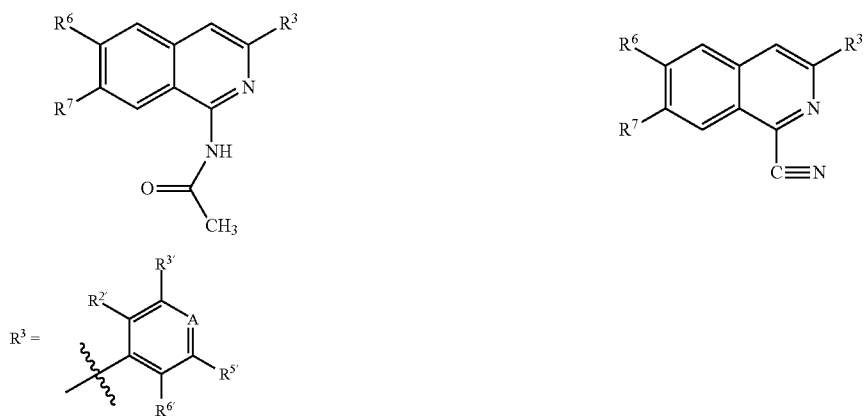

Scheme 34 illustrates how intermediate chloro compounds 4 and 5 can be preparing.

Scheme 34

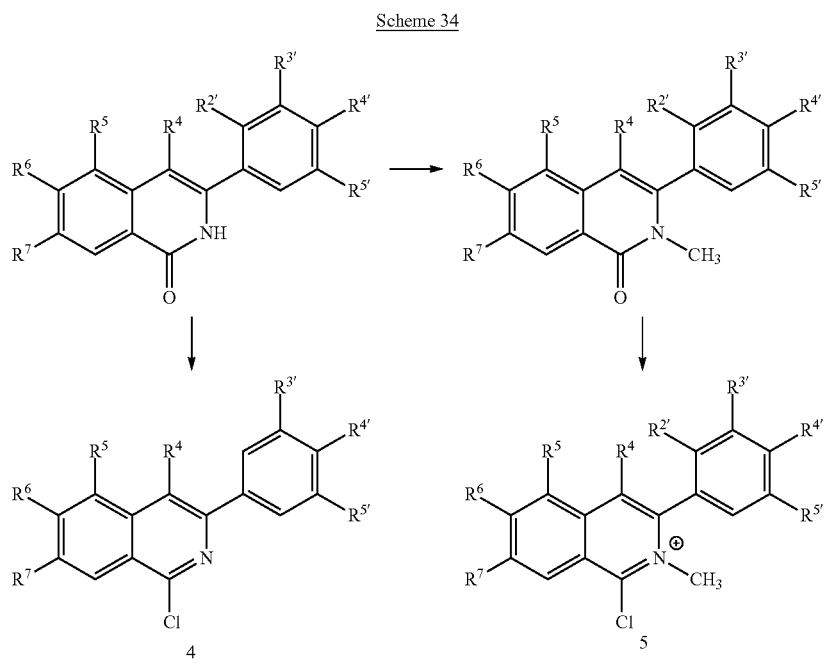

Scheme 35 illustrates the preparation of a representative compound of the invention wherein $R^{30}$ and $R^{3a}$ taken together with the atoms to which they are attached form a ring.

Scheme 35

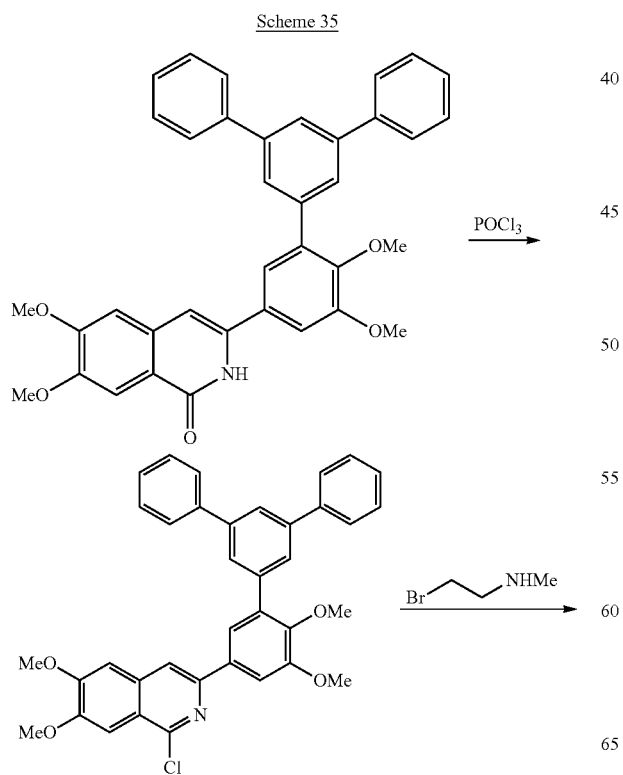

-continued

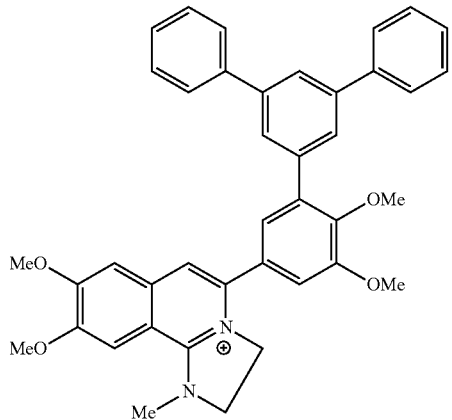

Scheme 36 illustrates the preparation of a representative compound of the invention wherein $R^{30}$ and $R^{3a}$ taken together with the atoms to which they are attached form a ring.

Scheme 36
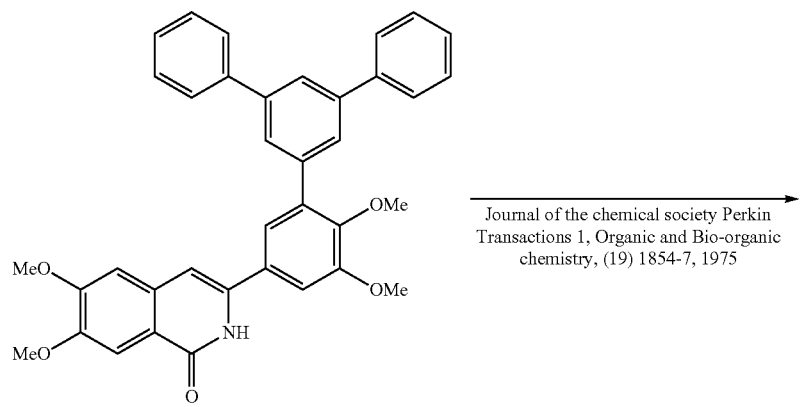
Journal of the chemical society Perkin Transactions 1, Organic and Bio-organic chemistry, (19) 1854-7, 1975
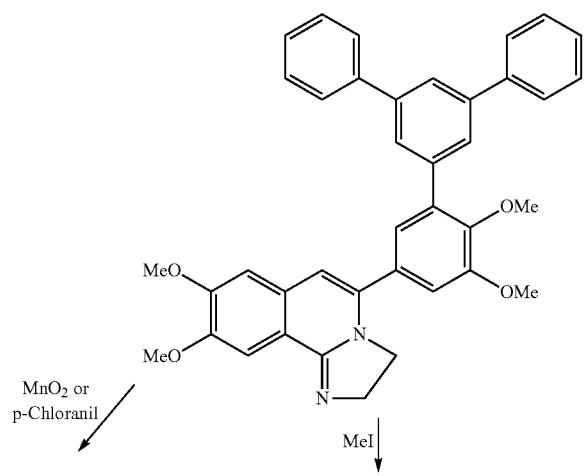
MnO$_2$ or p-Chloranil       MeI
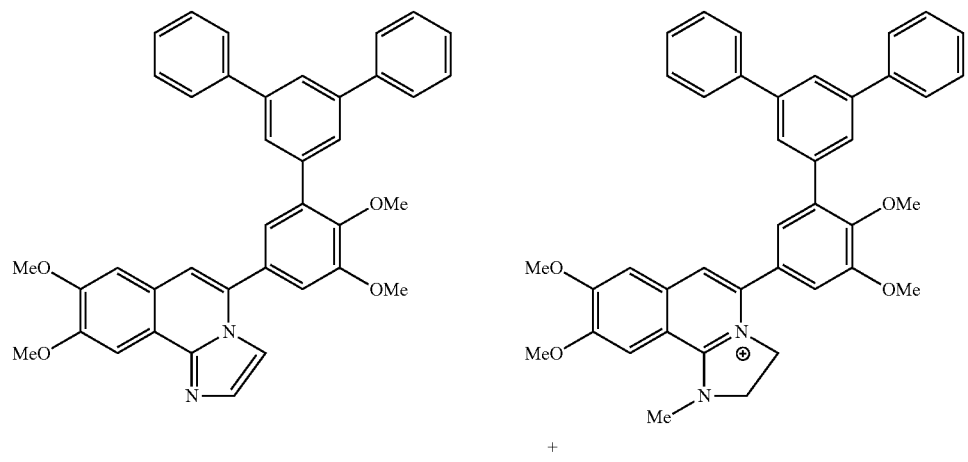
+

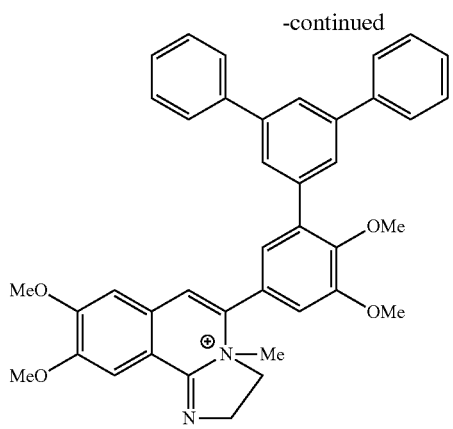
Scheme 37 illustrates a method for the preparation of various 2-substituted 8-oxo-5,6-dihydro-3,10,11-trimethoxydibenzo[a,g]quinolizines that are useful intermediates for preparing compounds of formula I using appropriately substituted phenethylamines and 2-bromobenzoic acids.
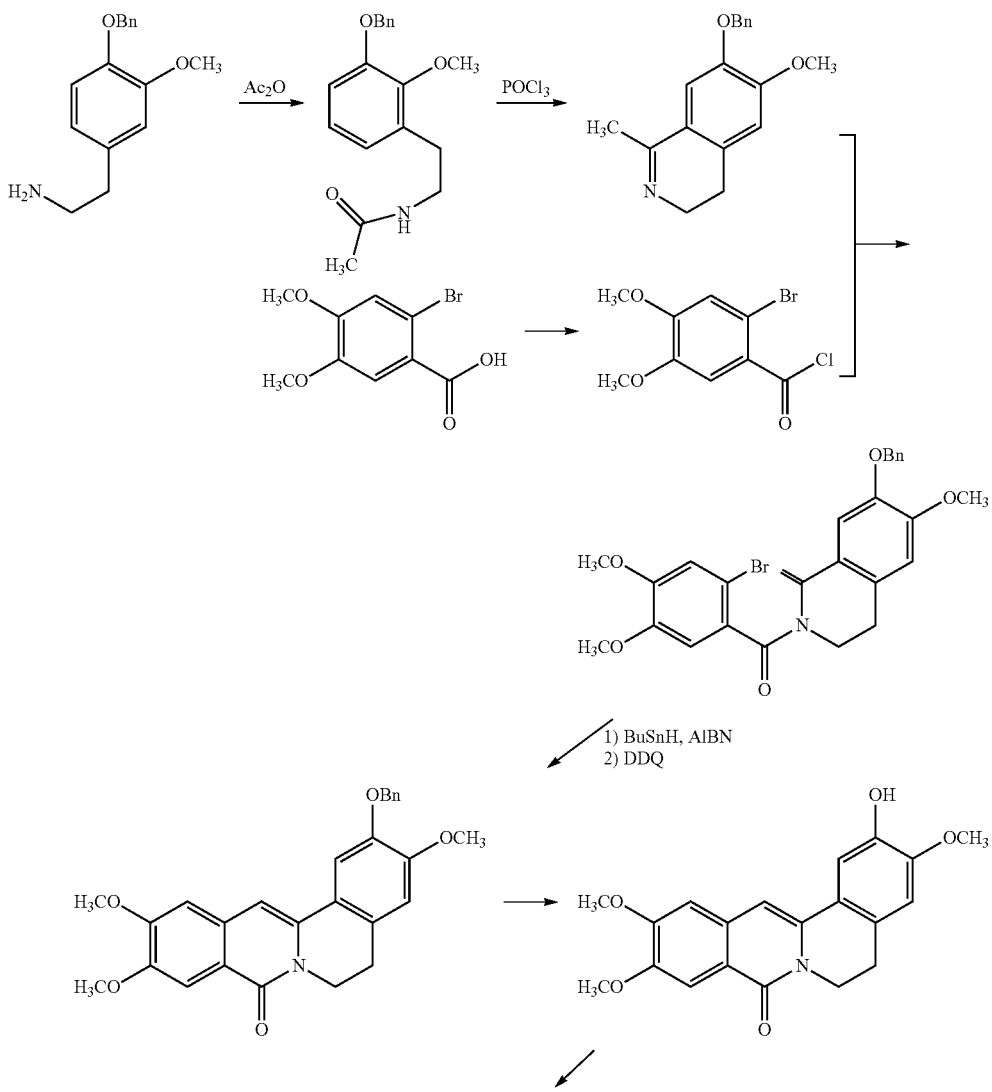

105
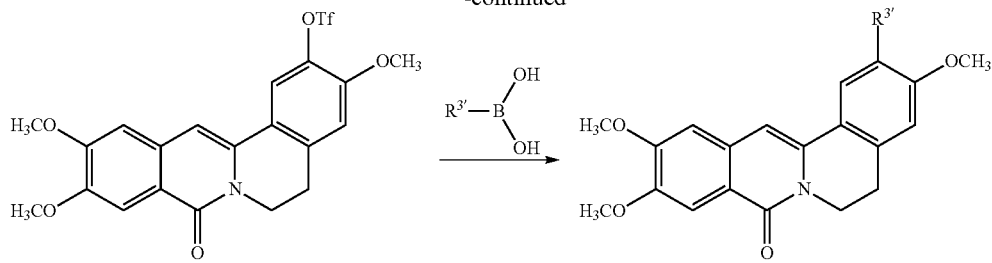
106
Scheme 38 illustrates a method for the preparation of various 2-substituted 8-oxo-5,6-dihydro-3-methoxy-9,10-dimethylenedibenzo[a,g]quinolizines that are useful intermediates for preparing compounds of formula I using appropriately substituted phenethylamines and 2-bromobenzoic acids.
Scheme 38
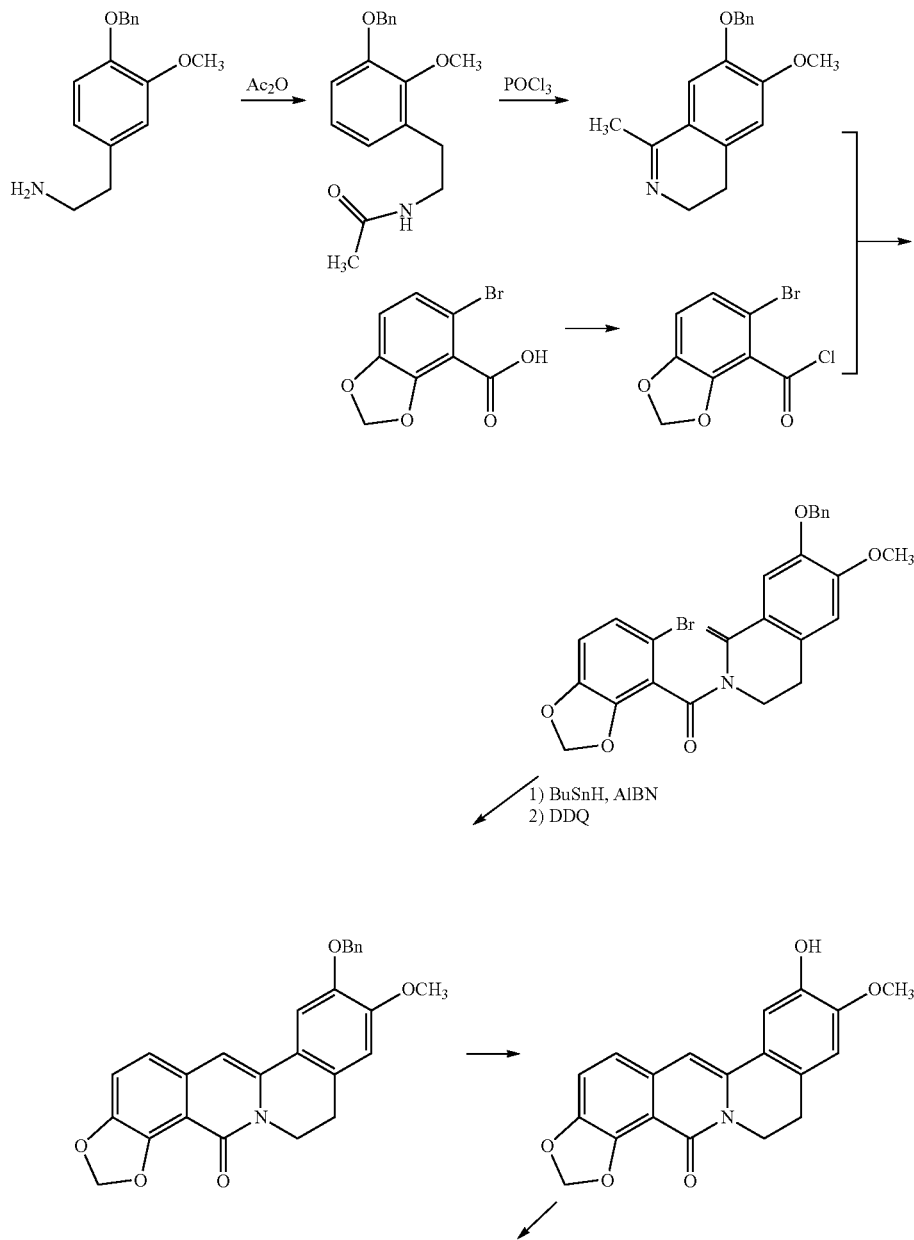

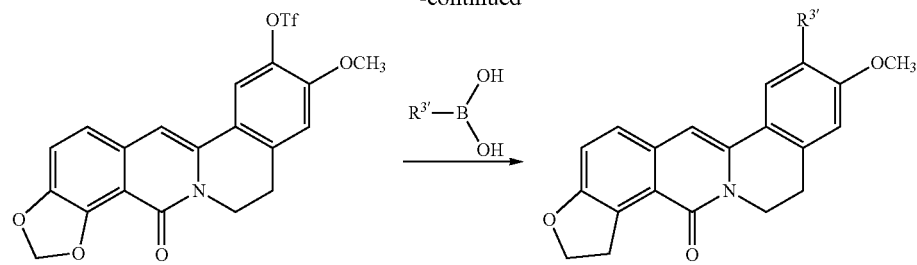
Scheme 39 illustrates a general method for the preparation of various 2-substituted-8-amino-5,6-dihydro-3,10,11-trimethoxydibenzo[a,g]quinolizium and 2-substituted-8-cyano-5,6-dihydro-3,10,11-trimethoxydibenzo[a,g]quinolizium compounds of formula I.
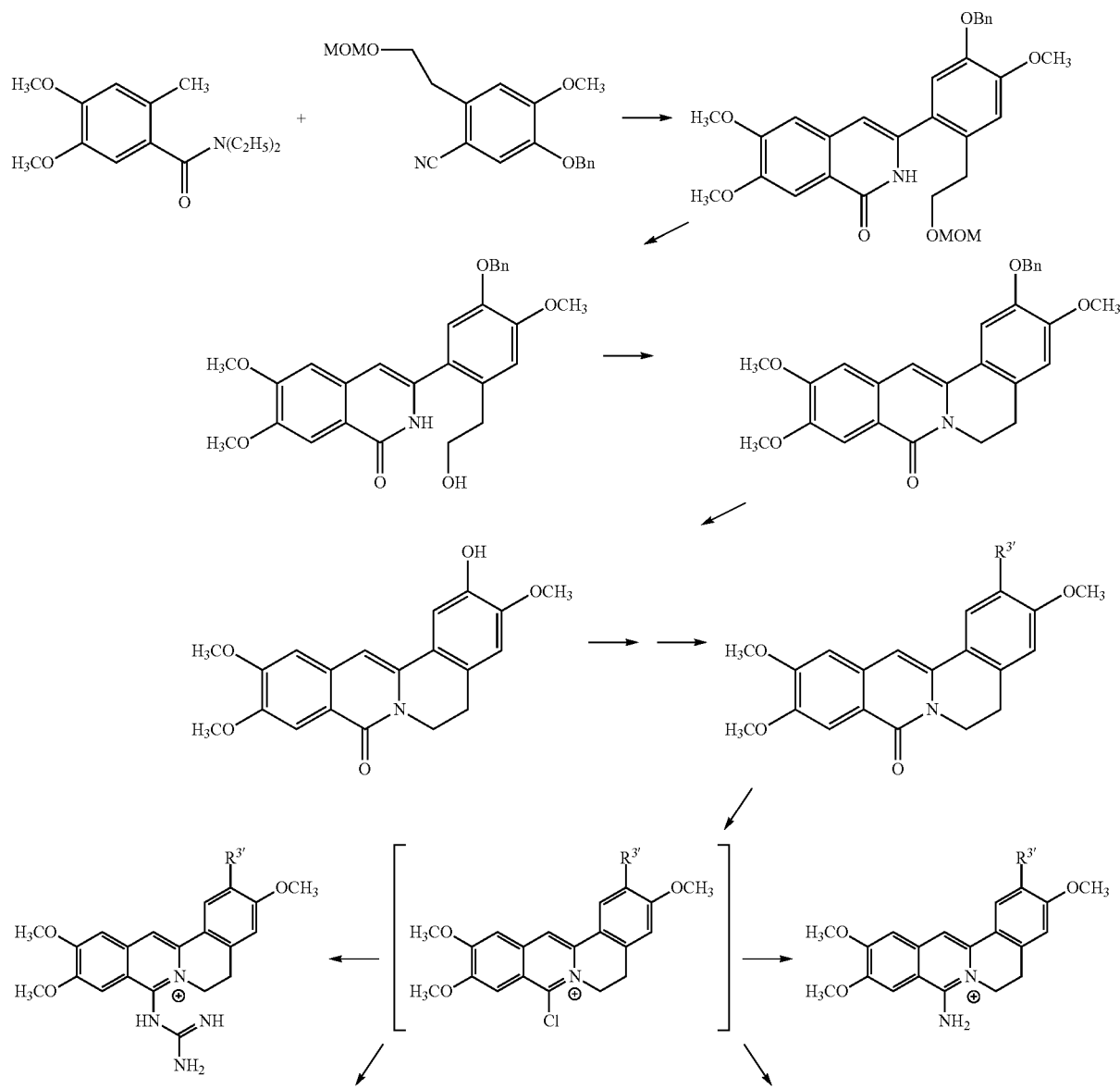
Scheme 39

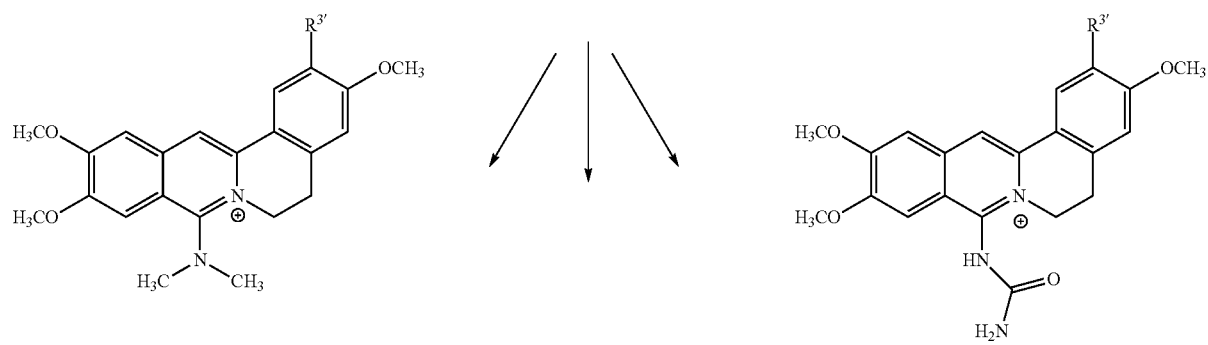

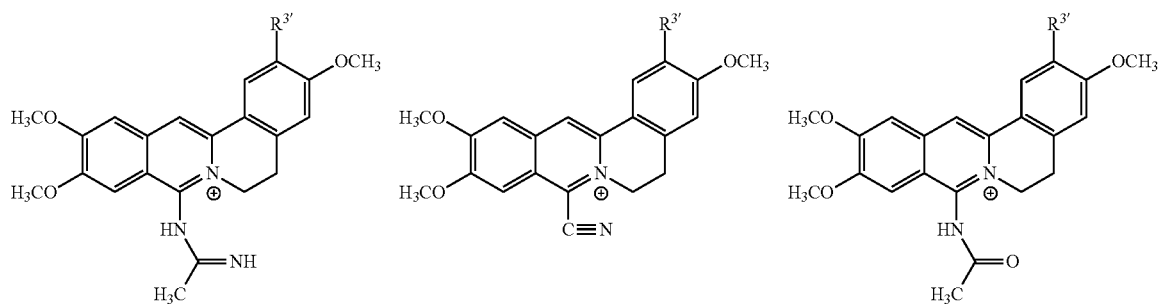

Scheme 40 illustrates the preparation of various 8-oxo-5,6-dihydro-dibenzo[a,g]quinolizines using appropriately substituted isoquinolin-1-ones and 1-bromo-2-(2-bromoethyl) benzene intermediates.

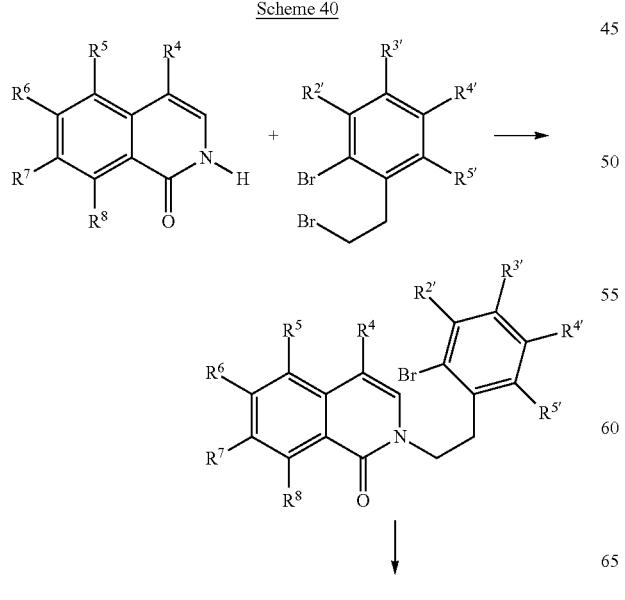

-continued

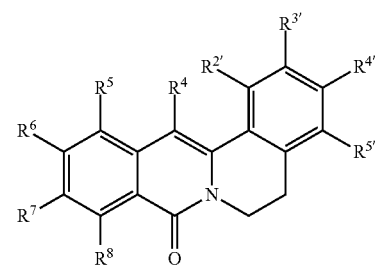

Scheme 41 illustrates the preparation of various 8-oxo-5,6-dihydro-dibenzo[a,g]quinolizines using appropriately substituted isoquinolines and 1-bromo-2-(2-bromoethyl)benzen derivatives. The 8-oxo-5,6-dihydrodibenzo[a,g]quinolizine intermediates are useful intermediates for preparing compounds of formula I.

Scheme 41
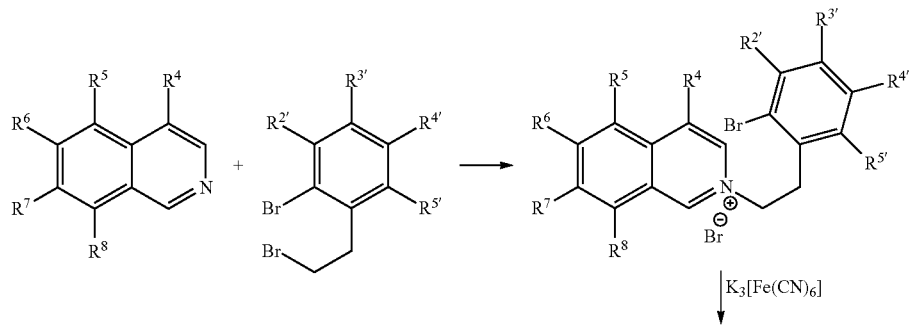
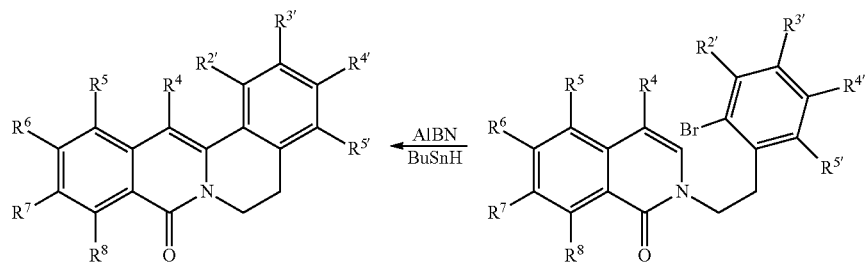
Scheme 42 illustrates general methods for preparing 8-oxo-5,6-dihydrodibenzo[a,g]-quinolizines that are useful for preparing compounds of formula I.
Scheme 42
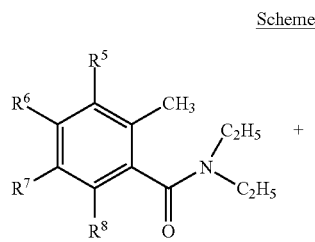
-continued
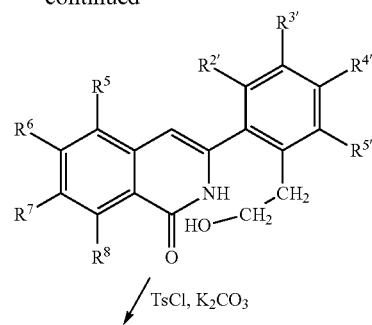
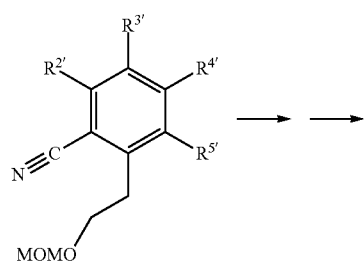
Scheme 43 illustrates methods for preparing 8-oxo-5,6-dihydrodibenzo[a,g]quinolizines that are useful for preparing compounds of formula I.

Scheme 43
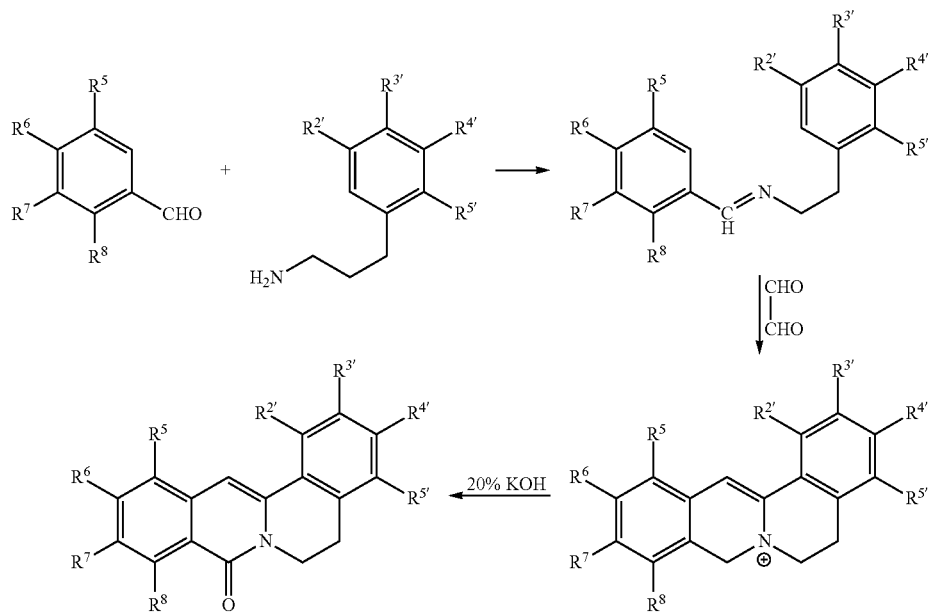
Scheme 44 illustrates a ring-closing metathesis method for preparing 8-oxo-dibenzo[a,g]quinolizine intermediates and their 5,6-dihydro analogs. These compounds are useful intermediates for preparing compounds of formula I.
Scheme 44
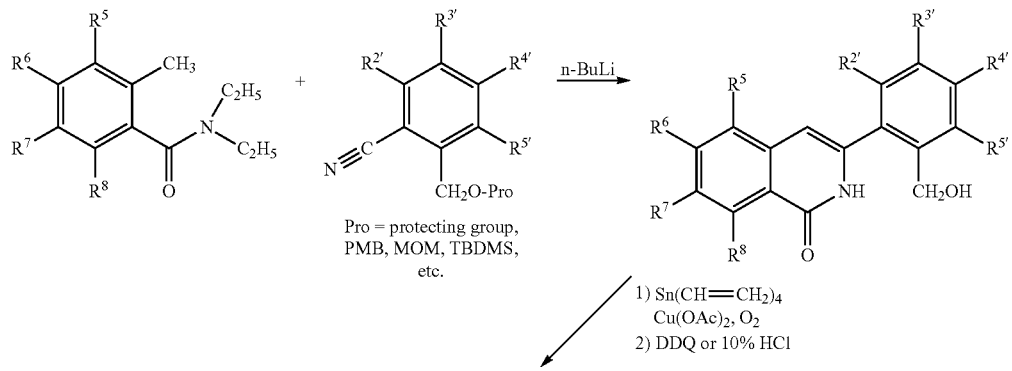
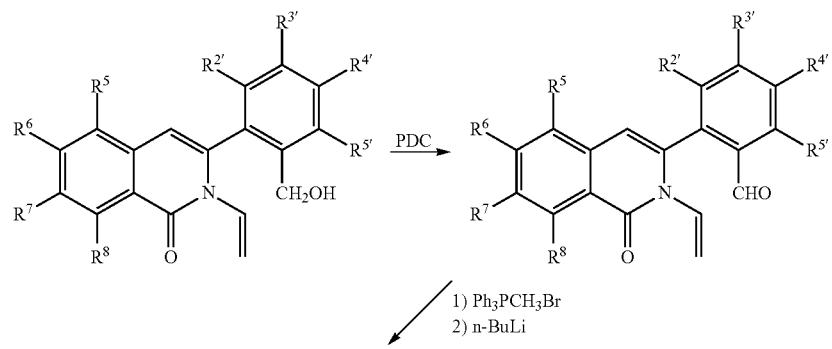

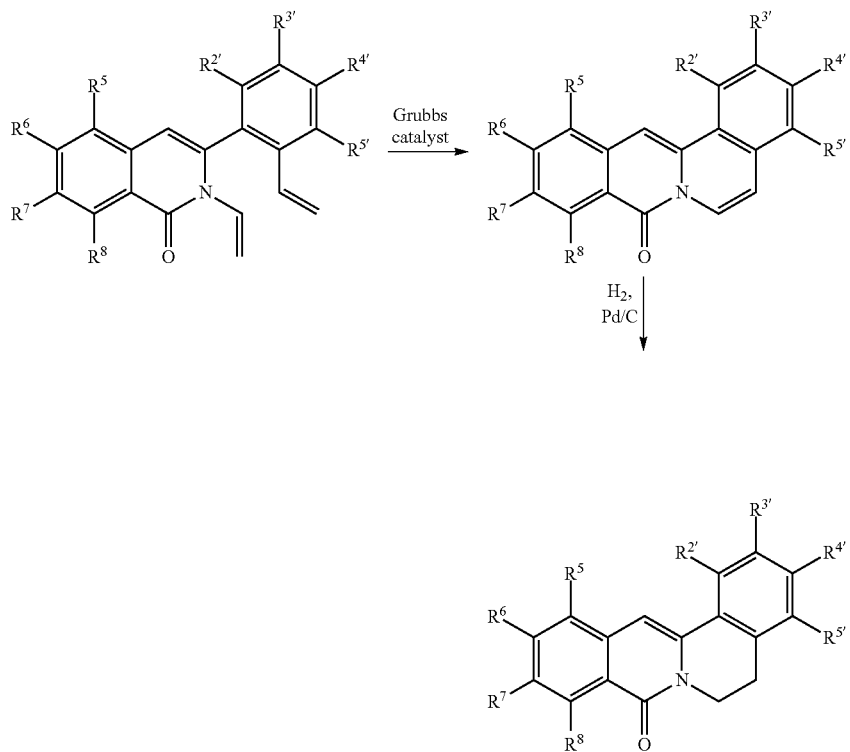
Scheme 45 illustrates a method for preparing varied $R^2$ substituents of 8-oxo-dibenzo[a,g]quinolizines and 5,6-dihydro-8-oxo-dibenzo[a,g]quinolizines that can be converted into the corresponding 8-chloro dibenzo[a,g]quinolizinium compounds.
Scheme 45
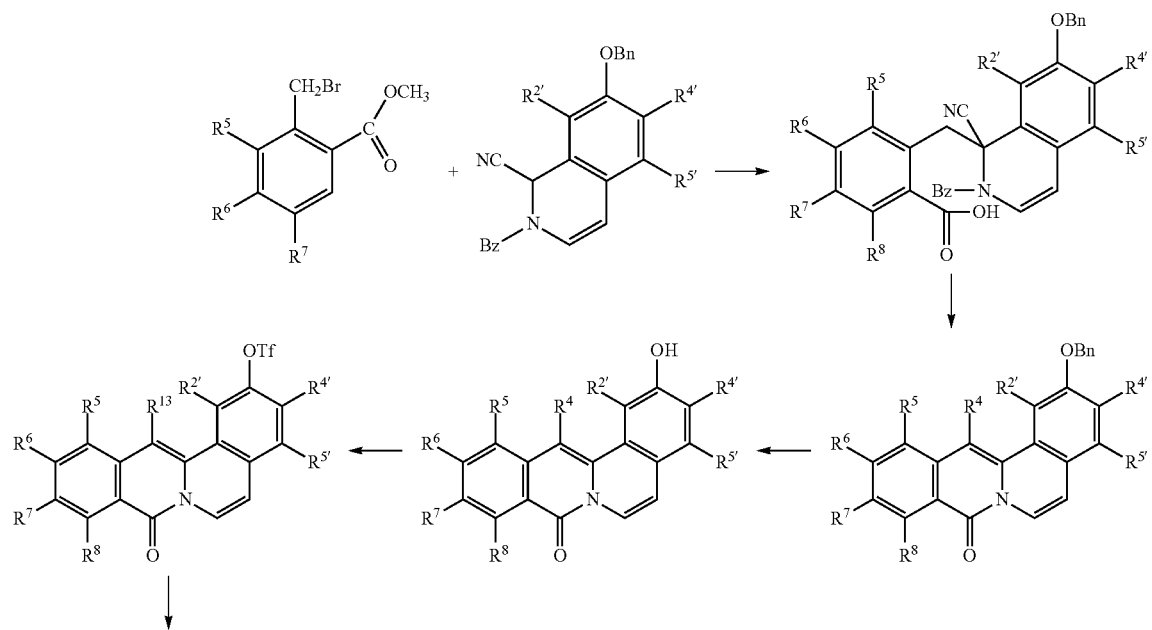

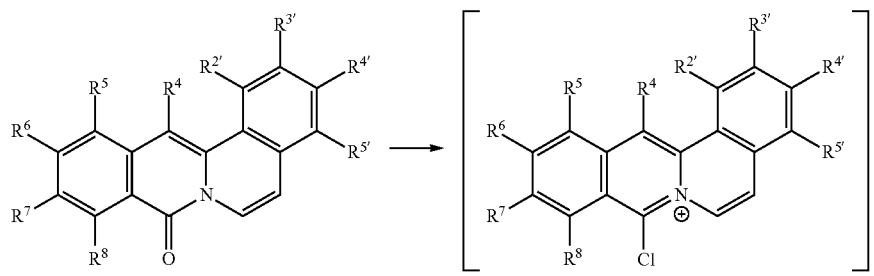
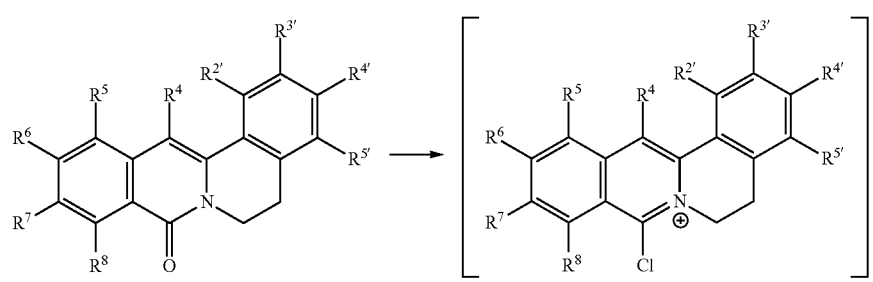
Scheme 46 illustrates a method for preparing varied $R^2$ substituents of 8-oxo-dibenzo[a,g]quinolizines and 5,6-dihydro-8-oxo-dibenzo[a,g]quinolizines that can be converted into the corresponding 8-chloro dibenzo[a,g]quinolizinium compounds.
Scheme 46
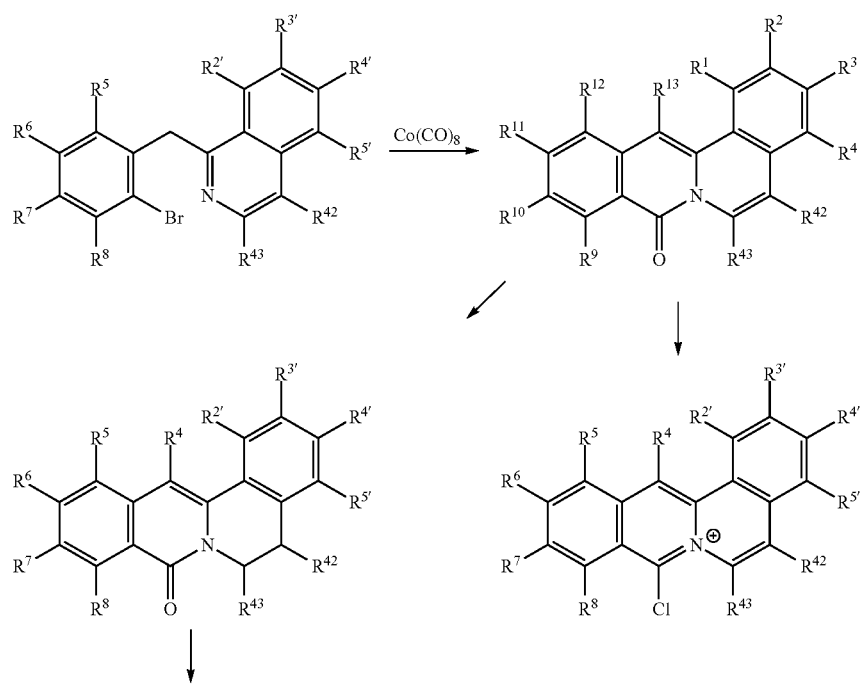

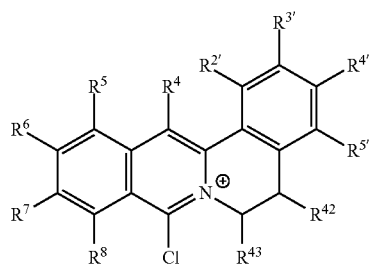

Scheme 47 illustrates a method for preparing 8-oxo-dibenzo[a,g]quinolizines and 5,6-dihydro-8-oxo-dibenzo[a,g]quinolizines using an intramolecular Wittig-Horner reaction.

Scheme 47

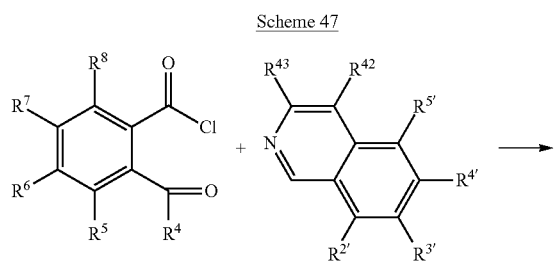

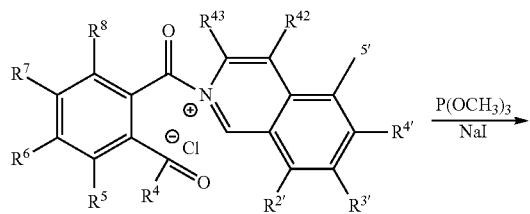

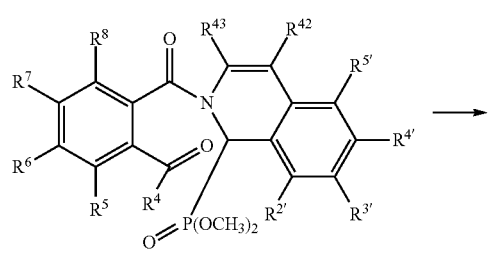

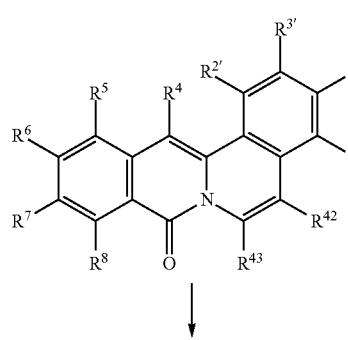

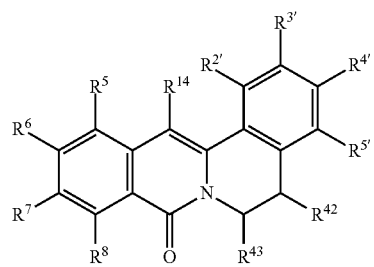

Scheme 48 illustrates a method for preparing 8-oxo-dibenzo[a,g]quinolizines and 5,6-dihydro-8-oxo-dibenzo[a,g]quinolizines that can ultimately be converted into the corresponding 8-chlorodibenzo[a,g]quinolizinium compounds.

Scheme 48

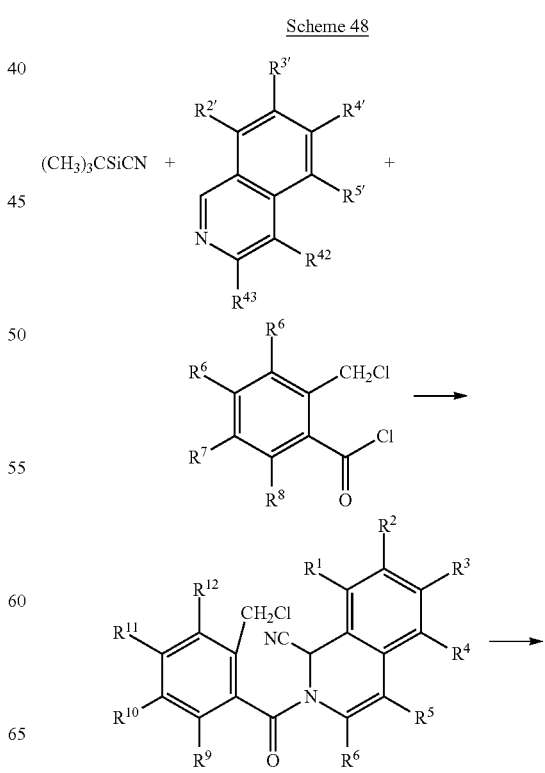

-continued

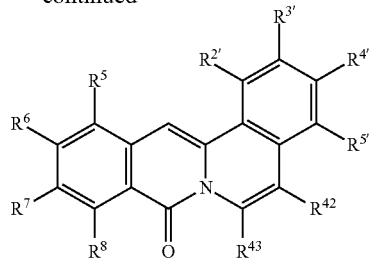

By binding to FtsZ, the compounds of the present invention inhibit the ability of the protein to hydrolyze GTP. This inhibition of FtsZ GTPase activity, in turn, inhibits the ability of the protein to polymerize into Z-rings, as Z-ring formation requires GTP hydrolysis as an energy source for driving the reaction. Since the Z-ring serves as the scaffold for recruitment of all other proteins that comprise the divisome complex, inhibition of Z-ring formation by the compounds of the present invention also results in a corresponding inhibition of divisome protein recruitment.

The compounds of the invention are useful to treat bacterial infections including infections by Gram-negative bacterial strains, Gram-positive bacterial strains and multiple drug-resistant bacterial strains Gram-negative bacterial strains include *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwofli, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenza*.

Gram-positive bacterial strains include *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Bacillus anthracis, Bacillus cereus, Micrococcus luteus, Mycobacterium tuberculosis, Clostridium difficile, Propionibacterium acnes, Streptococcus mutans, Actinomyces viscosus, Actinomyces naeslundii, Streptococcus sanguis, Streptococcus pneumoniae, Streptococcus viridans* and *Streptococcus salivarius*.

Multiple drug-resistant bacterial strains include methicillin-resistant *Staphylococcus aureus*, vancomycin-resistant Enterococci, multiple drug-resistant *Mycobacterium tuberculosis*, multidrug-resistant *Clostridium difficile*.

In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluororquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an antitussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself.

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases. In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $CF_3SO_3^-$, $p\text{-}CH_3C_6H_4SO_3^-$, citrate, tartrate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluents, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The ability of a compound of the invention to alter the polymerization dynamics of FtsZ can be determined using a method like Test A described below.

Test A. Determining the Impact of the Compounds of the Invention on FtsZ Polymerization Dynamics.

Compound-induced alteration in FtsZ polymerization dynamics can be tested using a light scattering-based competition binding assay using purified FtsZ. Upon addition of GTP, FtsZ self-associates to form polymeric structures that scatter light at 340 nm to a greater extent than the monomeric protein. The impact of the compounds of the invention on the polymerization dynamics of FtsZ can be detected by an increase of decrease in the extent of GTP-induced light scattering relative to that observed in the absence of compound. Quantitation of the overall extent of light scattering at a given compound concentration provides an indication of the potency of that compound at altering FtsZ polymerization dynamics.

The ability of a compound of the invention to inhibit FtsZ GTPase activity can be determined using a method like Test B described below.

Test B. Determining the FtsZ GTPase Inhibitory Activities of Compounds of the Invention.

Compound-induced inhibition of the FtsZ GTPase activity can be tested using a colorimetric assay in which the inorganic phosphate (Pi) released upon FtsZ-catalyzed hydrolysis of GTP reacts with malachite green and molybdate under acidic conditions to form a ternary complex that absorbs light at 650 nm, thus enabling quantitation of Pi levels by recording the absorbance at 650 nm (A650). All reactions are conducted in triplicate in 96-well microtiter plates. Differing concentrations (ranging from 0 to 1.5 mM) of compound are combined with 1 mM GTP and 20 mM $CaCl_2$, the latter being used because FtsZ GTPase activity requires the presence of $Ca2+$ ions. The reactions will be initiated by addition of 2 µM FtsZ and allowed to incubate for 60 minutes at room temperature. Following incubation, the reactions will be stopped by adding 80 µl of an acidic malachite green-molybdate solution containing 0.3 mg/ml malachite green oxalate, 2 mg/ml sodium molybdate, 0.5 mg/ml Triton X-100, and 0.7 N HCl. For the purposes of generating a standard curve, each experiment includes reactions containing known concentrations (ranging from 0 to 10 µM) of monobasic potassium phosphate (KH2PO4) in place of FtsZ. Ten minutes following addition of the acidic malachite green-molybdate solution, the A650 value for each reaction are recorded using a microtiter plate reader. A standard curve of A650 versus Pi concentration is constructed using the average A650 value obtained for each known KH2PO4 concentration. This standard curve is then fit by linear regression analysis to yield the quantitative relationship between A650 and Pi concentration. The resulting relationship as well as the average A650 value for each test reaction is used to calculate the concentrations of Pi released by the GTPase activity of FtsZ. The released Pi concentration in the absence of test compound is set as the mark for 100% GTPase activity, and is used to calculate the percent GTPase activities in reactions containing test compounds. The percent GTPase activity is then plotted as a function of log(compound concentration), with the resulting curves being fit using an appropriate sigmoidal relationship to obtain the compound concentrations at which GTPase activity is inhibited by 50% (IC50 values). These IC50 values provide quantitative measures of the potencies with which the test compounds of the invention inhibit FtsZ GTPase activity. Results from Test B for representative compounds of the invention are shown in the following Table.

| Inhibition of *S. aureus* FtsZ GTPase Activity by Representative Compounds of the Invention | |
|---|---|
| Compound | [1]$IC_{50}$ (µM) |
| Example 19 | <100 |
| Example 22 | <100 |

[1]$IC_{50}$ reflects the compound concentration at which FtsZ GTPase activity is inhibited by 50%.

The antibacterial activity of a compound of the invention can be determined using methods like Test C and Test D described below.

Test C. Planktonic (Free-Living) Antibacterial Assay.

Planktonic antibacterial activity can be determined using a broth microdilution assay in which log-phase bacteria are grown at 37° C. in appropriate medium containing two-fold serial dilutions of a compound to yield a final concentration ranging from 256 to 0.1 µg/ml. For determination of minimal inhibitory concentration (MIC) values, bacterial growth is monitored after 24 to 48 hours by measuring optical density at 600 nm. MIC values reflect the minimal compound concentrations at which bacterial growth is completely inhibited. The minimal inhibitory concentration against methicillin-Sensitive *Staphylococcus aureus* (MSSA) for each of the following representative compounds of the invention was determined to be less than 32 µg/ml. Data for representative compounds of the invention is provided below.

TABLE X

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 3 | 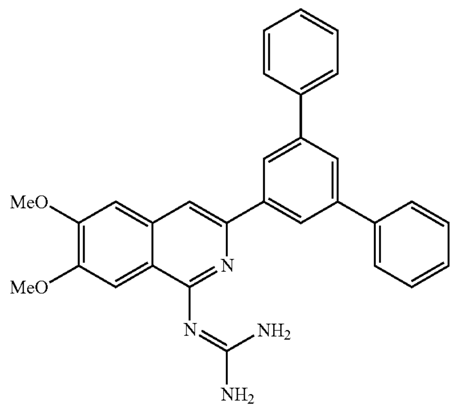 [SMILES: COc1cc2cc(-c3cc(-c4ccccc4)cc(-c4ccccc4)c3)nc(N=C(N)N)c2cc1OC] | | ≤32 |
| Example 5 | 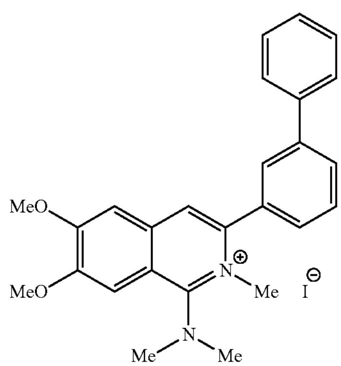 [SMILES: COc1cc2cc(-c3cccc(-c4ccccc4)c3)[n+](C)c(N(C)C)c2cc1OC ; [I-]] | | ≤8 |
| Example 7 | 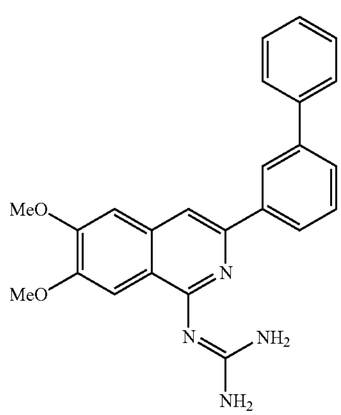 [SMILES: COc1cc2cc(-c3cccc(-c4ccccc4)c3)nc(N=C(N)N)c2cc1OC] | | ≤8 |

TABLE X-continued

Minimal Inhibitory Concentrations against MSSA for representative compounds of the Invention

| Example | Structure | MIC vs MSSA (ug/ml) | MIC vs MRSA (ug/ml) |
|---------|-----------|---------------------|---------------------|
| Example 9 | 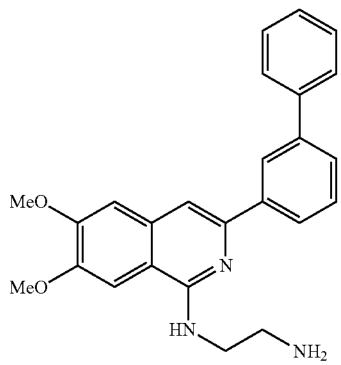 [SMILES: COc1cc2cc(-c3cccc(-c4ccccc4)c3)nc(NCCN)c2cc1OC] | ≤8 | |
| Example 10 | 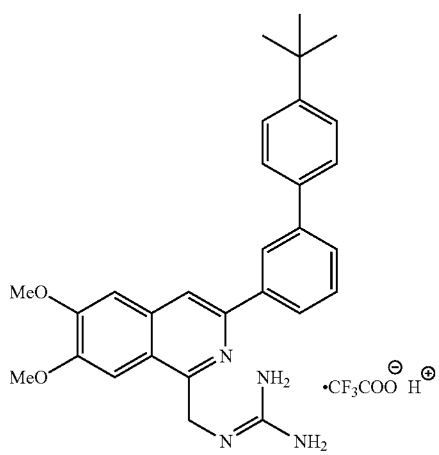 | ≤8 | ≤8 |
| Example 11 | 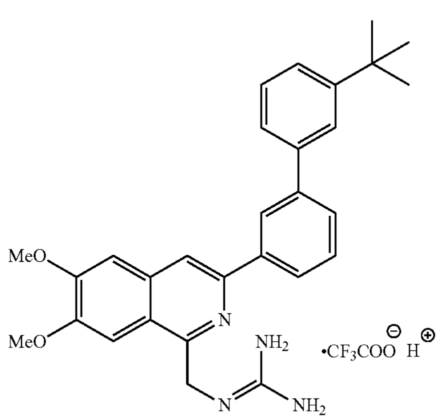 | ≤8 | ≤8 |

TABLE X-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 12 | (structure shown) | ≤8 | |
| Example 13 | (structure shown) | ≤8 | ≤8 |
| Example 15 | (structure shown) | ≤8 | ≤8 |
| Example 19 | (structure shown) | ≤8 | ≤8 |

TABLE X-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 22 | (structure: 3-(4'-fluoro-[1,1'-biphenyl]-3-yl)-4,5-dimethoxyphenyl isoquinolinium methiodide) | ≤8 | |
| Example 23 | (structure: 1-((N-methylguanidino)methyl)-3-(3-tert-butylphenyl)-6,7-dimethoxyisoquinoline) | ≤8 | |

Test D. Biofilm Antibacterial Assay

Bacteria growing in biofilms frequently exhibit altered sensitivities to antimicrobial agents relative to free-living bacteria. It is therefore important to assess the antibacterial activities of the compounds of the invention against bacteria growing as biofilms. Toward this end, well-established protocols can be used to determine biofilm susceptibilities to compounds. The biofilms are prepared by seeding overnight cultures of bacteria on top of sterile polycarbonate membranes resting on Tryptic Soy Agar (TSA) plates. The plates are inverted and incubated for 48 hours at 37° C. After 48 hours of incubation in the absence of antibiotic, colony biofilms are transferred to fresh TSA plates containing differing compound concentrations. These plates are incubated at 37° C. and the biofilms sampled every hour for four hours and after 24 hours. The biofilms are sampled by placing the membrane and associated bacteria into a tube containing phosphate-buffered water and vortexing at high speed. The resulting cell suspensions are serially diluted and the viable bacteria counted by drop-plating on R2A agar plates. The extent of bacterial killing is calculated relative to the cell count at time zero. Antibacterial potencies are defined by the minimum drug concentrations that eradicate the biofilm (i.e., minimum biofilm eradication concentrations, MBEC).

The invention will now be illustrated by the following non-limiting Examples.

EXAMPLES

Example 1

Preparation of Compound

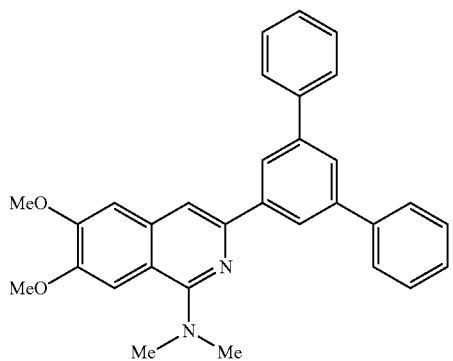 [SMILES: COc1cc2cc(-c3cc(-c4ccccc4)cc(-c4ccccc4)c3)nc(N(C)C)c2cc1OC]

3-([1,1':3',1''-Terphenyl]-5'-yl)-1-chloro-6,7-dimethoxyisoquinoline (25 mg) and chloro(2-di-t-butylphosphino-2',4',6'-tri-1-propyl-1,1'-biphenyl)[2-(2-aminoethyl)phenyl]PdII) (4 mg, 0.1 eq.) were combined in a flask and air was evacuated and replaced with $N_2$. Dimethylamine (2 mL) followed by LHMDS 1M in THF (0.02 mL, 1.5 eq.) was then added, and reaction was allowed to stir overnight at room temperature.

Reaction mixture was then diluted with EtOAc and washed with NH₄Cl. Organic layer was dried over sodium sulfate and concentrated. Chromatography achieved using ISCO max gradient 40% EtOAc/hexane yielding product as a tan solid (24 mg, 94% yield). ¹H NMR (400 MHz) (CDCl₃) δ 8.28 (m, 2H), 7.72 (m, 1H), 7.69-7.67 (m, 4H), 7.63 (s, 1H), 7.44-7.40 (m, 4H), 7.37 (s, 1H), 7.34-7.30 (m, 2H), 7.18 (s, 1H), 3.97 (s, 3H), 3.96 (s, 3H), 3.08 (s, 6H). ¹³C NMR (100 MHz) (CDCl₃) δ 160.49, 152.24, 148.90, 147.18, 142.05, 141.62, 141.26, 135.54, 128.79, 127.39, 127.36, 125.83, 124.55, 115.91, 106.06, 105.01, 56.03, 55.97, 42.99. MP: 102-104° C.

The requisite intermediate was prepared as follows:

a. Preparation of Compound

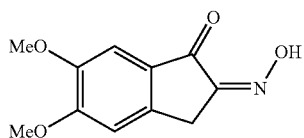 [SMILES: COc1cc2c(cc1OC)C(=O)/C(=N\O)C2]

To a solution of 5,6-dimethoxy-1-indanone (2 g) in 40 mL MeOH was added concentrated HCl (1.04 mL). Butyl nitrite (1.34 mL, 1.1 eq.) in 10 mL MeOH was then added at 40° C. and reaction mixture was allowed to stir for 2.5 hours. Reaction mixture was then cooled to room temperature and precipitate was filtered out and dried yielding a pale yellow solid (2.14 g, 93% yield). ¹H NMR (400 MHz) (DMSO-d₆) δ 12.44 (s, 1H), 7.18 (s, 2H), 3.90 (s, 3H), 3.82 (s, 3H), 3.66 (s, 2H). ¹³C NMR (100 MHz) (DMSO-d₆) δ 187.54, 155.96, 154.66, 149.29, 142.46, 130.48, 108.56, 104.49, 55.87, 55.67, 27.79. MP: 221-223° C.

b. Preparation of Compound

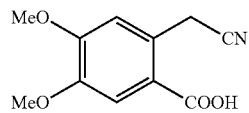

2-(Hydroxyimino)-5,6-dimethoxy-2,3-dihydro-1H-inden-1-one (2.14 g) was added to a 20 mL solution of 8% NaOH and heated to 50° C. p-toluenesulfonyl chloride (2.46 g, 1.33 eq.) was then added in portions. Reaction mixture was heated to 80° C. for 15 minutes the cooled to room temperature. Precipitate was filtered off and filtrate was collected and acidified with concentrated HCl to a pH of 3-4. Resulting precipitate was collected and dried yielding a tan solid (1.84 g, 86% yield). ¹H NMR (400 MHz) (DMSO-d₆) δ 13.05 (s, 1H), 7.51 (s, 1H), 7.15 (s, 1H), 4.19 (s, 2H), 3.86 (s, 3H), 3.81 (s, 3H). ¹³C NMR (100 MHz) (DMSO-d₆) δ 167.10, 151.86, 147.71, 126.36, 121.36, 119.07, 114.11, 113.94, 55.80, 5.62, 22.00. IR (thin film NaCl) 2982, 2945, 2634, 2255, 1686, 1601, 1573, 1535, 1524, 1468, 1456, 1441, 1395, 1322, 1300, 1283, 1224, 1199, 1174, 1701, 1026, 987, 928, 880, 862, 839, 787, 762, 742, 666, 600. MP: 153-156° C.

c. Preparation of Compound

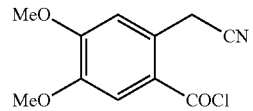

2-(Cyanomethyl)-4,5-dimethoxybenzoic acid (500 mg) was added to a 3-neck flask with a stir bar under N2 and dissolved in 7 mL anhydrous DCM. Oxalyl chloride (0.79 mL, 4 eq.) was then added followed by catalytic amount of anhydrous DMF. Reaction was allowed to stir for 2 hours at room temperature then solvents were evaporated and placed on vacuum pump for 30 minutes. Crude product was then taken immediately to the next step.

d. Preparation of Compound

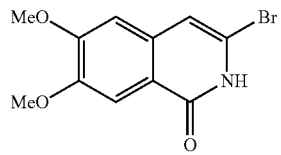 [SMILES: COc1cc2cc(Br)[nH]c(=O)c2cc1OC]

2-(Cyanomethyl)-4,5-dimethoxybenzoyl chloride was suspended in 30 mL anhydrous ether and HBr was bubbled through the solution for 2 hours. Reaction mixture was diluted with CHCl₃, washed with NaHCO₃, and organic layer was dried over sodium sulfate and concentrated. DCM was then added to precipitate product out. Precipitate was then filtered and dried yielding a brown solid (498 mg, 78% yield). ¹H NMR (400 MHz) (DMSO-d₆) δ 12.03 (s, 1H), 7.50 (s, 1H), 7.14 (s, 1H), 6.79 (s, 1H), 3.88 (s, 3H), 3.86 (s, 3H). ¹³C NMR (100 MHz) (DMSO-d₆) δ 161.52, 153.41, 148.78, 133.38, 128.86, 128.16, 107.71, 106.60, 106.33, 55.77, 55.53. MP: 249-253° C.

e. Preparation of Compound

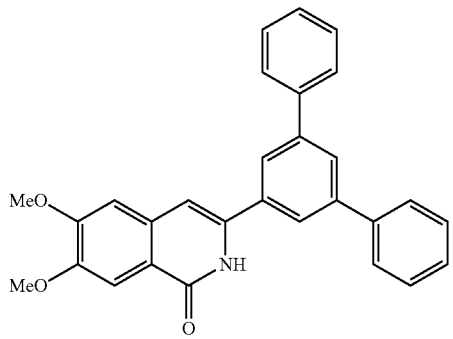 [SMILES: COc1cc2cc(-c3cc(-c4ccccc4)cc(-c4ccccc4)c3)[nH]c(=O)c2cc1OC]

3-Bromo-6,7-dimethoxyisoquinolin-1(2H)-one (100 mg) was combined with terphenyl boronic acid (193 mg, 2 eq.), Pd(OAc)₂ (8 mg, 0.1 eq.), XPhos (33.5 mg, 0.2 eq.), and K$_2$CO$_3$ (194 mg, 4 eq.) in a flask and degassed. 6 mL ACN and 3 mL of H$_2$O were then added and solution was heated at 100° C. for 1.5 hours. Reaction mixture was cooled to room temperature then diluted with EtOAc and washed with NaHCO$_3$. Organic layer was dried over sodium sulfate and concentrated. Chromatography achieved using ISCO max gradient 70% EtOAc/hexane yielding product as a white solid (108 mg, 71% yield). $^1$H NMR (400 MHz) (CDCl$_3$) δ 11.20 (s, 1H), 7.91 (d, J=4 Hz, 2H), 7.84 (t, J=4 Hz, 1H), 7.74-7.72 (m, 4H), 7.65 (s, 1H), 7.41-7.38 (m, 4H), 7.34-7.30 (m, 2H), 6.93 (s, 1H), 6.80 (s, 1H), 3.95 (s, 3H), 3.71 (s, 3H). $^{13}$C NMR (100 MHz) (CDCl$_3$) δ 163.60, 153.96, 149.32, 142.67, 140.46, 138.53, 135.62, 133.92, 128.97, 127.88, 127.30, 126.77, 124.01, 119.03, 107.41, 106.58, 104.45, 56.11, 53.38. MP: 256-260° C.

f. Preparation of Compound

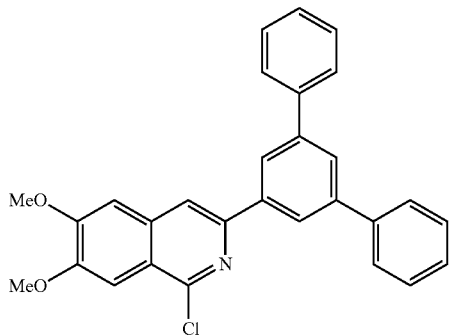 [SMILES: COc1cc2cc(-c3cc(-c4ccccc4)cc(-c4ccccc4)c3)nc(Cl)c2cc1OC]

3-([1,1':3',1''-Terphenyl]-5'-yl)-6,7-dimethoxyisoquinolin-1 (2H)-one (105 mg) was refluxed at 110° C. in 3 mL POCl$_3$ for 3 hours. POCl$_3$ was then removed under vacuum. Chromatography achieved using ISCO max gradient 70% EtOAc/hexane yielding product as a beige solid (84 mg, 77% yield). $^1$H NMR (400 MHz) (CDCl$_3$) δ 8.29 (d, J=4.0 Hz, 2H), 8.01 (s, 1H), 7.86 (t, J=4 Hz, 1H), 7.79-7.76 (m, 4H), 7.57 (s, 1H), 7.54-7.50 (m, 4H), 7.45-7.41 (m, 2H), 7.18 (s, 1H), 4.11 (s, 3H), 4.08 (s, 3H). $^{13}$C NMR (100 MHz) (CDCl$_3$) δ 153.77, 151.15, 149.17, 142.36, 141.16, 139.44, 135.32, 128.80, 127.53, 127.42, 126.45, 124.60, 121.84, 115.63, 105.47, 104.61, 56.23. MP: 183-184° C.

Example 2

Preparation of Compound

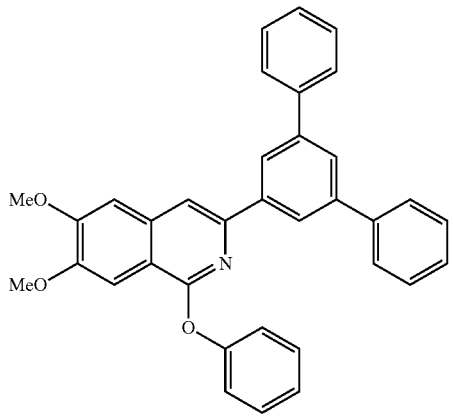 [SMILES: COc1cc2cc(-c3cc(-c4ccccc4)cc(-c4ccccc4)c3)nc(Oc3ccccc3)c2cc1OC]

3-([1,1':3',1''-Terphenyl]-5'-yl)-1-chloro-6,7-dimethoxyisoquinoline (25 mg) was refluxed at 185° C. for 2.5 hours in 3 mL phenol. Reaction mixture was then cooled to room temperature and diluted with H$_2$O, washed with 1N NaOH, and extracted with EtOAc. Organic layer was concentrated and remaining phenol was removed under reduced pressure. Chromatography achieved using ISCO max gradient 50% EtOAc/hexane yielding white solid (16 mg, 57% yield). $^1$H NMR (400 MHz) (CDCl$_3$) δ 8.08 (m, 2H), 7.73 (s, 1H), 7.68 (t, J=4.0 Hz, 1H), 7.63 (s, 1H), 7.57-7.55 (m, 4H), 7.43-7.36 (m, 6H), 7.34-7.28 (m, 4H), 7.28-7.20 (m, 1H), 7.10 (s, 1H), 4.01 (s, 3H), 3.98 (s, 3H). $^{13}$C NMR (100 MHz) (CDCl$_3$) δ 158.84, 154.27, 153.39, 150.13, 146.18, 141.80, 141.19, 139.93, 136.00, 129.20, 128.72, 127.38, 127.20, 125.54, 124.48, 124.18, 122.33, 113.81, 110.85, 105.59, 102.78, 56.20, 56.06. MP: 188-192° C.

Example 3

Preparation of Compound

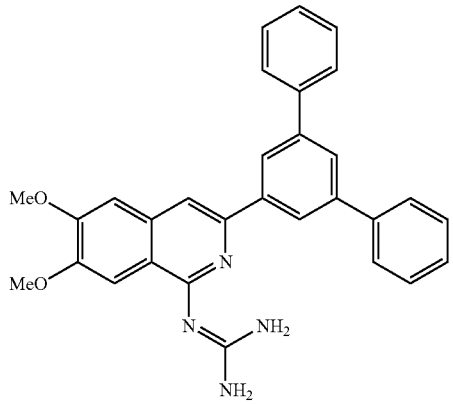 [SMILES: COc1cc2cc(-c3cc(-c4ccccc4)cc(-c4ccccc4)c3)nc(N=C(N)N)c2cc1OC]

Guanidine HCl (13 mg, 3 eq.) was added to a suspension of NaH 60% dispersion in mineral oil (6 mg, 3 eq.) in 2 mL anhydrous DMSO. Reaction was heated at 60° C. for 30 minutes then 3-([1,1'-biphenyl]-3-yl)-1-chloro-6,7-dimethoxyisoquinoline (20 mg) and chloro(2-di-t-butylphosphino-2',4',6'-tri-1-propyl-1,1'-biphenyl)[2-(2-aminoethyl)phenyl]PdII) (5 mg, 0.1 eq.) were then quickly added, and the reaction was heated at 100° C. overnight. Reaction mixture was cooled to room temperature, diluted with EtOAc, and washed with H$_2$O. Organic layer was dried over sodium sulfate and concentrated. Chromatography achieved using ISCO max gradient 5% MeOH/DCM yielding product as a brown solid (10.5 mg, 50%). $^1$H NMR (400 MHz) (DMSO-d$_6$) δ 8.28 (s, 1H), 8.28 (m, 2H), 8.11 (s, 1H), 7.97 (s, 1H), 7.90 (d, J=12 Hz, 4H), 7.56 (t, J=12 Hz, 4H), 7.51-7.44 (m, 3H), 4.04 (s, 3H), 3.99 (s, 3H).

Example 4

Preparation of Compound

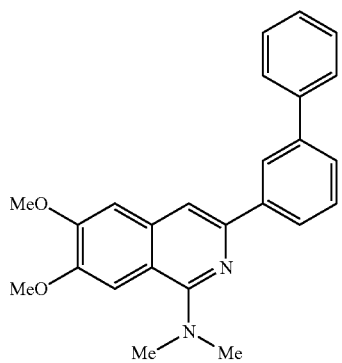 [SMILES: COc1cc2cc(-c3cccc(-c4ccccc4)c3)nc(N(C)C)c2cc1OC]

3-([1,1'-Biphenyl]-3-yl)-1-chloro-6,7-dimethoxyisoquinoline (20 mg) and chloro(2-di-t-butylphosphino-2',4',6'-tri-1-propyl-1,1'-biphenyl)[2-(2-aminoethyl)phenyl]PdII) (4 mg, 0.1 eq.) were combined in a flask and air was evacuated and replaced with $N_2$. Dimethylamine (2 mL) followed by LHMDS 1M in THF (0.02 mL, 1.5 eq.) was then added, and reaction was allowed to stir overnight at room temperature. Reaction mixture was then diluted with EtOAc and washed with $NH_4Cl$. Organic layer was dried over sodium sulfate and concentrated. Chromatography achieved using ISCO max gradient 40% EtOAc/hexane yielding product as a tan oil (20 mg, quantitative). $^1$H NMR (400 MHz) (CDCl$_3$) δ 8.30 (t, J=4 Hz, 1H), 8.05 (dt, J=8 Hz, J=4 Hz, 1H), 7.64-7.62 (m, 2H), 7.58 (s, 1H), 7.52-7.49 (m, 1H), 7.47-7.44 (m, 1H), 7.42-7.38 (m, 2H), 7.36 (s, 1H), 7.32-7.28 (m, 1H), 7.03 (s, 1H), 3.96 (s, 3H), 3.95 (s, 3H), 3.06 (s, 6H). $^{13}$C NMR (100 MHz) (CDCl$_3$) δ 152.23, 148.86, 147.21, 145.89, 141.65, 141.47, 140.68, 135.55, 128.94, 128.73, 127.27, 127.20, 126.75, 125.50, 125.43, 119.97, 115.85, 110.35, 106.06, 105.02, 56.02, 55.95, 42.95.

The requisite intermediate was prepared as follows:

a. Preparation of Compound

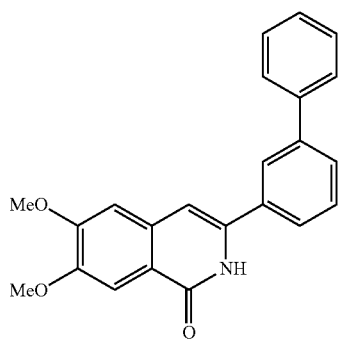 [SMILES: COc1cc2cc(-c3cccc(-c4ccccc4)c3)[nH]c(=O)c2cc1OC]

3-Bromo-6,7-dimethoxyisoquinolin-1(2H)-one (550 mg) was combined with 3-biphenyl boronic acid (768 mg, 2 eq.), Pd(OAc)$_2$ (43.5 mg, 0.1 eq.), XPhos (185 mg, 0.2 eq.), and K$_2$CO$_3$ (1.07 g, 4 eq.) in a flask and degassed. 15 mL ACN and 7.5 mL of H$_2$O were then added and solution was heated at 100° C. for 1.5 hours. Reaction mixture was cooled to room temperature then diluted with EtOAc and washed with NaHCO$_3$. Organic layer was dried over sodium sulfate and concentrated. Chromatography achieved using ISCO max gradient 70% EtOAc/hexane yielding product as a white solid (540 mg, 78% yield). $^1$H NMR (400 MHz) (CDCl$_3$) δ 9.98 (s, 1H), 7.97 (m, 1H), 7.78 (s, 1H), 7.75-7.67 (m, 4H), 7.60 (t, J=16 Hz, 1H), 7.50-7.46 (m, 2H), 7.43-7.39 (m, 1H), 7.01 (s, 1H), 6.81 (s, 1H), 4.05 (s, 3H), 3.96 (s, 3H). $^{13}$C NMR (100 MHz) (CDCl$_3$) δ 163.48, 153.93, 149.28, 142.03, 140.35, 138.47, 135.10, 133.92, 129.54, 128.93, 127.81, 127.75, 127.17, 125.07, 124.97, 118.99, 107.38, 106.57, 104.19, 56.11, 56.09. MP: 229-231° C.

b. Preparation of Compound

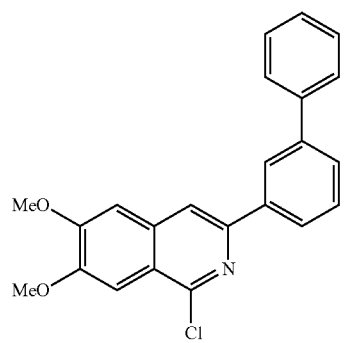

3-([1,1'-Biphenyl]-3-yl)-6,7-dimethoxyisoquinolin-1(2H)-one (130 mg) was refluxed at 110° C. in 3 mL POCl$_3$ for 3 hours. POCl$_3$ was then removed under vacuum. Chromatography achieved using ISCO max gradient 70% EtOAc/hexane yielding product as a beige solid (117 mg, 85% yield). $^1$H NMR (400 MHz) (CDCl$_3$) δ 8.32 (t, J=4 Hz, 1H), 8.10-8.07 (m, 1H), 7.96 (s, 1H), 7.73-7.71 (m, 2H), 7.66-7.64 (m, 1H), 7.57 (t, J=10 Hz, 2H), 7.52-7.48 (m, 1H), 7.18 (s, 1H), 4.11 (s, 3H), 4.08 (s, 3H). $^{13}$C NMR (100 MHz) (CDCl$_3$) δ 153.72, 151.09, 149.21, 149.11, 141.79, 141.17, 138.88, 135.32, 129.19, 128.76, 127.45, 127.40, 127.32, 125.64, 125.55, 121.75, 115.44, 105.43, 104.56, 56.22.

c. Preparation of Compound

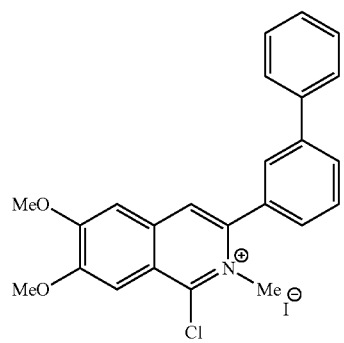 [SMILES: COc1cc2cc(-c3cccc(-c4ccccc4)c3)[n+](C)c(Cl)c2cc1OC ; [I-]]

3-([1,1'-Biphenyl]-3-yl)-1-chloro-6,7-dimethoxyisoquinoline (20 mg) in 1 mL MeI was heated in a sealed tube at 100° C. overnight. Solution was concentrated and salt was re-crystallized in EtOAc/hexane yielding product as an off-white solid (20 mg, 71% yield). $^1$H NMR (400 MHz)

(DMSO-d$_6$) δ 8.26 (s, 1H), 8.00 (s, 1H), 7.96 (d, J=8 Hz, 1H), 7.79-7.75 (m, 4H), 7.73 (s, 1H), 7.70 (s, 1H), 7.53-7.51 (m, 2H), 7.48-7.44 (m, 1H), 4.42 (s, 3H), 4.12 (s, 1H), 4.07 (s, 1H).

Example 5

Preparation of Compound

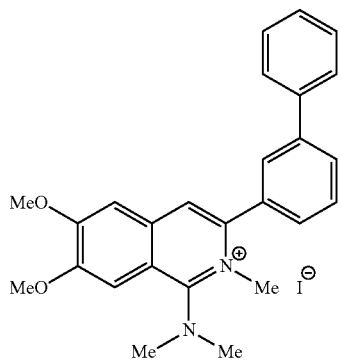 [SMILES: COc1cc2cc(-c3cccc(-c4ccccc4)c3)[n+](C)c(N(C)C)c2cc1OC ; [I-]]

3-([1,1'-Biphenyl]-3-yl)-1-chloro-6,7-dimethoxy-2-methyl-isoquinolin-2-ium iodide (28 mg) in 3 mL dimethylamine was stirred at room temperature overnight. Solution was concentrated and salt was re-crystallized in EtOAc/hexane yielding product as a tan solid (20 mg, 71% yield). $^1$H NMR (400 MHz) (CDCl$_3$) δ 7.87 (t, J=4 Hz, 1H), 7.79-7.77 (m, 1H), 7.75 (s, 1H), 7.73-7.69 (m, 3H), 7.67-7.63 (m, 1H), 7.56 (s, 1H), 7.52-7.48 (m, 2H), 7.44-7.42 (m, 1H), 7.39 (s, 1H), 4.15 (s, 3H), 4.12 (s, 3H), 3.63 (s, 6H). $^{13}$C NMR (100 MHz) (CDCl$_3$) δ 158.72, 156.93, 151.86, 144.86, 142.53, 139.56, 136.89, 134.22, 129.97, 129.06, 128.99, 128.15, 127.63, 127.31, 120.07, 119.40, 106.87, 106.64, 57.11, 45.58, 45.19, 34.54.

Example 6

Preparation of Compound

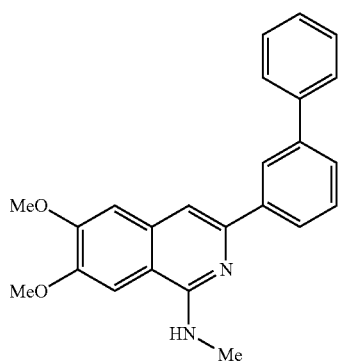 [SMILES: CNc1nc(-c2cccc(-c3ccccc3)c2)cc2cc(OC)c(OC)cc12]

3-([1,1'-Biphenyl]-3-yl)-1-chloro-6,7-dimethoxyisoquinoline (20 mg) and chloro(2-di-t-butylphosphino-2',4',6'-tri-1-propyl-1,1'-biphenyl)[2-(2-aminoethyl)phenyl]PdII) (4 mg, 0.1 eq.) were combined in a flask and air was evacuated and replaced with N$_2$. Methylamine (2 mL) followed by LHMDS 1M in THF (0.02 mL, 1.5 eq.) was then added, and reaction was allowed to stir overnight at room temperature. Reaction mixture was then diluted with EtOAc and washed with NH$_4$Cl. Organic layer was dried over sodium sulfate and concentrated. Chromatography achieved using ISCO max gradient 50% EtOAc/hexane yielding product as a clear oil (20 mg, quantitative). $^1$H NMR (400 MHz) (CDCl$_3$) δ 8.31 (t, J=4 Hz, 1H), 8.06 (dt, J=8 Hz, J=4 Hz, 1H), 7.64-7.62 (m, 2H), 7.51-7.49 (m, 1H), 7.46 7.43 (m, 1H), 7.41-7.37 (m, 2H), 7.34 (s, 1H), 7.31-7.27 (m, 1H), 6.99 (s, 1H), 6.91 (s, 1H), 4.92 (bs, 1H), 3.93 (s, 6H), 3.21 (s, 3H). $^{13}$C NMR (100 MHz) (CDCl$_3$) δ 154.47, 152.18, 149.09, 141.73, 141.37, 140.97, 134.06, 128.85, 128.72, 127.16, 126.67, 125.53, 125.46, 112.13, 106.62, 106.56, 101.17, 56.07, 55.92, 28.97.

Example 7

Preparation of Compound

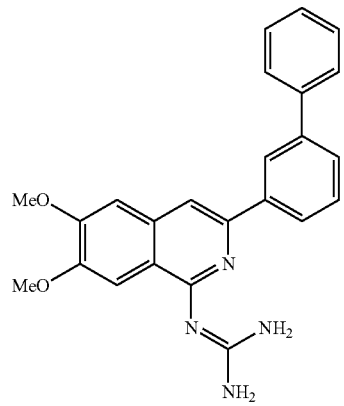 [SMILES: COc1cc2cc(-c3cccc(-c4ccccc4)c3)nc(N=C(N)N)c2cc1OC]

Guanidine HCl (38 mg, 3 eq.) was added to a suspension of NaH 60% dispersion in mineral oil (10 mg, 3 eq.) in 5 mL anhydrous DMSO. Reaction was heated at 60° C. for 30 minutes then 3-([1,1'-biphenyl]-3-yl)-1-chloro-6,7-dimethoxyisoquinoline (50 mg) and chloro(2-di-t-butylphosphino-2',4',6'-tri-1-propyl-1,1'-biphenyl)[2-(2-aminoethyl)phenyl]PdII) (9 mg, 0.1 eq.) were then quickly added, and the reaction was heated at 100° C. overnight. Reaction mixture was cooled to room temperature, diluted with EtOAc, and washed with H$_2$O. Organic layer was dried over sodium sulfate and concentrated. Chromatography achieved using ISCO max gradient 5% MeOH/DCM yielding product as a tan solid (20 mg, 38%). $^1$H NMR (400 MHz) (DMSO-d$_6$) δ 11.36 (bs, 1H), 8.26-8.19 (m, 3H), 7.96 (d, J=8 Hz, 1H), 7.81-7.74 (m, 3H), 7.64 (t, J=16 Hz, 1H), 7.55-7.50 (m, 3H), 7.43 (t, J=12 Hz, 1H), 4.05 (s, 3H), 3.98 (s, 3H). $^{13}$C NMR (100 MHz) (DMSO-d$_6$) δ 156.33, 153.35, 150.62, 145.03, 140.98, 140.00, 139.01, 135.06, 129.70, 128.97, 127.68, 126.86, 125.15, 124.51, 113.43, 113.15, 106.57, 102.93, 56.92, 55.82, 54.85. MP: 255-257° C.

Example 8

Preparation of Compound

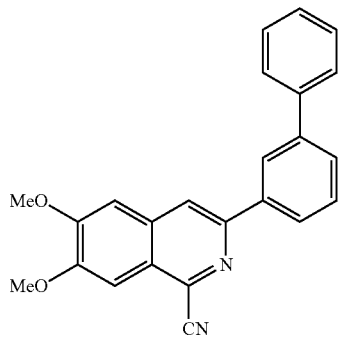 [SMILES: COc1cc2cc(-c3cccc(-c4ccccc4)c3)nc(C#N)c2cc1OC]

3-([1,1'-Biphenyl]-3-yl)-1-chloro-6,7-dimethoxyisoquinoline (50 mg) and CuCN (24 mg, 2 eq.) in 2 mL DMSO was heated at 140° C. for 3 hours. Reaction mixture was then cooled to room temperature, diluted with EtOAc, and washed with H$_2$O. Organic layer was dried over sodium sulfate and concentrated. Chromatography achieved using ISCO max gradient 30% EtOAc/hexane yielding product as a beige solid (13 mg, 27% yield). $^1$H NMR (400 MHz) (CDCl$_3$) δ 8.25 (t, J=4 Hz, 1H), 8.10 (s, 1H), 8.00-7.98 (m, 1H), 7.64-7.62 (m, 2H), 7.60-7.57 (m, 1H), 7.50 (t, J=16 Hz, 1H), 7.43-7.39 (m, 3H), 7.34-7.30 (m, 1H), 7.11 (s, 1H), 4.03 (s, 3H), 4.00 (s, 3H). $^{13}$C NMR (100 MHz) (CDCl$_3$) δ 154.28, 152.56, 150.73, 142.00, 140.98, 138.53, 134.11, 131.60, 129.34, 128.82, 127.86, 127.53, 127.28, 125.68, 125.63, 125.52, 118.91, 116.57, 105.18, 102.74, 56.46, 56.34.

Example 9

Preparation of Compound

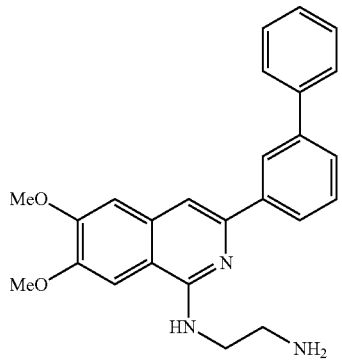 [SMILES: COc1cc2cc(-c3cccc(-c4ccccc4)c3)nc(NCCN)c2cc1OC]

3-([1,1'-Biphenyl]-3-yl)-1-chloro-6,7-dimethoxyisoquinoline (50 mg) in 0.5 mL ethylenediamine was heated at 150° C. in a sealed tube overnight. Solution was then cooled to room temperature and concentrated. Chromatography achieved using silica column max gradient 10% MeOH/DCM/1% NH$_4$OH yielding product as a beige oil (12 mg, 23% yield). $^1$H NMR (400 MHz) (CDCl$_3$) δ 8.26 (s, 1H), 8.03 (d, J=8 Hz, 1H), 7.62 (d, J=8 Hz, 2H), 7.50 (d, J=8 Hz, 1H), 7.45 (d, J=8 Hz, 1H), 7.42-7.38 (m, 2H), 7.34 (s, 1H), 7.30 (t, J=16 Hz, 1H), 6.99 (d, J=4 Hz, 2H), 5.50 (bs, 1H), 3.96 (s, 3H), 3.94 (s, 3H), 3.75 (q, J=16 Hz, 2H), 3.08 (t, J=12 Hz, 2H). $^{13}$C NMR (100 MHz) (CDCl$_3$) δ 154.01, 152.23, 149.13, 147.72, 141.68, 141.37, 140.93, 134.17, 128.88, 128.74, 127.27, 127.19, 126.66, 125.48, 125.39, 112.09, 106.70, 106.54, 101.33, 56.18, 55.93, 44.31, 41.44. IR (thin film NaCl) 3356, 2932, 1623, 1573, 1535, 1502, 1464, 1425, 1250, 1219, 1166, 1131, 1023, 859, 800, 760, 734, 701, 404.

Example 10

Preparation of Compound

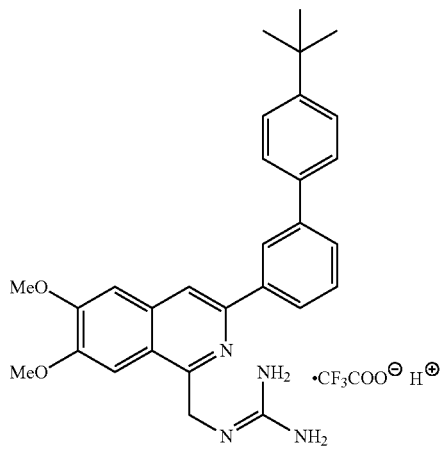

To a cooled solution of di-Boc protected guanidine compound (78 mg) in 1.5 mL DCM was added 1.5 mL trifluoroacetic acid. Reaction was removed from an ice bath and then allow to stir at room temperature for 2 hours. Solvents were evaporated. The solid residue was then taken back up in DCM and precipitate was filtered off yielding product as a grayish white solid (22 mg, 42% yield over 2 steps). $^1$H NMR (400 MHz) (MeOD$_4$) δ 8.25 (m, 1H), 8.08 (s, 1H), 8.04 (d, J=4 Hz, 1H), 7.58-7.56 (m, 3H), 7.47 (t, J=16 Hz, 1H), 7.43 (d, J=8 Hz, 2H), 7.33 (s, 1H), 7.29 (s, 1H), 4.95 (s, 2H), 3.95 (s, 3H), 3.93 (s, 3H), 1.28 (s, 9H).

The requisite intermediate was prepared as follows:

a. Preparation of Compound

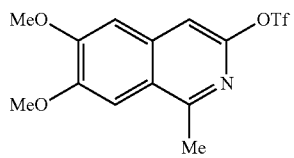 [SMILES: COc1cc2cc(OS(=O)(=O)C(F)(F)F)nc(C)c2cc1OC]

6,7-Dimethoxy-1-methylisoquinolin-3-ol (540 mg) and Et$_3$N (0.9 mL, 2 eq.) in DCM were cooled to −78° C. Tf$_2$O (0.64 mL, 1.2 eq.) was slowly added to the mixture and was stirred for 30 minutes at −78° C. Reaction was then quickly diluted with additional DCM and washed with saturated NaHCO$_3$. Organic layer was dried over sodium sulfate and concentrated. Chromatography achieved using ISCO max gradient 30% EtOAc/hexane yielding product as a white solid (737 mg, 85% yield). $^1$H NMR (400 MHz) (CDCl$_3$) δ 7.29 (s, 1H), 7.29 (s, 1H), 7.12 (s, 1H), 4.07 (s, 3H), 4.07 (s, 3H), 2.90 (s, 3H). $^{13}$C NMR (100 MHz) (CDCl$_3$) δ 156.54, 153.80, 150.67, 135.47, 123.35, 107.62, 105.39, 103.73, 56.23, 56.11, 22.03.

b. Preparation of Compound

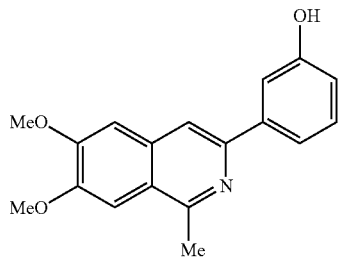 [SMILES: COc1cc2cc(-c3cccc(O)c3)nc(C)c2cc1OC]

6,7-Dimethoxy-1-methylisoquinolin-3-yl trifluoromethanesulfonate (200 mg), 3-hydroxyphenylboronic acid (157 mg, 2 eq.), Pd(OAc)$_2$ (13 mg, 0.1 eq.), XPhos (54 mg, 0.2 eq.), and Cs$_2$CO$_3$ (650 mg, 3.5 eq.) were combined in a flask with 9 mL ACN and 3 mL H$_2$O and degassed. Reaction mixture was then refluxed at 100° C. for 5 hours. Solution was cooled to room temperature then diluted with EtOAc and washed with saturated NaHCO$_3$. Organic layer was dried over sodium sulfate and concentrated. Chromatography achieved using ISCO max gradient 50% EtOAc/hexane yielding product as white solid (78 mg, 46% yield). $^1$H NMR (400 MHz) (CDCl$_3$) δ 7.66-7.63 (m, 2H), 7.38 (d, J=4 Hz, 1H), 7.20 (t, J=8 Hz, 1H), 7.17 (s, 1H), 7.00 (s, 1H), 6.73-6.71 (m, 1H), 3.95 (s, 3H), 3.94 (s, 3H), 2.87 (s, 3H). $^{13}$C NMR (100 MHz) (CDCl$_3$) δ 156.74, 156.12, 152.88, 149.93, 149.19, 141.46, 133.56, 129.85, 122.35, 118.72, 115.49, 115.25, 114.59, 105.66, 103.87, 56.05, 56.01, 22.20. IR (thin film NaCl) 3002, 2255, 1621, 1576, 1501, 1468, 1425, 1409, 1372, 1324, 1292, 1245, 1222, 1205, 1178, 1159, 1062, 1027, 995, 973, 924, 913, 896, 878, 846, 837, 781, 762, 745, 738, 726, 691, 645.

c. Preparation of Compound

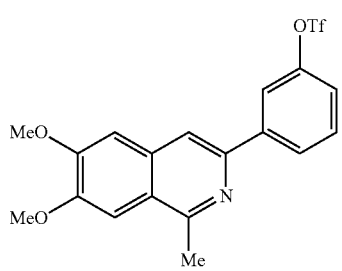 [SMILES: COc1cc2cc(-c3cccc(OS(=O)(=O)C(F)(F)F)c3)nc(C)c2cc1OC]

3-(6,7-Dimethoxy-1-methylisoquinolin-3-yl)phenol (175 mg) and Et$_3$N (0.16 mL, 2 eq.) in DCM were cooled to −78° C. Tf$_2$O (0.12 mL, 1.2 eq.) was slowly added to the mixture and was stirred for 30 minutes at −78° C. Reaction was then quickly diluted with additional DCM and washed with saturated NaHCO$_3$. Organic layer was dried over sodium sulfate and concentrated. Chromatography achieved using ISCO max gradient 30% EtOAc/hexane yielding product as a white solid (230 mg, 91% yield). $^1$H NMR (400 MHz) (CDCl$_3$) δ 8.14 (d, J=8 Hz, 1H), 8.09 (s, 1H), 7.82 (s, 1H), 7.56 (t, J=16 Hz, 1H), 7.31 (s, 1H), 7.29 (dd, J=8 Hz, J=4 Hz, 1H), 7.15 (s, 1H), 4.08 (s, 3H), 4.07 (s, 3H), 2.98 (s, 3H). $^{13}$C NMR (100 MHz) (CDCl$_3$) δ 156.31, 152.87, 150.31, 150.23, 146.60, 142.99, 133.24, 130.31, 126.31, 122.79, 120.29, 119.56, 117.23, 114.79, 105.81, 103.93, 56.07, 56.03, 22.68.

d. Preparation of Compound

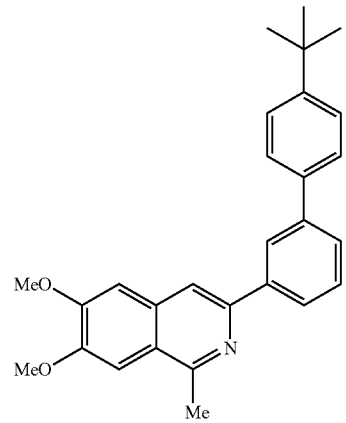 [SMILES: COc1cc2cc(-c3cccc(-c4ccc(C(C)(C)C)cc4)c3)nc(C)c2cc1OC]

3-(6,7-Dimethoxy-1-methylisoquinolin-3-yl)phenyl trifluoromethanesulfonate (130 mg), 4-t-butylphenylboronic acid (108 mg, 2 eq.), Pd(OAc)$_2$ (7 mg, 0.1 eq.), XPhos (29 mg, 0.2 eq.), and K$_2$CO$_3$ (147 mg, 3.5 eq.) in 3 mL ACN and 1.5 mL H$_2$O were combined in a flask and degassed. Reaction mixture was heated to 95° C. for 2 hours. Solution was then cooled to room temperature, diluted with EtOAc, and washed with saturated NaHCO$_3$. Organic layer was dried over sodium sulfate and concentrated. Chromatography achieved using ISCO max gradient 40% EtOAc/hexane yielding product as a white solid (121 mg, 97% yield). $^1$H NMR (400 MHz) (CDCl$_3$) δ 8.35-8.34 (m, 1H), 8.08 (d, J=8 Hz, 1H), 7.88 (s, 1H), 7.68 (d, J=8 Hz, 2H), 7.63 (d, J=8 Hz, 1H), 7.56 (t, J=16 Hz, 1H), 7.53 (d, J=8 Hz, 2H), 7.33 (s, 1H), 7.16 (s, 1H), 4.09 (s, 3H), 4.08 (s, 3H), 3.00 (s, 3H), 1.41 (s, 9H). $^{13}$C NMR (100 MHz) (CDCl$_3$) δ 155.95, 152.67, 150.26, 149.84, 149.25, 141.47, 140.63, 138.58, 133.47, 129.01, 126.95, 126.71, 125.69, 125.65, 125.53, 122.32, 114.47, 105.72, 103.97, 56.02, 34.55, 31.40, 22.74.

e. Preparation of Compound

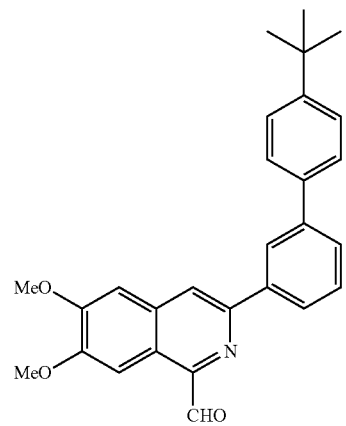 [SMILES: COc1cc2cc(-c3cccc(-c4ccc(C(C)(C)C)cc4)c3)nc(C=O)c2cc1OC]

3-(4'-(tert-Butyl)-[1,1'-biphenyl]-3-yl)-6,7-dimethoxy-1-methylisoquinoline (100 mg) and SeO$_2$ (32 mg, 1.2 eq.) in 5 mL anhydrous dioxane were refluxed at 102° C. for 3 hours. Solution was then cooled to room temperature and filtered to remove precipitate. Resulting filtrate was concentrated. Chromatography achieved using ISCO max gradient 30% EtOAc/hexane yielding product as a yellow solid (80 mg, 77% yield). $^1$H NMR (400 MHz) (CDCl$_3$) δ 10.40 (s, 1H), 8.68 (s, 1H), 8.34 (m, 1H), 8.14 (s, 1H), 8.07 (d, J=8 Hz, 1H), 7.59 (d, J=8 Hz, 3H), 7.52 (t, J=16 Hz, 1H), 7.45 (d, J=8 Hz, 2H), 7.13 (s, 1H), 4.05 (s, 3H), 4.00 (s, 3H), 1.32 (s, 9H). $^{13}$C NMR (100 MHz) (CDCl$_3$) δ 196.81, 153.33, 152.83, 149.76, 141.84, 139.20, 138.29, 135.44, 129.26, 127.43, 126.95, 125.76, 125.59, 125.35, 122.19, 120.01, 104.99, 103.59, 56.29, 56.02, 34.57, 31.38.

f. Preparation of Compound

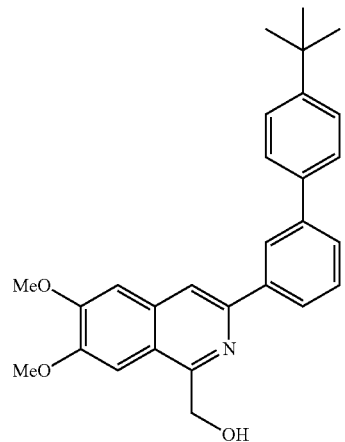 [SMILES: COc1cc2cc(-c3cccc(-c4ccc(C(C)(C)C)cc4)c3)nc(CO)c2cc1OC]

3-(4'-(tert-Butyl)-[1,1'-biphenyl]-3-yl)-6,7-dimethoxyisoquinoline-1-carboxaldehyde (76 mg) in 5 mL ethanol was treated slowly with NaBH$_4$ (20 mg, 3 eq.) at room temperature. Reaction was stirred for 1 hour then 2 mL acetone was added and solution was filtered through filter paper. Filtrate was concentrated then re-dissolved in DCM and washed with H$_2$O. Organic layer was dried over sodium sulfate and concentrated. Chromatography achieved using ISCO max gradient 50% EtOAc/hexane yielding product as a pearly, gold solid (59 mg, 78% yield). $^1$H NMR (400 MHz) (CDCl$_3$) δ 8.25-8.24 (m, 1H), 7.99-7.97 (m, 1H), 7.85 (s, 1H), 7.57-7.54 (m, 3H), 7.47 (t, J=12 Hz, 1H), 7.43 (d, J=8 Hz, 2H), 7.08 (s, 1H), 6.96 (s, 1H), 5.22 (t, J=12 Hz, 1H), 5.10 (d, J=4 Hz, 1H), 3.96 (s, 3H), 3.95 (s, 3H). $^{13}$C NMR (100 MHz) (CDCl$_3$) δ 154.63, 153.20, 150.49, 150.43, 147.65, 141.66, 139.60, 138.31, 133.81, 129.11, 127.11, 126.93, 125.76, 125.40, 125.27, 119.80, 115.29, 105.86, 101.30, 61.41, 56.12, 56.06, 34.57, 31.39.

g. Preparation of Compound

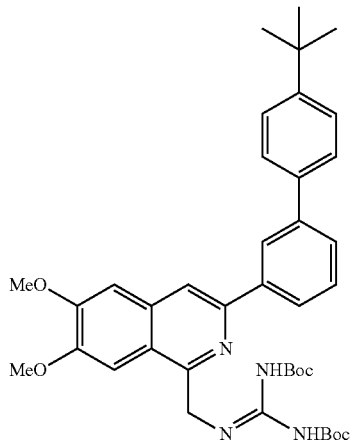 [SMILES: COc1cc2cc(-c3cccc(-c4ccc(C(C)(C)C)cc4)c3)nc(CN=C(NC(=O)OC(C)(C)C)NC(=O)OC(C)(C)C)c2cc1OC]

To a solution of (3-(4'-(tert-butyl)-[1,1'-biphenyl]-3-yl)-6,7-dimethoxyisoquinolin-1-yl)methanol (39 mg), PPh$_3$ (35 mg, 1.5 eq.), and 1,3-bis(tert-butoxycarbonyl)guanidine (47 mg, 2 eq.) in 3 mL toluene at 0° C. was added diisopropylazodicarboxylate (0.03 mL, 1.5 eq.) drop wise over 15 minutes. Reaction was stirred for 3 hours at room temperature then 2 drops H$_2$O were added, and the solution was concentrated. Solid was then re-dissolved in DCM and passed through silica column and resulting crude product was taken to next step.

Example 11

Preparation of Compound

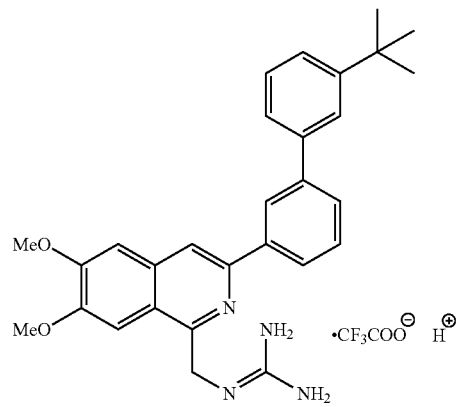

To a cooled solution of di-Boc protected guanidine compound (78 mg) in 1.5 mL DCM was added 1.5 mL trifluoroacetic acid. The reaction mixture was removed from the ice bath and then allowed to stir at room temperature for 2 hours. The solvent was evaporated. The solid residue was then taken back up in DCM and precipitate was filtered off yielding product as a grayish white solid (22 mg, 42% yield over 2 steps). $^1$H NMR (400 MHz) (MeOD$_4$) δ 8.21 (m, 1H), 8.11-8.07 (m, 2H), 7.61 (m, 1H), 7.55-7.47 (m, 2H), 7.43-7.41 (m, 1H), 7.36-7.30 (m, 3H), 7.27 (s, 1H), 4.92 (s, 2H), 3.94 (s, 3H), 3.92 (s, 3H), 1.31 (s, 9H).

The requisite intermediate was prepared as follows:

a. Preparation of Compound

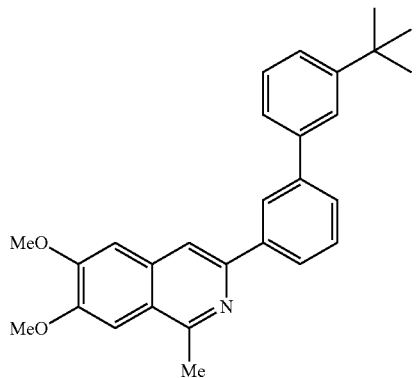 [SMILES: COc1cc2cc(-c3cccc(-c4cccc(C(C)(C)C)c4)c3)nc(C)c2cc1OC]

3-(6,7-Dimethoxy-1-methylisoquinolin-3-yl)phenyl trifluoromethanesulfonate (100 mg), 3-t-butylphenylboronic acid (50 mg, 1.2 eq.), Pd(OAc)$_2$ (5 mg, 0.1 eq.), XPhos (22 mg, 0.2 eq.), and K$_2$CO$_3$ (390 mg, 3.5 eq.) in 4 mL ACN and 2 mL H$_2$O were combined in a flask and degassed. Reaction mixture was heated to 95° C. for 2 hours. Solution was then cooled to room temperature, diluted with EtOAc, and washed with saturated NaHCO$_3$. Organic layer was dried over sodium sulfate and concentrated. Chromatography achieved using ISCO max gradient 30% EtOAc/hexane yielding product as a pearly oil (97 mg, quantitative). $^1$H NMR (400 MHz) (CDCl$_3$) δ 8.33 (m, 1H), 8.12-8.10 (m, 1H), 7.89 (s, 1H), 7.74 (s, 1H), 7.65-7.53 (m, 1H), 7.59 (d, J=8 Hz, 1H), 7.56-7.54 (m, 1H), 7.45-7.44 (m, 2H), 7.33 (s, 1H), 7.16 (s, 1H), 4.09 (s, 3H), 4.08 (s, 3H), 3.01 (s, 3H), 1.44 (s, 9H). $^{13}$C NMR (100 MHz) (CDCl$_3$) δ 155.98, 152.69, 151.55, 149.86, 149.26, 142.35, 141.33, 140.68, 133.48, 129.04, 129.01, 128.23, 127.06, 125.91, 125.72, 124.64, 124.50, 124.29, 122.34, 114.54, 105.74, 103.97, 56.04, 54.01, 34.89, 31.48, 22.75.

b. Preparation of Compound

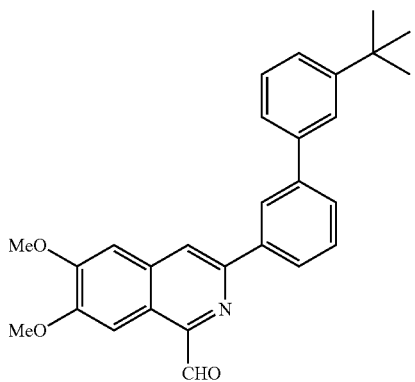 [SMILES: COc1cc2cc(-c3cccc(-c4cccc(C(C)(C)C)c4)c3)nc(C=O)c2cc1OC]

3-(3'-(tert-Butyl)-[1,1'-biphenyl]-3-yl)-6,7-dimethoxy-1-methylisoquinoline (92 mg) and SeO$_2$ (25 mg, 1.2 eq.) in 5 mL anhydrous dioxane were refluxed at 102° C. for 3 hours. Solution was then cooled to room temperature and filtered to remove precipitate. Resulting filtrate was concentrated. Chromatography achieved using ISCO max gradient 30% EtOAc/hexane yielding product as a yellow solid (55 mg, 58% yield). $^1$H NMR (400 MHz) (CDCl$_3$) δ 10.39 (s, 1H), 8.66 (s, 1H), 8.31 (s, 1H), 8.12 (s, 1H), 8.07 (d, J=4 Hz, 1H), 7.63 (s, 1H), 7.59 (d, J=8 Hz, 1H), 7.53 (t, J=12 Hz, 1H), 7.46-7.44 (m, 1H), 7.36-7.35 (m, 2H), 7.11 (s, 1H), 4.03 (s, 3H), 3.99 (s, 3H), 1.34 (s, 9H). $^{13}$C NMR (100 MHz) (CDCl$_3$) δ 196.86, 153.26, 152.79, 151.71, 149.69, 147.04, 142.67, 141.02, 139.21, 135.42, 129.29, 128.54, 127.80, 125.81, 125.52, 124.61, 124.54, 124.47, 122.19, 120.07, 104.99, 103.52, 56.31, 56.07, 34.89, 31.47.

c. Preparation of Compound

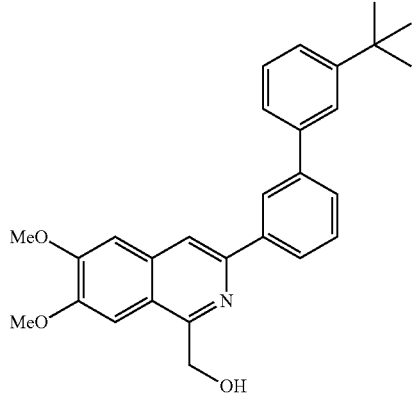 [SMILES: COc1cc2cc(-c3cccc(-c4cccc(C(C)(C)C)c4)c3)nc(CO)c2cc1OC]

3-(3'-(tert-Butyl)-[1,1'-biphenyl]-3-yl)-6,7-dimethoxyisoquinoline-1-carbaldehyde (52 mg) in 4 mL ethanol was treated slowly with NaBH$_4$ (14 mg, 3 eq.) at room temperature. Reaction was stirred for 1 hour then 2 mL acetone was added and solution was filtered through filter paper. Filtrate was concentrated then re-dissolved in DCM and washed with H$_2$O. Organic layer was dried over sodium sulfate and concentrated. Chromatography achieved using ISCO max gradient 50% EtOAc/hexane yielding product as a yellow oil (27 mg, 52% yield). $^1$H NMR (400 MHz) (CDCl$_3$) δ 8.24 (t, J=4 Hz, 1H), 8.03-8.01 (m, 1H), 7.88 (s, 1H), 7.62 (m, 1H), 7.57-7.55 (m, 1H), 7.51 (t, J=12 Hz, 1H), 7.45-7.42 (m, 1H), 7.36-7.35 (m, 2H), 7.12 (s, 1H), 6.98 (s, 1H), 5.39 (bs, 1H), 5.12 (s, 2H), 3.99 (s, 3H), 3.98 (s, 3H), 1.33 (s, 9H). $^{13}$C NMR (100 MHz) (CDCl$_3$) δ 154.60, 153.16, 151.69, 150.40, 147.62, 142.51, 141.06, 139.64, 133.80, 129.14, 128.55, 127.49, 125.67, 125.47, 124.61, 124.52, 124.46, 119.79, 115.38, 105.87, 101.22, 61.39, 56.13, 34.88, 31.47.

d. Preparation of Compound

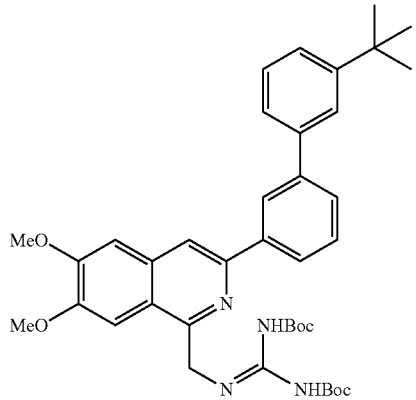 [SMILES: COc1cc2cc(-c3cccc(-c4cccc(C(C)(C)C)c4)c3)nc(CN=C(NC(=O)OC(C)(C)C)NC(=O)OC(C)(C)C)c2cc1OC]

(3-(3'-(tert-Butyl)-[1,1'-biphenyl]-3-yl)-6,7-dimethoxyisoquinolin-1-yl)methanol (27 mg), PPh$_3$ (25 mg, 1.5 eq.), and 1,3-bis(tert-butoxycarbonyl)guanidine (33 mg, 2 eq.) in 3 mL toluene at 0° C. was added diisopropylazodicarboxylate (0.02 mL, 1.5 eq.) drop wise over 15 minutes. Reaction was stirred for 3 hours at room temperature then 2 drops H$_2$O were added, and the solution was concentrated. Solid was then re-dissolved in DCM and passed through silica column and resulting crude product was taken to next step.

Example 12

Preparation of Compound

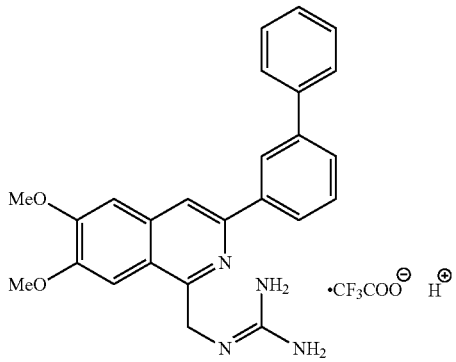

To a cooled solution of di-Boc protected guanidine compound (75 mg) in 1.5 mL DCM was added 1.5 mL trifluoroacetic acid. Reaction was taken off ice bath and stirred at room temperature for 2 hours then solvents were evaporated. Solid was then taken back up in DCM and precipitate was filtered off yielding product as a grayish white solid (40 mg, 93% yield over 2 steps). $^1$H NMR (400 MHz) (MeOD$_4$) δ 8.40 (m, 1H), 8.22 (s, 1H), 8.20 (m, 1H), 7.76-7.74 (m, 2H), 7.68 (dt, J=8 Hz, J=4 Hz, 1H), 7.61 (t, J=16 Hz, 1H), 7.53-7.49 (m, 2H), 7.46 (s, 1H), 7.42-7.38 (m, 2H), 5.07 (s, 2H), 4.07 (s, 3H), 4.05 (s, 3H). $^{13}$C NMR (100 MHz) (MeOD$_4$) δ 159.56, 155.01, 152.42, 151.82, 149.44, 143.09, 142.54, 141.25, 135.93, 130.32, 129.96, 128.54, 128.19, 128.10, 126.77, 122.05, 117.22, 107.35, 103.15, 56.64, 56.60, 45.08.
The requisite intermediate was prepared as follows:

a. Preparation of Compound

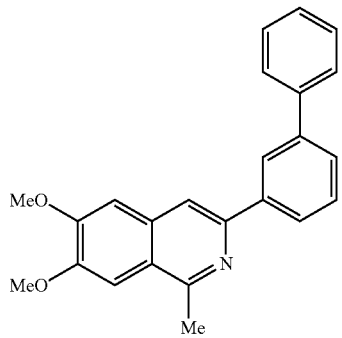 [SMILES: COc1cc2cc(-c3cccc(-c4ccccc4)c3)nc(C)c2cc1OC]

6,7-Dimethoxy-1-methylisoquinolin-3-yl trifluoromethanesulfonate (575 mg), 3-biphenylboronic acid (390 mg, 1.2 eq.), Pd(OAc)$_2$ (37 mg, 0.1 eq.), XPhos (156 mg, 0.2 eq.), and K$_2$CO$_3$ (792 mg, 3.5 eq.) were combined in a flask with 9 mL ACN and 3 mL H$_2$O and degassed. Reaction mixture was then refluxed at 100° C. for 5 hours. Solution was cooled to room temperature then diluted with EtOAc and washed with saturated NaHCO$_3$. Organic layer was dried over sodium sulfate and concentrated. Chromatography achieved using ISCO max gradient 30% EtOAc/hexane yielding product as white solid (473 mg, 81% yield). $^1$H NMR (400 MHz) (CDCl$_3$) δ 8.36 (m, 1H), 8.11-8.09 (m, 1H), 7.89 (s, 1H), 7.75-7.73 (m, 2H), 7.64-7.62 (m, 1H), 7.58 (t, J=12 Hz, 2H), 7.50 (t, J=16 Hz, 1H), 7.40 (t, J=12 Hz, 1H), 7.33 (s, 1H), 7.16 (s, 1H), 4.09 (s, 3H), 4.08 (s, 3H), 3.01 (s, 3H). $^{13}$C NMR (100 MHz) (CDCl$_3$) δ 155.99, 152.69, 149.87, 149.15, 141.64, 141.49, 140.71, 133.47, 129.08, 128.70, 127.33, 127.25, 126.83, 125.77, 122.35, 114.51, 105.72, 103.96, 56.02, 22.76.

b. Preparation of Compound

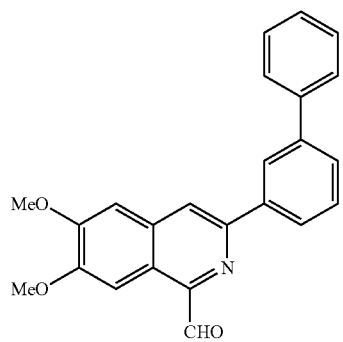 [SMILES: COc1cc2cc(-c3cccc(-c4ccccc4)c3)nc(C=O)c2cc1OC]

3-([1,1'-Biphenyl]-3-yl)-6,7-dimethoxy-1-methylisoquinoline (200 mg) and SeO$_2$ (75 mg, 1.2 eq.) in 10.5 mL anhydrous dioxane were refluxed at 102° C. for 3 hours. Solution was then cooled to room temperature and filtered to remove precipitate. Resulting filtrate was concentrated. Chromatography achieved using ISCO max gradient 30% EtOAc/hexane yielding product as a yellow solid (175 mg, 84% yield). $^1$H NMR (400 MHz) (CDCl$_3$) δ 10.50 (s, 1H), 8.77 (s, 1H), 8.44 (s, 1H), 8.23-8.18 (m, 2H), 7.75-7.66 (m, 3H), 7.63 (t, J=16 Hz, 1H), 7.52 (t, J=16 Hz, 2H), 7.44-7.42 (m, 1H), 7.22 (s, 1H), 4.14 (s, 3H), 4.09 (s, 3H). $^{13}$C NMR (100 MHz) (CDCl$_3$) δ 196.80, 153.30, 152.83, 149.61, 147.06, 141.98, 141.19, 139.26, 135.43, 129.34, 129.34, 128.83, 127.58, 127.49, 127.31, 125.66, 125.62, 122.19, 120.04, 104.99, 103.55, 56.30, 56.05.

c. Preparation of Compound

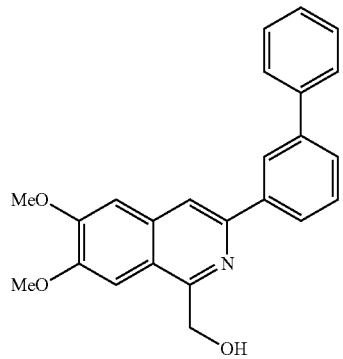 [SMILES: COc1cc2cc(-c3cccc(-c4ccccc4)c3)nc(CO)c2cc1OC]

3-([1,1'-Biphenyl]-3-yl)-6,7-dimethoxyisoquinoline-1-carboxaldehyde (160 mg) in 7 mL ethanol was treated slowly with NaBH$_4$ (50 mg, 3 eq.) at room temperature. Reaction was stirred for 1 hour then 2 mL acetone was added and solution was filtered through filter paper. Filtrate was concentrated then re-dissolved in DCM and washed with H₂O. Organic layer was dried over sodium sulfate and concentrated. Chromatography achieved using ISCO max gradient 50% EtOAc/hexane yielding product as a yellow solid (98 mg, 61% yield). ¹H NMR (400 MHz) (CDCl₃) δ 8.36-8.35 (m, 1H), 8.13-8.11 (m, 1H), 7.98 (s, 1H), 7.73 (d, J=8 Hz, 2H), 7.68-7.66 (m, 1H), 7.60 (t, J=16 Hz, 1H), 7.51 (t, J=16 Hz, 2H), 7.42 (t, J=12 Hz, 1H), 7.22 (s, 1H), 7.09 (s, 1H), 5.35 (bs, 1H), 5.32 (s, 2H), 4.08 (s, 3H), 4.07 (s, 3H). ¹³C NMR (100 MHz) (CDCl₃) δ 154.65, 141.81, 141.21, 129.19, 128.82, 127.44, 127.29, 127.25, 125.55, 125.51, 119.82, 115.35, 105.87, 101.29, 61.41, 56.14, 56.09.

d. Preparation of Compound

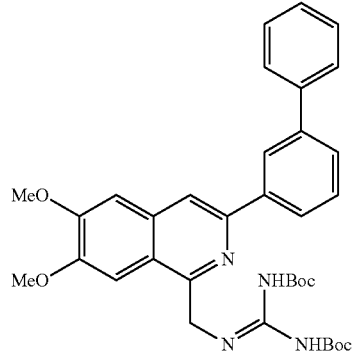 [SMILES: COc1cc2cc(-c3cccc(-c4ccccc4)c3)nc(CN=C(NC(=O)OC(C)(C)C)NC(=O)OC(C)(C)C)c2cc1OC]

(3-([1,1'-Biphenyl]-3-yl)-6,7-dimethoxyisoquinolin-1-yl) methanol (30 mg), PPh₃ (32 mg, 1.5 eq.), and 1,3-bis(tert-butoxycarbonyl)guanidine (42 mg, 2 eq.) in 3 mL toluene at 0° C. was added diisopropylazodicarboxylate (0.024 mL, 1.5 eq.) drop wise over 15 minutes. Reaction was stirred for 3 hours at room temperature then 2 drops H₂O were added, and the solution was concentrated. Solid was then re-dissolved in DCM and passed through silica column and resulting crude product was taken to next step.

Example 13

Preparation of Compound

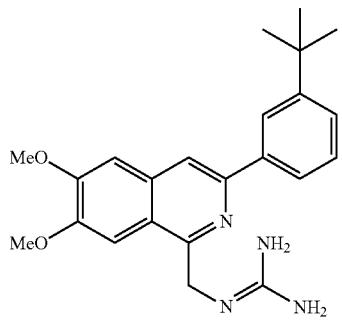 [SMILES: COc1cc2cc(-c3cccc(C(C)(C)C)c3)nc(CN=C(N)N)c2cc1OC]

To a cooled solution of di-Boc protected guanidine compound (80 mg) in 1.5 mL DCM was added 1.5 mL trifluoroacetic acid. Reaction mixture was removed from the ice bath and allowed to stirred at room temperature for 2 hours. Solvents was evaporated. The solid residue was then taken back up in DCM and precipitate was filtered off yielding product as a grayish white solid (52 mg, 95% yield over 2 steps). ¹H NMR (400 MHz) (CDCl₃) δ 9.69 (bm, 1H), 7.96 (s, 1H), 7.93 (s, 1H), 7.76-7.75 (m, 1H), 7.47-7.42 (m, 3H), 7.18 (s, 1H), 4.87 (d, J=4 Hz, 2H), 4.10 (s, 3H), 4.07 (s, 3H), 1.39 (s, 9H). ¹³C NMR (100 MHz) (CDCl₃) δ 159.07, 154.10, 151.87, 151.77, 151.39, 148.17, 137.74, 135.25, 128.77, 126.02, 123.91, 123.54, 121.52, 117.13, 105.62, 102.59, 56.34, 56.20, 44.66, 34.83, 31.31.

The requisite intermediate was prepared as follows:

a. Preparation of Compound 6,7-Dimethoxy-1-methylisoquinolin-3-yl trifluoromethanesulfonate (300 mg), 3-t-butylphenylboronic acid (183 mg, 1.2 eq.), Pd(OAc)₂ (19 mg, 0.1 eq.), XPhos (81 mg, 0.2 eq.), and K₂CO₃ (354 mg, 3 eq.) were combined in a flask with 9 mL dioxane and 3 mL H₂O and degassed. Reaction mixture was then refluxed at 100° C. for 2 hours. Solution was cooled to room temperature then diluted with EtOAc and washed with saturated NaHCO₃. Organic layer was dried over sodium sulfate and concentrated. Chromatography achieved using ISCO max gradient 40% EtOAc/hexane yielding product as a clear oil (245 mg, 83% yield). ¹H NMR (400 MHz) (CDCl₃) δ 8.14 (s, 1H), 7.92-7.89 (m, 1H), 7.81 (s, 1H), 7.45-7.44 (m, 2H), 7.31 (s, 1H), 7.15 (s, H), 4.08 (s, 3H), 4.07 (s, 3H), 3.00 (s, 3H), 1.44 (s, 9H). ¹³C NMR (100 MHz) (CDCl₃) δ 155.86, 152.59, 151.39, 149.88, 149.70, 139.95, 133.48, 128.37, 125.13, 124.16, 123.88, 122.16, 114.45, 105.67, 103.92, 56.03, 55.99, 34.88, 31.48, 22.79.

b. Preparation of Compound 3-(3-(tert-Butyl)phenyl)-6,7-dimethoxy-1-methylisoquinoline (153 mg) and SeO₂ (61 mg, 1.2 eq.) in 5 mL anhydrous dioxane were refluxed at 102° C. for 3 hours. Solution was then cooled to room temperature and filtered to remove precipitate. Resulting filtrate was concentrated. Chromatography achieved using ISCO max gradient 30% EtOAc/hexane yielding product as a yellow solid (97 mg, 62% yield). $^1$H NMR (400 MHz) (CDCl$_3$) δ 10.40 (s, 1H), 8.67 (s, 1H), 8.14 (s, 1H), 8.08 (s, 1H), 7.90 (dt, J=4 Hz, J=4 Hz, 1H), 7.42-7.40 (m, 2H), 7.13 (s, 1H), 4.04 (s, 3H), 4.00 (s, 3H), 1.36 (s, 9H). $^{13}$C NMR (100 MHz) (CDCl$_3$) δ 196.96, 153.20, 152.67, 151.82, 150.35, 146.98, 138.51, 135.43, 128.67, 125.91, 124.05, 123.78, 122.07, 120.08, 104.95, 103.49, 56.30, 56.07, 34.95, 31.46.

c. Preparation of Compound

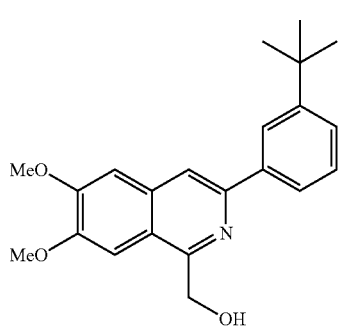 [SMILES: COc1cc2cc(-c3cccc(C(C)(C)C)c3)nc(CO)c2cc1OC]

3-(3-(tert-Butyl)phenyl)-6,7-dimethoxyisoquinoline-1-carboxaldehyde (97 mg) in 5 mL ethanol was treated slowly with NaBH$_4$ (26 mg, 3 eq.) at room temperature. Reaction was stirred for 1 hour then 2 mL acetone was added and solution was filtered through filter paper. Filtrate was concentrated then re-dissolved in DCM and washed with H$_2$O. Organic layer was dried over sodium sulfate and concentrated. Chromatography achieved using ISCO max gradient 50% EtOAc/hexane yielding product as a pale yellow solid (50 mg, 63% yield). $^1$H NMR (400 MHz) (CDCl$_3$) δ 8.07 (m, 1H), 7.86-7.83 (m, 1H), 7.82 (s, 1H), 7.39-7.37 (m, 2H), 7.13 (s, 1H), 6.98 (s, 1H), 5.12 (s, 2H), 3.99 (s, 3H), 3.98 (s, 3H), 1.35 (s, 9H). $^{13}$C NMR (100 MHz) (CDCl$_3$) δ 154.47, 153.14, 151.62, 150.31, 148.21, 138.90, 133.85, 128.51, 125.55, 123.97, 123.65, 119.64, 115.25, 105.84, 101.22, 61.32, 56.13, 56.10, 34.90, 31.45. IR (thin film NaCl) 3345, 2957, 1621, 1577, 1506, 1467, 1416, 1362, 1276, 1247, 1163, 1090, 1023, 991, 874, 834, 800, 701.

d. Preparation of Compound

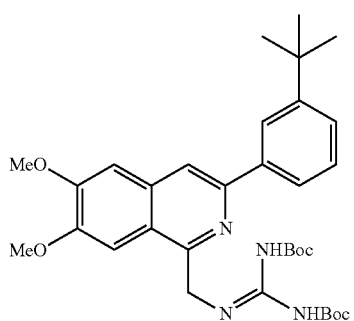 [SMILES: COc1cc2cc(-c3cccc(C(C)(C)C)c3)nc(CN=C(NC(=O)OC(C)(C)C)NC(=O)OC(C)(C)C)c2cc1OC]

(3-(3-(tert-butyl)phenyl)-6,7-dimethoxyisoquinolin-1-yl) methanol (50 mg), PPh$_3$ (56 mg, 1.5 eq.), and 1,3-bis(tert-butoxycarbonyl)guanidine (74 mg, 2 eq.) in 4 mL toluene at 0° C. was added diisopropylazodicarboxylate (0.04 mL, 1.5 eq.) drop wise over 15 minutes. Reaction was stirred for 3 hours at room temperature then 2 drops H$_2$O were added, and the solution was concentrated. Solid was then re-dissolved in DCM and passed through silica column and resulting crude product was taken to next step.

Example 14

Preparation of Compound

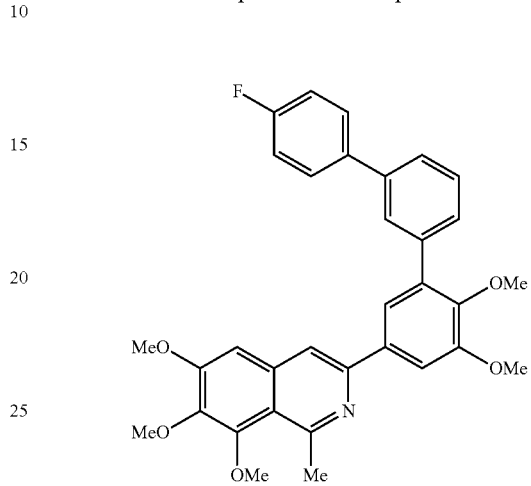

A 25-mL round bottom flask equipped with a magnetic stirrer, a condenser and a nitrogen in/outlet adapter was charged with 2,3-dimethoxy-5-(6,7,8-trimethoxy-1-methylisoquinolin-3-yl)phenyl trifluoromethanesulfonate (200 mg, 0.39 mmol), (4'-fluoro-[1,1'-biphenyl]-3-yl)boronic acid (99.3 mg, 0.58 mmol), water/acetonitrile (2 mL/6 ml), K$_2$CO$_3$ (106 mg, 0.77 mmol), 2-dicyclohexylphosphino-2',4',6'-triisopropylbiphenyl (20 mg, 0.039 mmol). The resulting solution was degassed for 5 min, then Pd(OAc)$_2$ (5.0 mg, 0.02 mmol) was added and the solution was carefully degassed. The reaction mixture was warmed to 90° C. and stirred for 12 hours. After cooling to room temperature, the reaction mixture was diluted with EtOAc (50 mL) and washed with saturated NaHCO$_3$ (10 mL), brine (10 mL), dried over Na$_2$SO$_4$. The organic layer was concentrated in rotavapor and purified on silica gel. Elution with 10% EtOAc/hexanes afforded the title compound (180 mg, 86%) as a white foam. $^1$H NMR (CDCl$_3$, 400 MHz) δ 7.85 (t, 1H, J=1.68 Hz), 7.82 (d, 1H, J=2.04 Hz), 7.76 (s, 1H), 7.62-7.68 (m, 4H), 7.51-7.59 (m, 2H), 7.14-7.18 (m, 2H), 6.95 (s, 1H), 4.09 (s, 3H), 4.05 (s, 3H), 4.02 (s, 3H), 3.99 (s, 3H), 3.70 (s, 3H), 3.16 (s, 3H).

The requisite intermediate was prepared as follows:

a. Preparation of Compound

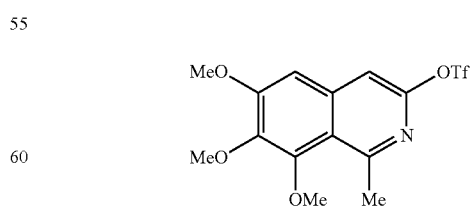

A 50-mL round bottom flask equipped with a magnetic stirrer under nitrogen was charged with 6,7,8-trimethoxy-1-methylisoquinolin-3-ol (200 mg, 0.80 mmol), CH$_2$Cl$_2$ (15 mL), and triethylamine (0.22 ml, 1.60 mmol). After cooling to −70° C., triflic anhydride (0.15 ml, 0.88 mmol) was added via a syringe. The resulting reaction mixture was stirred at −70 to −4° C. for 30 min, then diluted with CH$_2$Cl$_2$ (50 mL) and washed with saturated NaHCO$_3$ (20 mL), brine (20 mL), dried over MgSO$_4$, and concentrated to afford a brown solid. The brown solid was purified on silica gel, and elution with CH$_2$Cl$_2$ afforded the title compound (210 mg, 69%) as a white solid. $^1$H NMR (CDCl$_3$, 400 MHz) δ 7.13 (s, 1H), 6.83 (s, 1H), 3.96 (s, 3H), 3.94 (s, 3H), 3.88 (s, 3H), 2.96 (s, 3H).

b. Preparation of Compound

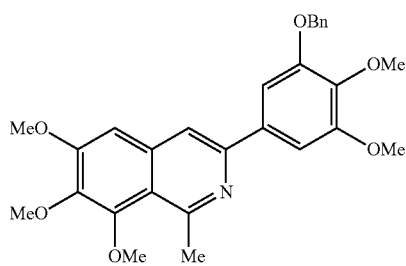 [SMILES: COc1cc(-c2cc3cc(OC)c(OC)c(OC)c3c(C)n2)cc(OCc2ccccc2)c1OC]

A 100-mL round bottom flask equipped with a magnetic stirrer, a condenser and a nitrogen in/outlet adapter was charged with 6,7,8-trimethoxy-1-methylisoquinolin-3-yl trifluoromethanesulfonate (1.7 g, 4.46 mmol), (3-(benzyloxy)-4,5-dimethoxyphenyl)boronic acid (1.54 g, 5.35 mmol), water/acetonitrile (10 mL/20 ml), K$_2$CO$_3$ (1.54 mg, 11.2 mmol), 2-dicyclohexylphosphino-2',4',6'-triisopropylbiphenyl (212 mg, 0.45 mmol). The resulting solution was degassed for 5 min, then Pd(OAc)$_2$ (50 mg, 0.22 mmol) was added and the solution was carefully degassed. The reaction mixture was heated to 90° C. for 4 hours. After cooling to room temperature, the reaction mixture was diluted with EtOAc (200 mL) and washed with saturated NaHCO$_3$ (50 mL), brine (50 mL), dried over Na$_2$SO$_4$, concentrated in rotavapor and purified on silica gel. Elution with 20% EtOAc/hexanes afforded the title compound (2.03 g, 96%) as a light yellow oil. $^1$H NMR (CDCl$_3$, 400 MHz) δ 7.66 (s, 1H), 7.73-7.55 (m, 2H), 7.39-7.44 (m, 4H), 7.33-7.37 (m, 1H), 6.95 (s, 1H), 5.28 (s, 2H), 4.05 (s, 3H), 4.04 (s, 3H), 4.02 (s, 3H), 3.99 (s, 314 3.94 (s, 3H), 3.15 (s, 3H).

c. Preparation of Compound

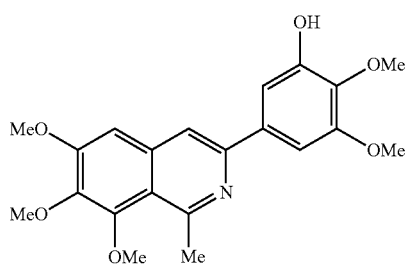 [SMILES: COc1cc(-c2cc3cc(OC)c(OC)c(OC)c3c(C)n2)cc(O)c1OC]

A 1-L round bottom flask equipped with a magnetic stirrer was charged with 3-(3-(benzyloxy)-4,5-dimethoxyphenyl)-6,7,8-trimethoxy-1-methylisoquinoline (2.3 g, 4.84 mmol), MeOH (250 mL), and Pd/C (10%, 200 mg). The reaction flask was sealed with septum and purge with N$_2$ three times; H$_2$ three times. The reaction mixture was stirred at room temperature under H$_2$ balloon for 3 hours. TLC showed the starting material was consumed. The reaction mixture was passed through a pad of Celite and washed with MeOH. The filtrate was concentrated to afford the crude title compound (1.67 g, 90%) as a grey foam. The crude product was used in next step without further purification. $^1$H NMR (CDCl$_3$, 400 MHz) δ 7.69 (s, 1H), 7.39 (d, 1H, J=1.92 Hz), 7.31 (d, 1H, J=1.96 Hz), 6.94 (s, 1H), 5.83 (s, 1H), 4.05 (s, 3H), 4.04 (s, 3H), 4.03 (s, 3H), 3.99 (s, 3H), 3.97 (s, 3H), 3.15 (s, 3H).

d. Preparation of Compound

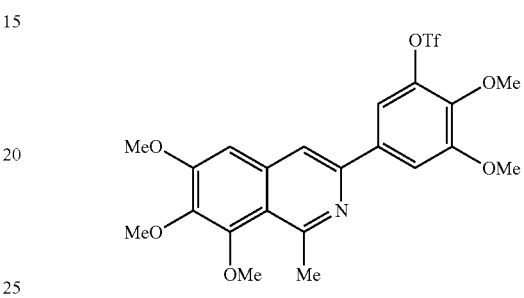

A 500-mL round bottom flask equipped with a magnetic stirrer under nitrogen was charged with 2,3-dimethoxy-5-(6,7,8-trimethoxy-1-methylisoquinolin-3-yl)phenol (1.66 g, 4.31 mmol), CH$_2$Cl$_2$ (100 mL), and triethylamine (1.20 ml, 8.62 mmol). After cooling to −70° C., triflic anhydride (0.80 ml, 4.74 mmol) was added via a syringe. The resulting reaction mixture was stirred at −70- to −30° C. for 30 min. The reaction mixture was diluted with CH$_2$Cl$_2$ (100 mL) and washed with saturated NaHCO$_3$ (50 ml), brine (50 mL), dried over Na$_2$SO$_4$, concentrated in rotavapor and purified on silica gel. Elution with 20% EtOAc/hexanes afforded the title compound (2.21 g, 99%) as a light yellow solid. $^1$H NMR (CDCl$_3$, 400 MHz) δ 7.72 (d, 1H, J=1.88 Hz), 7.59 (s, 1H), 7.45 (d, 1H, J=1.84 Hz), 6.89 (s, 1H), 3.96 (s, 6H), 3.95 (s, 3H), 3.92 (s, 3H), 3.90 (s, 3H), 3.06 (s, 3H).

Example 15

Preparation of Compound

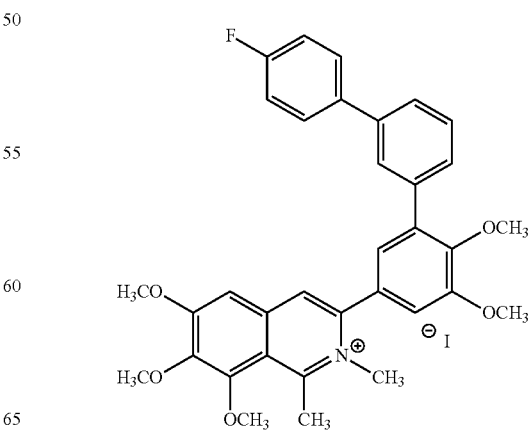

A solution of 3-(4"-fluoro-5,6-dimethoxy-[1,1':3',1"-terphenyl]-3-yl)-6,7,8-trimethoxy-1-methylisoquinoline (180 mg, 0.33 mmol) in iodomethane (3.0 mL) was stirred in a sealed vial at 100° C. for 12 hours. After cooled to room temperature, Et$_2$O (10 mL) was added and the solid was collected by filtration, then washed with Et$_2$O to afford the title compound (155 mg, 68%) as a light yellow solid. $^1$H NMR (CDCl$_3$, 400 MHz) δ 7.87 (s, 1H), 7.85 (d, 1H, J=2.04 Hz), 7.78 (m, 1H), 7.50-7.64 (m, 5H), 7.13-7.18 (m, 2H), 7.09-7.10 (m, 1H), 4.35 (s, 3H), 4.14 (s, 3H), 4.11 (s, 3H), 4.10 (s, 3H), 4.05 (s, 3H), 3.77 (s, 3H), 3.60 (s, 3H).

Example 16

Preparation of Compound

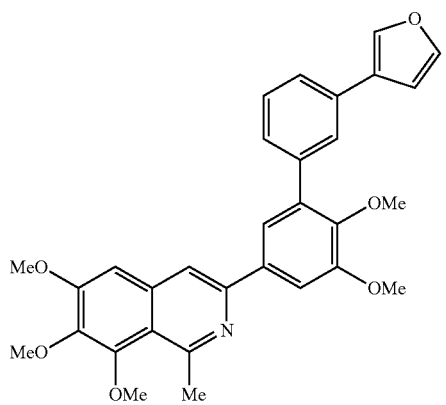 [SMILES: COc1cc(-c2cc3cc(OC)c(OC)c(OC)c3c(C)n2)cc(-c2cccc(-c3ccoc3)c2)c1OC]

A 25-mL round bottom flask equipped with a magnetic stirrer, a condenser and a nitrogen in/outlet adapter was charged with 2',3'-dimethoxy-5'-(6,7,8-trimethoxy-1-methylisoquinolin-3-yl)phenyl-3'-yltrifluoromethanesulfonate (43 mg, 0.07 mmol), 3-(3-furanyl)phenylboronic acid (12 mg, 0.11 mmol), water/acetonitrile (2 mL/4 ml), K$_2$CO$_3$ (24 mg, 0.18 mmol), 2-dicyclohexylphosphino-2',4',6'-triisopropylbiphenyl (6 mg, 0.014 mmol). The resulting solution was degassed for 5 min, then Pd(OAc)$_2$ (2.0 mg, 0.07 mmol) was added and the solution was carefully degassed. The reaction mixture was warmed to 100° C. and stirred for 1 hour. After cooling to room temperature, the reaction mixture was diluted with EtOAc (30 mL) and washed with saturated NaHCO$_3$ (10 mL), brine (10 mL), dried over Na$_2$SO$_4$. The organic layer was concentrated in rotavapor and purified on silica gel. Elution with 20% EtOAc/hexanes afforded the title compound (20 mg, 54%) as a white foam. $^1$H NMR (CDCl$_3$, 400 MHz) δ 7.67-7.73 (m, 4H), 7.57 (d, 1H, J=2.04 Hz), 7.36-7.47 (m, 4H), 6.86 (s, 1H), 6.70 (t, 1H, J=0.68 Hz), 3.99 (s, 2H), 3.96 (s, 3H), 3.93 (s, 3H), 3.90 (s, 3H), 3.58 (s, 3H), 3.07 (s, 3H).

Example 17

Preparation of Compound

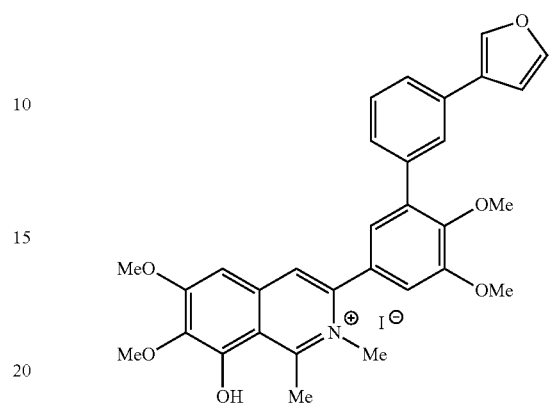

3-(3'-(Furan-3-yl)-5,6-dimethoxy-[1,1'-biphenyl]-3-yl)-6,7,8-trimethoxy-1-methylisoquinoline (15 mg, 0.03 mmol) in iodomethane (1.0 mL) was stirred in a sealed vial at 100° C. for 12 hours. After cooling to room temperature, the solvent was removed. The residue was triturated with EtOAc (5 mL). The solid was collected by filtration and washed with Et$_2$O to afford the title compound (10 mg, 53%) as light yellow solid. $^1$H NMR (CDCl$_3$, 400 MHz) δ 7.77-7.87 (m, 3H), 7.70 (s, 1H), 7.43-7.49 (m, 4H), 7.04-7.08 (m, 2H), 6.74 (s, 1H), 4.31 (s, 3H), 4.10 (s, 3H), 4.07 (s, 2H), 4.06 (s, 3H), 4.02 (s, 3H), 3.71 (s, 3H), 3.56 (s, 3H).

Example 18

Preparation of Compound

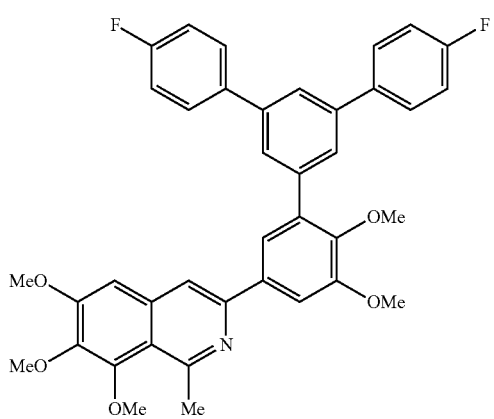 [SMILES: COc1cc(-c2cc3cc(OC)c(OC)c(OC)c3c(C)n2)cc(-c2cc(-c3ccc(F)cc3)cc(-c3ccc(F)cc3)c2)c1OC]

A 50-mL round bottom flask equipped with a magnetic stirrer, a condenser and a nitrogen in/outlet adapter was charged with 2,3-dimethoxy-5-(6,7,8-trimethoxy-1-methylisoquinolin-3-yl)phenyl trifluoromethanesulfonate (200 mg, 0.39 mmol), (4'-fluoro-[1,1'-biphenyl]-3-yl)boronic acid (180 mg, 0.58 mmol), water/acetonitrile (2 mL/6 ml), K$_2$CO$_3$ (106 mg, 0.77 mmol), 2-dicyclohexylphosphino-2',4',6'-triisopropylbiphenyl (20 mg, 0.039 mmol). The resulting solution was degassed for 5 min, then Pd(OAc)$_2$ (5.0 mg, 0.02 mmol) was added and the solution was carefully degassed. The reaction mixture was warmed to 100° C. and stirred for 2 hours. After cooling to room temperature, the reaction mixture was diluted with EtOAc (50 mL) and washed with saturated NaHCO$_3$ (10 mL), brine (10 mL), dried over Na$_2$SO$_4$. The organic layer was concentrated in rotavapor and purified on silica gel. Elution with 10% EtOAc/hexanes afforded the title compound (185 mg, 76%) as a white foam. $^1$H NMR (CDCl$_3$, 400 MHz) δ 7.58-7.75 (m, 10H), 7.07-7.10 (m, 4H), 6.85 (s, 1H), 4.00 (s, 3H), 3.96 (s, 3H), 3.92 (s, 3H), 3.89 (s, 3H), 3.65 (s, 3H), 3.07 (s, 3H).

Example 19

Preparation of Compound

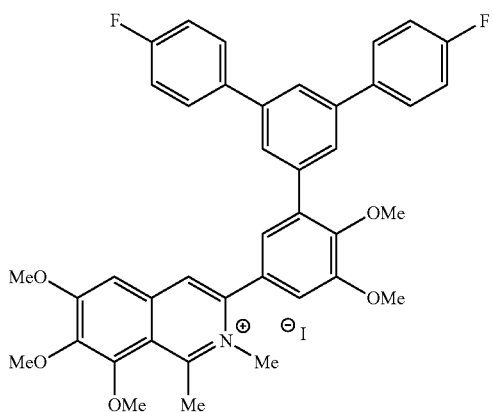 [SMILES: COc1cc(-c2cc3cc(OC)c(OC)c(OC)c3c(C)[n+]2C)cc(-c2cc(-c3ccc(F)cc3)cc(-c3ccc(F)cc3)c2)c1OC ; [I-]]

A solution of 3-(4"-fluoro-5'-(4-fluorophenyl)-5,6-dimethoxy-[1,1':3',1"-terphenyl]-3-yl)-6,7,8-trimethoxy-1-methylisoquinoline in iodomethane (3.0 mL) was stirred in a sealed vial at 100° C. for 2 days. After cooling to room temperature, Et$_2$O (10 mL) was added to the reaction mixture and the solid was collected by filtration to afford the title compound (156 mg, 73%) as a light yellow solid. $^1$H NMR (CDCl$_3$, 400 MHz) δ 7.88 (m, 2H), 7.76 (m, 2H), 7.73 (m, 1H), 7.66-7.70 (m, 4H), 7.16-7.20 (m, 5H), 7.10 (s, 1H), 4.35 (s, 3H), 4.14 (s, 3H), 4.11 (s, 3H), 4.10 (s, 3H), 4.06 (s, 3H), 3.82 (s, 3H), 3.60 (s, 3H).

Example 20

Preparation of Compound

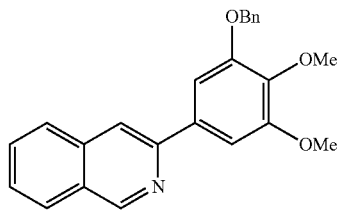

A 100-mL round bottom flask equipped with a magnetic stirrer, a condenser and a nitrogen in/outlet adapter was charged with isoquinolin-3-yl trifluoromethanesulfonate (500 mg, 1.88 mmol), (3-(benzyloxy)-4,5-dimethoxyphenyl) boronic acid (1.1 g, 3.77 mmol), water/acetonitrile (5 mL/20 ml), K$_2$CO$_3$ (650 mg, 4.70 mmol), 2-dicyclohexylphosphino-2',4',6'-triisopropylbiphenyl (90 mg, 0.19 mmol). The resulting solution was degassed for 5 min, then Pd(OAc)$_2$ (21 mg, 0.09 mmol) was added and the solution was carefully degassed. The reaction mixture was heated to 100° C. for 1 hour. After cooling to room temperature, the reaction mixture was diluted with EtOAc (100 mL) and washed with saturated NaHCO$_3$ (30 mL), brine (30 mL), dried over Na$_2$SO$_4$, concentrated in rotavapor and purified on silica gel. Elution with 10% EtOAc/hexanes afforded the title compound (300 mg, 43%) as a colorless oil. $^1$H NMR (CDCl$_3$, 400 MHz) δ 9.24 (s, 1H), 7.92 (d, 1H, J=8.20 Hz), 7.88 (s, 1H), 7.79 (d, 1H, J=8.24 Hz), 7.61-7.65 (m, 1H), 7.50-7.53 (m, 1H), 7.44-7.46 (m, 2H), 7.31-7.37 (m, 4H), 7.24-7.28 (m, 1H), 5.20 (s, 2H), 3.94 (s, 3H), 3.88 (s, 3H).

The requisite intermediate was prepared as follows:

a. Preparation of Compound

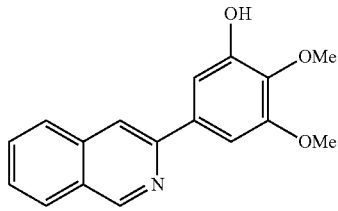 [SMILES: COc1cc(-c2cc3ccccc3cn2)cc(OS(=O)(=O)C(F)(F)F)c1OC]

A 100-mL round bottom flask equipped with a magnetic stirrer was charged with 3-(3-(benzyloxy)-4,5-dimethoxyphenyl)isoquinoline (300 mg, 0.81 mmol), MeOH (30 mL), and Pd/C (10%, 30 mg). The reaction flask was sealed with septum and purge with N$_2$ three times; H$_2$ three times. The reaction mixture was stirred at room temperature under H$_2$ balloon for 24 hours. TLC showed the starting material was consumed. The reaction mixture was passed through a pad of Celite and washed with MeOH. The filtrate was concentrated to afford the crude title compound (278 mg) as a greenish yellow foam. The crude product was used in next step without further purification and identification.

b. Preparation of Compound

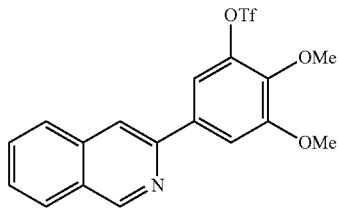

A 100-mL round bottom flask equipped with a magnetic stirrer under nitrogen was charged with 5-(isoquinolin-3-yl)-2,3-dimethoxyphenol (278 mg, 0.99 mmol), CH$_2$Cl$_2$ (20 mL), and triethylamine (0.28 ml, 1.98 mmol). After cooling to −70° C., triflic anhydride (0.18 ml, 1.1 mmol) was added via a syringe. The resulting reaction mixture was stirred at −70- TO −30° C. for 30 min. The reaction mixture was diluted with CH$_2$Cl$_2$ (30 mL) and washed with saturated NaHCO$_3$ (10 ml), brine (10 mL), dried over Na$_2$SO$_4$, concentrated in rotavapor and purified on silica gel. Elution with CH$_2$Cl$_2$ afforded the title compound (150 mg, 37%) as a white solid. $^1$H NMR (CDCl$_3$, 400 MHz) δ 9.23 (s, 1H), 7.93 (d, 1H, J=8.80 Hz), 7.92 (s, 1H), 7.82 (d, 1H, J=8.20 Hz), 7.73 (d, 1H, J=1.92 Hz), 7.65 (t, 1H, J=7.28 Hz), 7.54 (t, 1H, J=6.92 Hz), 7.50 (d, 1H, J=1.92 Hz), 3.97 (s, 3H), 3.94 (s, 3H).

Example 21

Preparation of Compound

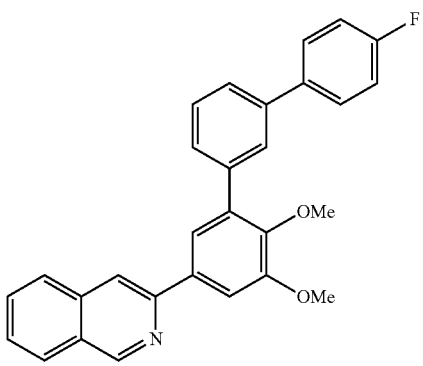 [SMILES: COc1cc(-c2cc3ccccc3cn2)cc(-c2cccc(-c3ccc(F)cc3)c2)c1OC]

A 25-mL round bottom flask equipped with a magnetic stirrer, a condenser and a nitrogen in/outlet adapter was charged with 5-(isoquinolin-3-yl)-2,3-dimethoxyphenyl trifluoromethanesulfonate (30 mg, 0.07 mmol), [1,1'-biphenyl]-4-ylboronic acid (20 mg, 0.12 mmol), water/acetonitrile (2 mL/4 ml), $K_2CO_3$ (21 mg, 0.15 mmol), 2-dicyclohexylphosphino-2',4',6'-triisopropylbiphenyl (6 mg, 0.013 mmol). The resulting solution was degassed for S min, then $Pd(OAc)_2$ (2.0 mg, 0.065 mmol) was added and the solution was carefully degassed. The reaction mixture was warmed to 100° C. and stirred for 1.0 hour. After cooling to room temperature, the reaction mixture was diluted with EtOAc (30 mL) and washed with saturated $NaHCO_3$ (10 mL), brine (10 mL), dried over $Na_2SO_4$. The organic layer was concentrated in rotavapor and purified on silica gel. Elution with 20% EtOAc/hexanes afforded the title compound (14 mg, 43%) as a white foam. $^1H$ NMR ($CDCl_3$, 400 MHz) δ 9.26 (s, 1H), 7.99 (s, 1H), 7.92 (d, 1H, J=8.16 Hz), 7.75-7.79 (m, 3H), 7.42-7.79 (m, 8H), 7.04-7.08 (m, 2H), 4.00 (s, 3H), 3.63 (s, 3H).

The requisite intermediate was prepared as follows:

a. Preparation of Compound

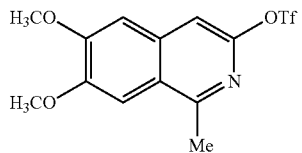 [SMILES: COc1cc2cc(OS(=O)(=O)C(F)(F)F)nc(C)c2cc1OC]

A 150-mL round bottom flask equipped with a magnetic stirrer under nitrogen was charged with 6,7-dimethoxy-1-methylisoquinolin-3-ol (1.26 g, 5.8 mmol), $CH_2Cl_2$ (30 mL), and triethylamine (1.6 ml, 11.5 mmol). After cooling to −70° C., triflic anhydride (1.1 ml, 6.3 mmol) was added via a syringe. The resulting reaction mixture was stirred at −70° C. for 30 min, then room temperature for 1 hour. The reaction mixture was diluted with $CH_2Cl_2$ (100 mL) and washed with saturated $NaHCO_3$ (30 ml), brine (30 mL), dried over $MgSO_4$, and concentrated to afford a crude product as a brown oil. The crude product was purified on silica gel. Elution with $CH_2Cl_2$ afforded the title compound (1.1 g, 54%) as a white solid. $^1H$ NMR ($CDCl_3$, 400 MHz) δ 7.30 (m, 3H), 4.06 (m, 6H), 2.90 (s, 3H).

Example 22

Preparation of Compound

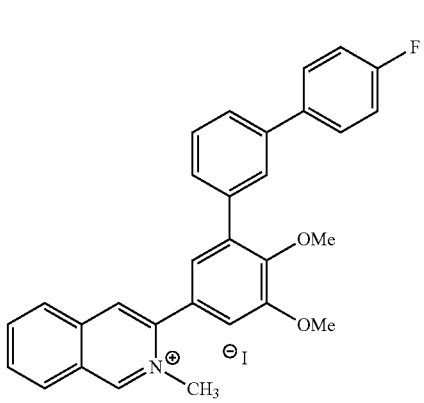 [SMILES: COc1cc(-c2cc3ccccc3c[n+]2C)cc(-c2cccc(-c3ccc(F)cc3)c2)c1OC ; [I-]]

A solution of 3-(4"-fluoro-5,6-dimethoxy-[1,1':3',1"-terphenyl]-3-yl)isoquinoline (14 mg, 0.03 mmol) in iodomethane (1.0 mL) was stirred in a sealed vial at 100° C. for 12 hours. After cooling to room temperature, the solvent was removed and the residue was triturated with EtOAc. The solid was collected by filtration to afford the title compound (10 mg, 55%) as a yellow solid. $^1H$ NMR ($CDCl_3$, 400 MHz) δ 11.0 (s, 1H), 8.78 (d, 1H, J=7.96 Hz), 8.14-8.19 (m, 2H), 8.07-8.09 (m, 1H), 8.00 (t, 1H, J=7.56 Hz), 7.76 (s, 1H), 7.54-7.63 (m, 5H), 7.28-7.32 (m, 1H), 7.13-7.17 (m, 3H), 4.63 (s, 3H), 4.04 (s, 3H), 3.80 (s, 3H).

Example 23

Preparation of Compound

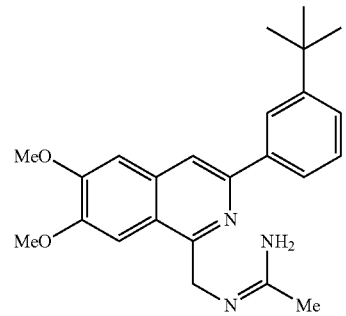 [SMILES: COc1cc2cc(-c3cccc(C(C)(C)C)c3)nc(C/N=C(/C)N)c2cc1OC]

1-(Bromomethyl)-3-(3-(tert-butyl)phenyl)-6,7-dimethoxy-isoquinoline (25 mg), acetamidine HCl (7 mg, 1.2 eq.), and $K_2CO_3$ (17 mg, 2 eq.) in 2 mL DMF were heated at 50° C. for 2 hours. Reaction mixture was then cooled to room temperature, diluted with EtOAc, and washed with 10% LiCl solution. Organic layer was dried over sodium sulfate and concentrated. Chromatography achieved using ISCO max gradient 10% MeOH/DCM yielding product as an off-white solid (18 mg, 78% yield). $^1H$ NMR (400 MHz) ($MeOD_4$) δ

8.22 (t, J=4 Hz, 1H), 8.13 (s, 1H), 7.94-7.72 (m, 1H), 7.50 (dt, J=8 Hz, J=4 Hz, 1H), 7.46-7.43 (m, 2H), 7.40 (s, 1H), 5.16 (s, 2H), 4.08 (s, 3H), 4.04 (s, 3H), 2.44 (s, 3H), 1.45 (s, 9H). $^{13}$C NMR (100 MHz) (MeOD$_4$) δ 167.29, 154.99, 152.81, 152.37, 150.66, 150.11, 140.33, 136.10, 129.60, 126.54, 124.84, 124.61, 122.19, 117.10, 107.30, 103.23, 56.72, 56.60, 46.29, 35.77, 31.92, 19.25.

The requisite intermediate was prepared as follows:

a. Preparation of Compound

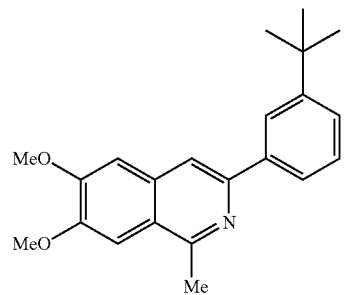 [SMILES: COc1cc2cc(-c3cccc(C(C)(C)C)c3)nc(C)c2cc1OC]

A 100-mL round bottom flask equipped with a magnetic stirrer, a condenser and a nitrogen in/outlet adapter was charged with 6,7-dimethoxy-1-methylisoquinolin-3-yl trifluoromethanesulfonate (700 mg, 1.99 mmol), (3-(tert-butyl)phenyl)boronic acid (426 mg, 2.39 mmol), water/acetonitrile (5 mL/15 ml), K$_2$CO$_3$ (550 mg, 3.99 mmol), 2-dicyclohexylphosphino-2',4',6'-triisopropylbiphenyl (95 mg, 0.20 mmol). The resulting solution was degassed for 5 min, then Pd(OAc)$_2$ (22.4 mg, 0.10 mmol) was added and the reaction mixture was carefully degassed. The reaction mixture was heated to 100° C. and stirred for 1 hour. The reaction mixture was warmed to 100° C. and stirred for 1 hour. After cooling to 20° C., the reaction mixture was diluted with EtOAc (100 mL) and washed with saturated NaHCO$_3$ (30 mL), brine (30 mL), dried over Na$_2$SO$_4$, concentrated in rotavapor and purified on silica gel. Elution with 20% EtOAc/hexanes afforded the title compound (600 mg, 90%) as a white foam. $^1$H NMR (CDCl$_3$, 400 MHz) δ 8.13 (m, 1H), 7.85-7.93 (m, 1H), 7.76 (s, 1H), 7.41-7.46 (m, 2H), 7.32 (s, 1H), 7.16 (s, 1H), 4.09 (s, 3H), 4.08 (s, 3H), 3.00 (s, 3H), 1.44 (s, 9H).

b. Preparation of Compound

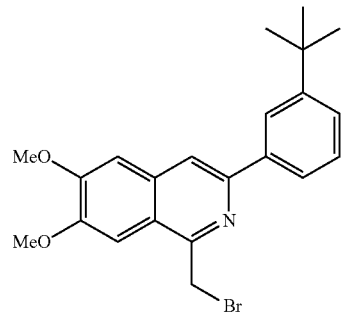 [SMILES: COc1cc2cc(-c3cccc(C(C)(C)C)c3)nc(CBr)c2cc1OC]

3-(3-(tert-Butyl)phenyl)-6,7-dimethoxy-1-methylisoquinoline (400 mg), NBS (223 mg, 1.05 eq.), and AIBN (20 mg, 0.1 eq.) in 7 mL CCl$_4$ were heated at 85° C. for 2 hours. Reaction mixture was then cooled to room temperature and diluted with hexane. Solid precipitate was filtered off and filtrate was concentrated. Chromatography achieved using ISCO max gradient 15% EtOAc/hexane yielding product as a white solid (350 mg, 71% yield). $^1$H NMR (400 MHz) (CDCl$_3$) δ 8.15-8.14 (m, 1H), 7.94-7.91 (m, 2H), 7.48-7.45 (m, 3H), 7.18 9s, 1H), 5.10 (s, 2H), 4.11 (s, 3H), 4.07 (s, 3H), 1.45 (s, 9H). $^{13}$C NMR (100 MHz) (CDCl$_3$) δ 153.03, 152.89, 151.50, 150.11, 149.96, 139.19, 134.59, 128.46, 125.45, 124.18, 123.86, 121.45, 116.56, 105.75, 103.56, 56.16, 56.10, 34.90, 32.97, 31.47.

Example 24

Alternative Preparation of the Compound of Example 13

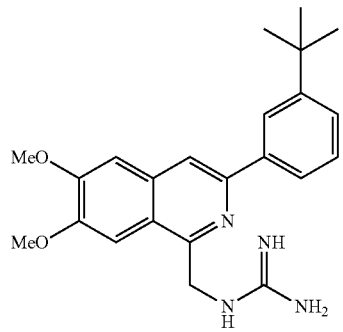 [SMILES: COc1cc2cc(-c3cccc(C(C)(C)C)c3)nc(CNC(=N)N)c2cc1OC]

A 20-mL vial was added methyl di-tert-butyl (((((3-(3-(tert-butyl)phenyl)-6,7-dimethoxyisoquinolin-1-yl)methyl)amino)methylene)dicarbamate (300 mg, 0.50 mmol), CH$_2$Cl$_2$ (3 mL), and TFA (3 mL). The sealed vial was stirred at 50° C. for 1 hour. The solvent was removed and the residue was purified on silica gel. Elution with CH$_2$Cl$_2$ to (10/89/1: MeOH/CHCl$_3$/ammonium hydroxide) afforded the title compound (163 mg, 82%) as a white solid. $^1$H NMR (CDCl$_3$, 400 MHz) δ 9.84 (t, 1H, J=5.84 Hz), 8.00 (s, 1H), 7.93 (s, 1H), 7.77-7.79 (m, 1H), 7.41-7.48 (m, 3H), 7.18 (s, 1H), 4.86 (d, 1H, J=5.76 Hz), 4.11 (s, 3H), 4.07 (s, 3H), 1.68 (broad s, 2H), 1.41 (s, 9H).

a. Preparation of Compound

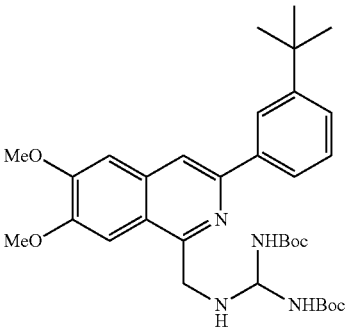 [SMILES: COc1cc2cc(-c3cccc(C(C)(C)C)c3)nc(CNC(NC(=O)OC(C)(C)C)NC(=O)OC(C)(C)C)c2cc1OC]

A 50-mL round bottom flask equipped with a magnetic stirrer, a condenser and a nitrogen in/outlet adapter was charged with 3-(3-(tert-butyl)phenyl)-6,7-dimethoxy-1-bromomethylisoquinoline (400 mg, 0.97 mmol), DMF (3 mL), K₂CO₃ (266 mg, 1.93 mmol), and 1,3-bis(tert-butoxycarbonyl)guanidine (300 mg, 1.16 mmol) The reaction mixture was stirred at room temperature for 12 hours. The reaction mixture was diluted with EtOAc (100 mL), washed with water (30 mL), 10% LiCl (30 mL), brine (30 mL), dried over Na₂SO₄, concentrated in rotavapor and purified on silica gel. Elution with 20% EtOAc/hexanes afforded the title compound (325 mg, 57%) as a white solid. ¹H NMR (CDCl₃, 400 MHz) δ 9.54 (broad s, 2H), 8.18 (s, 1H), 7.66-7.70 (m, 2H), 7.17-7.19 (m, 2H), 5.64 (s, 2H), 3.86 (s, 6H), 1.24 (s, 9H), 1.21 (s, 9H), 0.87 (s, 9H).

Example 25

The following can illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

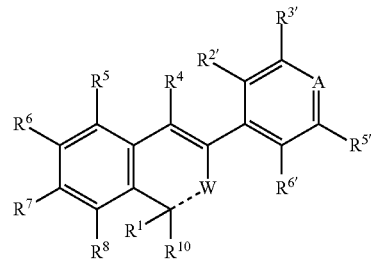

wherein:
the bond represented by - - - is a double bond, $R^{10}$ is absent, and W is $(NR^{30})^+D^-$;
$R^1$ is —$NR^{3a}R^{3b}$, —$C(=NR^{3cb})$—$NR^{3cc}R^{3cd}$, aryloxy, cyano, or ($C_1$-$C_6$)alkyl that is substituted with one or more —$NR3^{ce}$-$C(=NR^{3cb})R^{3ce}$, —$C(=NR^{3cb})$—$NR^{3cc}R^{3cd}$, —$NR^{3ce}$—$C(=NR^{3cb})$—$NR^{3cc}R^{3cd}$, and —$NR^{3ce}$—$C(=O)$—$NR^{3cc}R^{3cd}$;
at least one of $R^4$, $R^5$, $R^{2'}$, $R^{3'}$, and $R^{6'}$ is aryl or heteroaryl; and the remainder of $R^4$, $R^5$, $R^{2'}$, $R^{3'}$, and $R^{6'}$ is selected from hydrogen, halo, hydroxy, carboxy, cyano, $CF_3SO_3$—, ($C_1$-$C_6$)alkyl, ($C_2$-$C_6$)alkenyl, ($C_2$-$C_6$)alkynyl, ($C_1$-$C_6$)alkoxy, cycloalkyl, aryl($C_1$-$C_6$)alkyl, aryl, heteroaryl, hetero aryl ($C_1$-$C_6$)alkyl, aryl ($C_1$-$C_6$)alkanoyl, and heteroaryl ($C_1$-$C_6$)alkanoyl; wherein each ($C_1$-$C_6$)alkyl, ($C_2$-$C_6$)alkenyl, ($C_2$-$C_6$)alkynyl, ($C_1$-$C_6$)alkoxy, cycloalkyl, and ($C_1$-$C_6$)alkanoyl of $R^4$, $R^5$, $R^{2'}$, $R^{3'}$, and $R^{6'}$ is optionally substituted with one or more groups independently selected from halo, hydroxy, cyano, nitro, ($C_1$-$C_6$)alkoxy, cycloalkyl, oxo, carboxy, aryloxy, sulfo, —$S(O)_2NR^{3g}R^{3h}$, —$N(R^j)S(O)_2R^{3k}$, and —$NR^{3g}R^{3h}$; and wherein each aryl, and heteroaryl of $R^4$, $R^5$, $R^{2'}$, $R^{3'}$, and $R^{6'}$ is optionally substituted with one or more groups independently selected from ($C_1$-$C_6$)

alkyl, halo, hydroxy, cyano, nitro, $(C_1-C_6)$alkoxy, cycloalkyl, carboxy, aryloxy, nitro, sulfo, $R^{3aa}$, $—S(O)_2NR^{3g}R^{3h}$, $—N(R^{3j})S(O)_2R^{3k}$, and $—NR^{3g}R^{3h}$;

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, $R^{3bb}$, and $Z—R^{3x}$;

each Z is independently selected from $—O—$, $—S—$, and $—N(R^{3y})—$;

$R^{30}$ is absent and $D^-$ is absent; or $R^{30}$ is H or $(C_1-C_6)$alkyl and $D^-$ is counterion;

A is N or $C—R^{4'}$;

$R^{3a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^a$ is optionally substituted with one or more groups selected from halo, hydroxy, cyano, nitro, $(C_1-C_6)$alkoxy, cycloalkyl, oxo, carboxy, $—NR^{3da}R^{3db}$, and aryloxy, and wherein each aryl and heteroaryl of $R^{3a}$ is optionally substituted with one or more groups selected from $(C_1-C_6)$alkyl, halo, hydroxy, cyano, nitro, $(C_1-C_6)$alkoxy, cycloalkyl, carboxy, and aryloxy; and $R^{3b}$ is hydrogen, $(C_1-C_6)$alkyl, aryl, aryl$(C_1-C_6)$alkyl, heteroaryl, heteroaryl$(C_1-C_6)$alkyl, $—C(=NR^{3cb})—NR^{3cc}R^{3cd}$, $—C(=NR^{3cb})—R^{3ea}$, $—C(=O)—R^{3m}$, $—C(=O)—OR^{3n}$, $—C(=O)—SR^{3p}$, $—C(=O)—NR^{3q}R^{3r}$, $—C(=S)—R^{3m}$, $—C(=S)—OR^{3n}$, $—C(=S)—SR^{3p}$, or $—C(=S)—NR^{3q}R^{3r}$; wherein each $(C_1-C_6)$alkyl of $R^{3b}$ is optionally substituted with one or more groups independently selected from halo, hydroxy, cyano, nitro, $(C_1-C_6)$alkoxy, cycloalkyl, oxo, carboxy, $—NR^{3da}R^{3db}$, and aryloxy; and wherein each aryl, and heteroaryl of $R^b$ is optionally substituted with one or more groups independently selected from $(C_1-C_6)$alkyl, halo, hydroxy, cyano, nitro, $(C_1-C_6)$alkoxy, cycloalkyl, carboxy, and aryloxy; or $R^{3a}$ and $R^{3b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{3c}$ is hydrogen, $(C_1-C_6)$alkyl, aryl, or heteroaryl;

$R^{3d}$ is hydrogen, $(C_1-C_6)$alkyl, $(C_1-C_6)$alkoxy, $(C_1-C_6)$alkylthio, $(C_1-C_6)$alkanoyl, or $—NR^{3e}R^{3f}$;

$R^{3e}$ and $R^{3f}$ are each independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; or $R^{3e}$ and $R^{3f}$ together with the nitrogen to which they are attached form a aziridino, azetidino, morpholino, piperazino, pyrrolidino or piperidino;

each $R^{3g}$ and $R^{3h}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$ alkyl; or $R^{3g}$ and $R^{3h}$ together with the nitrogen to which they are attached form a aziridino, azetidino, morpholino, piperazino, pyrrolidino or piperidino;

each $R^{3j}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3k}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3m}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl;

each $R^{3n}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $—S(O)_2NR^{3g}R^{3h}$, $—N(R^{3j})S(O)_2R^{3k}$, and $—NR^{3g}R^{3h}$;

each $R^{3p}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $—S(O)_2NR^{3g}R^{3h}$, $—N(R^{3j})S(O)_2R^{3k}$, and $—NR^{3g}R^{3h}$;

each $R^{3q}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; and each $R^{3r}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$alkyl; or $R^{3q}$ and $R^{3r}$ together with the nitrogen to which they are attached form a aziridino, azetidino, morpholino, piperazino, pyrrolidino or piperidino;

each $R^{3u}$ and $R^{3v}$ is independently selected from H and $(C_1-C_6)$alkyl;

each $R^{3x}$ is independently selected from $(C_1-C_6)$alkyl, $(C_1-C_6)$alkanoyl, and $—C(=O)NR^{3u}R^{3v}$;

each $R^{3y}$ is independently selected from H and $(C_1-C_6)$ alkyl;

each $R^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$ alkoxy, cycloalkyl, carboxy, aryloxy, nitro, sulfo, $—S(O)_2NR^{3g}R^{3h}$, $—N(R^{3j})S(O)_2R^{3k}$, and $—NR^{3g}R^{3h}$; and each $R^{3bb}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$ alkoxy, cycloalkyl, carboxy, aryloxy, nitro, sulfo, $—S(O)_2NR^{3g}R^{3h}$, $—N(R^{3j})S(O)_2R^{3k}$, and $—NR^{3g}R^{3h}$;

each $R^{3cb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3cc}$ and $R^{3cd}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl $(C_1-C_6)$ alkyl; or $R^{3cc}$ and $R^{3cd}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl $(C_1-C_6)$ alkyl or heteroaryl$(C_1-C_6)$alkyl of $R^{3cc}$ and $R^{3cd}$ is optionally substituted with one or more groups independently selected from hydroxy, carboxy, and $NR^{3cm}R^{3cn}$;

each $R^{3ce}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3cg}$ and $R^{3ch}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl $(C_1-C_6)$ alkyl; or $R^{3cg}$ and $R^{3ch}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{3cg}$ and $R^{3ch}$ is optionally substituted with one or more groups independently selected from hydroxy, carboxy, and $NR^{3cm}R^{3cn}$;

each $R^{3cm}$ and $R^{3cn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl $(C_1-C_6)$ alkyl; or $R^{cm}$ and $R^{cn}$ together with the nitrogen to which they are attached form a aziridino, azetidino, morpholino, piperazino, pyrrolidino or piperidino;

each $R^{3da}$ and $R^{3db}$ is independently selected from H, $(C_1-C_6)$alkyl, cycloalkyl, cycloalkyl$(C_1-C_6)$alkyl, aryl, heteroaryl, aryl$(C_1-C_6)$ alkyl and heteroaryl$(C_1-C_6)$ alkyl; or $R^{3da}$ and $R^{3db}$ together with the nitrogen to which they are attached form a aziridino, azetidino, morpholino, piperazino, pyrrolidino or piperidino; and $R^{ea}$ is H, $(C_1-C_6)$alkyl, $(C_1-C_6)$alkoxy, $(C_1-C_6)$alkylthio, or $(C_1-C_6)$alkanoyl; or a salt thereof.

2. The compound of claim 1 which is:

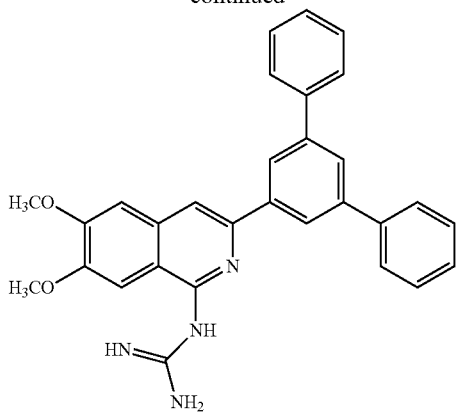

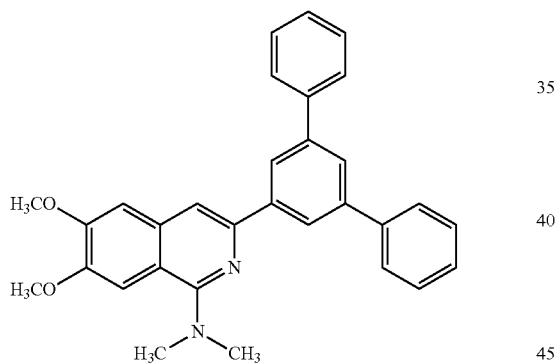

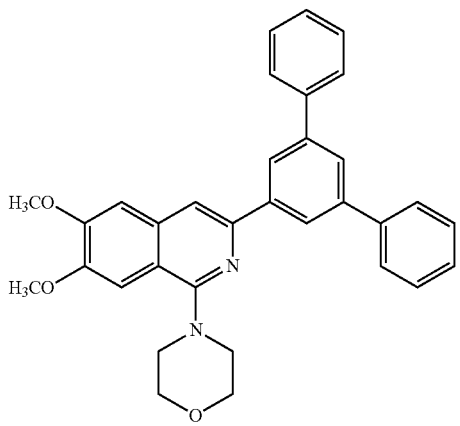

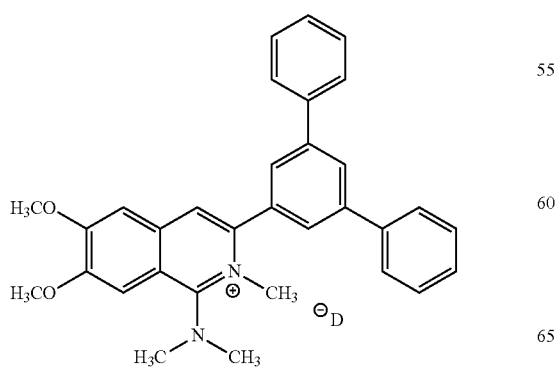

173
-continued
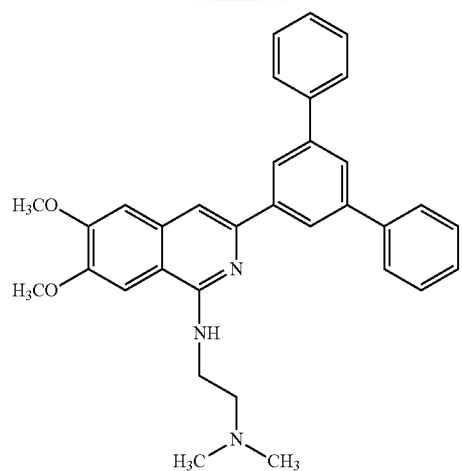
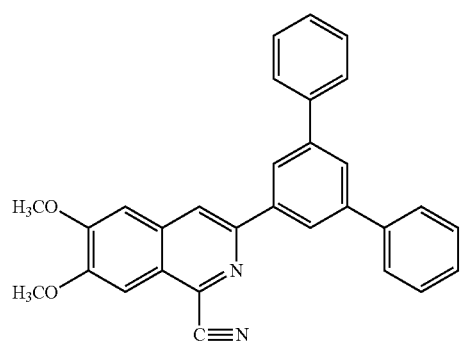
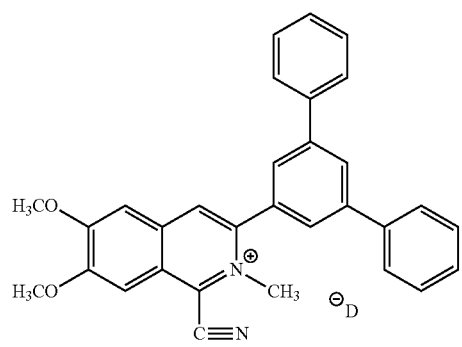
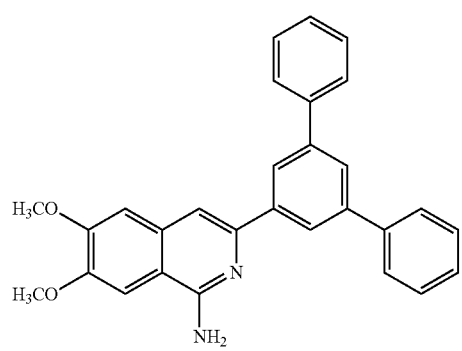
174
-continued
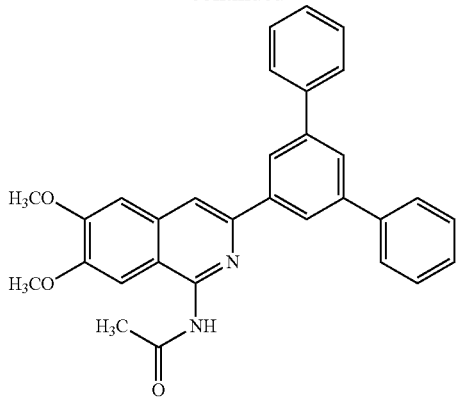
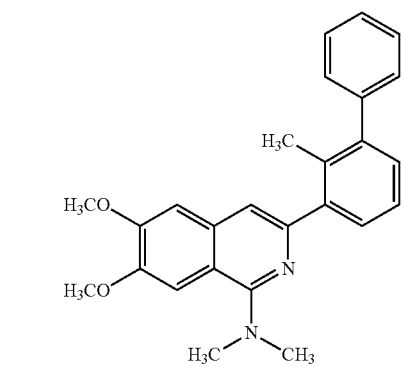
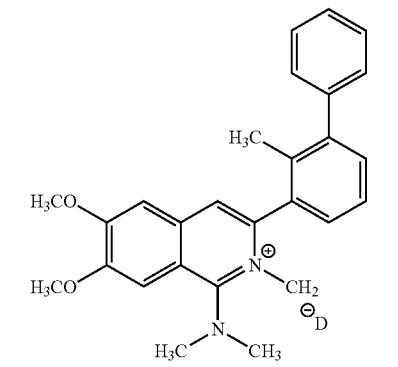
or
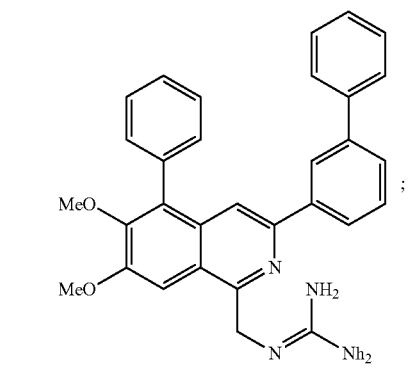
;
or a salt thereof.

3. The compound of claim 1 which is:
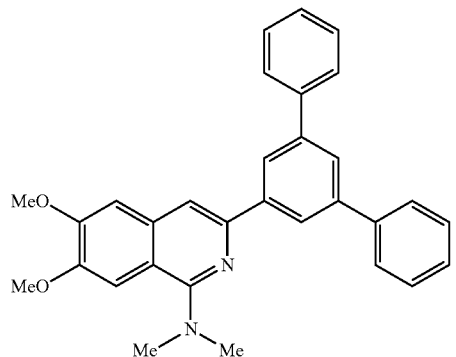
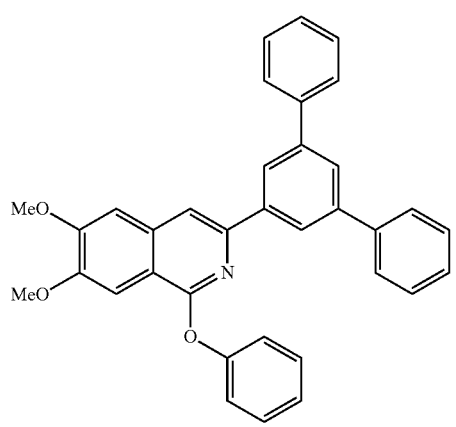
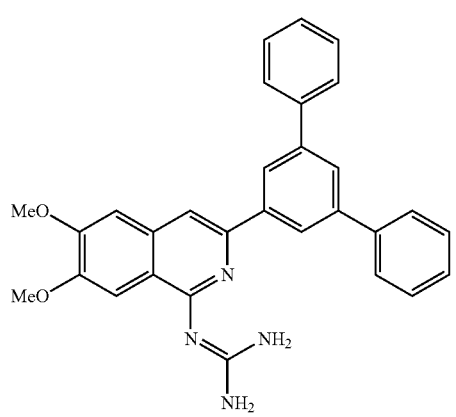
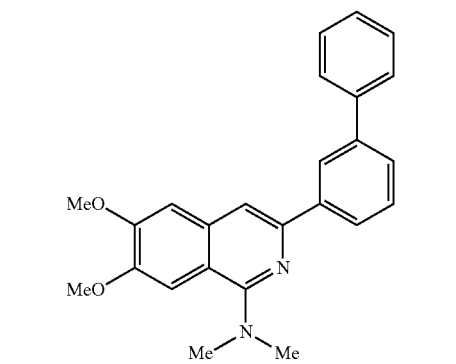
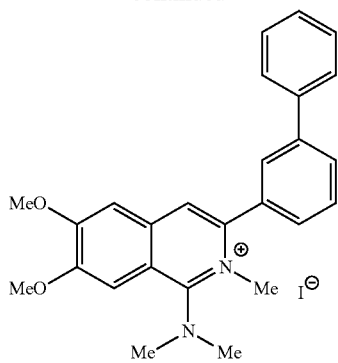
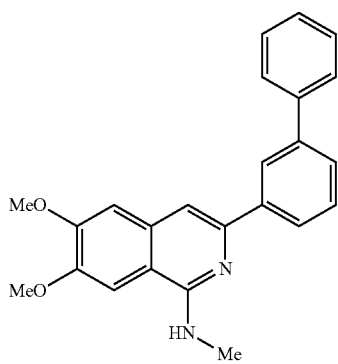
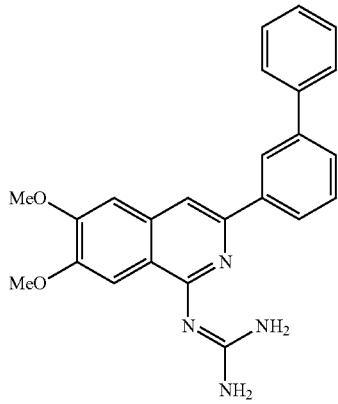
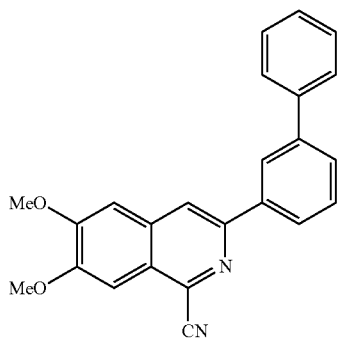

177
-continued
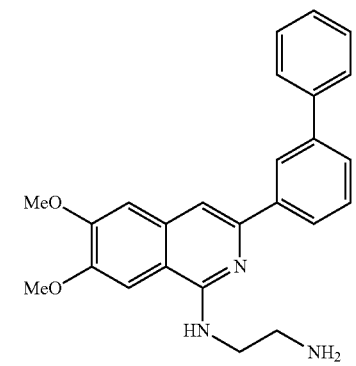
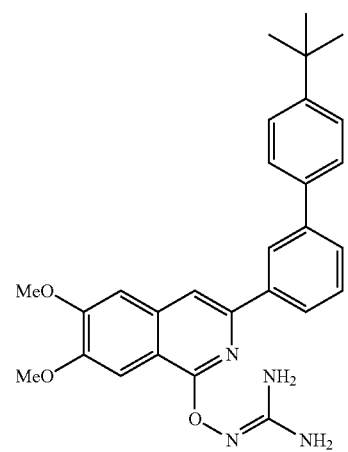
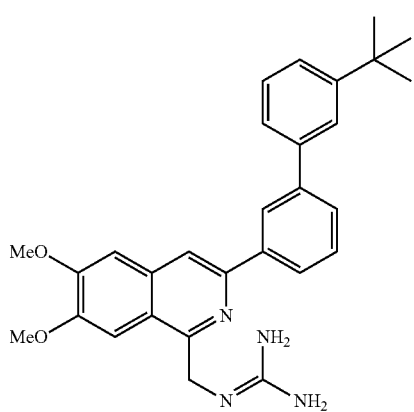
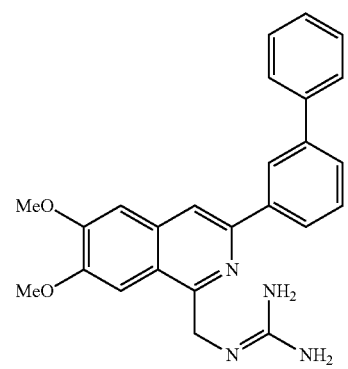
178
-continued
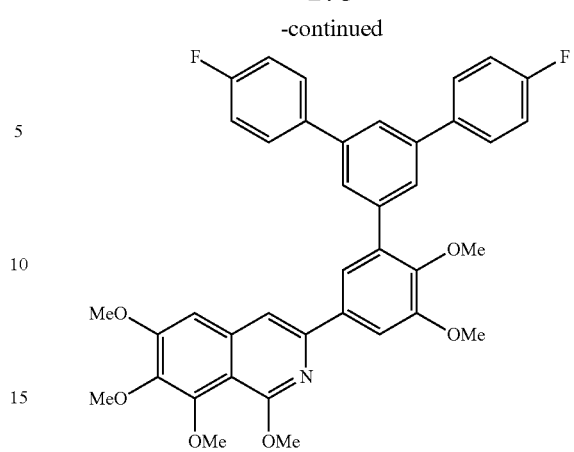
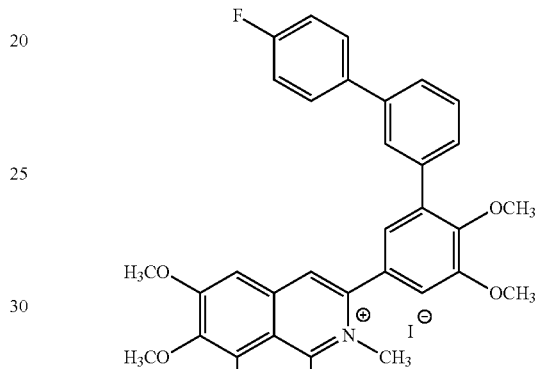
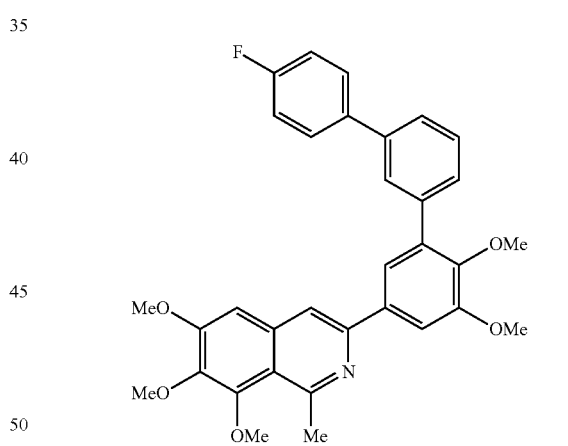
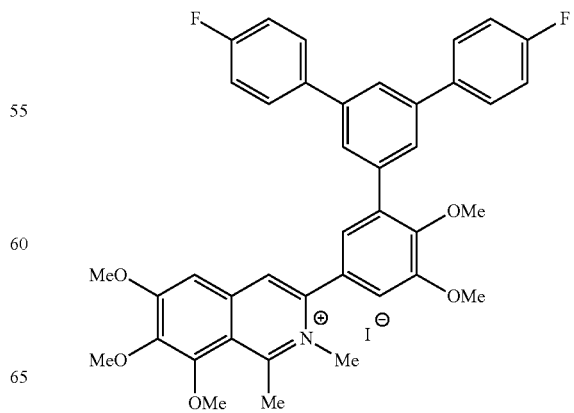

-continued

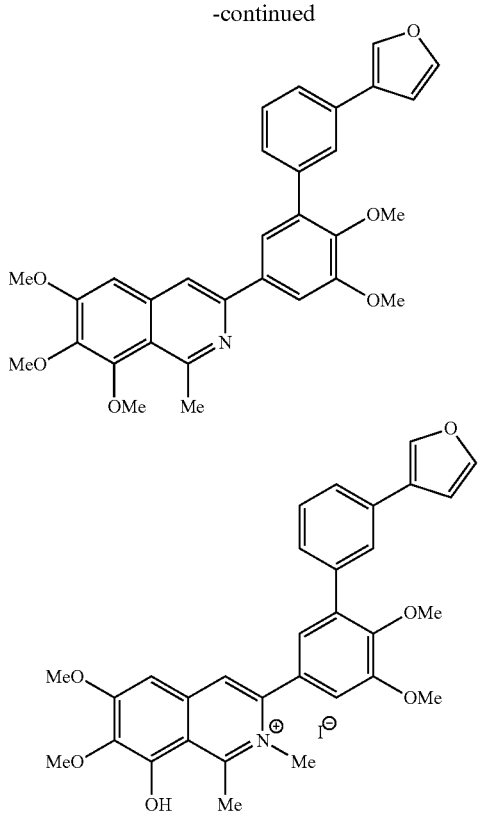

or a salt thereof.

4. The compound of claim 1 wherein:
the bond represented by - - - is present, $R^{10}$ is absent, and W is $(NR^{30})^+D^-$;
$R^6 R^7, R^8, R^{4'}$ and $R^{5'}$ are each independently selected from H and Z—$R^x$; or $R^6$ and $R^7$ taken together are methylenedioxy and $R^8, R^{4'}$, and $R^{5'}$ are each independently selected from H and Z—$R^x$; or $R^7$ and $R^8$ taken together are methylenedioxy and $R^6 R^{4'}$ and $R^{5'}$ are each independently selected from H and Z—$R^x$; or $R^{4'}$ and $R^{5'}$ taken together are methylenedioxy and $R^6 R^7$, and $R^8$ are each independently selected from H and —Z—$R^x$;
each Z is independently selected from —O—, —S—, and —N($R^y$)—;
at least one of $R^4, R^5, R^{2'}, R^{3'}$, and $R^{6'}$ is aryl or heteroaryl;
and the remainder of $R^4, R^5, R^{2'}, R^{3'}$, and $R^{6'}$ is selected from hydrogen, hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$ alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl of $R^4, R^5, R^{2'}, R^{3'}$, and $R^{6'}$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, —$S(O)_2NR^{3g}R^{3h}$, —$N(R^{3j})S(O)_2R^{3k}$, and —$NR^{3g}R^{3h}$; and wherein each aryl, and heteroaryl of $R^4, R^5, R^{2'}, R^{3'}$, and $R^{6'}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —$S(O)_2NR^{3g}R^{3h}$, —$N(R^{3j})S(O)_2R^{3k}$, and —$NR^{3g}R^{3h}$;

$R^{30}$ is absent and $X^-$ is absent; or $R^{30}$ is H or $(C_1-C_6)$alkyl and $X^-$ is counterion;
$R^{11}$ is —$NR^{3a}R^{3b}$ or cyano;
$R^{3a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^{3a}$ is optionally substituted with one or more groups selected from halo, hydroxy, cyano, nitro, $(C_1-C_6)$alkoxy, $(C_3-C_6)$cycloalkyl, oxo, carboxy, and aryloxy, and wherein each aryl and heteroaryl of $R^{3a}$ is optionally substituted with one or more groups selected from $(C_1-C_6)$alkyl, halo, hydroxy, cyano, nitro, $(C_1-C_6)$alkoxy, $(C_3-C_6)$cycloalkyl, carboxy, and aryloxy; and $R^{3b}$ is hydrogen, $(C_1-C_6)$alkyl, aryl, aryl$(C_1-C_6)$alkyl, heteroaryl, heteroaryl$(C_1-C_6)$alkyl, —$C(=O)$—$R^{3m}$, —$C(=O)$—$OR^{3n}$, —$C(=O)$—$S3p^p$, —$C(=O)$—$NR^{3q}R^{3r}$, —$C(=S)$—$R^{3m}$, —$C(=S)$—$OR^{3n}$, —$C(=S)$—$SR^{3p}$, —$C(=S)$—$NR^{3q}R^{3r}$, or —$C(=NR^{3c})$—$R^{3d}$; wherein each $(C_1-C_6)$alkyl of $R^{3b}$ is optionally substituted with one or more groups independently selected from halo, hydroxy, cyano, nitro, $(C_1-C_6)$alkoxy, $(C_3-C_6)$cycloalkyl, oxo, carboxy, and aryloxy; and wherein each aryl, and heteroaryl of $R^{3b}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, and aryloxy; or $R^{3a}$ and $R^{3b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one or more $(C_1-C_6)$alkyl;
$R^{3c}$ is hydrogen, $(C_1-C_6)$alkyl, aryl, or heteroaryl;
$R^{3d}$ is hydrogen, $(C_1-C_6)$alkyl, $(C_1-C_6)$alkoxy, $(C_1-C_6)$alkylthio, $(C_1-C_6)$alkanoyl, or —$NR^{3e}R^{3f}$;
$R^{3e}$ and $R^{3f}$ are each independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^e$ and $R^f$ together with the nitrogen to which they are attached form a aziridino, azetidino, morpholino, piperazino, pyrrolidino or piperidino;
each $R^{3g}$ and $R^{3h}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{3g}$ and $R^{3h}$ together with the nitrogen to which they are attached form a aziridino, azetidino, morpholino, piperazino, pyrrolidino or piperidino;
each $R^{3j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;
each $R^{3k}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;
each $R^{3m}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;
each $R^{3n}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;
each $R^{3p}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{3q}$ is independently selected from H, $(C_1$-$C_6)$alkyl, $(C_3$-$C_6)$cycloalkyl, $(C_3$-$C_6)$cycloalkyl$(C_1$-$C_6)$alkyl, aryl, heteroaryl, aryl$(C_1$-$C_6)$ alkyl and heteroaryl$(C_1$-$C_6)$alkyl; and each $R^{3r}$ is independently selected from H, $(C_1$-$C_6)$alkyl, $(C_3$-$C_6)$cycloalkyl, $(C_3$-$C_6)$cycloalkyl $(C_1$-$C_6)$alkyl, aryl, heteroaryl, aryl$(C_1$-$C_6)$ alkyl and heteroaryl$(C_1$-$C_6)$alkyl; or $R^{3q}$ and $R^{3r}$ together with the nitrogen to which they are attached form a aziridino, azetidino, morpholino, piperazino, pyrrolidino or piperidino;

each $R^{3u}$ and $R^{3v}$ is independently selected from H and $(C_1$-$C_6)$alkyl;

each $R^{3x}$ is independently selected from $(C_1$-$C_6)$alkyl, $(C_1$-$C_6)$alkanoyl, and —C(=O)NR$^{3u}$R$^{3v}$; and each $R^{3y}$ is independently selected from H and $(C_1$-$C_6)$ alkyl;

or a salt thereof.

5. The compound of claim 1 which is a compound of formula (IIIa):

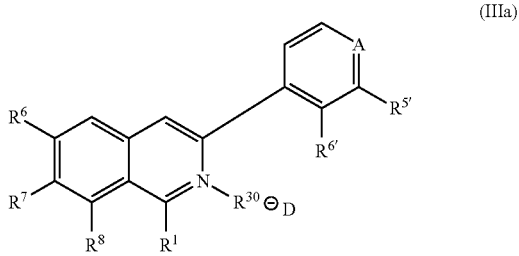

(IIIa)

wherein $R^{6'}$ is selected from hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, arylalkanoyl, and heteroarylalkanoyl; wherein each $(C_1$-$C_6)$alkyl, $(C_2$-$C_6)$alkenyl, $(C_2$-$C_6)$alkynyl, $(C_1$-$C_6)$alkoxy, cycloalkyl, and $(C_1$-$C_6)$alkanoyl of $R^{6'}$ is optionally substituted with one or more groups independently selected from halo, hydroxy, cyano, nitro, $(C_1$-$C_6)$alkoxy, cycloalkyl, oxo, carboxy, aryloxy, sulfo, —S(O)$_2$NR$^{3g}$R$^{3h}$, —N(R$^{3j}$)S(O)$_2$R$^{3k}$, and —NR$^{3g}$R$^{3h}$; and wherein each aryl, and heteroaryl of $R^{6'}$ is optionally substituted with one or more groups independently selected from $(C_1$-$C_6)$ alkyl, halo, hydroxy, cyano, nitro, $(C_1$-$C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; or a salt thereof.

6. The compound of claim 1 which is a compound of formula (IIIb):

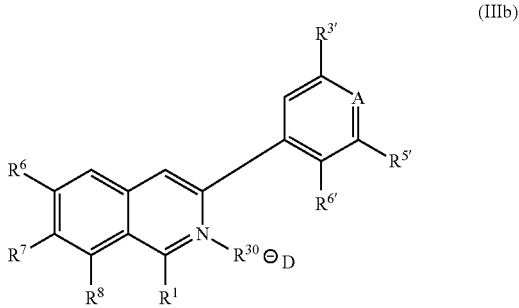

(IIIb)

wherein $R^{3'}$ is selected from hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, arylalkanoyl, and heteroarylalkanoyl; wherein each $(C_1$-$C_6)$alkyl, $(C_2$-$C_6)$alkenyl, $(C_2$-$C_6)$alkynyl, $(C_1$-$C_6)$alkoxy, cycloalkyl, and $(C_1$-$C_6)$alkanoyl of $R^{3'}$ is optionally substituted with one or more groups independently selected from halo, hydroxy, cyano, nitro, $(C_1$-$C_6)$ alkoxy, cycloalkyl, oxo, carboxy, aryloxy, sulfo, —S(O)$_2$NR$^{3g}$R$^{3h}$, —N(R$^{3j}$)S(O)$_2$R$^{3k}$, and —NR$^{3g}$R$^{3h}$; and wherein each aryl, and heteroaryl of $R^{3'}$ is optionally substituted with one or more groups independently selected from $(C_1$-$C_6)$ alkyl, halo, hydroxy, cyano, nitro, $(C_1$-$C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$;

or a salt thereof.

7. The compound of claim 1 which is a compound of formula (IIIc):

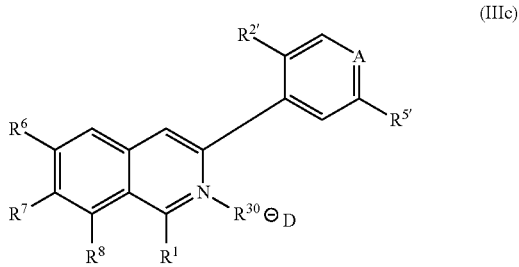

(IIIc)

wherein $R^{2'}$ is selected from hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, arylalkanoyl, and heteroarylalkanoyl; wherein each $(C_1$-$C_6)$alkyl, $(C_2$-$C_6)$alkenyl, $(C_2$-$C_6)$alkynyl, $(C_1$-$C_6)$alkoxy, cycloalkyl, and $(C_1$-$C_6)$alkanoyl of $R^{2'}$ is optionally substituted with one or more groups independently selected from halo, hydroxy, cyano, nitro, $(C_1$-$C_6)$ alkoxy, cycloalkyl, oxo, carboxy, aryloxy, sulfo, —S(O)$_2$NR$^{3g}$R$^{3h}$, —N(R$^{3j}$)S(O)$_2$Rv$^k$, and —NR$^{3g}$R$^{3h}$; and wherein each aryl, and heteroaryl of $R^{2'}$ is optionally substituted with one or more groups independently selected from $(C_1$-$C_6)$ alkyl, halo, hydroxy, cyano, nitro, $(C_1$-$C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; or a salt thereof.

8. The compound of claim 1 which is a compound of formula (IIId):

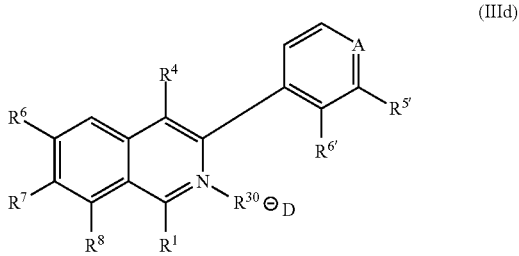

(IIId)

wherein $R^4$ is selected from hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, arylalkanoyl, and heteroarylalkanoyl; wherein each $(C_1$-$C_6)$alkyl, $(C_2$-$C_6)$alkenyl, $(C_2$-$C_6)$alkynyl, $(C_1$-$C_6)$alkoxy, cycloalkyl, and $(C_1$-$C_6)$alkanoyl of $R^4$ is optionally substituted with one or more groups independently selected from halo, hydroxy, cyano, nitro, $(C_1-C_6)$ alkoxy, cycloalkyl, oxo, carboxy, aryloxy, sulfo, —S(O)$_2$NR$^{3g}$R$^{3h}$, —N(R$^{3j}$)S(O)$_2$R$^{3k}$, and —NR$^{3g}$R$^{3h}$; and wherein each aryl, and heteroaryl of R$^4$ is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; or a salt thereof.

9. The compound of claim 1 which is a compound of formula (IIIe):

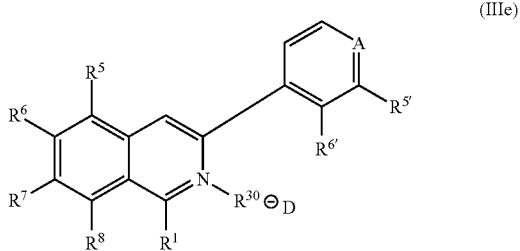

wherein R$^5$ is selected from hydroxy, carboxy, cyano, CF$_3$SO$_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; wherein each $(C_1-C_6)$alkyl, $(C_2-C_6)$alkenyl, $(C_2-C_6)$ alkynyl, $(C_1-C_6)$alkoxy, cycloalkyl, and $(C_1-C_6)$alkanoyl of R$^5$ is optionally substituted with one or more groups independently selected from halo, hydroxy, cyano, nitro, $(C_1-C_6)$ alkoxy, cycloalkyl, oxo, carboxy, aryloxy, sulfo, —S(O)$_2$NR$^{3g}$R$^{3h}$, —N(R$^{3j}$)S(O)$_2$R$^{3k}$, and —NR$^{3g}$R$^{3h}$; and wherein each aryl, and heteroaryl of R$^5$ is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; or a salt thereof.

10. The compound of claim 1 wherein R$^6$, R$^7$, R$^8$, R$^{4'}$ and R$^{5'}$ are each independently $(C_1-C_3)$alkoxy.

11. The compound of claim 1 wherein R$^6$, R$^7$, R$^8$, R$^{4'}$ and R$^{5'}$ are each methoxy.

12. The compound of claim 1 wherein R$^7$, R$^8$, R$^{4'}$ and R$^{5'}$ are each methoxy.

13. The compound of claim 1 wherein R$^{6'}$ is selected from phenyl, pyridyl and furanyl and is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; and each R$^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{3g}$Rv$^h$, —N(R$^{3j}$)S(O)$_2$R$^{3k}$, and —NR$^{3g}$Rv$^h$.

14. The compound of claim 1 wherein R$^{3'}$ is selected from phenyl, pyridyl and furanyl and is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; and each R$^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

15. The compound of claim 1 wherein R$^{2'}$ is selected from phenyl, pyridyl and furanyl and is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g3}$R$^h$; and each R$^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

16. The compound of claim 1 wherein R$^4$ is selected from phenyl, pyridyl and furanyl and is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; and each R$^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

17. The compound of claim 1 wherein R$^5$ is selected from phenyl, pyridyl and furanyl and is optionally substituted with one or more groups independently selected from $(C_1-C_6)$ alkyl, halo, hydroxy, cyano, nitro, $(C_1-C_6)$alkoxy, cycloalkyl, carboxy, aryloxy, nitro, sulfo, R$^{3aa}$, —S(O)$_2$NR$^{3g}$R$^{3h}$, —N(R$^{3j}$)S(O)$_2$R$^{3k}$, and —NR$^{3g}$R$^{3h}$; and each R$^{3aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{3g}$R$^{3h}$, —N(R$^{3j}$)S(O)$_2$R$^{3k}$, and —NR$^{3g}$R$^{3h}$.

18. The compound of claim 1 wherein at least one of R$^4$, R$^5$, R$^{2'}$, R$^{3'}$, and R$^{6'}$ is selected from 3-biphenyl, 3-(4'-fluoro) biphenyl, 4-biphenyl, 4-(4'-fluoro)biphenyl, 3,5-bis(4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenyl)phenyl, 4-(3-furanyl)phenyl, 2-phenylpyrid-4-yl, 2-(3-methoxyphenyl)pyrid-3-yl, 2-phenylfur-4-yl, and 2-pyrid-4-yl)pyrid-5-yl.

19. A composition comprising a compound of formula I as described in claim 1, or a pharmaceutically acceptable salt thereof, and a pharmaceutically acceptable vehicle.

20. A method for inhibiting FtsZ polymerization in a bacterium comprising contacting the bacterium with an amount of a compound of formula I as described in claim 1, or a pharmaceutically acceptable salt thereof, effective to inhibit FtsZ polymerization.

21. A method for inhibiting FtsZ Z-ring formation in a bacterium comprising contacting the bacterium with an amount of a compound of formula I as described in claim 1, or a pharmaceutically acceptable salt thereof, effective to inhibit FtsZ Z-ring formation.

22. A method for inhibiting the recruitment of divisome proteins in a bacterium comprising contacting the bacterium with an amount of a compound of formula I as described in claim 1, or a pharmaceutically acceptable salt thereof, effective to inhibit the recruitment of divisome proteins.

23. A method for treating a bacterial infection in a mammal comprising administering to the mammal an effective amount of a compound of formula I as described in claim 1, or a pharmaceutically acceptable salt thereof.

24. The method of claim 23 wherein the bacterial infection is a Gram-negative bacterial strain infection.

25. The method of claim 23 wherein the bacterial infection is a Gram-positive bacterial strain infection.

26. The method of claim 23 wherein the bacterial infection is a multiple drug-resistant bacterial strain infection.

27. The method of claim 26 wherein the multiple drug-resistance bacterial strain is selected from the group consisting of methicillin-resistant *Staphylococcus aureus*, vancomycin-resistant *Enterococcus*, multiple drug-resistant tuberculosis and multidrug-resistant *Clostridium difficile*.

* * * * *

UNITED STATES PATENT AND TRADEMARK OFFICE
CERTIFICATE OF CORRECTION

PATENT NO. : 8,933,096 B2
APPLICATION NO. : 13/702936
DATED : January 13, 2015
INVENTOR(S) : LaVoie et al.

It is certified that error appears in the above-identified patent and that said Letters Patent is hereby corrected as shown below:

On the Title Page

Under Item (75) Inventors:

Replace:

"Ajit Parhi, Highland Park, NJ"

With:

-- Ajit Parhi, New Brunswick, NJ --

Under Item (57) Abstract, in the first line:

Replace:

"The invention provides a compound of formula (I): or a salt or"

With:

-- The invention provides a compound of formula (I), or a salt or --

In the Claims

In Claim 1, Column 168, Lines 57-58:

Replace:

Signed and Sealed this
Twenty-eighth Day of July, 2015

Michelle K. Lee
*Director of the United States Patent and Trademark Office*

"heteroaryl, hetero aryl ($C_1$-$C_6$)alkyl, aryl ($C_1$-$C_6$)alkanoyl, and heteroaryl ($C_1$-$C_6$) alkanoyl;"

With:

-- heteroaryl, heteroaryl($C_1$-$C_6$)alkyl, aryl($C_1$-$C_6$)alkanoyl, and heteroaryl ($C_1$-$C_6$) alkanoyl; --

In Claim 1, Column 169, Line 33-34:

Replace:

"and wherein each aryl, and heteroaryl of $R^b$ is"

With:

-- and wherein each aryl and heteroaryl of $R^b$ is --

In Claim 1, Column 169, Line 41:

Replace:

"pyrrolidino pyrrole,"

With:

-- pyrrolidino, pyrrole, --

In Claim 1, Column 169, Line 51:

Replace:

"form a aziridino,"

With:

-- form an aziridino, --

In Claim 1, Column 169, Line 57:

Replace:

"form a aziridino,"

CERTIFICATE OF CORRECTION (continued)
U.S. Pat. No. 8,933,096 B2

Page 3 of 7

With:

-- form an aziridino, --

In Claim 1, Column 170, Line 25:

Replace:

"form a aziridino,"

With:

-- form an aziridino, --

In Claim 1, Column 170, Line 56:

Replace:

"form a aziridino,"

With:

-- form an aziridino, --

In Claim 1, Column 171, Line 18:

Replace:

"form a aziridino,"

With:

-- form an aziridino, --

In Claim 1, Column 171, Line 25:

Replace:

"form a aziridino,"

With:

-- form an aziridino, --
In Claim 2, Column 177, Lines 18-35:
Replace:
" 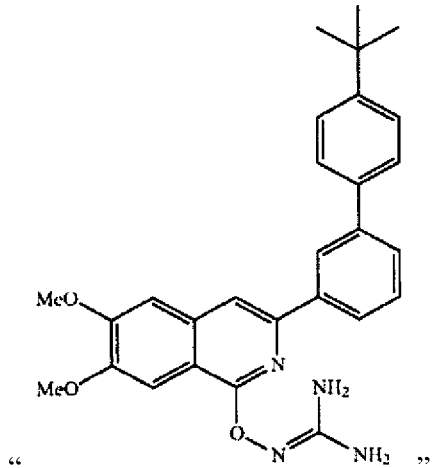 "
With:
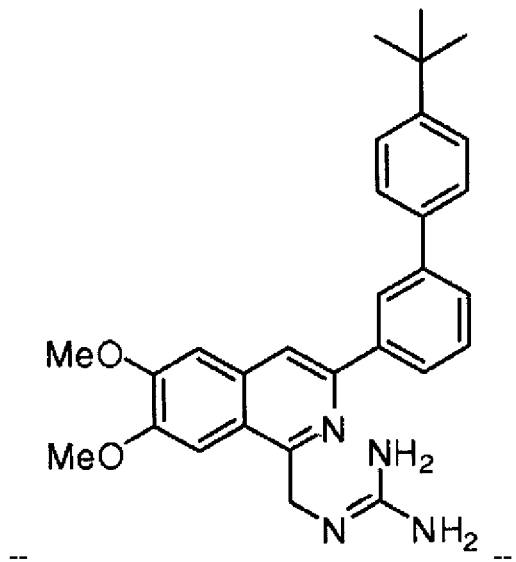
--  --
In Claim 2, Column 178, Lines 1-17:
Replace:

"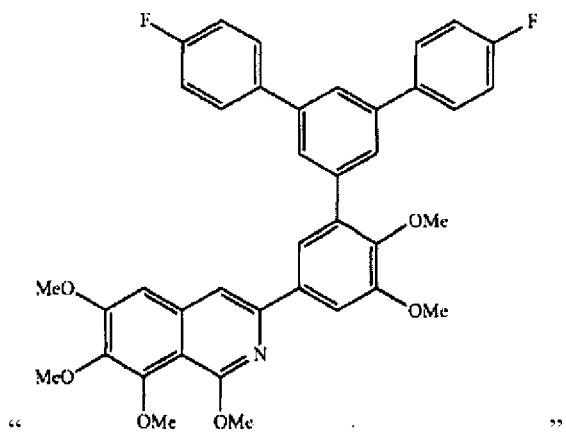"

With:

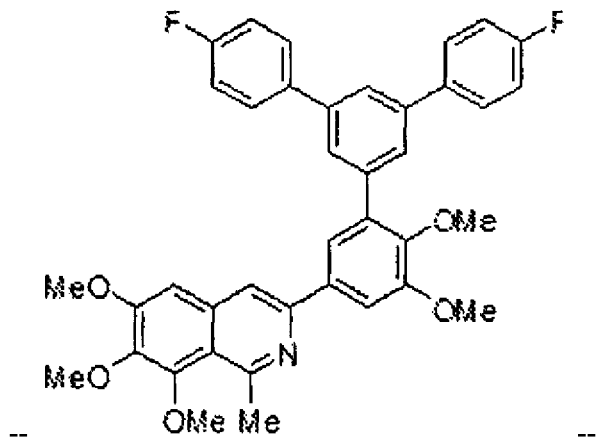

In Claim 4, Column 179, Lines 42-43:

Replace:

"are methylenedioxy and $R^6$ $R^{4'}$ and $R^{5'}$ are each independently selected from H and Z-$R^x$; or $R^{4'}$ and $R^{5'}$ taken together are methylenedioxy and $R^6$ $R^7$, and R8 are"

With:

-- are methylenedioxy and $R^6$, $R^{4'}$ and $R^{5'}$ are each independently selected from H and Z-$R^x$; or $R^{4'}$ and $R^{5'}$ taken together are methylenedioxy and $R^6$, $R^7$, and R8 are --

In Claim 4, Column 180, Line 16:

Replace:

"–C(=O) –S3$p^p$,"

With:

-- –C (=O) –SR$^{3p}$, --

In Claim 4, Column 180, Line 27:

Replace:

"form aziridino,"

With:

-- form an aziridino, --

In Claim 4, Column 180, Line 40:

Replace:

"form a aziridino,"

With:

-- form an aziridino, --

In Claim 4, Column 180, Line 45:

Replace:

"form a aziridino,"

With:

-- form an aziridino, --

In Claim 4, Column 181, Line 8:

Replace:

"form a aziridino,"

With:

-- form an aziridino, --

In Claim 6, Column 182, Line 9:

Replace:

"each aryl, and heteroaryl"

With:

-- each aryl and heteroaryl --

In Claim 8, Column 183, Line 4:

Replace:

"each aryl, and heteroaryl"

With:

-- each aryl and heteroaryl --

In Claim 9, Column 183, Line 35:

Replace:

"each aryl, and heteroaryl"

With:

-- each aryl and heteroaryl --

In Claim 15, Column 184, Line 9:

Replace:

"$NR^{3g3}R^{h}$;"

With:

-- $NR^{3g}R^{3h}$; --